United States Patent
Brown et al.

(10) Patent No.: US 7,361,495 B2
(45) Date of Patent: Apr. 22, 2008

(54) POLYPEPTIDE FROM A CELLULOLYTIC FUNGUS HAVING CELLULOLYTIC ENHANCING ACTIVITY

(75) Inventors: Kimberly Brown, Elk Grove, CA (US); Paul Harris, Carnation, WA (US); Elizabeth Zaretsky, Reno, NV (US); Edward Re, Davis, CA (US); Elena Vlasenko, Davis, CA (US); Keith McFarland, Davis, CA (US); Alfredo Lopez de Leon, Davis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 11/046,124

(22) Filed: Jan. 28, 2005

(65) Prior Publication Data

US 2005/0191736 A1 Sep. 1, 2005

Related U.S. Application Data

(60) Provisional application No. 60/540,661, filed on Jan. 30, 2004.

(51) Int. Cl.
C12N 9/42 (2006.01)
C12N 9/14 (2006.01)
C07K 14/37 (2006.01)

(52) U.S. Cl. ............ 435/209; 435/195; 530/371; 510/392

(58) Field of Classification Search ........... 435/209, 435/195; 530/371; 510/392
See application file for complete search history.

(56) References Cited

U.S. PATENT DOCUMENTS

2002/0028449 A1 3/2002 Ruben et al.

FOREIGN PATENT DOCUMENTS

| EP | 1 482 033 | 12/2004 |
|---|---|---|
| WO | WO 93/11249 | 6/1993 |
| WO | WO 99/06423 | 2/1999 |
| WO | WO 03/070940 | 8/2003 |
| WO | WO 2004/031378 | 4/2004 |

OTHER PUBLICATIONS

UniProt database search, Result 1, sequence alignment of SEQ ID No. 2 with the protein of record No. Q7RWN7, Galagan et al., "The genome sequence of the filamentous fungus *Neurospora crassa*," Nature 422:859-868, 2003, searched Aug. 5, 2006.*

Result 1, Uniprot protein database search, alignment of Applicants' SEQ ID No. 2 with Uniprot database record No. Q7RWN7, protein from *Neurospora crassa* having cellulolytic activity, Galagan et al., Nature 422:859-868, 2003, search performed on Aug. 5, 2006.*

(Continued)

*Primary Examiner*—Rebecca Prouty
*Assistant Examiner*—Rosanne Kosson
(74) *Attorney, Agent, or Firm*—Robert L. Starnes

(57) ABSTRACT

The present invention relates to isolated polypeptides having cellulolytic enhancing activity and isolated polynucleotides encoding the polypeptides. The invention also relates to nucleic acid constructs, vectors, and host cells comprising the polynucleotides as well as methods for producing and using the polypeptides.

16 Claims, 37 Drawing Sheets

OTHER PUBLICATIONS

Altenschmidt et al., Evidence that enzymes of a novel aerobic 2-amino-benzoate metabolism in denitrifying *Pseudomonas* are coded on a small plasmid, *Eur. J. Biochem.*, 1990, v. 194, pp. 647-653.

Saloheimo et al., cDNA cloning of a *Trichoderma reesei* cellulase and demonstration of endoglucanase activity by expression in yeast, *Eur. J. Biochemistry.*, 1997, v. 249, pp. 584-591.

Lev Sophie et al., A mitogen-activated protein kinase pathway modulates the expression of two cellulase genes in *Cochliobolus heterostrophus* during plant infection, *Plant Cell*, 2003, v. 15, pp. 835-844.

Galagan et al., The genome sequence of the filamentous fungus *Neurospora crassa, Nature*, 2003, v. 422, pp. 859-868.

Database UniProt, Dec. 15, 2003 XP002415905, Accession No. Q7RWN7, Galagan et al., The Genome Sequence of the Filamentous Fungus *Neurospora crassa*, Nature 422:859-868, 2003.

* cited by examiner

```
AATTGAAGGAGGGAGTGGCGGAGTGGCCACCAAGTCAGGCGGCTGTCAACTAACCAAGGATGGGAACAGTTCGGCTGCCTTGCCCGAGG    90
GCAGCGTTCCCTGATGGGGACGAACATGGACTGGGTCAGCTGGGTCAGCTGCTGTATAAAAGTTCAATGATGATCTCTGAGATGCGCTGCTGG   180
GGTGTTCTGCGCTTTTCCATCCTCGCAACCTGTATCCAGCGTTCGGCACGTTGGCACCATGAAGTCGTTCACCATTGCCGCCTTGGCA   270
                                                  M   K   S   F   T   I   A   A   L   A
GCCCTATGGGCCCAGGAGCCGCCCACGGAGGCCGCCCACGGAGGCGCTCGATGATGGAGTCGACTACGGCGTCGCAATGTGTCCGCTC   360
 A   L   W   A   Q   E   A   A   A   H   A   T   F   Q   D   L   W   I   D   G   V   D   Y   G   S   Q   C   V   R   L
CCGGGCGTCCAACTCCCCCGTCACCAATGTTGCGTCGACGATATCGGACAATGTCGGACACCTCGGCACCGTCAAGTGCCCGGTC   450
 P   A   S   N   S   P   V   T   N   V   A   S   D   D   I   R   C   N   V   G   T   S   R   P   T   V   K   C   P   V
AAGGCCGGCTCCACGGTCACGATGAGAATCGAGACCAGTTGCGCACGCCCTCTCTGCGTTAGGCCCCCCAGCTACTATATGGCACTAACACGAC   540
 K   A   G   S   T   V   T   I   E   M   H   Q
CTCCAGCAACCTGGCGACCGGTCTTGCGCCAACGAGGCTATCGGCGGCGACCACTACGGCCCCGTAATGTGTACATGTCAAGTCGAT   630
     Q   P   G   D   R   S   C   A   N   E   A   I   G   G   D   H   Y   G   P   V   M   V   Y   M   S   K   V   D
GACGCGGTGACAGCCGACGGTTCATCGGGCTGGTTCAAGGTGTTCCAGGACAGCTGGGCCAAGAACCCGTCGGGTTCGACGGGCGACGAC   720
 D   A   V   T   A   D   G   S   S   G   W   F   K   V   F   Q   D   S   W   A   K   N   P   S   G   S   T   G   D   D
GACTACTGGGGCACCAAGGACCTCAACTCGTGTGCGCAAGATGAACATCGAGCCGGGCGACTACCTGCTC   810
 D   Y   W   G   T   K   D   L   N   S   C   C   G   S   V   L   Y   T   D   I   E   P   G   D   Y   L   L
CGGGCCGAGGTTATCGCGCTGCACGTGGCCCAGTCTGGGGGCGCCTACTCGGCGACCGTGAATTCCGGCGGCCCTGAACATCAACCACCGCCCATGTCG   900
 R   A   E   V   I   A   L   H   V   A   A   S   S   G   G   A   Q   F   Y   M   S   C   Y   Q   L   T   V   T   G   S
GGCAGCGCGCCACCCCCTGACCGTGAATTCCGGGGCCGAYSASDPGILINIHAPMS                  990
 G   S   A   T   P   S   T   V   N   F   P   G   A   Y   S   A   S   D   P   G   I   L   I   N   I   H   A   P   M   S
ACCTACGTCGTCCCGGGCCCCGACCGTGTAGCAGCCGGCCAAGTCGGCTGCAGTCGGCTGCGAGGCGACCTGCACG  1080
 T   Y   V   V   P   G   P   T   V   Y   A   G   G   S   T   K   S   A   G   S   S   C   E   A   T   C   T
GTTGGTTCCGGCCCCCAGCGCGACACTGACGCGAGCCAGCCCACCTCCACCTGCGGCGCCCCTCCGGCTCCGGCTGCACG  1170
 V   G   S   G   P   S   A   T   L   T   Q   P   T   S   T   A   T   S   A   P   G   G   G   S   G   C   T
GCGCCAAGTACCAGCAGTGCGGCGGCACCGGCTACGTCCGGTAGTCCCGTAGTTCCCTCGTAAGTTCCCTCGTGATATGCCAGTGCCTCTAAGCCGGG  1260
 A   A   K   Y   Q   Q   C   G   G   T   G   Y   T   G   C   T   T   C   A
TCTGGACTGTTTTGCTAACTCGGCGTCACTGACTTATTTCAAGTCAGGGGT
AGCGCTTGCTCAGCGGGCTGCTGTGAAGGAGCTCCCATGTCCCATGCCGGAGTACCGGGCTGAGCGCTGAGCGCTGAGCCGCTTCTTGTATA  1440
TAGTTGAGTTTTCCCAATCATGATGAACAATACATATGCATGACTGTTGCGTCGTCAGTCTTTTTGCTCCACTGAACTGTGAGA         1530
CCCATGTCATCCGACCATTCGATCGTCGCTCTACCATTCGGTTGATGAGAGTCTTGAGAGTCACTGGCACGTCCTCGGCG       1620
GTAATGAAATGTGAGGAAAGATACTTCAAGGATGTGAGCTGTCTGACGCTGTGAGCTCGATGTAGCTGCCCAGACGATATCAGGGATGGCAAATACAGTGCTTCTGTAAGCC    1710
AGCACACAAAAGAATACTCAAGGATGGCCATAGCGGCAAATATACAGTATCAGGGATGCAAAAGTGCAAAAGTAAGGGCTCAATCGG          1800
GGATCGAACCCGAGACCTCGCACATGACTTATTTCAAGTCAGGGGT
```

Fig. 1

```
ACCCCGGGATCACTGCCCCTAGGAACCAGCACACCTCGGTCCAATCATGCGGTTCGACGCCCTCTCCGCCCTCGCTCTTG  80
                                            M  R  F  D  A  L  S  A  L  A  L
CGCCGCTTGTGGCTGGCCACGGCGCCGTGACCAGCTACATCATCGGCGGCAAAACCTATCCCGGCTACGAGGGCTTCTCG 160
 A  P  L  V  A  G  H  G  A  V  T  S  Y  I  I  G  G  K  T  Y  P  G  Y  E  G  F  S
CCTGCCTCGAGCCCGCCGACGATCCAGTACCAGTGGCCCGACTACAACCCGACCCTGAGCGTGACCGACCCGAAGATGCG 240
 P  A  S  S  P  P  T  I  Q  Y  Q  W  P  D  Y  N  P  T  L  S  V  T  D  P  K  M  R
CTGCAACGGCGGCACCTCGGCAGAGCTCAGCGCGCCCGTCCAGGCCGGCGAGAACGTGACGGCCGTCTGGAAGCAGTGGA 320
   C  N  G  G  T  S  A  E  L  S  A  P  V  Q  A  G  E  N  V  T  A  V  W  K  Q  W
CCCACCAGCAAGGCCCCGTCATGGTCTGGATGTTCAAGTGCCCCGGCGACTTCTCGTCGTGCCACGGCGACGGCAAGGGC 400
 T  H  Q  Q  G  P  V  M  V  W  M  F  K  C  P  G  D  F  S  S  S  H  G  D  G  K  G
TGGTTCAAGATCGACCAGCTGGGCCTGTGGGGCAACAACCTCAACTCGAACAACTGGGGCACCGCGATCGTCTACAAGAC 480
 W  F  K  I  D  Q  L  G  L  W  G  N  N  L  N  S  N  N  W  G  T  A  I  V  Y  K  T
CCTCCAGTGGAGCAACCCGATCCCCAAGAACCTCGCGCCGGGCAACTACCTCATCCGCCACGAGCTGCTCGCCCTGCACC 560
   L  Q  W  S  N  P  I  P  K  N  L  A  P  G  N  Y  L  I  R  H  E  L  L  A  L  H
AGGCCAACACGCCGCAGTTCTACGCCGAGTGCGCCCAGCTGGTCGTCTCCGGCAGCGGCTCCGCCCTGCCCCCGTCCGAC 640
 Q  A  N  T  P  Q  F  Y  A  E  C  A  Q  L  V  V  S  G  S  G  S  A  L  P  P  S  D
TACCTCTACAGCATCCCCGTCTACGCGCCCCAGAACGACCCCGGCATCACCGTGAGTGGGCTTCCGTTCCGCGGCGAGCT 720
   Y  L  Y  S  I  P  V  Y  A  P  Q  N  D  P  G  I  T
CTGTGGAAATCTTGCTGACGATGGGCTAGGTTGACATCTACAACGGCGGGCTTACCTCCTACACCCCGCCCGGCGGCCCC 800
                                   V  D  I  Y  N  G  G  L  T  S  Y  T  P  P  G  P
GTCTGGTCTGGCTTCGAGTTTTAGGCGCATTGAGTCGGGGGCTACGAGGGGAAGGCATCTGTTCGCATGAGCGTGGGTAC 880
 V  W  S  G  F  E  F
```

MRFDALSALALAPLVAGHGAVTSYIIGGKTYPGYEGFSPASSPPTIQYQWPDYNPTLSVTDPKMRCNGGTSAELSAPVQA
GENVTAVWKQWTHQQGPVMVWMFKCPGDFSSSHGDGKGWFKIDQLGLWGNNLNSNNWGTAIVYKTLQWSNPIPKNLAPGN
YLIRHELLALHQANTPQFYAECAQLVVSGSGSALPPSDYLYSIPVYAPQNDPGITVDIYNGGLTSYTPPGGPVWSGFEF

Fig. 2

```
CTCCTGTTCCTGGGCCACCGCTTGTTGCCTGCACTATTGGTAGAGTTGGTCTATTGCTAGAGTTGGCCATGCTTCTCACA  80
                                                                    M  L  L  T
TCAGTCCTCGGCTCGGCTGCCCTGCTTGCTAGCGGCGCTGCGGCACACGGCGCCGTGACCAGCTACATCATCGCCGGCAA 160
 S  V  L  G  S  A  A  L  L  A  S  G  A  A  A  H  G  A  V  T  S  Y  I  I  A  G  K
GAATTACCCGGGGTGGGTAGCTGATTATTGAGGGCGCATTCAAGGTTCATACCGGTGTGCATGGCTGACAACCGGCTGGC 240
 N  Y  P  G
AGATACCAAGGCTTTTCTCCTGCAACTCGCCGAACGTCATCCAATGGCAATGGCATGACTACAACCCCGTCTTGTCGTG 320
    Y  Q  G  F  S  P  A  N  S  P  N  V  I  Q  W  Q  W  H  D  Y  N  P  V  L  S  C
CAGCGACTCGAAGCTTCGCTGCAACGGCGGCACGTCGGCCACCCTGAACGCCACGGCCGCACCGGGCGACACCATCACCG 400
    S  D  S  K  L  R  C  N  G  G  T  S  A  T  L  N  A  T  A  A  P  G  D  T  I  T
CCATCTGGGCGCAGTGGACGCACAGCCAGGGCCCCATCCTGGTGTGGATGTACAAGTGCCCGGGCTCCTTCAGCTCCTGT 480
 A  I  W  A  Q  W  T  H  S  Q  G  P  I  L  V  W  M  Y  K  C  P  G  S  F  S  S  C
GACGGCTCCGGCGCTGGCTGGTTCAAGATCGACGAGGCCGGCTTCCACGGCGACGGCGTCAAGGTCTTCCTCGACACCGA 560
 D  G  S  G  A  G  W  F  K  I  D  E  A  G  F  H  G  D  G  V  K  V  F  L  D  T  E
GAACCCGTCCGGCTGGGACATCGCCAAGCTCGTCGGCGGCAACAAGCAGTGGAGCAGCAAGGTCCCCGAGGGCCTCGCCC 640
    N  P  S  G  W  D  I  A  K  L  V  G  G  N  K  Q  W  S  S  K  V  P  E  G  L  A
CCGGCAACTACCTCGTCCGCCACGAGTTGATCGCCCTGCACCAGGCCAACAACCCGCAGTTCTACCCGGAGTGCGCCCAG 720
 P  G  N  Y  L  V  R  H  E  L  I  A  L  H  Q  A  N  N  P  Q  F  Y  P  E  C  A  Q
GTCGTCATCACCGGCTCCGGCACCGCGCAGCCGGATGCCTCATACAAGGCGGCTATCCCCGGCTACTGCAACCAGAATGA 800
    V  V  I  T  G  S  G  T  A  Q  P  D  A  S  Y  K  A  A  I  P  G  Y  C  N  Q  N  D
CCCGAACATCAAGGTGAGATCCAGGCGTAATGCAGTCTACTGCTGGAAAGAAAGTGGTCCAAGCTAAACCGCGCTCCAGG 880
    P  N  I  K
TGCCCATCAACGACCACTCCATCCCTCAGACCTACAAGATTCCCGGCCCTCCCGTCTTCAAGGGCACCGCCAGCAAGAAG 960
 V  P  I  N  D  H  S  I  P  Q  T  Y  K  I  P  G  P  P  V  F  K  G  T  A  S  K  K
GCCCGGGACTTCACCGCCTGAAGTTGTTGAATCGATGGAG 1000
 A  R  D  F  T  A

MLLTSVLGSAALLASGAAAHGAVTSYIIAGKNYPGYQGFSPANSPNVIQWQWHDYNPVLSCSDSKLRCNGGTSATLNATA
APGDTITAIWAQWTHSQGPILVWMYKCPGSFSSCDGSGAGWFKIDEAGFHGDGVKVFLDTENPSGWDIAKLVGGNKQWSS
KVPEGLAPGNYLVRHELIALHQANNPQFYPECAQVVITGSGTAQPDASYKAAIPGYCNQNDPNIKVPINDHSIPQTYKIP
GPPVFKGTASKKARDFTA
```

Fig. 3

```
ATGCTCGCAAACGGTGCCATCGTCTTCCTGGCCGCCGCCCTCGGCGTCAGTGGCCACTACACCTGGCCACGGGTTAACGA  80
 M   L   A   N   G   A   I   V   F   L   A   A   A   L   G   V   S   G   H   Y   T   W   P   R   V   N   D
CGGCGCCGACTGGCAACAGGTCCGTAAGGCGGACAACTGGCAGGACAACGGCTACGTCGGGGATGTCACGTCGCCACAGA 160
   G   A   D   W   Q   Q   V   R   K   A   D   N   W   Q   D   N   G   Y   V   G   D   V   T   S   P   Q
TCCGCTGTTTCCAGGCGACCCCGTCCCCGGCCCCATCCGTCCTCAACACCACGGCCGGCTCGACCGTGACCTACTGGGCC 240
 I   R   C   F   Q   A   T   P   S   P   A   P   S   V   L   N   T   T   A   G   S   T   V   T   Y   W   A
AACCCCGACGTCTACCACCCCGGGCCTGTGCAGTTTTACATGGCCCGCGTGCCCGATGGCGAGGACATCAACTCGTGGAA 320
 N   P   D   V   Y   H   P   G   P   V   Q   F   Y   M   A   R   V   P   D   G   E   D   I   N   S   W   N
CGGCGACGGCGCCGTGTGGTTCAAGGTGTACGAGGACCATCCTACCTTTGGCGCTCAGCTCACATGGCCCAGCACGGGCA 400
   G   D   G   A   V   W   F   K   V   Y   E   D   H   P   T   F   G   A   Q   L   T   W   P   S   T   G
AGAGCTCGTTCGCGGTTCCCATCCCCCCGTGCATCAAGTCCGGCTACTACCTCCTCCGGGCGGAGCAAATCGGCCTGCAC 480
 K   S   S   F   A   V   P   I   P   P   C   I   K   S   G   Y   Y   L   L   R   A   E   Q   I   G   L   H
GTCGCCCAGAGCGTAGGCGGAGCGCAGTTCTACATCTCATGCGCCCAGCTCAGCGTCACCGGCGGCGGCAGCACCGAGCC 560
   V   A   Q   S   V   G   G   A   Q   F   Y   I   S   C   A   Q   L   S   V   T   G   G   G   S   T   E   P
GCCGAACAAGGTGGCCTTCCCCGGCGCTTACAGTGCGACGGACCCGGGCATTCTGATCAACATCTACTACCCTGTTCCCA 640
   P   N   K   V   A   F   P   G   A   Y   S   A   T   D   P   G   I   L   I   N   I   Y   Y   P   V   P
CGTCCTACCAGAACCCCGGCCCGGCCGTCTTCAGCTGCTGA 681
 T   S   Y   Q   N   P   G   P   A   V   F   S   C

MLANGAIVFLAAALGVSGHYTWPRVNDGADWQQVRKADNWQDNGYVGDVTSPQIRCFQATPSPAPSVLNTTAGSTVTYWA
NPDVYHPGPVQFYMARVPDGEDINSWNGDGAVWFKVYEDHPTFGAQLTWPSTGKSSFAVPIPPCIKSGYYLLRAEQIGLH
VAQSVGGAQFYISCAQLSVTGGGSTEPPNKVAFPGAYSATDPGILINIYYPVPTSYQNPGPAVFSC
```

Fig. 4

```
ATGAAGGGACTTTTCAGTGCCGCCGCCCTCTCCCTGGCCGTCGGCCAGGCTTCGGCCCATTACATCTTCCAGCAACTCTC    80
 M  K  G  L  F  S  A  A  A  L  S  L  A  V  G  Q  A  S  A  H  Y  I  F  Q  Q  L  S
CATCAACGGGAACCAGTTTCCGGTGTACCAATATATTCGCAAGAACACCAATTATAACAGTCCCGTTACCGATCTCACGT   160
 I  N  G  N  Q  F  P  V  Y  Q  Y  I  R  K  N  T  N  Y  N  S  P  V  T  D  L  T
CCGACGATCTTCGGTGCAATGTCGGCGCCCAGGGTGCTGGGACAGACACCGTCACGGTGAAGGCCGGCGACCAGTTCACC   240
 S  D  D  L  R  C  N  V  G  A  Q  G  A  G  T  D  T  V  T  V  K  A  G  D  Q  F  T
TTCACCCTTGACACCCCTGTTTACCACCAGGGGCCCATCTCCATCTACATGTCCAAGGCCCCGGGCGCGGCGTCAGACTA   320
 F  T  L  D  T  P  V  Y  H  Q  G  P  I  S  I  Y  M  S  K  A  P  G  A  A  S  D  Y
CGATGGCAGCGGCGGCTGGTTCAAGATCAAGGACTGGGGCCCGACTTTCAACGCCGACGGCACGGCCACCTGGGACATGG   400
 D  G  S  G  G  W  F  K  I  K  D  W  G  P  T  F  N  A  D  G  T  A  T  W  D  M
CCGGCTCATACACCTACAACATCCCGACCTGCATTCCCGACGGCGACTATCTGCTCCGCATCCAGTCGCTGGCCATCCAC   480
 A  G  S  Y  T  Y  N  I  P  T  C  I  P  D  G  D  Y  L  L  R  I  Q  S  L  A  I  H
AACCCCTGGCCGGCGGGCATCCCGCAGTTCTACATCTCCTGCGCCCAGATCACCGTGACCGGCGGCGGCAACGGCAACCC   560
 N  P  W  P  A  G  I  P  Q  F  Y  I  S  C  A  Q  I  T  V  T  G  G  G  N  G  N  P
TGGCCCGACGGCCCTCATCCCCGGCGCCTTCAAGGACACCGACCCGGGCTACACGGTGAACATCTACACGAACTTCCACA   640
 G  P  T  A  L  I  P  G  A  F  K  D  T  D  P  G  Y  T  V  N  I  Y  T  N  F  H
ACTACACGGTTCCCGGCCCGGAGGTCTTCAGCTGCAACGGCGGCGGCTCGAACCCGCCCCCGCCGGTGAGTAGCAGCACG   720
 N  Y  T  V  P  G  P  E  V  F  S  C  N  G  G  G  S  N  P  P  P  P  V  S  S  T
CCCGCGACCACGACGCTGGTCACGTCGACGCGCACCACGTCCTCCACGTCCTCCGCCTCGACGCCGGCCTCGACCGGCGG   800
 P  A  T  T  T  L  V  T  S  T  R  T  T  S  S  T  S  S  A  S  T  P  A  S  T  G  G
CTGCACCGTCGCCAAGTGGGGCCAGTGCGGCGGCAACGGGTACACCGGCTGCACGACCTGCGCGGCCGGGTCCACCTGCA   880
 C  T  V  A  K  W  G  Q  C  G  G  N  G  Y  T  G  C  T  T  C  A  A  G  S  T  C
GCAAGCAGAACGACTACTACTCGCAGTGCTTGTAAGGGAGGCCGCAAAGCATGAGGTGTTTGAAGAGGAGGAGGGGGTC   960
 S  K  Q  N  D  Y  Y  S  Q  C  L

MKGLFSAAALSLAVGQASAHYIFQQLSINGNQFPVYQYIRKNTNYNSPVTDLTSDDLRCNVGAQGAGTDTVTVKAGDQFT
FTLDTPVYHQGPISIYMSKAPGAASDYDGSGGWFKIKDWGPTFNADGTATWDMAGSYTYNIPTCIPDGDYLLRIQSLAIH
NPWPAGIPQFYISCAQITVTGGGNGNPGPTALIPGAFKDTDPGYTVNIYTNFHNYTVPGPEVFSCNGGGSNPPPPVSSST
PATTTLVTSTRTTSSTSSASTPASTGGCTVAKWGQCGGNGYTGCTTCAAGSTCSKQNDYYSQCL
```

```
TTGCGAACAGCGTGTCTTTGTGTTTGTTCAACGCCGACTCTGGAGAGGGTTTCATCAGTGTCGACGGCAACGAGGGTGACCGCAAAAATCTCACTCTGTG  2000
 V  S  L  V  F  V  N  A  D  S  G  E  G  F  I  S  V  D  G  N  E  G  D  R  K  N  L  T  L  W
GAAGAACGGGCGAGGCCGTCATTGACACTGTTGTCAGCCACTGCAACACGATTGTGGTTATTCACAGTGTGGGCCCGTCTTGATCGACCGGTGGTAT     2100
 K  N  G  E  A  V  I  D  T  V  V  S  H  C  N  T  I  V  V  I  H  S  V  G  P  V  L  I  D  R  W  Y
GATAACCCCAACGTCACTGCCATCATCTGGGCCCTTGCCCGGTCGCAAGAGTGGCAACTCCCTGGTCGACGTGCTCTATGGCCGCGTCAACCCAGCG     2200
 D  N  P  N  V  T  A  I  I  W  A  G  L  P  G  Q  E  S  G  N  S  L  V  D  V  L  Y  G  R  V  N  P  S
CCAAGACCCCCGTTCACCTGGGGCAAGACTCGGGAGTCTTACGGGCCATCTTGACAAGGCAATGAGAGCATGGCCTGAGCTACACCACCTTTGGTTACTCT   2300
 A  K  T  P  F  T  W  G  K  T  R  E  S  Y  G  A  P  L  L  T  E  P  N  N  G  A  P  Q  D  D  F  N
CGAGGGCGTCTTCATTGACTACCGTCATTTCGAGTTCGGCATATGTCCGACTGGAGACCAAGCCTGCGCCAACCTATGAGATCGTAGTGCCG        2400
 R  G  V  F  I  D  Y  R  H  F  D  K  R  N  E  T  P  I  Y  E  F  G  H  G  L  S  Y  T  T  F  G  Y  S
CACTTCGGGGTTCAGGCCCTCAATAGTTCGAGTGCCTGTGCATAGTTCCGAGACTGGGAGAGCAAGCCTCGCCAACCTATGAGATCGTAGTGCCG       2500
 H  L  R  V  Q  A  L  N  S  S  S  A  Y  V  P  T  S  G  E  T  K  P  A  P  T  Y  G  E  I  G  S  A
CCGACTACCTGTATCCCGAGGGTCTCAAAAGAATTACCAAGTTTATTACCCTTGGCTCAACTCGAGAGATTCTTCTGACGACCGAACTA            2600
 A  D  Y  L  Y  P  E  G  L  K  R  I  T  K  F  I  Y  P  W  L  N  S  T  D  L  E  D  S  D  D  P  N  Y
CGGCTGGGAGGACTCGGAGTACATTCCCGGAGTACATAGGCGGTCGGATGGGTCTCTCAACCCTCCTCGAAGGCTGGCGGCCTCTCCGGTGTAACCCTT   2700
 G  W  E  D  S  E  Y  I  P  E  G  A  R  D  G  S  P  Q  P  L  L  K  A  G  G  A  P  G  G  N  P  T  L
TATCAGGAATCTTGTTAGGGTGTCGGCCACCATAACCAACACTGTAACGTCGCCGGGTTATGAAGTCCCTCAATTGGTGACCGCCATGTTCCTTGCG    2800
 Y  Q  D  L  V  R  V  S  A  T  I  T  N  T  G  N  V  A  G  Y  E  V  P  Q  L
TTGCAATTGGCTAACTCGCTTCTAGTGTTCACTGGGCGCGAACGAGCGAACGAACGAGCCGAAGTTCGACCGAATCTTCCTGGCTCCTGG          2900
           Y  V  S  L  G  P  N  E  P  R  V  L  R  K  F  D  R  I  F  L  A  P  G
GGAGCAAAAGGTTTGGACCACGACTCTTAACCGTCGTGATCTCGCCAATTGGGATGTGGAGGCTCAGGACTGGGTCATCACAAAGTACCCCAAGAAAGTG   3000
 E  Q  K  V  W  T  T  L  N  R  R  D  L  A  N  W  D  V  E  A  Q  D  W  V  I  T  K  Y  P  P  K  K  V
CACGTCGGCAGCTCCTCGCGTAAGCTCCCTCTGAGAGCCGCCCTCGCCCCGTGTCTACTAG     3060
 H  V  G  S  S  R  K  L  P  L  R  A  P  L  P  P  R  V  Y

Fig. 32B
```

POLYPEPTIDE FROM A CELLULOLYTIC FUNGUS HAVING CELLULOLYTIC ENHANCING ACTIVITY

CROSS-REFERENCE TO RELATED APPLICATION

This application claims the benefit of U.S. Provisional Application No. 60/540,661, filed Jan. 30, 2004, which application is incorporated herein by reference.

STATEMENT AS TO RIGHTS TO INVENTIONS MADE UNDER FEDERALLY SPONSORED RESEARCH AND DEVELOPMENT

This invention was made with Government support under NREL Subcontract No. ZCO-30017-02, Prime Contract DE-AC36-98GO10337 awarded by the Department of Energy. The government has certain rights in this invention.

BACKGROUND OF THE INVENTION

1. Field of the Invention

The present invention relates to isolated polypeptides having cellulolytic enhancing activity and isolated polynucleotides encoding the polypeptides. The invention also relates to nucleic acid constructs, vectors, and host cells comprising the polynucleotides as well as methods for producing and using the polypeptides.

2. Description of the Related Art

Cellulose is a polymer of the simple sugar glucose covalently bonded by beta-1,4-linkages. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

It would be advantageous in the art to improve the conversion of cellulosic feedstocks.

It is an object of the present invention to provide isolated polypeptides having cellulolytic enhancing activity and isolated nucleic acid sequences encoding the polypeptides to improve the conversion of cellulosic feedstocks.

SUMMARY OF THE INVENTION

The present invention relates to isolated polypeptides having cellulolytic enhancing activity selected from the group consisting of:

(a) a polypeptide having an amino acid sequence which has at least 75% identity with amino acids 20 to 326 of SEQ ID NO: 2, amino acids 18 to 240 of SEQ ID NO: 4, amino acids 20 to 258 of SEQ ID NO: 6, amino acids 19 to 226 of SEQ ID NO: 8, or amino acids 20 to 304 of SEQ ID NO: 10;

(b) a polypeptide which is encoded by a nucleotide sequence which hybridizes under at least medium stringency conditions with (i) nucleotides 388 to 1332 of SEQ ID NO: 1, nucleotides 98 to 821 of SEQ ID NO: 3, nucleotides 126 to 978 of SEQ ID NO: 5, nucleotides 55 to 678 of SEQ ID NO: 7, or nucleotides 58 to 912 of SEQ ID NO: 9, (ii) the cDNA sequence contained in nucleotides 388 to 1332 of SEQ ID NO: 1, nucleotides 98 to 821 of SEQ ID NO: 3, or nucleotides 126 to 978 of SEQ ID NO: 5, or the genomic DNA sequence comprising nucleotides 55 to 678 of SEQ ID NO: 7 or nucleotides 58 to 912 of SEQ ID NO: 9, or (iii) a complementary strand of (i) or (ii); and (c) a variant comprising a conservative substitution, deletion, and/or insertion of one or more amino acids of amino acids 20 to 326 of SEQ ID NO: 2, amino acids 18 to 240 of SEQ ID NO: 4, amino acids 20 to 258 of SEQ ID NO: 6, amino acids 19 to 226 of SEQ ID NO: 8, or amino acids 20 to 304 of SEQ ID NO: 10.

The present invention also relates to isolated polynucleotides encoding polypeptides having cellulolytic enhancing activity, selected from the group consisting of:

(a) a polynucleotide encoding a polypeptide having an amino acid sequence which has at least 75% identity with amino acids 20 to 326 of SEQ ID NO: 2, amino acids 18 to 240 of SEQ ID NO: 4, amino acids 20 to 258 of SEQ ID NO: 6, amino acids 19 to 226 of SEQ ID NO: 8, or amino acids 20 to 304 of SEQ ID NO: 10, amino acids 18 to 240 of SEQ ID NO: 4, amino acids 20 to 258 of SEQ ID NO: 6, amino acids 19 to 226 of SEQ ID NO: 8, or amino acids 20 to 304 of SEQ ID NO: 10;

(b) a polynucleotide having at least 75% identity with nucleotides 388 to 1332 of SEQ ID NO: 1, nucleotides 98 to 821 of SEQ ID NO: 3, nucleotides 126 to 978 of SEQ ID NO: 5, nucleotides 55 to 678 of SEQ ID NO: 7, or nucleotides 58 to 912 of SEQ ID NO: 9; and (c) a polynucleotide which hybridizes under at least medium stringency conditions with (i) nucleotides 388 to 1332 of SEQ ID NO: 1, nucleotides 98 to 821 of SEQ ID NO: 3, nucleotides 126 to 978 of SEQ ID NO: 5, nucleotides 55 to 678 of SEQ ID NO: 7, or nucleotides 58 to 912 of SEQ ID NO: 9, (ii) the cDNA sequence contained in nucleotides 388 to 1332 of SEQ ID NO: 1, nucleotides 98 to 821 of SEQ ID NO: 3, or nucleotides 126 to 978 of SEQ ID NO: 5, or the genomic DNA sequence comprising nucleotides 55 to 678 of SEQ ID NO: 7 or nucleotides 58 to 912 of SEQ ID NO: 9, or (iii) a complementary strand of (i) or (ii).

The present invention also relates to nucleic acid constructs, recombinant expression vectors, and recombinant host cells comprising the polynucleotides.

The present invention also relates to methods for producing such a polypeptide having cellulolytic enhancing activity comprising (a) cultivating a recombinant host cell comprising a nucleic acid construct comprising a polynucleotide encoding the polypeptide under conditions conducive for production of the polypeptide; and (b) recovering the polypeptide.

The present invention also relates to nucleic acid constructs comprising a gene encoding a protein, wherein the gene is operably linked to a nucleotide sequence encoding a signal peptide consisting of nucleotides 330 to 387 of SEQ ID NO: 1, nucleotides 47 to 97 of SEQ ID NO: 3, nucleotides 69 to 125 of SEQ ID NO: 5, nucleotides 1 to 54 of SEQ ID NO: 7, or nucleotides 1 to 57 of SEQ ID NO: 9', wherein the gene is foreign to the nucleotide sequence.

The present invention also relates to methods for degrading or converting a cellulosic material, comprising: treating the cellulosic material with an effective amount of a cellulolytic protein in the presence of an effective amount of a polypeptide having cellulolytic enhancing activity, wherein the presence of the polypeptide having cellulolytic enhancing activity increases the degradation of cellulosic material compared to the absence of the polypeptide having cellulolytic enhancing activity.

The present invention further relates to methods for producing an organic substance, comprising:

(a) saccharifying a cellulosic material with an effective amount of a cellulolytic protein in the presence of an effective amount of a polypeptide having cellulolytic enhancing activity, wherein the presence of the polypeptide having cellulolytic enhancing activity increases the degradation of cellulosic material compared to the absence of the polypeptide having cellulolytic enhancing activity;

(b) fermenting the saccharified cellulosic material of step (a) with one or more fermentating microorganisms; and (c) recovering the organic substance from the fermentation.

BRIEF DESCRIPTION OF THE FIGURES

FIG. 1 shows the genomic DNA sequence and the deduced amino acid sequence of a *Thielavia terrestris* NRRL 8126 GH61B polypeptide having cellulolytic enhancing activity (SEQ ID NOs: 1 and 2, respectively). Predicted introns are italicized. The predicted signal peptide is underlined.

FIG. 2 shows the genomic DNA sequence and the deduced amino acid sequence of a *Thielavia terrestris* NRRL 8126 GH61C polypeptide having cellulolytic enhancing activity (SEQ ID NOs: 3 and 4, respectively). Predicted introns are italicized. The predicted signal peptide is underlined.

FIG. 3 shows the genomic DNA sequence and the deduced amino acid sequence of a *Thielavia terrestris* NRRL 8126 GH61D polypeptide having cellulolytic enhancing activity (SEQ ID NOs: 5 and 6, respectively). Predicted introns are italicized. The predicted signal peptide is underlined.

FIG. 4 shows the cDNA sequence and the deduced amino acid sequence of a *Thielavia terrestris* NRRL 8126 GH61E polypeptide having cellulolytic enhancing activity (SEQ ID NOs: 7 and 8, respectively). The predicted signal peptide is underlined.

FIG. 5 shows the cDNA sequence and the deduced amino acid sequence of a *Thielavia terrestris* NRRL 8126 GH61G polypeptide having cellulolytic enhancing activity (SEQ ID NOs: 9 and 10, respectively). The predicted signal peptide is underlined.

FIGS. 32A and 32B show the genomic DNA sequence and the deduced amino acid sequence of an *Aspergillus fumigatus* beta-glucosidase (SEQ ID NOs: 75 and 76, respectively). The predicted signal peptide is underlined and predicted introns are italicized.

Definitions

Figure 6:
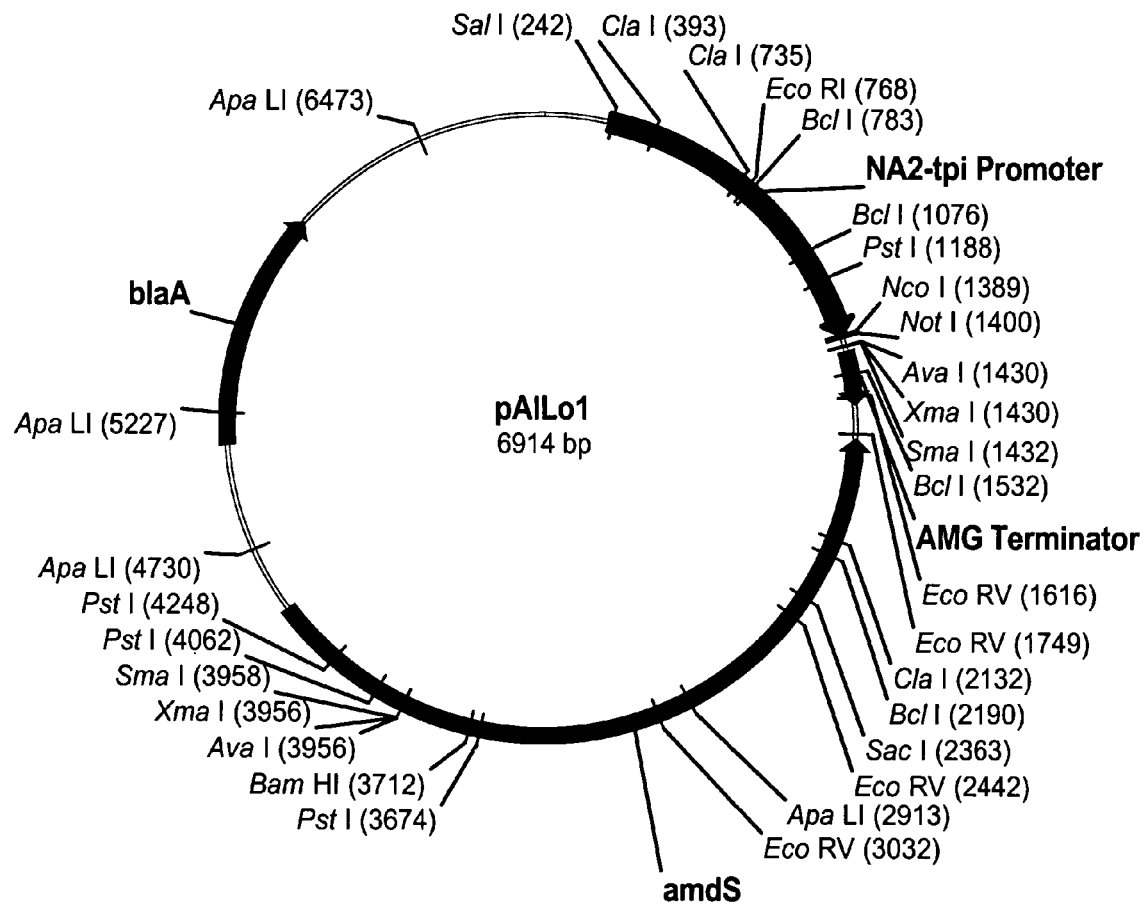
FIG. 6 shows a restriction map of pAlLo1.

The term "cellulolytic enhancing activity" is defined herein as a biological activity which enhances the hydrolysis of a cellulosic material by proteins having cellulolytic activity. For purposes of the present invention, cellulolytic enhancing activity is determined by measuring the increase in reducing sugars from the hydrolysis of a cellulosic material by cellulolytic protein under the following conditions: 5.0 mg of cellulolytic protein/g of cellulose in PCS for 5-7 day at 50° C. in the presence and absence of 0.01-2.5 mg of cellulolytic enhancing activity per g of cellulose in PCS compared to a control hydrolysis with equal total protein loading without cellulolytic enhancing activity (5.01-7.5 mg of cellulolytic protein/g of cellulose in PCS). In a preferred aspect, a mixture of Celluclast® 1.5 L sample (Novozymes A/S, Bagsvaerd, Denmark) in the presence of 3% *Aspergillus oryzae* beta-glucosidase (recombinantly produced in *Aspergillus oryzae* according to WO 02/095014) or 3% *Aspergillus fumigatus* beta-glucosidase (recombinantly produced in *Aspergillus oryzae* according to Example 22) of cellulase protein loading is used as the source of the cellulolytic activity.

The term "cellulolytic activity" is defined herein as a biological activity which hydrolyzes a cellulosic material. For purposes of the present invention, cellulolytic activity is determined by measuring the increase in hydrolysis of a cellulosic material by a cellulolytic mixture under the following conditions: 1-10 mg of cellulolytic protein/g of cellulose in PCS for 5-7 day at 50° C. compared to a control hydrolysis without addition of cellulolytic protein. In a preferred aspect, a mixture of Celluclast® 1.5 L sample (Novozymes A/S, Bagsvaerd, Denmark) in the presence of 3% *Aspergillus oryzae* beta-glucosidase (recombinantly produced in *Aspergillus oryzae* according to WO 02/095014) or 3% *Aspergillus fumigatus* beta glucosidase (recombinantly produced in *Aspergillus oryzae* according to Example 22) of cellulase protein loading as the source of the cellulolytic activity.

The term "PCS" or "Pre-treated Corn Stover" is defined herein as a cellulosic material derived from corn stover by treatment with heat and dilute acid. For purposes of the present invention, PCS is made by the method described in Example 24, or variations thereof in time, temperature and amount of acid.

The term "Family 61 glycoside hydrolase" or "Family GH61" is defined herein as a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. Presently, Henrissat lists the GH61 Family as unclassified indicating that properties such as mechanism, catalytic nucleophile/base, catalytic proton donors, and 3-D structure are not known for polypeptides belonging to this family.

The cellulosic material can be any material containing cellulose. Cellulose is generally found, for example, in the stems, leaves, hulls, husks, and cobs of plants or leaves, branches, and wood of trees. The cellulosic material can also be, but is not limited to, herbaceous material, agricultural residues, forestry residues, municipal solid wastes, waste paper, and pulp and paper mill residues. It is understood herein that the cellulose may be in the form of lignocellulose, a plant cell wall material containing lignin, cellulose, and hemicellulose in a mixed matrix.

In a preferred embodiment, the cellulosic material is corn stover. In another preferred embodiment, the cellulosic material is corn fiber. In another preferred embodiment, the cellulosic material is rice straw. In another preferred embodiment, the cellulosic material is paper and pulp processing waste. In another preferred embodiment, the cellulosic material is woody or herbaceous plants. In another preferred embodiment, the cellulosic material is bagasse.

The cellulosic material may be used as is or may be subjected to pretreatment, using conventional methods known in the art. For example, physical pretreatment techniques can include various types of milling, irradiation, steaming/steam explosion, and hydrothermolysis; chemical pretreatment techniques can include dilute acid, alkaline, organic solvent, ammonia, sulfur dioxide, carbon dioxide, and pH-controlled hydrothermolysis; and biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh, P., and Singh, A., 1993, Physicochemical and biological treatments for enzymatic/microbial conversion of lignocellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson, L., and Hahn-Hagerdal, B., 1996, Fermentation of lignocellulosic hydrolysates for ethanol production, *Enz. Microb. Tech.* 18: 312-331; and Vallander, L., and Eriksson, K.-E. L., 1990, Production of ethanol from lignocellulosic materials: State of the art, *Adv. Biochem. Eng./Biotechnol.* 42: 63-95).

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the cellulolytic enhancing activity of the polypeptide consisting of the amino acid sequence shown as amino acids 20 to 326 of SEQ ID NO: 2, amino acids 18 to 240 of SEQ ID NO: 4, amino acids 20 to 258 of SEQ ID NO: 6, amino acids 19 to 226 of SEQ ID NO: 8, or amino acids 20 to 304 of SEQ ID NO: 10.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Identity: The relatedness between two amino acid sequences or between two nucleotide sequences is described by the parameter "identity".

For purposes of the present invention, the degree of identity between two amino acid sequences can be determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5. The degree of identity between two amino acid sequences can also be determined by the Smith-Waterman algorithm (Waterman et al., 1976, *Adv. Math.* 20: 367) with a gap open penalty of 11, a gap extension penalty of 1, and the BLOSUM62 matrix.

For purposes of the present invention, the degree of identity between two nucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Polypeptide Fragment: The term "polypeptide fragment" is defined herein as a polypeptide having one or more amino acids deleted from the amino and/or carboxyl terminus of amino acids 20 to 326 of SEQ ID NO: 2, amino acids 18 to 240 of SEQ ID NO: 4, amino acids 20 to 258 of SEQ ID NO: 6, amino acids 19 to 226 of SEQ ID NO: 8, or amino acids 20 to 304 of SEQ ID NO: 10; or a homologous sequence thereof, wherein the fragment has cellulolytic enhancing activity. Preferably, a fragment of amino acids 20 to 326 of SEQ ID NO: 2 contains at least 277 amino acid residues, more preferably at least 287 amino acid residues, and most preferably at least 297 amino acid residues. Preferably, a fragment of amino acids 18 to 240 of SEQ ID NO: 4 contains at least 185 amino acid residues, more preferably at least 195 amino acid residues, and most preferably at least 205 amino acid residues. Preferably, a fragment of amino acids 20 to 258 of SEQ ID NO: 6 contains at least 200 amino acid residues, more preferably at least 212 amino acid residues, and most preferably at least 224 amino acid residues. Preferably, a fragment of amino acids 19 to 226 of SEQ ID NO: 8 contains at least 175 amino acid residues, more preferably at least 185 amino acid residues, and most preferably at least 195 amino acid residues. Preferably, a fragment of amino acids 20 to 304 of SEQ ID NO: 10 contains at least 240 amino acid residues, more preferably at least 255 amino acid residues, and most preferably at least 270 amino acid residues.

Subsequence: The term "subsequence" is defined herein as a nucleotide sequence having one or more nucleotides deleted from the 5' and/or 3' end of nucleotides 388 to 1332 of SEQ ID NO: 1, nucleotides 98 to 821 of SEQ ID NO: 3, nucleotides 126 to 978 of SEQ ID NO: 5, nucleotides 55 to 678 of SEQ ID NO: 7, or nucleotides 58 to 912 of SEQ ID NO: 9; or a homologous sequence thereof, wherein the subsequence encodes a polypeptide fragment having cellulolytic enhancing activity. Preferably, a subsequence of nucleotides 388 to 1332 of SEQ ID NO: 1 contains at least 831 nucleotides, more preferably at least 861 nucleotides, and most preferably at least 891 nucleotides. Preferably, a subsequence of nucleotides 98 to 821 of SEQ ID NO: 3 contains at least 555 nucleotides, more preferably at least 585 nucleotides, and most preferably at least 615 nucleotides. Preferably, a subsequence of nucleotides 126 to 978 of SEQ ID NO: 5 contains at least 600 nucleotides, more preferably at least 636 nucleotides, and most preferably at least 672 nucleotides. Preferably, a subsequence of nucleotides 55 to 678 of SEQ ID NO: 7 contains at least 525 nucleotides, more preferably at least 555 nucleotides, and most preferably at least 585 nucleotides. Preferably, a subsequence of nucleotides 58 to 912 of SEQ ID NO: 9 contains at least 720 nucleotides, more preferably at least 765 nucleotides, and most preferably at least 810 nucleotides.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide which is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TM, TAG and TGA. The coding sequence may be a DNA, cDNA, or recombinant nucleotide sequence.

Expression: The term "expression" includes any step involved in the production of a polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct or expression vector comprising a polynucleotide of the present invention.

Modification: The term "modification" means herein any chemical modification of the polypeptide comprising or consisting of amino acids 20 to 326 of SEQ ID NO: 2, amino acids 18 to 240 of SEQ ID NO: 4, amino acids 20 to 258 of SEQ ID NO: 6, amino acids 19 to 226 of SEQ ID NO: 8, or amino acids 20 to 304 of SEQ ID NO: 10; or a homologous sequence thereof, as well as genetic manipulation of the DNA encoding that polypeptide. The modification can be substitutions, deletions and/or insertions of one or more amino acids as well as replacements of one or more amino acid side chains.

Artificial variant: When used herein, the term "artificial variant" means a polypeptide having cellulolytic enhancing activity produced by an organism expressing a modified nucleotide sequence of SEQ ID NO: 1, 3, 5, 7, or 9; or a homologous sequence thereof, or the mature coding region thereof. The modified nucleotide sequence is obtained through human intervention by modification of the nucleotide sequence disclosed in SEQ ID NO: 1, 3, 5, 7, or 9; or a homologous sequence thereof, or the mature coding region thereof.

DETAILED DESCRIPTION OF THE INVENTION

Polypeptides Having Cellulolytic Enhancing Activity

In a first aspect, the present invention relates to isolated polypeptides having cellulolytic enhancing activity, comprising the following motifs:

[ILMV]-P-X(4,5)-G-X-Y-[ILMV]-X-R-X-[EQ]-X(4)-[HNQ] and [FW]-[TF]-K-[AIV], wherein X is any amino acid, X(4,5) is any amino acid at 4 or 5 contiguous positions, and X(4) is any amino acid at 4 contiguous positions.

The isolated polypeptide comprising the above-noted motifs may further comprise:
H-X(1,2)-G-P-X(3)-[YW]-[AILMV],
[EQ]-X-Y-X(2)-C-X-[EHQN]-[FILV]-X-[ILV], or
H-X(1,2)-G-P-X(3)-[YW]-[AILMV] and [EQ]-X-Y-X(2)-C-X-[EHQN]-[FILV]-X-[ILV], wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In a preferred embodiment, the isolated polypeptide having cellulolytic enhancing activity further comprises H-X(1,2)-G-P-X(3)-[YW]-[AILMV]. In another preferred embodiment, the isolated polypeptide having cellulolytic enhancing activity further comprises [EQ]-X-Y-X(2)-C-X-[EHQN]-[FILV]-X-[ILV]. In another preferred embodiment, the isolated polypeptide having cellulolytic enhancing activity further comprises H-X(1,2)-G-P-X(3)-[YW]-[AILMV] and [EQ]-X-Y-X(2)-C-X-[EHQN]-[FILV]-X-[ILV].

In a second aspect, the present invention relates to isolated polypeptides having an amino acid sequence which has a degree of identity to amino acids 20 to 326 of SEQ ID NO: 2, amino acids 18 to 240 of SEQ ID NO: 4, amino acids 20 to 258 of SEQ ID NO: 6, amino acids 19 to 226 of SEQ ID NO: 8, or amino acids 20 to 304 of SEQ ID NO: 10 (i.e., the mature polypeptide) of at least 75%, preferably at least 80%, more preferably at least 85%, even more preferably at least 90%, most preferably at least 95%, and even most preferably at least 97%, 98%, or 99%, which have cellulolytic enhancing activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from amino acids 20 to 326 of SEQ ID NO: 2, amino acids 18 to 240 of SEQ ID NO: 4, amino acids 20 to 258 of SEQ ID NO: 6, amino acids 19 to 226 of SEQ ID NO: 8, or amino acids 20 to 304 of SEQ ID NO: 10.

A polypeptide of the present invention preferably comprises the amino acid sequence of SEQ ID NO: 2 or an allelic variant thereof; or a fragment thereof that has cellulolytic enhancing activity. In a preferred aspect, a polypeptide comprises the amino acid sequence of SEQ ID NO: 2. In another preferred aspect, a polypeptide comprises amino acids 20 to 326 of SEQ ID NO: 2, or an allelic variant thereof; or a fragment thereof that has cellulolytic enhancing activity. In another preferred aspect, a polypeptide comprises amino acids 20 to 326 of SEQ ID NO: 2. In another preferred aspect, a polypeptide consists of the amino acid sequence of SEQ ID NO: 2 or an allelic variant thereof; or a fragment thereof that has cellulolytic enhancing activity. In another preferred aspect, a polypeptide consists of the amino acid sequence of SEQ ID NO: 2. In another preferred aspect, a polypeptide consists of amino acids 20 to 326 of SEQ ID NO: 2 or an allelic variant thereof; or a fragment thereof that has cellulolytic enhancing activity. In another preferred aspect, a polypeptide consists of amino acids 20 to 326 of SEQ ID NO: 2.

A polypeptide of the present invention preferably comprises the amino acid sequence of SEQ ID NO: 4 or an allelic variant thereof; or a fragment thereof that has cellulolytic enhancing activity. In a preferred aspect, a polypeptide comprises the amino acid sequence of SEQ ID NO: 4. In another preferred aspect, a polypeptide comprises amino acids 18 to 240 of SEQ ID NO: 4, or an allelic variant thereof; or a fragment thereof that has cellulolytic enhancing activity. In another preferred aspect, a polypeptide comprises amino acids 18 to 240 of SEQ ID NO: 4. In another preferred aspect, a polypeptide consists of the amino acid sequence of SEQ ID NO: 4 or an allelic variant thereof; or a fragment thereof that has cellulolytic enhancing activity. In another preferred aspect, a polypeptide consists of the amino acid sequence of SEQ ID NO: 4. In another preferred aspect, a polypeptide consists of amino acids 18 to 240 of SEQ ID NO: 4 or an allelic variant thereof; or a fragment thereof that has cellulolytic enhancing activity. In another preferred aspect, a polypeptide consists of amino acids 18 to 240 of SEQ ID NO: 4.

A polypeptide of the present invention preferably comprises the amino acid sequence of SEQ ID NO: 6 or an allelic variant thereof; or a fragment thereof that has cellulolytic enhancing activity. In a preferred aspect, a polypeptide comprises the amino acid sequence of SEQ ID NO: 6. In another preferred aspect, a polypeptide comprises amino acids 20 to 258 of SEQ ID NO: 6, or an allelic variant thereof; or a fragment thereof that has cellulolytic enhancing activity. In another preferred aspect, a polypeptide comprises amino acids 20 to 258 of SEQ ID NO: 6. In another preferred aspect, a polypeptide consists of the amino acid sequence of SEQ ID NO: 6 or an allelic variant thereof; or a fragment thereof that has cellulolytic enhancing activity. In another preferred aspect, a polypeptide consists of the amino acid sequence of SEQ ID NO: 6. In another preferred aspect, a polypeptide consists of amino acids 20 to 258 of SEQ ID NO: 6 or an allelic variant thereof; or a fragment thereof that has cellulolytic enhancing activity. In another preferred aspect, a polypeptide consists of amino acids 20 to 258 of SEQ ID NO: 6.

A polypeptide of the present invention preferably comprises the amino acid sequence of SEQ ID NO: 8 or an allelic variant thereof; or a fragment thereof that has cellulolytic enhancing activity. In a preferred aspect, a polypeptide comprises the amino acid sequence of SEQ ID NO: 8. In another preferred aspect, a polypeptide comprises amino acids 19 to 226 of SEQ ID NO: 8, or an allelic variant thereof; or a fragment thereof that has cellulolytic enhancing activity. In another preferred aspect, a polypeptide comprises amino acids 19 to 226 of SEQ ID NO: 8. In another preferred aspect, a polypeptide consists of the amino acid sequence of SEQ ID NO: 8 or an allelic variant thereof; or a fragment thereof that has cellulolytic enhancing activity. In another preferred aspect, a polypeptide consists of the amino acid sequence of SEQ ID NO: 8. In another preferred aspect, a polypeptide consists of amino acids 19 to 226 of SEQ ID NO: 8 or an allelic variant thereof; or a fragment thereof that has cellulolytic enhancing activity. In another preferred aspect, a polypeptide consists of amino acids 19 to 226 of SEQ ID NO: 8.

A polypeptide of the present invention preferably comprises the amino acid sequence of SEQ ID NO: 10 or an allelic variant thereof; or a fragment thereof that has cellulolytic enhancing activity. In a preferred aspect, a polypeptide comprises the amino acid sequence of SEQ ID NO: 10. In another preferred aspect, a polypeptide comprises amino acids 20 to 304 of SEQ ID NO: 10, or an allelic variant thereof; or a fragment thereof that has cellulolytic enhancing activity. In another preferred aspect, a polypeptide comprises amino acids 20 to 304 of SEQ ID NO: 10. In another preferred aspect, a polypeptide consists of the amino acid sequence of SEQ ID NO: 10 or an allelic variant thereof; or a fragment thereof that has cellulolytic enhancing activity. In another preferred aspect, a polypeptide consists of the amino acid sequence of SEQ ID NO: 10. In another preferred aspect, a polypeptide consists of amino acids 20 to 304 of SEQ ID NO: 10 or an allelic variant thereof; or a fragment thereof that has cellulolytic enhancing activity. In another preferred aspect, a polypeptide consists of amino acids 20 to 304 of SEQ ID NO: 10.

In a third aspect, the present invention relates to isolated polypeptides having cellulolytic enhancing activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 388 to 1332 of SEQ ID NO: 1, nucleotides 98 to 821 of SEQ ID NO: 3, nucleotides 126 to 978 of SEQ ID NO: 5, nucleotides 55 to 678 of SEQ ID NO: 7, or nucleotides 58 to 912 of SEQ ID NO: 9, (ii) the cDNA sequence contained in nucleotides 388 to 1332 of SEQ ID NO: 1, nucleotides 98 to 821 of SEQ ID NO: 3, or nucleotides 126 to 978 of SEQ ID NO: 5, or the genomic DNA sequence comprising nucleotides 55 to 678 of SEQ ID NO: 7 or nucleotides 58 to 912 of SEQ ID NO: 9, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). A subsequence of SEQ ID NO: 1, 3, 5, 7, or 9 contains at least 100 contiguous nucleotides or preferably at least 200 contiguous nucleotides. Moreover, the subsequence may encode a polypeptide fragment which has cellulolytic enhancing activity.

The nucleotide sequence of SEQ ID NO: 1, 3, 5, 7, or 9; or a subsequence thereof; as well as the amino acid sequence of SEQ ID NO: 2, 4, 6, 8, or 10; or a fragment thereof, may be used to design a nucleic acid probe to identify and clone DNA encoding polypeptides having cellulolytic enhancing activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may, therefore, be screened for DNA which hybridizes with the probes described above and which encodes a polypeptide having cellulolytic enhancing activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, 3, 5, 7, or 9, or a subsequence thereof, the carrier material is used in a Southern blot.

For purposes of the present invention, hybridization indicates that the nucleotide sequence hybridizes to a labeled nucleic acid probe corresponding to the nucleotide sequence shown in SEQ ID NO: 1, 3, 5, 7, or 9, the cDNA sequence contained in SEQ ID NO: 1, 3, or 5, or the genomic sequence comprising SEQ ID NO: 7 or 9, its complementary strand, or a subsequence thereof, under very low to very high stringency conditions. Molecules to which the nucleic acid probe hybridizes under these conditions can be detected using X-ray film.

In a preferred embodiment, the nucleic acid probe is a nucleic acid sequence which encodes the polypeptide of SEQ ID NO: 2, or a subsequence thereof. In another preferred embodiment, the nucleic acid probe is SEQ ID NO: 1. In another preferred embodiment, the nucleic acid probe is the mature polypeptide coding region of SEQ ID NO: 1. In another preferred embodiment, the nucleic acid probe is the nucleic acid sequence contained in plasmid pEJG120 which is contained in *Escherichia coli* NRRL B-30699, wherein the nucleic acid sequence encodes a polypeptide having cellulolytic enhancing activity. In another preferred embodiment, the nucleic acid probe is the mature polypeptide coding region contained in plasmid pEJG120 which is contained in *Escherichia coli* NRRL B-30699.

In another preferred embodiment, the nucleic acid probe is a nucleic acid sequence which encodes the polypeptide of SEQ ID NO: 4, or a subsequence thereof. In another preferred embodiment, the nucleic acid probe is SEQ ID NO: 3. In another preferred embodiment, the nucleic acid probe is the mature polypeptide coding region of SEQ ID NO: 3. In another preferred embodiment, the nucleic acid probe is the nucleic acid sequence contained in plasmid pTter61C which is contained in *Escherichia coli* NRRL B-30813, wherein the nucleic acid sequence encodes a polypeptide having cellulolytic enhancing activity. In another preferred embodiment, the nucleic acid probe is the mature polypeptide coding region contained in plasmid pTter61C which is contained in *Escherichia coli* NRRL B-30813.

In another preferred embodiment, the nucleic acid probe is a nucleic acid sequence which encodes the polypeptide of SEQ ID NO: 6, or a subsequence thereof. In another preferred embodiment, the nucleic acid probe is SEQ ID NO: 5. In another preferred embodiment, the nucleic acid probe is the mature polypeptide coding region of SEQ ID NO: 5. In another preferred embodiment, the nucleic acid probe is the nucleic acid sequence contained in plasmid pTter61D which is contained in *Escherichia coli* NRRL B-30812, wherein the nucleic acid sequence encodes a polypeptide having cellulolytic enhancing activity. In another preferred embodiment, the nucleic acid probe is the mature polypeptide coding region contained in plasmid pTter61D which is contained in *Escherichia coli* NRRL B-30812.

In another preferred embodiment, the nucleic acid probe is a nucleic acid sequence which encodes the polypeptide of SEQ ID NO: 8, or a subsequence thereof. In another preferred embodiment, the nucleic acid probe is SEQ ID NO: 7. In another preferred embodiment, the nucleic acid probe is the mature polypeptide coding region of SEQ ID NO: 7. In another preferred embodiment, the nucleic acid probe is the nucleic acid sequence contained in plasmid pTter61E which is contained in *Escherichia coli* NRRL B-30814, wherein the nucleic acid sequence encodes a polypeptide having cellulolytic enhancing activity. In another preferred embodiment, the nucleic acid probe is the mature polypeptide coding region contained in plasmid pTter61E which is contained in *Escherichia coli* NRRL B-30814.

In another preferred embodiment, the nucleic acid probe is a nucleic acid sequence which encodes the polypeptide of SEQ ID NO: 10, or a subsequence thereof. In another preferred embodiment, the nucleic acid probe is SEQ ID NO: 9. In another preferred embodiment, the nucleic acid probe is the mature polypeptide coding region of SEQ ID NO: 9. In another preferred embodiment, the nucleic acid probe is the nucleic acid sequence contained in plasmid pTter61G which is contained in *Escherichia coli* NRRL B-30811, wherein the nucleic acid sequence encodes a polypeptide having cellulolytic enhancing activity. In another preferred embodiment, the nucleic acid probe is the mature polypeptide coding region contained in plasmid pTter61G which is contained in *Escherichia coli* NRRL B-30811.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a fourth aspect, the present invention relates to artificial variants comprising a conservative substitution, deletion, and/or insertion of one or more amino acids of SEQ ID NO: 2 or a homologous sequence thereof; or the mature polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., cellulolytic enhancing activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of amino acids 20 to 326 of SEQ ID NO: 2, amino acids 18 to 240 of SEQ ID NO: 4, amino acids 20 to 258 of SEQ ID NO: 6, amino acids 19 to 226 of SEQ ID NO: 8, or amino acids 20 to 304 of SEQ ID NO: 10 is 10, preferably 9, more preferably 8, more preferably 7, more preferably at most 6, more preferably 5, more preferably 4, even more preferably 3, most preferably 2, and even most preferably 1.

Sources of Polypeptides Having Cellulolytic Enhancing Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may also be a fungal polypeptide, and more preferably a yeast polypeptide such as a *Candida, Kluyveromyces, Pichia, Saccharomyces, Schizosaccharomyces*, or *Yarrowia* polypeptide; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* polypeptide.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having cellulolytic enhancing activity.

In another preferred aspect, the polypeptide is an *Aspergillus aculeatus, Aspergillus awamori, Aspergillus*

*fumigatus, Aspergillus foetidus, Aspergillus japonicus, Aspergillus nidulans, Aspergillus niger, Aspergillus oryzae, Coprinus cinereus, Diplodia gossyppina, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Magnaporthe grisea, Mucor miehei, Myceliophthora thermophila, Neurospora crassa, Penicillium purpurogenum, Phanerochaete chrysosporium, Pseudoplectania nigrella, Thermoascus aurantiacus, Trichoderma harzianum, Trichoderma koningii, Trichoderma longibrachiatum, Trichoderma reesei, Trichoderma viride*, or *Trichophaea saccata* polypeptide.

In a more preferred aspect, the polypeptide is a *Thielavia terrestris* polypeptide. In a most preferred embodiment, the polypeptide is a *Thielavia terrestris* NRRL 8126 polypeptide, e.g., the polypeptide with the amino acid sequence of SEQ ID NO: 2, 4, 6, 8, or 10, or fragments thereof, e.g., the mature protein.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having nucleotide sequences which encode polypeptides of the present invention.

In a preferred aspect, the nucleotide sequence is set forth in SEQ ID NO: 1. In another more preferred aspect, the nucleotide sequence is the sequence contained in plasmid pEJG120 that is contained in *Escherichia coli* NRRL B-30699. In another preferred aspect, the nucleotide sequence is the mature polypeptide coding region of SEQ ID NO: 1. In another more preferred aspect, the nucleotide sequence is the mature polypeptide coding region contained in plasmid pEJG120 that is contained in *Escherichia coli* NRRL B-30699. The present invention also encompasses nucleotide sequences which encode a polypeptide having the amino acid sequence of SEQ ID NO: 2 or the mature polypeptide thereof, which differ from SEQ ID NO: 1 by virtue of the degeneracy of the genetic code. The present invention also relates to subsequences of SEQ ID NO: 1 which encode fragments of SEQ ID NO: 2 that have cellulolytic enhancing activity.

In another preferred aspect, the nucleotide sequence is set forth in SEQ ID NO: 3. In another more preferred aspect, the nucleotide sequence is the sequence contained in plasmid pTter61C that is contained in *Escherichia coli* NRRL B-30813. In another preferred aspect, the nucleotide sequence is the mature polypeptide coding region of SEQ ID NO: 3. In another more preferred aspect, the nucleotide sequence is the mature polypeptide coding region contained in plasmid pTter61C that is contained in *Escherichia coli* NRRL B-30813. The present invention also encompasses nucleotide sequences which encode a polypeptide having the amino acid sequence of SEQ ID NO: 4 or the mature polypeptide thereof, which differ from SEQ ID NO: 3 by virtue of the degeneracy of the genetic code. The present invention also relates to subsequences of SEQ ID NO: 3 which encode fragments of SEQ ID NO: 4 that have cellulolytic enhancing activity.

In another preferred aspect, the nucleotide sequence is set forth in SEQ ID NO: 5. In another more preferred aspect, the nucleotide sequence is the sequence contained in plasmid pTter61D that is contained in *Escherichia coli* NRRL B-30812. In another preferred aspect, the nucleotide sequence is the mature polypeptide coding region of SEQ ID NO: 5. In another more preferred aspect, the nucleotide sequence is the mature polypeptide coding region contained in plasmid pTter61D that is contained in *Escherichia coli* NRRL B-30812. The present invention also encompasses nucleotide sequences which encode a polypeptide having the amino acid sequence of SEQ ID NO: 6 or the mature polypeptide thereof, which differ from SEQ ID NO: 5 by virtue of the degeneracy of the genetic code. The present invention also relates to subsequences of SEQ ID NO: 5 which encode fragments of SEQ ID NO: 6 that have cellulolytic enhancing activity.

In another preferred aspect, the nucleotide sequence is set forth in SEQ ID NO: 7. In another more preferred aspect, the nucleotide sequence is the sequence contained in plasmid pTter61E that is contained in *Escherichia coli* NRRL B-30814. In another preferred aspect, the nucleotide sequence is the mature polypeptide coding region of SEQ ID NO: 7. In another more preferred aspect, the nucleotide sequence is the mature polypeptide coding region contained in plasmid pTter61E that is contained in *Escherichia coli* NRRL B-30814. The present invention also encompasses nucleotide sequences which encode a polypeptide having the amino acid sequence of SEQ ID NO: 8 or the mature polypeptide thereof, which differ from SEQ ID NO: 7 by virtue of the degeneracy of the genetic code. The present invention also relates to subsequences of SEQ ID NO: 7 which encode fragments of SEQ ID NO: 8 that have cellulolytic enhancing activity.

In another preferred aspect, the nucleotide sequence is set forth in SEQ ID NO: 9. In another more preferred aspect, the nucleotide sequence is the sequence contained in plasmid pTter61G that is contained in *Escherichia coli* NRRL B-30811. In another preferred aspect, the nucleotide sequence is the mature polypeptide coding region of SEQ ID NO: 9. In another more preferred aspect, the nucleotide sequence is the mature polypeptide coding region contained in plasmid pTter61G that is contained in *Escherichia coli* NRRL B-30811. The present invention also encompasses nucleotide sequences which encode a polypeptide having the amino acid sequence of SEQ ID NO: 10 or the mature polypeptide thereof, which differ from SEQ ID NO: 9 by virtue of the degeneracy of the genetic code. The present invention also relates to subsequences of SEQ ID NO: 9 which encode fragments of SEQ ID NO: 10 that have cellulolytic enhancing activity.

The present invention also relates to mutant polynucleotides comprising at least one mutation in the mature polypeptide coding sequence of SEQ ID NO: 1, 3, 5, 7, or 9 in which the mutant nucleotide sequence encodes a polypeptide which consists of amino acids 20 to 326 of SEQ ID NO: 2, amino acids 18 to 240 of SEQ ID NO: 4, amino acids 20 to 258 of SEQ ID NO: 6, amino acids 19 to 226 of SEQ ID NO: 8, or amino acids 20 to 304 of SEQ ID NO: 10, respectively.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Thielavia*, or another or related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO: 1 (i.e., nucleotides 388 to 1332) of at least 75%, preferably at least 80%, more preferably at least 85%, even more preferably at least 90%, most preferably at least 95%, and even most preferably at least 97% identity, which encode an active polypeptide.

The present invention also relates to polynucleotides having nucleotide sequences which have a degree of identity to the mature polypeptide coding sequence of SEQ ID NO: 3 (i.e., nucleotides 98 to 821) of at least 75%, preferably at least 80%, more preferably at least 85%, even more preferably at least 90%, most preferably at least 95%, and even most preferably at least 97% identity, which encode an active polypeptide.

The present invention also relates to polynucleotides having nucleotide sequences which have a degree of identity to the mature polypeptide coding sequence of SEQ ID NO: 5 (i.e., nucleotides 126 to 978) of at least 75%, preferably at least 80%, more preferably at least 85%, even more preferably at least 90%, most preferably at least 95%, and even most preferably at least 97% identity, which encode an active polypeptide.

The present invention also relates to polynucleotides having nucleotide sequences which have a degree of identity to the mature polypeptide coding sequence of SEQ ID NO: 7 (i.e., nucleotides 55 to 678) of at least 75%, preferably at least 80%, more preferably at least 85%, even more preferably at least 90%, most preferably at least 95%, and even most preferably at least 97% identity, which encode an active polypeptide.

The present invention also relates to polynucleotides having nucleotide sequences which have a degree of identity to the mature polypeptide coding sequence of SEQ ID NO: 9 (i.e., nucleotides 58 to 912) of at least 75%, preferably at least 80%, more preferably at least 85%, even more preferably at least 90%, most preferably at least 95%, and even most preferably at least 97% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 1, 3, 5, 7, or 9, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for cellulolytic enhancing activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated polynucleotides encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 388 to 1332 of SEQ ID NO: 1, nucleotides 98 to 821 of SEQ ID NO: 3, nucleotides 126 to 978 of SEQ ID NO: 5, nucleotides 55 to 678 of SEQ ID NO: 7, or nucleotides 58 to 912 of SEQ ID NO: 9, (ii) the cDNA sequence contained in nucleotides 388 to 1332 of SEQ ID NO: 1, nucleotides 98 to 821 of SEQ ID NO: 3, or nucleotides 126 to 978 of SEQ ID NO: 5, or the genomic DNA sequence comprising nucleotides 55 to 678 of SEQ ID NO: 7 or nucleotides 58 to 912 of SEQ ID NO: 9, or (iii) a complementary strand of (i) or (ii); or allelic variants and subsequences thereof (Sambrook et al., 1989, supra), as defined herein.

The present invention also relates to isolated polynucleotides obtained by (a) hybridizing a population of DNA under very low, low, medium, medium-high, high, or very high stringency conditions with (i) nucleotides 388 to 1332 of SEQ ID NO: 1, nucleotides 98 to 821 of SEQ ID NO: 3, nucleotides 126 to 978 of SEQ ID NO: 5, nucleotides 55 to 678 of SEQ ID NO: 7, or nucleotides 58 to 912 of SEQ ID NO: 9, (ii) the cDNA sequence contained in nucleotides 388 to 1332 of SEQ ID NO: 1, nucleotides 98 to 821 of SEQ ID NO: 3, or nucleotides 126 to 978 of SEQ ID NO: 5, or the genomic DNA sequence comprising nucleotides 55 to 678 of SEQ ID NO: 7 or nucleotides 58 to 912 of SEQ ID NO: 9, or (iii) a complementary strand of (i) or (ii); and (b) isolating the hybridizing polynucleotide, which encodes a polypeptide having cellulolytic enhancing activity.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the E. coli lac operon, Streptomyces coelicolor agarase gene (dagA), Bacillus subtilis levansucrase gene (sacB), Bacillus licheniformis alpha-amylase gene (amyL), Bacillus stearothermophilus maltogenic amylase gene (amyM), Bacillus amyloliquefaciens alpha-amylase gene (amyQ), Bacillus licheniformis penicillinase gene (penP), Bacillus subtilis xyla and xylB genes, and prokaryotic beta-lactamase gene (Villa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for Aspergillus oryzae TAKA amylase, Rhizomucor miehei aspartic proteinase, Aspergillus niger neutral alpha-amylase, Aspergillus niger acid stable alpha-amylase, Aspergillus niger or Aspergillus awamori glucoamylase (glaA), Rhizomucor miehei lipase, Aspergillus oryzae alkaline protease, Aspergillus oryzae triose phosphate isomerase, Aspergillus nidulans acetamidase, Fusarium venenatum amyloglucosidase (WO 00/56900), Fusarium venenatum Daria (WO 00/56900), Fusarium venenatum Quinn (WO 00/56900), Fusarium oxysporum trypsin-like protease (WO 96/00787), Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase III, Trichoderma reesei endoglucanase IV, Trichoderma reesei endoglucanase V, Trichoderma reesei xylanase I, Trichoderma reesei xylanase II, Trichoderma reesei beta-xylosidase, as well as the NA2-tpi promoter (a hybrid of the promoters from the genes for Aspergillus niger neutral alpha-amylase and Aspergillus oryzae triose phosphate isomerase); and mutant, truncated, and hybrid promoters thereof.

In a yeast host, useful promoters are obtained from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH1,ADH2/GAP), Saccharomyces cerevisiae triose phosphate isomerase (TPI), Saccharomyces cerevisiae metallothionein (CUP1), and Saccharomyces cerevisiae 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for Aspergillus oryzae TAKA amylase, Aspergillus niger glucoamylase, Aspergillus nidulans anthranilate synthase, Aspergillus niger alpha-glucosidase, and Fusarium oxysporum trypsin-like protease.

Preferred terminators for yeast host cells are obtained from the genes for Saccharomyces cerevisiae enolase, Saccharomyces cerevisiae cytochrome C (CYC1), and Saccharomyces cerevisiae glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice, i.e., secreted into a culture medium, may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

In a preferred aspect, the signal peptide coding region is nucleotides 330 to 387 of SEQ ID NO: 1 which encode amino acids 1 to 19 of SEQ ID NO: 2.

In a preferred aspect, the signal peptide coding region is nucleotides 47 to 97 of SEQ ID NO: 3 which encode amino acids 1 to 17 of SEQ ID NO: 4.

In a preferred aspect, the signal peptide coding region is nucleotides 69 to 125 of SEQ ID NO: 5 which encode amino acids 1 to 19 of SEQ ID NO: 6.

In a preferred aspect, the signal peptide coding region is nucleotides 1 to 54 of SEQ ID NO: 7 which encode amino acids 1 to 18 of SEQ ID NO: 8.

In a preferred aspect, the signal peptide coding region is nucleotides 1 to 57 of SEQ ID NO: 9 which encode amino acids 1 to 19 of SEQ ID NO: 10.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMAL and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus,* or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9,1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Thielavia*, and more preferably *Thielavia terrestris*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a mutant nucleotide sequence having at least one mutation in the mature polypeptide coding region of SEQ ID NO: 1, wherein the mutant nucleotide sequence encodes a polypeptide which consists of amino acids 20 to 326 of SEQ ID NO: 2, amino acids 18 to 240 of SEQ ID NO: 4, amino acids 20 to 258 of SEQ ID NO: 6, amino acids 19 to 226 of SEQ ID NO: 8, or amino acids 20 to 304 of SEQ ID NO: 10, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides haing cellulolytic enhancing activity are detected using the methods described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to a transgenic plant, plant part, or plant cell which has been transformed with a nucleotide sequence encoding a polypeptide having cellulolytic enhancing activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome or chloroplast genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a polynucleotide encoding a polypeptide having cellulolytic enhancing activity of the present invention under conditions conducive for production of the polypeptide; and (b) recovering the polypeptide.

Removal or Reduction of Cellulolytic Enhancing Activity

The present invention also relates to methods for producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence which is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred embodiment, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell which comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous proteins. Therefore, the present invention further relates to methods for producing a native or heterologous protein comprising (a) cultivating the mutant cell under conditions conducive for production of the protein; and (b) recovering the polypeptide. The term "heterologous proteins" is defined herein as proteins which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of cellulolytic enhancing activity by fermentation of a cell which produces both a polypeptide of the present invention as well as the protein product of interest by adding an effective amount of an agent capable of inhibiting cellulolytic enhancing activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of cellulolytic enhancing activity by cultivating the cell under conditions permitting the expression of the product, subjecting the resultant culture broth to a combined pH and temperature treatment so as to reduce the cellulolytic enhancing activity substantially, and recovering the product from the culture broth. Alternatively, the combined pH and temperature treatment may be performed on an enzyme preparation recovered from the culture broth. The combined pH and temperature treatment may optionally be used in combination with a treatment with a cellulolytic enhancing inhibitor.

In accordance with this aspect of the invention, it is possible to remove at least 60%, preferably at least 75%, more preferably at least 85%, still more preferably at least 95%, and most preferably at least 99% of the cellulolytic enhancing activity. Complete removal of cellulolytic enhancing activity may be obtained by use of this method.

The combined pH and temperature treatment is preferably carried out at a pH of 4-5 and a temperature of 80-90° C. for a sufficient period of time to attain the desired effect.

The methods used for cultivation and purification of the product of interest may be performed by methods known in the art.

The methods of the present invention for producing an essentially cellulolytic enhancing-free product are of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The cellulolytic enhancing-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from cellulolytic enhancing activity which is produced by a method of the present invention.

Compositions

The present invention also relates to compositions comprising a polypeptide of the present invention. Preferably, the compositions are enriched in such a polypeptide. The term "enriched" indicates that the cellulolytic enhancing activity of the composition has been increased, e.g., with an enrichment factor of at least 1.1.

The composition may comprise a polypeptide of the present invention as the major component, e.g., a monocomponent composition. Alternatively, the composition may further comprise one or more enzymatic activities, such as an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Degradation or Conversion of Biomass to Monosaccharides, Disaccharides, and Polysaccharides The present invention also relates to methods for degrading or converting a cellulosic material, comprising: treating the cellulosic material with an effective amount of a cellulolytic protein in the presence of an effective amount of the polypeptide having cellulolytic enhancing activity, wherein the presence of the polypeptide having cellulolytic enhancing activity increases the degradation of cellulosic material compared to the absence of the polypeptide having cellulolytic enhancing activity.

The polypeptides and host cells of the present invention may be used in the production of monosaccharides, disaccharides, and polysaccharides as chemical or fermentation feedstocks from biomass for the production of ethanol, plastics, other products or intermediates. In particular, the polypeptides and host cells of the present invention may be used to increase the value of processing residues (dried distillers grain, spent grains from brewing, sugarcane bagasse, etc.) by partial or complete solubilization of cellulose or hemicellulose. In boosting the processing by cellulolytic proteins of cellulosic material to glucose, xylose, mannose, galactose, and arabinose, their polymers, or products derived from them as described below. The polypeptides may be in the form of a crude fermentation broth with or without the cells or in the form of a semi-purified or purified enzyme preparation. The cellulolytic enhancing protein may be a monocomponent preparation, e.g., a Family 61 protein, a multicomponent protein preparation, e.g., a number of Family 61 proteins or a combination of multicomponent and monocomponent protein preparations. The cellulolytic enhancing proteins may boost the activity of cellulolytic proteins, either in the acid, neutral, or alkaline pH-range. Alternatively, a host cell of the present invention may be used as a source of the polypeptide in a fermentation process with the biomass. The host cell may also contain native or heterologous genes that encode cellulolytic protein as well as other enzymes useful in the processing of biomass.

Biomass can include, but is not limited to, wood resources, municipal solid waste, wastepaper, crops, and crop residues (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York).

The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

In the methods of the present invention, the cellulolytic protein may be any protein involved in the processing of cellulosic material to glucose, or hemicellulose to xylose, mannose, galactose, and arabinose, their polymers, or products derived from them as described below. The cellulolytic protein may be a monocomponent preparation, e.g., a cellulase, a multicomponent preparation, e.g., endoglucanase, cellobiohydrolase, glucohydrolase, beta-glucosidase, as defined below or a combination of multicomponent and monocomponent protein preparations. The cellulolytic proteins may have activity, i.e., hydrolyze cellulose, either in the acid, neutral, or alkaline pH-range.

The cellulolytic protein may be of fungal or bacterial origin, which may be obtainable or isolated and purified from microorganisms which are known to be capable of producing cellulolytic enzymes, e.g., species of *Bacillus, Pseudomonas, Humicola, Coprinus, Thielavia, Fusarium, Myceliophthora, Acremonium, Cephalosporium, Scytalidium, Penicillium* or *Aspergillus* (see, for example, EP 458162), especially those produced by a strain selected from the species *Humicola insolens* (reclassified as *Scytalidium thermophilum*, see for example, U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum,* and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic proteins may also be obtained from *Trichoderma* (particularly *Trichoderma viride, Trichoderma reesei,* and *Trichoderma koningii*), alkalophilic *Bacillus* (see, for example, U.S. Pat. No. 3,844,890 and EP 458162), and *Streptomyces* (see, for example, EP 458162). Chemically modified or protein engineered mutants are included.

Especially suitable cellulolytic proteins are the alkaline or neutral cellulases. Examples of such cellulases are cellulases described in EP 495,257, EP 531,372, WO 96/11262, WO 96/29397, WO 98/08940. Other examples are cellulase variants such as those described in WO 94/07998, EP 531,315, U.S. Pat. Nos. 4,435,307, 5,457,046, 5,648,263, 5,686,593, 5,691,178, 5,763,254, 5,776,757, WO 89/09259, WO 95/24471, WO 98/12307, and PCT/DK98/00299.

The cellulolytic proteins and cellulolytic enhancing proteins used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), More *Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and cellulolytic protein production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of a cellulolytic protein or cellulolytic enhancing protein. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the cellulolytic protein or cellulolytic enhancing protein to be expressed or isolated.

The resulting cellulolytic proteins or cellulolytic enhancing proteins produced by the methods described above may be recovered from the fermentation medium by conventional procedures including, but not limited to, centrifugation, filtration, spray-drying, evaporation, or precipitation. The recovered protein may then be further purified by a variety of chromatographic procedures, e.g., ion exchange chromatography, gel filtration chromatography, affinity chromatography, or the like.

Cellulolytic protein may hydrolyze or hydrolyzes carboxymethyl cellulose (CMC), thereby decreasing the viscosity of the incubation mixture. The resulting reduction in viscosity may be determined by a vibration viscosimeter (e.g., MIVI 3000 from Sofraser, France). Determination of cellulase activity, measured in terms of Cellulase Viscosity Unit (CEVU), quantifies the amount of catalytic activity present in a sample by measuring the ability of the sample to reduce the viscosity of a solution of carboxymethyl cellulose (CMC). The assay is performed at the temperature and pH suitable for the cellulolytic protein and substrate. For Celluclast™ (Novozymes A/S, Bagsvaerd, Denmark) the assay is carried out at 40° C. in 0.1 M phosphate pH 9.0 buffer for 30 minutes with CMC as substrate (33.3 g/L carboxymethyl cellulose Hercules 7 LFD) and an enzyme concentration of approximately 3.3-4.2 CEVU/ml. The CEVU activity is calculated relative to a declared enzyme standard, such as CELLUZYME™ Standard 17-1194 (obtained from Novozymes A/S, Bagsvaerd, Denmark).

Examples of cellulolytic preparations suitable for use in the present invention include, for example, CELLUCLAST™ (available from Novozymes A/S) and NOVOZYM™ 188 (available from Novozymes A/S). Other commercially available preparations comprising cellulase which may be used include CELLUZYME™, CEREFLO™ and ULTRAFLO™ (Novozymes A/S), LAMINEX™ and SPEZYME™ CP (Genencor Int.), and ROHAMENT™ 7069 W (Röhm GmbH). The cellulase enzymes are added in amounts effective from about 0.001% to about 5.0% wt. of solids, more preferably from about 0.025% to about 4.0% wt. of solids, and most preferably from about 0.005% to about 2.0% wt. of solids.

As mentioned above, the cellulolytic proteins or cellulolytic enhancing proteins used in the methods of the present invention may be monocomponent preparations, i.e., a component essentially free of other cellulolytic components. The single component may be a recombinant component, i.e., produced by cloning of a DNA sequence encoding the single component and subsequent cell transformed with the DNA sequence and expressed in a host (see, for example, WO 91/17243 and WO 91/17244). Other examples of monocomponent cellulolytic proteins include, but are not limited to, those disclosed in JP-07203960-A and WO-9206209. The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

Examples of monocomponent cellulolytic proteins useful in practicing the methods of the present invention include, but are not limited to, endoglucanase, cellobiohydrolase, glucohydrolase, and beta-glucosidase.

The term "endoglucanase" is defined herein as an endo-1,4-(1,3;1,4)-beta-D-glucan 4-glucanohydrolase (E.C. No. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, *Pure and Appl. Chem.* 59: 257-268.

The exo-1,4-beta-D-glucanases include both cellobiohydrolases and glucohydrolases.

The term "cellobiohydrolase" is defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain. For purposes of the present invention, cellobiohydrolase activity is determined according to the procedures described by Lever et al., 1972, *Anal. Biochem.* 47: 273-279 and by van Tilbeurgh et al., 1982, *FEBS Letters* 149: 152-156; van Tilbeurgh and Claeyssens, 1985, *FEBS Letters* 187: 283-288. In the present invention, the Lever et al. method was employed to assess hydrolysis of cellulose in corn stover, while the method of van Tilbeurgh et al. was used to determine the cellobiohydrolase activity on a fluorescent disaccharide derivative.

The term "glucohydrolase" is defined herein as a 1,4-beta-D-glucan glucohydrolase (E.C. 3.2.1.74), which catalyzes the hydrolysis of 1,4-linkages (O-glycosyl bonds) in 1,4-beta-D-glucans so as to remove successive glucose units. For purposes of the present invention, exoglucanase activity is determined according to the procedure described by Himmel et al., 1986, *J. Biol. Chem.* 261: 12948-12955.

The term "beta-glucosidase" is defined herein as a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, *J. Basic Microbiol.* 42: 55-66, except different conditions were employed as described herein. One unit of beta-glucosidase activity is defined as 1.0 µmole of p-nitrophenol produced per minute at 50° C., pH 5 from 4 mM p-nitrophenyl-beta-D-glucopyranoside as substrate in 100 mM sodium citrate, 0.01% Tween-20.

The polypeptides of the present invention are used in conjunction with cellulolytic proteins to degrade the cellulosic component of the biomass substrate, (see, for example, Brigham et al., 1995, in *Handbook on Bioethanol* (Charles E. Wyman, editor), pp. 119-141, Taylor & Francis, Washington D.C.; Lee, 1997, *Journal of Biotechnology* 56: 1-24).

The optimum amounts of a polypeptide having cellulolytic enhancing activity and of cellulolytic proteins depends on several factors including, but not limited to, the mixture of component cellulolytic proteins, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation). The term "cellulolytic proteins" is defined herein as those proteins or mixtures of proteins shown as being capable of hydrolyzing or converting or degrading cellulose under the conditions tested. Their amounts are usually measured by a common assay such as BCA (bicinchoninic acid, P. K. Smith et al., 1985, *Anal. Biochem.* 150: 76), and the preferred amount added in proportion to the amount of biomass being hydrolyzed.

In a preferred aspect, the amount of polypeptide having cellulolytic enhancing activity per g of cellulosic material is about 0.01 to about 2.0 mg, preferably about 0.025 to about 1.5 mg, more preferably about 0.05 to about 1.25 mg, more preferably about 0.075 to about 1.25 mg, more preferably about 0.1 to about 1.25 mg, even more preferably about 0.15 to about 1.25 mg, and most preferably about 0.25 to about 1.0 mg per g of cellulosic material.

In another preferred aspect, the amount of cellulolytic proteins per g of cellulosic material is about 0.5 to about 50 mg, preferably about 0.5 to about 40 mg, more preferably about 0.5 to about 25 mg, more preferably about 0.75 to about 20 mg, more preferably about 0.75 to about 15 mg, even more preferably about 0.5 to about 10 mg, and most preferably about 2.5 to about 10 mg per g of cellulosic material.

In a preferred aspect, the amount of polypeptide having cellulolytic enhancing activity per g of cellulolytic proteins is about 0.005 to about 1.0 g, preferably about 0.01 to about 1.0 g, more preferably at about 0.15 to about 0.75 g, more preferably about 0.15 to about 0.5 g, more preferably about 0.1 to about 0.5 g, even more preferably about 0.1 to about 0.5 g, and most preferably about 0.05 to about 0.2 g per g of cellulolytic proteins.

The methods of the present invention may be used to process a cellulosic material to many useful organic products, chemicals and fuels. In addition to ethanol, some commodity and specialty chemicals that can be produced from cellulose include xylose, acetone, acetate, glycine, lysine, organic acids (e.g., lactic acid), 1,3-propanediol, butanediol, glycerol, ethylene glycol, furfural, polyhydroxyalkanoates, cis, cis-muconic acid, and animal feed (Lynd, L. R., Wyman, C. E., and Gerngross, T. U., 1999, *Biocommodity Engineering, Biotechnol. Prog.*, 15: 777-793; Philippidis, G. P., 1996, Cellulose bioconversion technology, in *Handbook on Bioethanol: Production and Utilization*, Wyman, C. E., ed., Taylor & Francis, Washington, D.C., 179-212; and Ryu, D. D. Y., and Mandels, M., 1980, Cellulases: biosynthesis and applications, *Enz. Microb. Technol.*, 2: 91-102). Potential coproduction benefits extend beyond the synthesis of multiple organic products from fermentable carbohydrate. Lignin-rich residues remaining after biological processing can be converted to lignin-derived chemicals, or used for power production.

Conventional methods used to process the cellulosic material in accordance with the methods of the present invention are well understood to those skilled in the art. The methods of the present invention may be implemented using any conventional biomass processing apparatus configured to operate in accordance with the invention.

Such an apparatus may include a batch-stirred reactor, a continuous flow stirred reactor with ultrafiltration, a continuous plug-flow column reactor (Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153).

The conventional methods include, but are not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to glucose and then ferment glucose to ethanol. In SSF, the enzymatic hydrolysis of cellulose and the fermentation of glucose to ethanol is combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF includes the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF includes two separate steps carried out in the same reactor but at different temperatures, ie., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577).

"Fermentation" or "fermentation process" refers to any fermentation process or any process comprising a fermentation step. A fermentation process includes, without limitation, fermentation processes used to produce fermentation products including alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)). Fermentation processes also include fermentation processes used in the consumable alcohol industry (e.g., beer and wine), dairy industry (e.g., fermented dairy products), leather industry, and tobacco industry.

The present invention further relates to methods for producing an organic substance, comprising: (a) saccharifying a cellulosic material with an effective amount of a cellulolytic protein in the presence of an effective amount of a polypeptide having cellulolytic enhancing activity, wherein the presence of the polypeptide having cellulolytic enhancing activity increases the degradation of cellulosic material compared to the absence of the polypeptide having cellulolytic enhancing activity; (b) fermenting the saccharified cellulosic material of step (a) with one or more fermentating microorganisms; and (c) recovering the organic substance from the fermentation. The polypeptide having cellulolytic enhancing activity may be in the form of a crude fermentation broth with or without the cells or in the form of a semi-purified or purified enzyme preparation. The cellulolytic enhancing protein may be a monocomponent preparation, e.g., a Family 61 protein, a multicomponent protein preparation, e.g., a number of Family 61 proteins, or a combination of multicomponent and monocomponent protein preparations.

The organic substance can be any substance derived from the fermentation. In a preferred embodiment, the organic substance is an alcohol. It will be understood that the term "alcohol" encompasses an organic substance that contains one or more hydroxyl moieties. In a more preferred embodiment, the alcohol is arabinitol. In another more preferred embodiment, the alcohol is butanol. In another more preferred embodiment, the alcohol is ethanol. In another more preferred embodiment, the alcohol is glycerol. In another more preferred embodiment, the alcohol is methanol. In another more preferred embodiment, the alcohol is 1,3-propanediol. In another more preferred embodiment, the alcohol is sorbitol. In another more preferred embodiment, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred embodiment, the organic substance is an organic acid. In another more preferred embodiment, the organic acid is acetic acid. In another more preferred embodiment, the organic acid is acetonic acid. In another more preferred embodiment, the organic acid is adipic acid. In another more preferred embodiment, the organic acid is ascorbic acid. In another more preferred embodiment, the organic acid is citric acid. In another more preferred embodiment, the organic acid is 2,5-diketo-D-gluconic acid. In another more preferred embodiment, the organic acid is formic acid. In another more preferred embodiment, the organic acid is fumaric acid. In another more preferred embodiment, the organic acid is glucaric acid. In another more preferred embodiment, the organic acid is gluconic acid. In another more preferred embodiment, the organic acid is glucuronic acid. In another more preferred embodiment, the organic acid is glutaric acid. In another preferred embodiment, the organic acid is 3-hydroxypropionic acid. In another more preferred embodiment, the organic acid is itaconic acid. In another more preferred embodiment, the organic acid is lactic acid. In another more preferred embodiment, the organic acid is malic acid. In another more preferred embodiment, the organic acid is malonic acid. In another more preferred embodiment, the organic acid is oxalic acid. In another more preferred embodiment, the organic acid is propionic acid. In another more preferred embodiment, the organic acid is succinic acid. In another more preferred embodiment, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred embodiment, the organic substance is a ketone. It will be understood that the term "ketone" encompasses an organic substance that contains one or more ketone moieties. In another more preferred embodiment, the ketone is acetone. See, for example, Qureshi and Blaschek, 2003, supra.

In another preferred embodiment, the organic substance is an amino acid. In another more preferred embodiment, the organic acid is aspartic acid. In another more preferred embodiment, the amino acid is glutamic acid. In another more preferred embodiment, the amino acid is glycine. In another more preferred embodiment, the amino acid is lysine. In another more preferred embodiment, the amino acid is serine. In another more preferred embodiment, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred embodiment, the organic substance is a gas. In another more preferred embodiment, the gas is methane. In another more preferred embodiment, the gas is $H_2$. In another more preferred embodiment, the gas is $CO_2$. In another more preferred embodiment, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Production of an organic substance from cellulosic material typically requires four major steps. These four steps are pretreatment, enzymatic hydrolysis, fermentation, and recovery. Exemplified below is a process for producing ethanol, but it will be understood that similar processes can be used to produce other organic substances, for example, the substances described above.

Pretreatment. In the pretreatment or pre-hydrolysis step, the cellulosic material is heated to break down the lignin and carbohydrate structure, solubilize most of the hemicellulose, and make the cellulose fraction accessible to cellulolytic enzymes. The heating is performed either directly with steam or in slurry where a catalyst may also be added to the material to speed up the reactions. Catalysts include strong acids, such as sulfuric acid and $SO_2$, or alkali, such as sodium hydroxide. The purpose of the pre-treatment stage is to facilitate the penetration of the enzymes and microorganisms. Cellulosic biomass may also be subject to a hydrothermal steam explosion pre-treatment (See U.S. Patent Application No. 20020164730).

Saccharification. In the enzymatic hydrolysis step, also known as saccharification, enzymes as described herein are added to the pretreated material to convert the cellulose fraction to glucose and/or other sugars. The saccharification is generally performed in stirred-tank reactors or fermentors under controlled pH, temperature, and mixing conditions. A saccharification step may last up to 200 hours. Saccharification may be carried out at temperatures from about 30° C. to about 65° C., in particular around 50° C., and at a pH in the range between about 4 and about 5, especially around pH 4.5. To produce glucose that can be metabolized by yeast, the hydrolysis is typically performed in the presence of a beta-glucosidase.

Fermentation. In the fermentation step, sugars, released from the cellulosic material as a result of the pretreatment and enzymatic hydrolysis steps, are fermented to ethanol by a fermenting organism, such as yeast. The fermentation can also be carried out simultaneously with the enzymatic hydrolysis in the same vessel, again under controlled pH, temperature, and mixing conditions. When saccharification and fermentation are performed simultaneously in the same vessel, the process is generally termed simultaneous saccharification and fermentation or SSF.

Any suitable cellulosic substrate or raw material may be used in a fermentation process of the present invention. The substrate is generally selected based on the desired fermentation product, i.e., the organic substance to be obtained from the fermentation, and the process employed, as is well known in the art. Examples of substrates suitable for use in the methods of present invention, include cellulose-containing materials, such as wood or plant residues or low molecular sugars DP1-3 obtained from processed cellulosic material that can be metabolized by the fermenting microorganism, and which may be supplied by direct addition to the fermentation medium.

The term "fermentation medium" will be understood to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism suitable for use in a desired fermentation process. Suitable fermenting microorganisms according to the invention are able to ferment, i.e., convert, sugars, such as glucose, xylose, arabinose, mannose, galactose, or oligosaccharides directly or indirectly into the desired fermentation product. Examples of fermenting microorganisms include fungal organisms, such as yeast. Preferred yeast includes strains of the *Saccharomyces* spp., and in particular, *Saccharomyces cerevisiae*. Commercially available yeast include, e.g., Red Star®/™/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

In a preferred embodiment, the yeast is a *Saccharomyces* spp. In a more preferred embodiment, the yeast is *Saccharomyces cerevisiae*. In another more preferred embodiment, the yeast is *Saccharomyces distaticus*. In another more preferred embodiment, the yeast is *Saccharomyces uvarum*. In another preferred embodiment, the yeast is a *Kluyveromyces*. In another more preferred embodiment, the yeast is *Kluyveromyces marxianus*. In another more preferred embodiment, the yeast is *Kluyveromyces fragilis*. In another preferred embodiment, the yeast is a *Candida*. In another more preferred embodiment, the yeast is *Candida pseudotropicalis*. In another more preferred embodiment, the yeast is *Candida brassicae*. In another preferred embodiment, the yeast is a *Clavispora*. In another more preferred embodiment, the yeast is *Clavispora lusitaniae*. In another more preferred embodiment, the yeast is *Clavispora opuntiae*. In another preferred embodiment, the yeast is a *Pachysolen*. In another more preferred embodiment, the yeast is *Pachysolen tannophilus*. In another preferred embodiment, the yeast is a *Bretannomyces*. In another more preferred embodiment, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment glucose to ethanol include, for example, *Zymomonas mobilis* and *Clostridium thermocellum* (Philippidis, 1996, supra).

It is well known in the art that the organisms described above can also be used to produce other organic substances, as described herein.

The cloning of heterologous genes in *Saccharomyces cerevisiae* (Chen, Z., Ho, N. W. Y., 1993, Cloning and improving the expression of *Pichia stipitis* xylose reductase gene in *Saccharomyces cerevisiae, Appl. Biochem. Biotechnol.* 39-40: 135-147; Ho, N. W. Y., Chen, Z, Brainard, A. P., 1998, Genetically engineered *Saccharomyces* yeast capable of effectively cofermenting glucose and xylose, *Appl. Environ. Microbiol.* 64: 1852-1859), or in bacteria such as *Escherichia coli* (Beall, D. S., Ohta, K., Ingram, L. O., 1991, Parametric studies of ethanol production from xylose and other sugars by recombinant *Escherichia coli*, *Biotech. Bioeng.* 38: 296-303), *Klebsiella oxytoca* (Ingram, L. O., Gomes, P. F., Lai, X., Moniruzzaman, M., Wood, B. E., Yomano, L. P., York, S. W., 1998, Metabolic engineering of bacteria for ethanol production, *Biotechnol. Bioeng.* 58: 204-214), and *Zymomonas mobilis* (Zhang, M., Eddy, C., Deanda, K., Finkelstein, M., and Picataggio, S., 1995, Metabolic engineering of a pentose metabolism pathway in ethanologenic *Zymomonas mobilis, Science* 267: 240-243; Deanda, K., Zhang, M., Eddy, C., and Picataggio, S., 1996, Development of an arabinose-fermenting *Zymomonas mobilis* strain by metabolic pathway engineering, *Appl. Environ. Microbiol.* 62: 4465-4470) has led to the construction of organisms capable of converting hexoses and pentoses to ethanol (cofermentation).

Yeast or another microorganism typically is added to the degraded cellulose or hydrolysate and the fermentation is ongoing for about 24 to about 96 hours, such as about 35 to about 60 hours. The temperature is typically between about 26° C. to about 40° C., in particular at about 32° C., and at about pH 3 to about pH 6, in particular around pH 4-5.

In a preferred embodiment, yeast or another microorganism is applied to the degraded cellulose or hydrolysate and the fermentation is ongoing for about 24 to about 96 hours, such as typically 35-60 hours. In a preferred embodiments, the temperature is generally between about 26 to about 40° C., in particular about 32° C., and the pH is generally from about pH 3 to about pH 6, preferably around pH 4-5. Yeast or another microorganism is preferably applied in amounts of approximately $10^5$ to $10^{12}$, preferably from approximately $10^7$ to $10^{10}$, especially approximately $5 \times 10^7$ viable count per ml of fermentation broth. During an ethanol producing phase the yeast cell count should preferably be in the range from approximately $10^7$ to $10^{10}$, especially around approximately $2 \times 10^8$. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

The most widely used process in the art is the simultaneous saccharification and fermentation (SSF) process where there is no holding stage for the saccharification, meaning that yeast and enzyme are added together.

For ethanol production, following the fermentation the mash is distilled to extract the ethanol. The ethanol obtained according to the process of the invention may be used as, e.g., fuel ethanol; drinking ethanol, i.e., potable neutral spirits, or industrial ethanol.

A fermentation stimulator may be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, e.g., Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Recovery. The alcohol is separated from the fermented cellulosic material and purified by conventional methods of distillation. Ethanol with a purity of up to about 96 vol. % ethanol can be obtained, which can be used as, for example, fuel ethanol, drinking ethanol, i.e., potable neutral spirits, or industrial ethanol.

For other organic substances, any method known in the art can be used including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, distillation, or extraction.

In the methods of the present invention, the cellulolytic protein(s) and cellulolytic enhancing polypeptide(s) may be supplemented by one or more additional enzyme activities to improve the degradation of the cellulosic material. Preferred additional enzymes are hemicellulases, esterases (e.g., lipases, phospholipases, and/or cutinases), proteases, laccases, peroxidases, or mixtures thereof.

In the methods of the present invention, the additional enzyme(s) may be added prior to or during fermentation, including during or after the propagation of the fermenting microorganism(s).

The enzymes referenced herein may be derived or obtained from any suitable origin, including, bacterial, fungal, yeast or mammalian origin. The term "obtained" means herein that the enzyme may have been isolated from an organism which naturally produces the enzyme as a native enzyme. The term "obtained" also means herein that the enzyme may have been produced recombinantly in a host organism, wherein the recombinantly produced enzyme is either native or foreign to the host organism or has a modified amino acid sequence, e.g., having one or more amino acids which are deleted, inserted and/or substituted, i.e., a recombinantly produced enzyme which is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

The enzymes may also be purified. The term "purified" as used herein covers enzymes free from other components from the organism from which it is derived. The term "purified" also covers enzymes free from components from the native organism from which it is obtained. The enzymes may be purified, with only minor amounts of other proteins being present. The expression "other proteins" relate in particular to other enzymes. The term "purified" as used herein also refers to removal of other components, particularly other proteins and most particularly other enzymes present in the cell of origin of the enzyme of the invention. The enzyme may be "substantially pure," that is, free from other components from the organism in which it is produced, that is, for example, a host organism for recombinantly produced enzymes. In a preferred embodiment, the enzymes are at least 75% (w/w), preferably at least 80%, more preferably at least 85%, more preferably at least 90%, more preferably at least 95%, more preferably at least 96%, more preferably at least 97%, even more preferably at least 98%, or most preferably at least 99% pure. In another preferred embodiment, the enzyme is 100% pure.

The enzymes used in the present invention may be in any form suitable for use in the processes described herein, such as, for example, a crude fermentation broth with or without cells, a dry powder or granulate, a non-dusting granulate, a liquid, a stabilized liquid, or a protected enzyme. Granulates may be produced, e.g., as disclosed in U.S. Pat. Nos. 4,106,991 and 4,661,452, and may optionally be coated by process known in the art. Liquid enzyme preparations may, for instance, be stabilized by adding stabilizers such as a sugar, a sugar alcohol or another polyol, and/or lactic acid or another organic acid according to established process. Protected enzymes may be prepared according to the process disclosed in EP 238,216.

Hemicellulases

Enzymatic hydrolysis of hemicelluloses can be performed by a wide variety of fungi and bacteria. Similar to cellulose degradation, hemicellulose hydrolysis requires coordinated action of many enzymes. Hemicellulases can be placed into three general categories: the endo-acting enzymes that attack internal bonds within the polysaccharide chain, the exo-acting enzymes that act processively from either the reducing or nonreducing end of polysaccharide chain, and the accessory enzymes, acetylesterases and esterases that hydrolyze lignin glycoside bonds, such as coumaric acid esterase and ferulic acid esterase (Wong, K. K. Y., Tan, L. U. L., and Saddler, J. N., 1988, Multiplicity of β-1,4-xylanase in microorganisms: Functions and applications, *Microbiol. Rev.* 52: 305-317; Tenkanen, M., and Poutanen, K., 1992, Significance of esterases in the degradation of xylans, in *Xylans and Xylanases*, Visser, J., Beldman, G., Kuster-van Someren, M. A., and Voragen, A. G. J., eds., Elsevier, New York, N.Y., 203-212; Coughlan, M. P., and Hazlewood, G. P., 1993, *Hemicellulose and hemicellulases*, Portland, London, UK; Brigham, J. S., Adney, W. S., and Himmel, M. E., 1996, Hemicellulases: Diversity and applications, in *Handbook on Bioethanol: Production and Utilization*, Wyman, C. E., ed., Taylor & Francis, Washington, D.C., 119-141).

Hemicellulases include xylanases, arabinofuranosidases, acetyl xylan esterase, glucuronidases, endo-galactanase, mannanases, endo or exo arabinases, exo-galactanses, and mixtures thereof. Examples of endo-acting hemicellulases and ancillary enzymes include endoarabinanase, endoarabinogalactanase, endoglucanase, endomannanase, endoxylanase, and feraxan endoxylanase. Examples of exo-acting hemicellulases and ancillary enzymes include α-L-arabinosidase, β-L-arabinosidase, α-1,2-L-fucosidase, α-D-galactosidase, β-D-galactosidase, β-D-glucosidase, β-D-glucuronidase, β-D-mannosidase, β-D-xylosidase, exoglucosidase, exocellobiohydrolase, exomannobiohydrolase, exomannanase, exoxylanase, xylan α-glucuronidase, and coniferin β-glucosidase. Examples of esterases include acetyl esterases (acetylgalactan esterase, acetylmannan esterase, and acetylxylan esterase) and aryl esterases (coumaric acid esterase and ferulic acid esterase).

Preferably, the hemicellulase is an exo-acting hemicellulase, and more preferably, an exo-acting hemicellulase which has the ability to hydrolyze hemicellulose under acidic conditions of below pH 7. An example of a hemicellulase suitable for use in the present invention includes VISCOZYME™ (available from Novozymes A/S, Denmark). The hemicellulase is added in an effective amount from about 0.001% to about 5.0% wt. of solids, more preferably from about 0.025% to about 4.0% wt. of solids, and most preferably from about 0.005% to about 2.0% wt. of solids.

A xylanase (E.C. 3.2.1.8) may be obtained from any suitable source, including fungal and bacterial organisms, such as *Aspergillus, Disporotrichum, Penicillium, Neurospora, Fusarium, Trichoderma, Humicola, Thermomyces*, and *Bacillus*. Preferred commercially available preparations comprising xylanase include SHEARZYME®, BIOFEED WHEAT®, BIO-FEED Plus® L, CELLUCLAST®, ULTRAFLO®, VISCOZYME®, PENTOPAN MONO® BG, and PULPZYME® HC (Novozymes A/S); and LAMINEX® and SPEZYME® CP (Genencor Int.).

Esterases

Esterases that can be used for bioconversion of cellulose include acetyl esterases such as acetylgalactan esterase, acetylmannan esterase, and acetylxylan esterase, and esterases that hydrolyze lignin glycoside bonds, such as coumaric acid esterase and ferulic acid esterase.

As used herein, an "esterase" also known as a carboxylic ester hydrolyase, refers to enzymes acting on ester bonds, and includes enzymes classified in EC 3.1.1 Carboxylic Ester Hydrolases according to Enzyme Nomenclature (*Enzyme Nomenclature,* 1992, Academic Press, San Diego, Calif., with Supplement 1 (1993), Supplement 2 (1994), Supplement 3 (1995), Supplement 4 (1997) and Supplement 5, in *Eur. J. Biochem.* 223: 1-5, 1994; *Eur. J. Biochem.* 232: 1-6, 1995; *Eur. J. Biochem.* 237: 1-5, 1996; *Eur. J. Biochem.* 250: 1-6, 1997, and *Eur. J. Biochem.* 264: 610-650, 1999; respectively). Non-limiting examples of esterases include arylesterase, triacylglycerol lipase, acetylesterase, acetylcholinesterase, cholinesterase, tropinesterase, pectinesterase, sterol esterase, chlorophyllase, L-arabinonolactonase, gluconolactonase, uronolactonase, tannase, retinyl-palmitate esterase, hydroxybutyrate-dimer hydrolase, acylglycerol lipase, 3-oxoadipate enol-lactonase, 1,4-lactonase, galactolipase, 4-pyridoxolactonase, acylcarnitine hydrolase, aminoacyl-tRNA hydrolase, D-arabinonolactonase, 6-phosphogluconolactonase, phospholipase A1, 6-acetylglucose deacetylase, lipoprotein lipase, dihydrocoumarin lipase, limonin-D-ring-lactonase, steroid-lactonase, triacetate-lactonase, actinomycin lactonase, orsellinate-depside hydrolase, cephalosporin-C deacetylase, chlorogenate hydrolase, alpha-amino-acid esterase, 4-methyloxaloacetate esterase, carboxymethylenebutenolidase, deoxylimonate A-ring-lactonase, 2-acetyl-1-alkylglycerophosphocholine esterase, fusarinine-C ornithinesterase, sinapine esterase, wax-ester hydrolase, phorbol-diester hydrolase, phosphatidylinositol deacylase, sialate O-acetylesterase, acetoxybutynyl-bithiophene deacetylase, acetylsalicylate deacetylase, methylumbelliferyl-acetate deacetylase, 2-pyrone-4,6-dicarboxylate lactonase, N-acetylgalactosaminoglycan deacetylase, juvenile-hormone esterase, bis(2-ethylhexyl)phthalate esterase, protein-glutamate methylesterase, 11-cis-retinyl-palmitate hydrolase, all-trans-retinyl-palmitate hydrolase, L-rhamnono-1,4-lactonase, 5-(3,4-diacetoxybut-1-ynyl)-2, 2'-bithiophene deacetylase, fatty-acyl-ethyl-ester synthase, xylono-1,4-lactonase, N-acetylglucosaminylphosphatidylinositol deacetylase, cetraxate benzylesterase, acetylalkylglycerol acetylhydrolase, and acetylxylan esterase.

Preferred esterases for use in the present invention are lipolytic enzymes, such as, lipases (classified as EC 3.1.1.3, EC 3.1.1.23, and/or EC 3.1.1.26) and phospholipases (classified as EC 3.1.1.4 and/or EC 3.1.1.32, including lysophospholipases classified as EC 3.1.1.5). Other preferred esterases are cutinases (classified as EC 3.1.1.74).

The esterase may be added in an amount effective to obtain the desired benefit to improve the performance of the fermenting microorganism, for example, to change the lipid composition/concentration inside and/or outside of the fermenting microorganism or in the cell membrane of the fermenting microorganism, to result in an improvement in the movement of solutes into and/or out of the fermenting microorganisms during fermentation and/or to provide more metabolizable energy sources (such as, for example, by converting components, such as, oil from the corn substrate, to components useful the fermenting microorganism, e.g., unsaturated fatty acids and glycerol), to increase ethanol yield. Examples of effective amounts of esterase are from about 0.01 to about 400 LU/g DS (Dry Solids). Preferably, the esterase is used in an amount of about 0.1 to about 100 LU/g DS, more preferably about 0.5 to about 50 LU/g DS, and even more preferably about 1 to about 20 LU/g DS. Further optimization of the amount of esterase can hereafter be obtained using standard procedures known in the art.

One Lipase Unit (LU) is the amount of enzyme which liberates 1.0 μmol of titratable fatty acid per minute with tributyrin as substrate and gum arabic as an emulsifier at 30(C, pH 7.0 (phosphate buffer).

In a preferred embodiment, the esterase is a lipolytic enzyme, more preferably, a lipase. As used herein, a "lipolytic enzyme" refers to lipases and phospholipases (including lyso-phospholipases). The lipolytic enzyme is preferably of microbial origin, in particular of bacterial, fungal or yeast origin. The lipolytic enzyme used may be derived from any source, including, for example, a strain of *Absidia*, in particular *Absidia blakesleena* and *Absidia corymbifera*, a strain of *Achromobacter*, in particular *Achromobacter iophagus*, a strain of *Aeromonas*, a strain of *Altemaria*, in particular *Alternaria brassiciola*, a strain of *Aspergillus*, in particular *Aspergillus niger, Aspergillus oryzae, Aspergillus fumigatus*, and *Aspergillus flavus*, a strain of *Achromobacter*, in particular *Achromobacter iophagus*, a strain of *Aureobasidium*, in particular *Aureobasidium pullulans*, a strain of *Bacillus*, in particular *Bacillus pumilus, Bacillus stearothermophilus*, and *Bacillus subtilis*, a strain of *Beauveria*, a strain of *Brochothrix*, in particular *Brochothrix thermosohata*, a strain of *Candida*, in particular *Candida cylindracea (Candida rugosa), Candida paralipolytica*, and *Candida antarctica*, a strain of *Chromobacter*, in particular *Chromobacter viscosum*, a strain of *Coprinus*, in particular *Coprinus cinereus*, a strain of *Fusarium*, in particular *Fusarium graminearum, Fusarium oxysporum, Fusarium solani, Fusarium solani pisi, Fusarium roseum culmorum*, and *Fusarium venenatum*, a strain of *Geotricum*, in particular *Geotricum penicillatum*, a strain of *Hansenula*, in particular *Hansenula anomala*, a strain of *Humicola*, in particular *Humicola brevispora, Humicola brevis* var. *thermoidea*, and *Humicola insolens*, a strain of *Hyphozyma*, a strain of *Lactobacillus*, in particular *Lactobacillus curvatus*, a strain of *Metarhizium*, a strain of *Mucor*, a strain of *Paecilomyces*, a strain of *Penicillium*, in particular *Penicil-* lium cyclopium, Penicillium crustosum and Penicillium expansum, a strain of Pseudomonas in particular Pseudomonas aeruginosa, Pseudomonas alcaligenes, Pseudomonas cepacia (syn. Burkholderia cepacia), Pseudomonas fluorescens, Pseudomonas fragi, Pseudomonas maltophilia, Pseudomonas mendocina, Pseudomonas mephitica lipolytica, Pseudomonas alcaligenes, Pseudomonas plantari, Pseudomonas pseudoalcaligenes, Pseudomonas putida, Pseudomonas stutzeri, and Pseudomonas wisconsinensis, a strain of Rhizooctonia, in particular Rhizooctonia solani, a strain of Rhizomucor, in particular Rhizomucor miehei, a strain of Rhizopus, in particular Rhizopus japonicus, Rhizopus microsporus, and Rhizopus nodosus, a strain of Rhodosporidium, in particular Rhodosporidium toruloides, a strain of Rhodotorula, in particular Rhodotorula glutinis, a strain of Sporobolomyces, in particular Sporobolomyces shibatanus, a strain of Thermomyces, in particular Thermomyces lanuginosus (formerly Humicola lanuginosa), a strain of Thiarosporella, in particular Thiarosporella phaseolina, a strain of Trichoderma, in particular, Trichoderma harzianum and Trichoderma reesei, and/or a strain of Verticillium.

In a preferred embodiment, the lipolytic enzyme is derived from a strain of Aspergillus, Achromobacter, Bacillus, Candida, Chromobacter, Fusarium, Humicola, Hyphozyma, Pseudomonas, Rhizomucor, Rhizopus, or Thermomyces.

In more preferred embodiments, the lipolytic enzyme is a lipase. Lipases may be applied herein for their ability to modify the structure and composition of triglyceride oils and fats in the fermentation media (including fermentation yeast), for example, resulting from a corn substrate. Lipases catalyze different types of triglyceride conversions, such as hydrolysis, esterification, and transesterification. Suitable lipases include acidic, neutral, and basic lipases, as are well-known in the art, although acidic lipases (such as, e.g., the lipase G AMANO 50, available from Amano) appear to be more effective at lower concentrations of lipase as compared to either neutral or basic lipases. Preferred lipases for use in the present invention include Candida antarcitca lipase and Candida cylindracea lipase. More preferred lipases are purified lipases such as Candida antarcitca lipase (lipase A), Candida antarcitca lipase (lipase B), Candida cylindracea lipase, and Penicillium camembertii lipase.

The lipase may be the one disclosed in EP 258,068-A or may be a lipase variant such as a variant disclosed in WO 00/60063 or WO 00/32758, hereby incorporated by reference. Preferred commercial lipases include LECITASE™, LIPOLASE™, and LIPEX™ (available from Novozymes A/S, Denmark) and G AMANO™ 50 (available from Amano).

Lipases are preferably added in amounts from about 1 to about 400 LU/g DS, preferably about 1 to about 10 LU/g DS, and more preferably about 1 to about 5 LU/g DS.

In another preferred embodiment of the present invention, the esterase is a cutinase. Cutinases are enzymes which are able to degrade cutin. The cutinase may be derived from any source. In a preferred embodiment, the cutinase is derived from a strain of Aspergillus, in particular Aspergillus oryzae, a strain of Alternaria, in particular Alternaria brassiciola, a strain of Fusarium, in particular Fusarium solani, Fusarium solani pisi, Fusarium roseum culmorum, or Fusarium roseum sambucium, a strain of Helminthosporum, in particular Helminthosporum sativum, a strain of Humicola, in particular Humicola insolens, a strain of Pseudomonas, in particular Pseudomonas mendocina or Pseudomonas putida, a strain of Rhizooctonia, in particular Rhizooctonia solani, a strain of Streptomyces, in particular Streptomyces scabies, or a strain of Ulocladium, in particular Ulocladium consortiale. In a most preferred embodiment the cutinase is derived from a strain of Humicola insolens, in particular the strain Humicola insolens DSM 1800. Humicola insolens cutinase is described in WO 96/13580, which is hereby incorporated by reference. The cutinase may be a variant such as one of the variants disclosed in WO 00/34450 and WO 01/92502, which are hereby incorporated by reference. Preferred cutinase variants include variants listed in Example 2 of WO 01/92502 which are hereby specifically incorporated by reference. An effective amount of cutinase is from about 0.01 to about 400 LU/g DS, preferably from about 0.1 to about 100 LU/g DS, and more preferably from about 1 to about 50 LU/g DS. Further optimization of the amount of cutinase can hereafter be obtained using standard procedures known in the art.

In another preferred embodiment, the esterase is a phospholipase. As used herein, the term "phospholipase" is an enzyme which has activity towards phospholipids, e.g., hydrolytic activity. Phospholipids, such as lecithin or phosphatidylcholine, consist of glycerol esterified with two fatty acids in an outer (sn-1) and the middle (sn-2) positions and esterified with phosphoric acid in the third position. The phosphoric acid may be esterified to an amino-alcohol. Several types of phospholipase activity can be distinguished, including phospholipases A1 and A2 which hydrolyze one fatty acyl group (in the sn-1 and sn-2 position, respectively) to form lysophospholipid; and lysophospholipase (or phospholipase B) which hydrolyzes the remaining fatty acyl group in lysophospholipid. Phospholipase C and phospholipase D (phosphodiesterases) release diacyl glycerol or phosphatidic acid respectively.

The term "phospholipase" includes enzymes with phospholipase activity, e.g., phospholipase A (A1 or A2), phospholipase B activity, phospholipase C activity, or phospholipase D activity. The term "phospholipase A" as used herein is intended to cover an enzyme with phospholipase A1 and/or phospholipase A2 activity. The phospholipase activity may be provided by enzymes having other activities as well, such as, e.g., a lipase with phospholipase activity. The phospholipase activity may, for example, be from a lipase with phospholipase side activity. In other embodiments, the phospholipase enzyme activity is provided by an enzyme having essentially only phospholipase activity and wherein the phospholipase enzyme activity is not a side activity.

The phospholipase may be of any origin, for example, of animal origin (e.g., mammalian, for example, bovine or porcine pancreas), or snake venom or bee venom. Alternatively, the phospholipase may be of microbial origin, for example, from filamentous fungi, yeast or bacteria, such as Aspergillus, e.g., A. awamori, A. foetidus, A. japonicus, A. niger, or A. oryzae, Dictyostelium, e.g., D. discoideum; Fusarium, e.g., F. culmorum, F. graminearum, F. heterosporum, F. solani, F. oxysporum, or F. venenatum; Mucor, e.g., M. javanicus, M. mucedo, or M. subtilissimus; Neurospora, e.g., N. crassa; Rhizomucor, e.g., R. pusillus; Rhizopus, e.g., R. arrhizus, R. japonicus, or R. stolonifer; Sclerotinia, e.g., S. libertiana; Trichophyton, e.g., T. rubrum; Whetzelinia, e.g., W. sclerotiorum; Bacillus, e.g., B. megaterium or B. subtilis; Citrobacter, e.g., C. freundii; Enterobacter, e.g., E. aerogenes or E. cloacae; Edwardsiella, E. tarda; Erwinia, e.g., E. herbicola; Escherichia, e.g., E. coli; Klebsiella, e.g., K. pneumoniae; Proteus, e.g., P. vulgaris; Providencia, e.g., P. stuartii; Salmonella, e.g., S. typhimurium; Serratia, e.g., S. liquefasciens, S. marcescens; Shigella, e.g., S. flexneri; Streptomyces, e.g., S. violeceoruber; or Yersinia, e.g., Y. enterocolitica.

Preferred commercial phospholipases include LECITASE™ and LECITASE™ ULTRA (available from Novozymes A/S, Denmark).

An effective amount of phospholipase is from about 0.01 to about 400 LU/g DS, preferably from about 0.1 to about 100 LU/g DS, and more preferably from about 1 to about 50 LU/g DS. Further optimization of the amount of phospholipase can hereafter be obtained using standard procedures known in the art.

Proteases

In another preferred embodiment of the invention, at least one surfactant and at least one carbohydrate generating enzyme is used in combination with at least one protease. The protease may be used, e.g., to digest protein to produce free amino nitrogen (FAN). Such free amino acids function as nutrients for the yeast, thereby enhancing the growth of the yeast and, consequently, the production of ethanol.

The fermenting microorganism for use in a fermentation process may be produced by propagating the fermenting microorganism in the presence of at least one protease. Although not limited to any one theory of operation, it is believed that the propagation of the fermenting microorganism with an effective amount of at least one protease reduces the lag time of the fermenting microorganism when the fermenting microorganism is subsequently used in a fermentation process as compared to a fermenting microorganism that was propogated under the same conditions without the addition of the protease. The action of the protease in the propagation process is believed to directly or indirectly result in the suppression or expression of genes which are detrimental or beneficial, respectively, to the fermenting microorganism during fermentation, thereby decreasing lag time and resulting in a faster fermentation cycle.

Proteases are well known in the art and refer to enzymes that catalyze the cleavage of peptide bonds. Suitable proteases include fungal and bacterial proteases. Preferred proteases are acidic proteases, i.e., proteases characterized by the ability to hydrolyze proteins under acidic conditions below pH 7. Suitable acid fungal proteases include fungal proteases derived from *Aspergillus, Mucor, Rhizopus, Candida, Coriolus, Endothia, Enthomophtra, Irpex, Penicillium, Sclerotium*, and *Torulopsis*. Especially contemplated are proteases derived from *Aspergillus niger* (see, e.g., Koaze et al., 1964, *Agr. Biol. Chem. Japan* 28: 216), *Aspergillus saitoi* (see, e.g., Yoshida, 1954, *J. Agr. Chem. Soc. Japan* 28: 66), *Aspergillus awamori* (Hayashida et al., 1977, *Agric. Biol. Chem.* 42: 927-933, *Aspergillus aculeatus* (WO 95/02044), or *Aspergillus oryzae*; and acidic proteases from *Mucor pusillus* or *Mucor miehei*.

Bacterial proteases, which are not acidic proteases, include the commercially available products ALCALASE™ and NEUTRASE™ (available from Novozymes A/S). Other proteases include GC106 from Genencor International, Inc., USA and NOVOZYM™ 50006 from Novozymes A/S.

Preferably, the protease is an aspartic acid protease, as described, for example, in *Handbook of Proteolytic Enzymes*, Edited by A. J. Barrett, N. D. Rawlings and J. F. Woessner, Academic Press, San Diego, 1998, Chapter 270). Suitable examples of aspartic acid protease include, e.g., those disclosed by Berka et al., 1990, *Gene* 96: 313; Berka et al., 1993, *Gene* 125: 195-198; and Gomi et al., 1993, *Biosci. Biotech. Biochem.* 57: 1095-1100.

Peroxidases

Other compounds possessing peroxidase activity may be any peroxidase (EC 1.11.1.7), or any fragment having peroxidase activity derived therefrom, exhibiting peroxidase activity.

Preferably, the peroxidase is produced by plants (e.g., horseradish or soybean peroxidase) or microorganisms such as fungi or bacteria.

Some preferred fungi include strains belonging to the subdivision Deuteromycotina, class Hyphomycetes, e.g., *Fusarium, Humicola, Tricoderma, Myrothecium, Verticillum, Arthromyces, Caldariomyces, Ulocladium, Embellisia, Cladosporium*, or *Dreschlera*, in particular, *Fusarium oxysporum* (DSM 2672), *Humicola insolens, Trichoderma reesei, Myrothecium verrucaria* (IFO 6113), *Verticillum alboatrum, Verticillum dahlie, Arthromyces ramosus* (FERM P-7754), *Caldariomyces fumago, Ulocladium chartarum, Embellisia alli*, or *Dreschlera halodes*.

Other preferred fungi include strains belonging to the subdivision Basidiomycotina, class Basidiomycetes, e.g., *Coprinus, Phanerochaete, Coriolus*, or *Trametes*, in particular *Coprinus cinereus* f. *microsporus* (IFO 8371), *Coprinus macrorhizus, Phanerochaete chrysosporium* (e.g. NA-12), or *Trametes* (previously called *Polyporus*), e.g., *T. versicolor* (e.g., PR4 28-A).

Further preferred fungi include strains belonging to the subdivision Zygomycotina, class Mycoraceae, e.g., *Rhizopus* or *Mucor*, in particular *Mucor hiemalis*.

Some preferred bacteria include strains of the order Actinomycetales, e.g. *Streptomyces spheroides* (ATTC 23965), *Streptomyces thermoviolaceus* (IFO 12382), or *Streptoverticillum verticillium* ssp. *verticillium*.

Other preferred bacteria include *Rhodobacter sphaeroides, Rhodomonas palustri, Streptococcus lactis, Pseudomonas purrocinia* (ATCC 15958), *Pseudomonas fluorescens* (NRRL B-11), and *Bacillus* strains, e.g., *Bacillus pumilus* (ATCC 12905) and *Bacillus stearothermophilus*.

Further preferred bacteria include strains belonging to *Myxococcus*, e.g., *M. virescens*.

The peroxidase may also be one which is produced by a method comprising cultivating a host cell transformed with a recombinant DNA vector which carries a DNA sequence encoding the peroxidase as well as DNA sequences for expression of the DNA sequence encoding the peroxidase, in a culture medium under conditions permitting the expression of the peroxidase and recovering the peroxidase from the culture.

In a preferred embodiment, a recombinantly produced peroxidase is a peroxidase derived from a *Coprinus* sp., in particular *C. macrorhizus* or *C. cinereus* according to WO 92/16634.

In the present invention, compounds possessing peroxidase activity comprise peroxidase enzymes and peroxidase active fragments derived from cytochromes, haemoglobin, or peroxidase enzymes.

One peroxidase unit (POXU) is the amount of enzyme which under the following conditions catalyzes the conversion of 1 μmole hydrogen peroxide per minute at 30° C. in 0.1 M phosphate buffer pH 7.0, 0.88 mM hydrogen peroxide, and 1.67 mM 2,2'-azino-bis(3-ethylbenzothiazoline-6-sulfonate) (ABTS). The reaction is followed for 60 seconds (15 seconds after mixing) by the change in absorbance at 418 nm, which should be in the range of 0.15 to 0.30. For calculation of activity, an absorption coefficient of oxidized ABTS of 36 mM−1 cm−1 and a stoichiometry of one μmole $H_2O_2$ converted per two μmole ABTS oxidized are used.

Laccases

In the present invention, laccases and laccase related enzymes comprise any laccase enzyme classified as EC 1.10.3.2, any catechol oxidase enzyme classified as EC 1.10.3.1, any bilirubin oxidase enzyme classified as EC 1.3.3.5, or any monophenol monooxygenase enzyme classified as EC 1.14.18.1.

The above-mentioned enzymes may be microbial, i.e., obtained from bacteria or fungi (including filamentous fungi and yeasts), or they may be derived from plants.

Suitable examples from fungi include a laccase obtained from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizooctonia*, e.g., *R. solani, Coprinus*, e.g., *C. cinereus, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Pycnoporus*, e.g., *P. cinnabarinus, Phlebia*, e.g., *P. radita* (WO 92/01046), or *Coriolus*, e.g., *C. hirsutus* (JP 2-238885).

Suitable examples from bacteria include a laccase obtained from a strain of *Bacillus*.

A laccase obtained from *Coprinus, Myceliophthora, Polyporus, Pycnoporus, Scytalidium* or *Rhizoctonia* is preferred; in particular a laccase obtained from *Coprinus cinereus, Myceliophthora thermophila, Polyporus pinsitus, Pycnoporus cinnabarinus, Scytalidium thermophilum*, or *Rhizoctonia solani*.

Commercially available laccases are NS51001 (a *Polyporus pinsitius* laccase, available from Novozymes A/S, Denmark) and NS51002 (a *Mycelioptora thermophila* laccase, available from Novozymes A/S, Denmark).

The laccase or the laccase related enzyme may also be one which is produced by a method comprising cultivating a host cell transformed with a recombinant DNA vector which carries a DNA sequence encoding the laccase as well as DNA sequences for expression of the DNA sequence encoding the laccase, in a culture medium under conditions permitting the expression of the laccase enzyme, and recovering the laccase from the culture.

Laccase activity (LACU) is determined from the oxidation of syringaldazin under aerobic conditions at pH 5.5. The violet color produced is photometered at 530 nm. The analytical conditions are 19 mM syringaldazin, 23 mM acetate buffer, pH 5.5, 30° C., 1 minute reaction time. One laccase unit (LACU) is the amount of enzyme that catalyses the conversion of 1.0 μmole syringaldazin per minute under the above conditions.

Laccase activity (LAMU) is determined from the oxidation of syringaldazin under aerobic conditions at pH 7.5. The violet color produced is photometered at 530 nm. The analytical conditions are 19 mM syringaldazin, 23 mM Tris/maleate pH 7.5, 30° C., 1 minute reaction time. One laccase unit (LAMU) is the amount of enzyme that catalyses the conversion of 1.0 μmole syringaldazin per minute under the above conditions.

The polypeptides of the present invention may be used in conjunction with the above-noted enzymes and/or cellulolytic proteins to further degrade the cellulose component of the biomass substrate, (see, for example, Brigham et al., 1995, in *Handbook on Bioethanol* (Charles E. Wyman, editor), pp. 119-141, Taylor & Francis, Washington D.C.; Lee, 1997, *Journal of Biotechnology* 56: 1-24).

The optimum amounts a polypeptide having cellulolytic enhancing activity and of cellulolytic proteins depends on several factors including, but not limited to, the mixture of component enzymes, the cellulosic substrate, concentration of cellulosic substrate, pretreatment of cellulosic substrate, temperature, time, pH, and inclusion of fermenting organism (e.g., yeast for SSF).

In a preferred aspect, an effective amount of polypeptide(s) having cellulolytic enhancing activity to cellulosic material is about 0.01 to about 2.0 mg, preferably at about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulosic material.

In another preferred aspect, an effective amount of cellulolytic protein(s) to cellulosic material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulosic material.

In a preferred aspect, an effective amount of polypeptide(s) having cellulolytic enhancing activity to cellulolytic protein(s) is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic protein(s).

Detergent Compositions

The polypeptides of the present invention having cellulolytic enhancing activity may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the invention. The detergent additive as well as the detergent composition may comprise one or more enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include Alcalase™, Savinase™, Primase™, Duralase™, Esperase™, and Kannase™ (Novozymes A/S), Maxatase™, Maxacal™, MaxapeM™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from Humicola (synonym Thermomyces), e.g., from H. lanuginosa (T. lanuginosus) as described in EP 258 068 and EP 305 216 or from H. insolens as described in WO 96/13580, a Pseudomonas lipase, e.g., from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012), a Bacillus lipase, e.g., from B. subtilis (Dartois et al., 1993, Biochemica et Biophysica Acta, 1131: 253-360), B. stearothermophilus (JP 64/744992) or B. pumilus (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novozymes A/S).

Amylases: Suitable amylases ($\alpha$ and/or $\beta$) include those of bacterial or fungal origin. Chemically modified or protein engineered mutants are included. Amylases include, for example, $\alpha$-amylases obtained from Bacillus, e.g., a special strain of Bacillus licheniformis, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, FungaMyl™ and BAN™ (Novozymes A/S), Rapidase™ and Purastar™ (from Genencor International Inc.).

Peroxidases/Oxidases: Suitable peroxidases/oxidases include those of plant, bacterial or fungal origin. Chemically modified or protein engineered mutants are included.

Examples of useful peroxidases include peroxidases from Coprinus, e.g., from C. cinereus, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions, any enzyme may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

In the detergent compositions, a polypeptide of the present invention having cellulolytic enhancing activity may be added in an amount corresponding to 0.001-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

A polypeptide of the invention having cellulolytic enhancing activity may also be incorporated in the detergent formulations disclosed in WO 97/07202, which is hereby incorporated by reference.

Other Uses

In general, treatment of any plant cell wall material may be enhanced by supplementing the polypeptides of the present invention having Cellulolytic enhancing activity.

Signal Peptide

The present invention also relates to nucleic acid constructs comprising a gene encoding a protein operably linked to a nucleic acid sequence consisting of nucleotides 241 to 1331 of SEQ ID NO: 1 encoding a signal peptide consisting of amino acids 1 to 19 of SEQ ID NO: 2, nucleotides 47 to 97 of SEQ ID NO: 3 encoding a signal peptide consisting of amino acids 1 to 17 of SEQ ID NO: 4, nucleotides 69 to 125 of SEQ ID NO: 5 encoding a signal peptide consisting of amino acids 1 to 19 of SEQ ID NO: 6, nucleotides 1 to 54 of SEQ ID NO: 7 encoding a signal peptide consisting of amino acids 1 to 18 of SEQ ID NO: 8, or nucleotides 1 to 57 of SEQ ID NO: 9 encoding a signal peptide consisting of amino acids 1 to 19 of SEQ ID NO: 10, which allows secretion of the protein into a culture medium, wherein the gene is foreign to the nucleic acid sequence.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Materials

Chemicals used as buffers and substrates were commercial products of at least reagent grade.

Strains

*Thielavia terrestris* NRRL 8126 was used as the source of the Family 61 polypeptides having cellulolytic enhancing activity. *Aspergillus oryzae* JaL250 strain (WO 99/61651) and *Trichoderma reesei* RutC30 (ATCC 56765; Montenecourt and Eveleigh, 1979, *Adv. Chem. Ser.* 181: 289-301) were used for expression of the Family 61 polypeptides having cellulolytic enhancing activity.

Media

YEG medium was composed per liter of 0.5% yeast extract and 2% glucose.

Potato dextrose medium was composed per liter of 39 grams of potato dextrose (Difco).

PDA plates were composed per liter of 39 grams of potato dextrose agar.

MDU2BP medium was composed per liter of 45 g of maltose, 1 g of $MgSO_4.7H_2O$, 1 g of NaCl, 2 g of $K_2SO_4$, 12 g of $KH_2PO_4$, 7 g of yeast extract, 2 g of urea, and 0.5 ml of AMG trace metals solution, pH to 5.0.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3 g of citric acid.

COVE plates were composed per liter of 342.3 g of sucrose, 20 ml of COVE salt solution, 10 ml of 1 M acetamide, 10 ml of 1.5 M $CsCl_2$, and 25 g of Noble agar.

COVE salt solution was composed per liter of 26 g of KCl, 26 g of $MgSO_4.7H_2O$, 76 g of $KH_2PO_4$, and 50 ml of COVE trace metals solution.

COVE trace metals solution was composed per liter of 0.04 g of $Na_2B_4O_7 \cdot 10H_2O$, 0.4 g of $CuSO_4 \cdot 5H_2O$, 1.2 g of $FeSO_4 \cdot 7H_2O$, 0.7 g of $MnSO_4 \cdot H_2O$, 0.8 g of $Na_2MoO_2 \cdot 2H_2O$, and 10 g of $ZnSO_4 \cdot 7H_2O$.

CIM medium was composed per liter of 20 g of cellulose, 10 g of corn steep solids, 1.45 g of $(NH_4)_2SO_4$, 2.08 g of $KH_2PO_4$, 0.28 g of $CaCl_2$, 0.42 g of $MgSO_4 \cdot 7H_2O$, and 0.42 ml of trace metals solution, pH to 6.0.

Trace metals solution was composed per liter of 41.2 mg of $FeCl_3 \cdot 6H_2O$, 11.6 mg of $ZnSO_4 \cdot 7H_2O$, 5.4 mg of $MnSO_4 \cdot H_2O$, 2.0 mg of $CuSO_4 \cdot 5H_2O$, 0.48 mg of $H_3BO_3$, and 67.2 mg of citric acid.

NNCYP medium was composed per liter of 5.0 g of $NH_4NO_3$, 0.5 g of $MgSO_4 \cdot 7H_2O$, 0.3 g of $CaCl_2$, 2.5 g of citric acid, 1.0 g of Bacto Peptone, 5.0 g of yeast extract, COVE trace metals solution, and sufficient $K_2HPO_4$ to achieve the final pH of approximately 5.4.

NNCYPmod medium was composed per liter of 1.0 g of NaCl, 5.0 g of $NH_4NO_3$, 0.2 g of $MgSO_4 \cdot 7H_2O$, 0.2 g of $CaCl_2$, 2.0 g of citric acid, 1.0 g of Bacto Peptone, 5.0 g of yeast extract, COVE trace metals solution, and sufficient $K_2HPO_4$ to achieve the final pH of approximately 5.4.

LB plates were composed per liter of 10 g of tryptone, 5 g of yeast extract, 5 g of sodium chloride, and 15 g of Bacto Agar.

SOC medium was composed of 2% tryptone, 0.5% yeast extract, 10 mM NaCl, 2.5 mM KCl, 10 mM $MgCl_2$, and 10 mM $MgSO_4$, and filter-sterilized glucose to 20 mM added after autoclaving.

Freezing medium was composed of 60% SOC and 40% glycerol.

2×YT medium was composed per liter of 16 g of tryptone, 10 g of yeast extract, 5 g of NaCl, and 15 g of Bacto agar.

Example 1

Identification of Polypeptides Having Cellulolytic Enhancing Activity from *Thielavia terrestris* NRRL 8126

An agarose plug from a fresh plate of *Thielavia terrestris* NRRL 8126 grown on NNCYPmod medium supplemented with 1% Sigmacell (Sigma Chemical Co., St. Louis, Mo.) was inoculated into 50 ml of NNCYPmod medium supplemented with 1% glucose and incubated at 45° C. and 200 rpm for 25 hours. Two-ml of this culture was used to inoculate 15×100 ml (500 ml flask) and 2×50 ml (250 ml flask) of NNCYPmod medium supplemented with 2% Sigmacell-20 and was incubated at 45° C., 200 rpm for 4 days. Pooled cultures were centrifuged at 3000×g for 10 minutes and the supernatant was filtered through a Nalgene 281-5000 glass fiber prefilter (Nalge Nunc Int'l., Rochester, N.Y.). The filtrate was cooled to 4° C. for storage.

Two-dimensional polyacrylamide gel electrophoresis. One ml of filtrate was precipitated by adding 100 μl of saturated trichloroacetic acid (TCA) at 4° C. and incubating for 10 minutes on ice followed by addition of 9 ml of ice-cold acetone and further incubation on ice for 20 minutes. The precipitated solution was centrifuged at 10,000×g for 10 minutes at 4° C., the supernatant decanted, and the pellet rinsed twice with ice-cold acetone and air dried. The dried pellet was dissolved in 0.2 ml of isoelectric focusing (IEF) sample buffer (9.0 M urea, 3.1% (wt/v) 3-[(3-cholamidopropyl)dimethyl-ammonium]-1-propanesulfonate (CHAPS, Pierce Chemical Co. Rockford, Ill.), 1% (v/v) pH 4-7 ampholytes, 50 mM dithiothreitol (DTT), and 0.005% bromophenol blue in distilled water). Urea stock solution was de-ionized using AG 501-X8 (D), 20-5-mesh, mixed bed resin from BioRad Laboratories (Hercules, Calif.). The de-ionized solution was stored at −20° C. The resulting mixture was allowed to solubilize for several hours with gentle mixing on a LabQuake™ Shaker (Lab Industries, Berkeley, Calif.). Two hundred 11 of each IEF sample buffer-protein mixture was applied to an 11 cm IPG strip (BioRad Laboratories, Hercules, Calif.) in an IPG rehydration tray (Amersham Biosciences, Piscataway, N.J.). A 750 μl aliquot of dry-strip cover fluid (Amersham Biosciences, Piscataway, N.J.) was layered over the IPG strips to prevent evaporation and allowed to rehydrate for 12 hours while applying 30 volts using an IPGPhor Isoelectric Focusing Unit (Amersham Biosciences, Piscataway, N.J.) at 20° C. The IPGPhor Unit was programmed for constant voltage but with a maximum current of 50 μA per strip. After 12 hours of rehydration, the isoelectric focusing conditions were as follows: 1 hour at 200 volts, 1 hour at 500 volts, and 1 hour at 1000 volts. Then a gradient was applied from 1000 volts to 8000 volts for 30 minutes and isoelectric focusing was programmed to run at 8000 volts and was complete when >30,000 volt hours was achieved. IPG gel strips were reduced and alkylated before the second dimension analysis by first reducing for 15 minutes in 100 mg of dithiothreitol per 10 ml of SDS-equilibration buffer (50 mM Tris HCl pH 8.8, 6.0 M urea, 2% (w/v) sodium dodecylsulfate (SDS), 30% glycerol, and 0.002% (w/v) bromophenol blue) followed by 15 minutes of alkylation in 250 mg iodoacetamide per 10 ml of equilibration buffer in the dark. The IPG strips were rinsed quickly in SDS-PAGE running buffer (Invitrogen/Novex, Carlsbad, Calif.) and placed on an 11 cm, 1 well 8-16% Tris-Glycine SDS-PAGE gel (BioRad Laboratories, Hercules, Calif.) and electrophoresed using a Criterion electrophoresis unit (BioRad Laboratories, Hercules, Calif.) at 50 volts until the sample entered the gel and then the voltage was increased to 200 volts and allowed to run until the bromophenol blue dye reached the bottom of the gel.

Polypeptide detection. The two dimensional gel was stained with a fluorescent SYPRO Orange Protein Stain (Molecular Probes, Eugene, Oreg.). Fluorescent staining methods were optimized and adapted from Malone et al., 2001, *Electrophoresis*, 22, 919-932. SDS-PAGE gels were fixed in 40% ethanol, 2% acetic acid, and 0.0005% SDS on a platform rocker for 1 hour to overnight. Fixing solution was removed and replaced with three repeated wash steps consisting of 2% acetic acid and 0.0005% SDS for 30 minutes each. Gels were stained for 1.5 hours to overnight in the dark with 2% acetic acid, 0.0005% SDS, and 0.02% SYPRO Orange Protein Stain. Staining and de-staining was further optimized to improve reproducibility and automation on a Hoefer Processor Plus staining unit (Amersham Biosciences, Piscataway, N.J.). Images of the fluorescent stained SDS-PAGE gels were obtained by scanning on a Molecular Dynamics STORM 860 Imaging System (Amersham Biosciences, Piscataway, N.J.) using blue fluorescence and 200 μm pixel sizes and a photomultiplier tube gain of 800 V. Images were viewed and adjusted using ImageQuant version 5.0 (Amersham Biosciences, Piscataway, N.J.). Gels were further visualized on a Dark Reader Blue transilluminator with orange filter (Clare Chemical Co, Denver, Colo.). Observed protein gel spots were excised using a 2 mm Acu-Punch Biopsy Punch (Acuderm Inc., Ft. Lauderdale, Fla.) and stored in ninety-six well plates that were prewashed with 0.1% trifluoroacetic acid (TFA) in 60% acetonitrile followed by two additional washes with HPLC grade water. The stained two-dimensional gel spots were stored in 25-50 µl of water in the pre-washed plates at −20° C. until digested.

In-gel digestion of polypeptides for peptide sequencing. A MultiPROBE® II Liquid Handling Robot (PerkinElmer Life and Analytical Sciences, Boston, Mass.) was used to perform the in-gel digestions. Two dimensional gel spots containing polypeptides of interest were reduced with 50 µl of 10 mM DTT in 100 mM ammonium bicarbonate pH 8.0 for 30 minutes. Following reduction, the gel pieces were alkylated with 50 µl of 55 mM iodoacetamide in 100 mM ammonium bicarbonate pH 8.0 buffer for 20 minutes. The dried gel pieces were allowed to swell in a trypsin digestion solution (6 ng/µl sequencing grade trypsin (Promega, Madison, Wis.) in 50 mM ammonium bicarbonate pH 8 buffer) for 30 minutes at room temperature, followed by an 8 hour digestion at 40° C. Each of the reaction steps described was followed by numerous washes and pre-washes with the appropriate solutions following the manufactures standard protocol. Fifty µl of acetonitrile was used to de-hydrate the gel between reactions and gel pieces were air dried between steps. Peptides were extracted twice with 1% formic acid/2% acetonitrile in HPLC grade water for 30 minutes. Peptide extraction solutions were transferred to a 96 well skirted PCR type plate (ABGene, Rochester, N.Y.) that had been cooled to 10-15° C. and covered with a 96-well plate lid (PerkinElmer Life and Analytical Sciences, Boston, Mass.) to prevent evaporation. Plates were further stored at 4° C. until mass spectrometry analysis could be performed.

Peptide sequencing by tandem mass spectrometry. For peptide sequencing by tandem mass spectrometry, a Q-Tof micro™ hybrid orthogonal quadrupole time-of-flight mass spectrometer (Waters Micromass® MS Technologies, Milford, Mass.) was used for LC-MS/MS analysis. The Q-Tof micro™ mass spectrometer was fitted with an Ultimate™ capillary and nano-flow HPLC system (Dionex, Sunnyvale, Calif.) which had been coupled with a FAMOS micro autosampler (Dionex, Sunnyvale, Calif.) and a Switchos II column switching device (Dionex, Sunnyvale, Calif.) for concentrating and desalting samples. Samples were loaded onto a guard column (300 µm ID×5 cm, C18 PepMap™) (Dionex, Sunnyvale, Calif.) fitted in the injection loop and washed with 0.1% formic acid in water at 40 µl/minute for 2 minutes using a Switchos II pump (Dionex, Sunnyvale, Calif.). Peptides were separated on a 75 µm ID×15 cm, C18, 3 µm, 100 Å PepMap™ nanoflow fused capillary column (Dionex, Sunnyvale, Calif.) at a flow rate of 175 nl/minute from a split flow of 175 µl/minute using a NAN-75 calibrator (Dionex, Sunnyvale, Calif.). The linear elution gradient was 5% to 60% acetonitrile in 0.1% formic acid applied over a 45 minute period. The column eluent was monitored at 215 nm and introduced into the Q-Tof micro™ mass spectrometer through an electrospray ion source fitted with the nanospray interface. The Q-Tof micro™ mass spectrometer was fully microprocessor controlled using MassLynx™ software version 3.5 (Waters Micromass® MS Technologies, Milford, Mass.). Data was acquired in survey scan mode and from a mass range of 50 to 2000 m/z with switching criteria for MS to MS/MS to include an ion intensity of greater than 10.0 counts/second and charge states of +2, +3, and +4. Analysis spectra of up to 4 co-eluting species with a scan time of 1.9 seconds and inter-scan time of 0.1 seconds could be obtained. A cone voltage of 65 volts was typically used and the collision energy was programmed to be varied according to the mass and charge state of the eluting peptide and in the range of 10-60 volts. The acquired spectra were combined, smoothed, and centered in an automated fashion and a peak list generated. The generated peak list was searched against selected databases using ProteinLynx™ Global Server 1.1 software (Waters Micromass® MS Technologies, Milford, Mass.). Results from the ProteinLynx™ searches were evaluated and un-identified proteins were analyzed further by evaluating the MS/MS spectrums of each ion of interest and de novo sequence determined by identifying the y and b ion series and matching mass differences to the appropriate amino acid.

Peptide sequences of *Thielavia terrestris* GH61B from de novo sequencing by mass spectrometry were obtained from several multiply charged ions for an approximately 40 kDa polypeptide gel spot. A doubly charged tryptic peptide ion of 878.422 m/z sequence was determined to be [Ile or Leu]-Pro-Ala-Ser-Asn-Ser-Pro-Val-Thr-Asn-Val-Ala-Ser-Asp-Asp-[Ile or Leu]-Arg (SEQ ID NO: 11). A second doubly charged tryptic peptide ion of 765.460 was determined to be [Ile or Leu]-Pro-Glu-Asp-[Ile or Leu]-Glu-Pro-Gly-Asp-Tyr-[Ile or Leu]-[Ile or Leu]-Arg (SEQ ID NO: 12).

Twenty µl of the pooled fraction containing the highest cellulolytic enhancing activity after the Phenyl Sepharose purification step described in Example 24 was mixed with 20 µl of 2×SDS-PAGE loading buffer with 50 mM DTT and boiled for 4 minutes. Forty µl was separated by SDS-PAGE using a 11 cm 8-16% Tris-Glycine SDS-PAGE gradient gel (BioRad Laboratories, Hercules, Calif.) and Tris-Glycine running buffer (Invitrogen, Carlsbad, Calif.). The SDS-PAGE was run under reducing conditions and the manufacturer's recommended protocol (BioRad Laboratories, Hercules, Calif.). The gel was removed from the cassette and rinsed 3 times with water for at least 5 minutes each and stained with Bio-Safe Coomassie Stain (BioRad Laboratories, Hercules, Calif.) for 1 hour followed by destaining with doubly-distilled water for more than 30 minutes. A protein band visible at approximately 27 kDa was in-gel digested with trypsin as described above. The peptides recovered from the digest were subjected to peptide sequencing by tandem mass spectrometry as described above. A doubly charged tryptic peptide ion of 903.895 m/z was determined to have a sequence of Cys-Pro-Gly-Ser-Phe-Ser-Ser-Cys-Asp-Gly-Ser-Gly-Ala-Gly-Trp-Phe-Lys (SEQ ID NO: 13, Family GH61D). A triply charged tryptic peptide ion of 415.553 m/z was determined to be [Ile or Leu]-Asp-Glu-Ala-Gly-Phe-His-Gly-Asp-Gly-Val-Lys (SEQ ID NO: 14, Family GH61D). Another doubly charged tryptic peptide ion of 565.857 m/z was determined to be X-X-Ala-Pro-Gly-Asn-Tyr-[Ile or Leu]-[Ile or Leu]-Arg (SEQ ID NO: 15, Family GH61C). These peptide sequences were used for designing primers for cloning.

Example 2

*Thielavia terrestris* Genomic DNA Extraction

*Thielavia terrestris* NRRL 8126 was grown in 25 ml of YEG medium at 37° C. and 250 rpm for 24 hours. Mycelia were then collected by filtration through Miracloth™ (Calbiochem, La Jolla, Calif.) and washed once with 25 ml of 10 mM Tris-1 mM EDTA (TE) buffer. Excess buffer was drained from the mycelia preparation, which was subsequently frozen in liquid nitrogen. The frozen mycelia preparation was ground to a fine powder in an electric coffee grinder, and the powder was added to a disposable plastic centrifuge tube containing 20 ml of TE buffer and 5 ml of 20% w/v sodium dodecylsulfate (SDS). The mixture was gently inverted several times to ensure mixing, and extracted twice with an equal volume of phenol:chloroform:isoamyl alcohol (25:24:1 v/v/v). Sodium acetate (3 M solution) was added to the extracted sample to a final concentration of 0.3 M followed by 2.5 volumes of ice cold ethanol to precipitate the DNA. The tube was centrifuged at 15,000×g for 30 minutes to pellet the DNA. The DNA pellet was allowed to air-dry for 30 minutes before resuspension in 0.5 ml of TE buffer. DNase-free ribonuclease A was added to the resuspended DNA pellet to a concentration of 100 μg per ml and the mixture was then incubated at 37° C. for 30 minutes. Proteinase K (200 μg/ml) was added and the tube was incubated an additional one hour at 37° C. Finally, the sample was centrifuged for 15 minutes at 12,000×g, and the supernatant was applied to a Qiaprep 8 manifold (QIAGEN Inc., Valencia, Calif.). The columns were washed twice with 1 ml of PB (QIAGEN Inc., Valencia, Calif.) and 1 ml of PE (QIAGEN Inc., Valencia, Calif.) under vacuum. The isolated DNA was eluted with 100 μl of TE, precipitated with ethanol, washed with 70% ethanol, dried under vacuum, resuspended in TE buffer, and stored at 4° C.

To generate genomic DNA for PCR amplification, *Thielavia terrestris* was grown in 50 ml of NNCYP medium supplemeted with 1% glucose in a baffled shake flask at 42° C. and 200 rpm for 24 hours. Mycelia were harvested by filtration, washed twice in TE (10 mM Tris-1 mM EDTA), and frozen under liquid nitrogen. A pea-size piece of frozen mycelia was suspended in 0.7 ml of 1% lithium dodecyl sulfate in TE and disrupted by agitation with an equal volume of 0.1 mm zirconia/silica beads (Biospec Products, Inc., Bartlesville, Okla.) for 45 seconds in a FastPrep FP120 (ThermoSavant, Holbrook, N.Y.). Debris was removed by centrifugation at 13,000×g for 10 minutes and the cleared supernatant was brought to 2.5 M ammonium acetate and incubated on ice for 20 minutes. After the incubation period, the nucleic acids were precipitated by addition of 2 volumes of ethanol. After centrifugation for 15 minutes in a microfuge at 4° C., the pellet was washed in 70% ethanol and air dried. The DNA was resuspended in 120 μl of 0.1×TE and incubated with 1 μl of DNase-free RNase A at 37° C. for 20 minutes. Ammonium acetate was added to 2.5 M and the DNA was precipitated with 2 volumes of ethanol. The pellet was washed in 70% ethanol, air dried, and resuspended in TE buffer.

Example 3

Construction of pAlLo2 Expression Vector

Expression vector pAlLo1 was constructed by modifying pBANe6 (U.S. Pat. No. 6,461,837), which comprises a hybrid of the promoters from the genes for *Aspergillus niger* neutral alpha-amylase and *Aspergillus oryzae* triose phosphate isomerase (NA2-tpi promoter), *Aspergillus niger* amyloglucosidase terminator sequence (AMG terminator), and *Aspergillus nidulans* acetamidase gene (amdS). All mutagenesis steps were verified by sequencing using BigDye™ terminator chemistry (Applied Biosystems, Inc., Foster City, Calif.). Modification of pBANe6 was performed by first eliminating three NcoI restriction sites at positions 2051, 2722, and 3397 bp from the amdS selection marker by site-directed mutagenesis. All changes were designed to be "silent" leaving the actual protein sequence of the amdS gene product unchanged. Removal of these three sites was performed simultaneously with a GeneEditor™ in vitro Site-Directed Mutagenesis Kit (Promega, Madison, Wis.) according to the manufacturer's instructions using the following primers (underlined nucleotide represents the changed base):

```
AMDS3NcoMut (2050):
5'-GTGCCCCATGATACGCCTCCGG-3'      (SEQ ID NO: 16)

AMDS2NcoMut (2721):
5'-GAGTCGTATTTCCAAGGCTCCTGACC-3'  (SEQ ID NO: 17)

AMDS1NcoMut (3396):
5'-GGAGGCCATGAAGTGGACCAACGG-3'    (SEQ ID NO: 18)
```

A plasmid comprising all three expected sequence changes was then submitted to site-directed mutagenesis, using a QuickChange™ Site-Directed Mutagenesis Kit (Stratagene, La Jolla, Calif.), to eliminate the NcoI restriction site at the end of the AMG terminator at position 1643. The following primers (underlined nucleotide represents the changed base) were used for mutagenesis:

```
Upper Primer to mutagenize the AMG terminator
sequence:
                                  (SEQ ID NO: 19)
5'-CACCGTGAAAGCCATGCTCTTTCCTTCGTGTAGAAGA
CCAGACAG-3'

Lower Primer to mutagenize the AMG terminator
sequence:
                                  (SEQ ID NO: 20)
5'-CTGGTCTTCTACACGAAGGAAAGAGCATGGCTTTCAC
GGTGTCTG-3'
```

The last step in the modification of pBANe6 was the addition of a new NcoI restriction site at the beginning of the polylinker using a QuickChange™ Site-Directed Mutagenesis Kit and the following primers (underlined nucleotides represent the changed bases) to yield pAlLo1 (FIG. 6).

```
Upper Primer to mutagenize the NA2-tpi promoter:
                                  (SEQ ID NO: 21)
5'-CTATATACACAACTGGATTTACCATGGGCCCGCGGCCGCAGATC-3'

Lower Primer to mutagenize the NA2-tpi promoter:
                                  (SEQ ID NO: 22)
5'-GATCTGCGGCCGCGGGCCCATGGTAAATCCAGTTGTGTATATAG-3'
```

Figure 7:
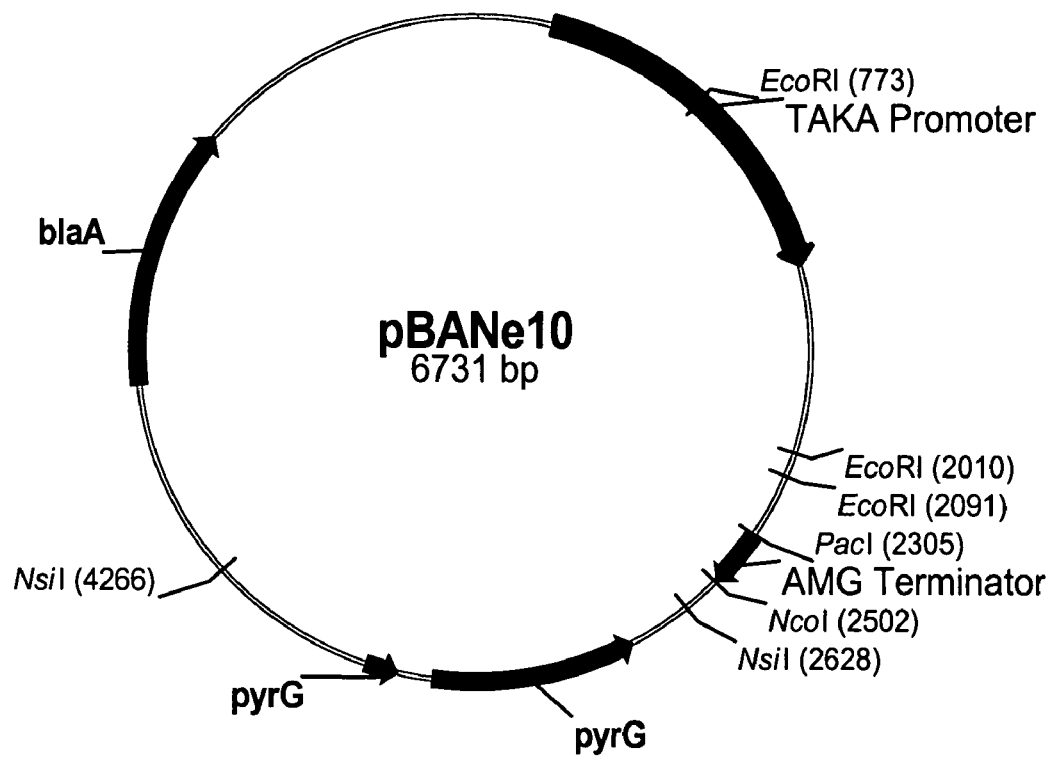
FIG. 7 shows a restriction map of pBANe10.
Figure 8:
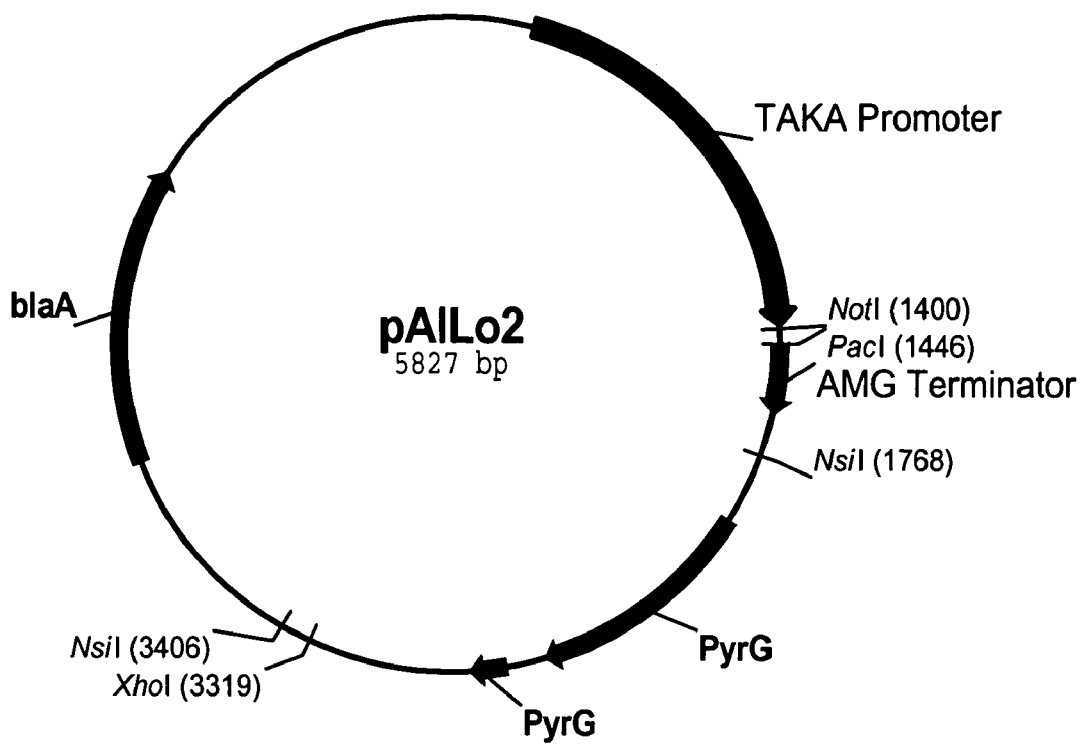
FIG. 8 shows a restriction map of pAlLo2.

The amdS gene of pAlLo1 was swapped with the *Aspergillus nidulans* pyrG gene. Plasmid pBANe10 (FIG. 7) was used as a source for the pyrG gene as a selection marker. Analysis of the sequence of pBANe10 showed that the pyrG marker was contained within an Nsi I restriction fragment and does not contain either Nco I or Pac I restriction sites. Since the amdS is also flanked by NsiI restriction sites the strategy to switch the selection marker was a simple swap of Nsi I restriction fragments. Plasmid DNA from pAlLo1 and pBANe10 were digested with the restriction enzyme Nsi I and the products purified by agarose gel electrophoresis. The Nsi I fragment from pBANe10 containing the pyrG gene was ligated to the backbone of pAlLo1 to replace the original Nsi I DNA fragment containing the amdS gene. Recombinant clones were analyzed by restriction enzyme digestion to determine that they had the correct insert and also its orientation. A clone with the pyrG gene transcribed in the counterclockwise direction was selected. The new plasmid was designated pAlLo2 (FIG. 8).

Example 4

PCR Amplification of a GH61B Gene Fragment from Thielavia terrestris NRRL 8126 Genomic DNA Primers were designed based upon peptide sequences obtained through tandem mass spectrometry as described in Example 1. The specific peptide sequences were as follows:

```
[L,I]PASNSPVTNVASDD[L,I]R      (SEQ ID NO: 23)

[L,I]PED[L,I]EPGDY[L,I][L,I]R  (SEQ ID NO: 24)
```

The regions of the sequences shown in bold were selected for DNA primer design. A longer 5' extension for the second sequence was engineered on the assumption that the next amino acid in the sequence was alanine (based on sequence conservation in homologs). The primers were:

```
Sense Primer:
5'-CCTCCAACTCCCCCGTCACNAAYGTNGC-3' (SEQ ID NO: 25)

Antisense Primer:
5'-GGCGCGGAGGAGGTARTCNCCNGGYTC-3'  (SEQ ID NO: 26)
```

Figure 9:
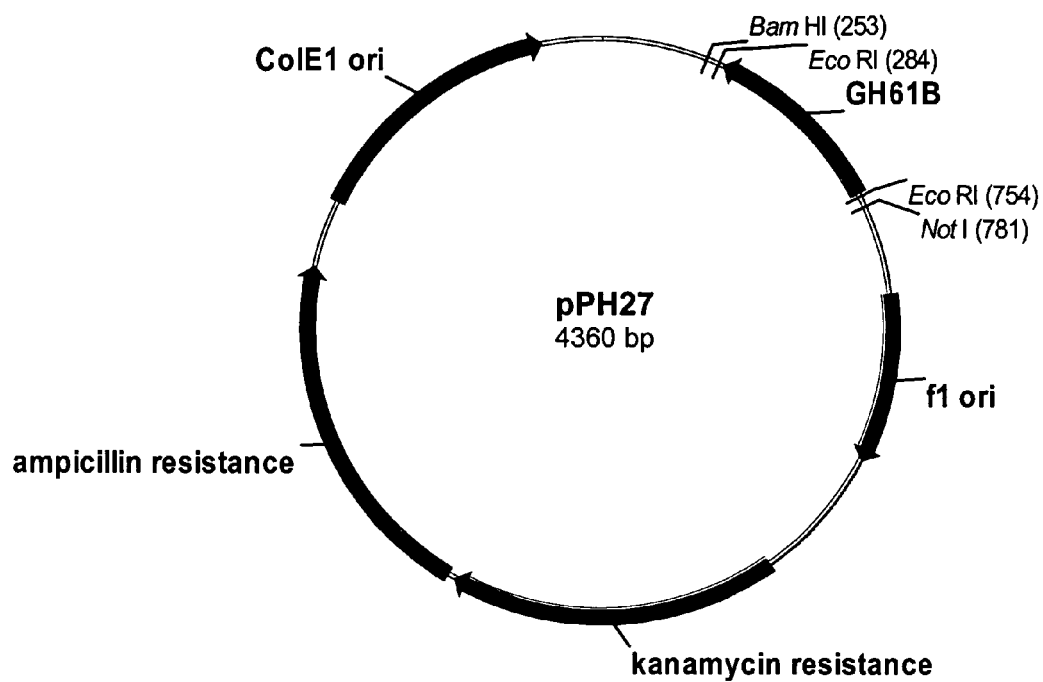
FIG. 9 shows a restriction map of pPH27.

PCR amplification was performed in a volume of 50 µl containing 1×AmpliTaq buffer (Applied Biosystems, Foster City, Calif.), 2.5 units of AmpliTaq DNA polymerase (Applied Biosystems, Foster City, Calif.), 1 µM each sense and antisense primer, and approximately 1 µg of genomic DNA from Thielavia terrestris NRRL 8126. Amplification was performed in a Robocycler (Stratagene, La Jolla, Calif.) using cycling parameters of 3 minutes at 96° C. and 3 minutes at 72° C. (during which DNA polymerase was added), 35 cycles of 45 seconds at 94° C., 45 seconds at 58° C., and 1 minute at 72° C., followed by a final extension of 7 minutes at 72° C. The reaction products were fractionated on a 3% agarose gel using 40 mM Tris base-20 mM sodium acetate-1 mM disodium EDTA (TAE) buffer and a band of approximately 450 bp was excised, purified using a QIAEX II Gel Extraction Kit (QIAGEN Inc., Valencia, Calif.), and subcloned using a TOPO TA Kit (Invitrogen, Carlsbad, Calif.). The plasmid from one E. coli transformant was sequenced and found to contain an insert of 452 bp coding for a Family 61 protein (GH61B). This plasmid was designated pPH27 (FIG. 9).

Example 5

PCR Amplification of a GH61C and GH61D Gene Fragment from Genomic DNA

Primers were designed based upon peptide sequences obtained through tandem mass spectrometry as described in Example 1, with the exception that the source of the polypeptides was an approximately 27 kDa band excised from a one-dimensional SDS-PAGE gel (Novex 4-12% Bis-Tris, Invitrogen, Carlsbad, Calif.) following partial purification through Q Sepharose as described in Example 24. The similar molecular mass of the GH61C and GH61D polypeptides resulted in cross-contamination of the polypeptides in the gel slice used for mass spectrometry and thus the peptide sequences determined during the mass spectrometry analysis were derived from both polypeptides. One primer was designed to the sequence of two likely adjacent tryptic peptides with combined sequence SGAGWFKIDEAGF-HGD (SEQ ID NO: 27). This turned out to be the correct sequence for GH61D, however the designed primer was sufficiently close to the GH61C sequence (GDGWFKIDE) to also amplify that gene as well. The antisense primer was based on the mass spectrometry-derived sequence APGNY[I,L][I,L]R (SEQ ID NO: 28). This was extended and refined based upon conservation in a multiple sequence alignment to APGNYLIRHEL (SEQ ID NO: 29). This turned out to be the correct sequence for GH61C, but was sufficiently close to the GH61D sequence (APGNYLVRHEL, SEQ ID NO: 30) to also amplify that gene. The specific peptide sequences used for primer design were as follows:

```
GAGWFKIDE   (SEQ ID NO: 31)

APGNYLIRHEL (SEQ ID NO: 29)
```

The primers were:

```
Sense primer:
                                 (SEQ ID NO: 32)
5'-CGGCGCGGGCTGGTTTAARATHGAYGA-3'

Antisense primer:
                                 (SEQ ID NO: 33)
5' AGTTCATGGCGAATCAGATARTTNCCNGGNGC-3'
```

Figure 10:
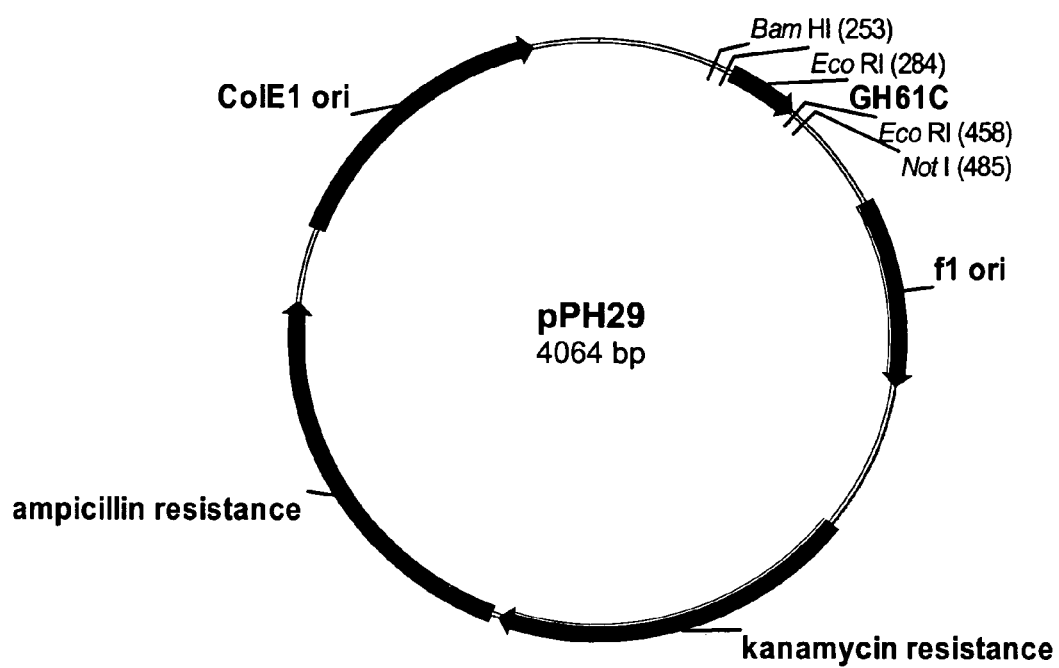
FIG. 10 shows a restriction map of pPH29.
Figure 11:
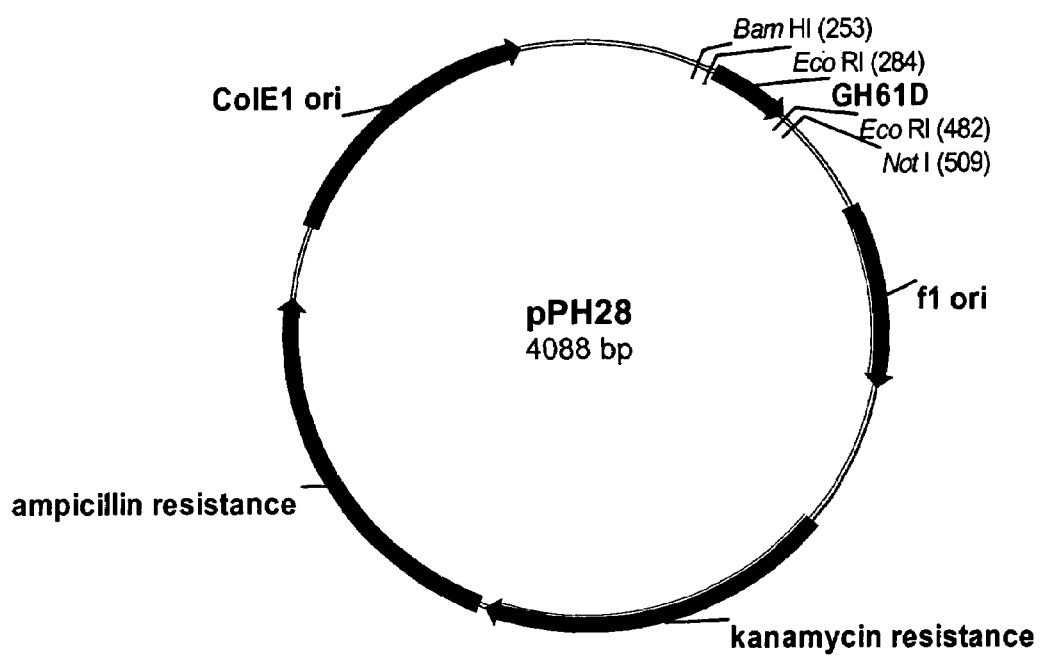
FIG. 11 shows a restriction map of pPH28.

PCR amplification was performed in a volume of 50 µl containing 1×AmpliTaq buffer, 2.5 units of AmpliTaq DNA polymerase, 1 µM each sense and antisense primer, and approximately 1 µg of genomic DNA from Thielavia terrestris NRRL 8126. Amplification was performed in a Stratagene Robocycler using cycling parameters of 3 minutes at 96° C. and 3 minutes at 72° C. (during which DNA polymerase was added), 35 cycles of 45 sec at 94° C., 45 sec at 53, 56, or 59° C. and 1 minute at 72° C., followed by a final extension of 7 minutes at 72° C. The reaction products were fractionated on a 3% agarose gel and two bands of approximately 150-200 bp were excised, purified using the QIAEX II Gel Extraction Kit (QIAGEN Inc., Valencia, Calif.), and subcloned together using the Topo TA kit (Invitrogen, Carlsbad, Calif.). The plasmid from one E. coli transformant was sequenced and found to contain an insert of 156 bp coding for a Family 61 protein (GH61C). This plasmid was designated pPH29 (FIG. 10). The plasmid from another E. coli transformant was sequenced and found to contain an insert of 180 bp coding for another Family 61 protein (GH61D). This plasmid was designated pPH28 (FIG. 11).

Example 6

Genomic DNA Library Construction

Genomic DNA libraries were constructed using the bacteriophage cloning vector λZipLox (Life Technologies, Gaithersburg, Md.) with E. coli Y1090ZL cells (Life Technologies, Gaithersburg, Md.) as a host for plating and purification of recombinant bacteriophage and E. coli DH10Bzip (Life Technologies, Gaithersburg, Md.) for excision of individual pZL1 clones containing the GH61B gene.

Thielavia terrestris NRRL 8126 genomic DNA was partially digested with Tsp 509I and size-fractionated on 1% agarose gels using TAE buffer. DNA fragments migrating in the size range 3-7 kb were excised and eluted from the gel using Prep-a-Gene reagents (BioRad Laboratories, Hercules, Calif.). The eluted DNA fragments were ligated with EcoRI-cleaved and dephosphorylated λZipLox vector arms (Life Technologies, Gaithersburg, Md.), and the ligation mixtures were packaged using commercial packaging extracts (Stratagene, La Jolla, Calif.). The packaged DNA libraries were plated and amplified in *E. coli* Y1090ZL cells. The unamplified genomic DNA library contained $3.1 \times 10^6$ pfu/ml (background titers with no DNA were $2.0 \times 10^4$ pfu/ml.

Example 7

Identification of *Thielavia terrestris* GH61B, GH61C, and GH61D Clones

*Thielavia terrestris* GH61B, GH61C, and GH61D probe fragments were amplified from pPH27, pPH29 and pPH28, respectively, using primers homologous to the TOPO vector and Herculase DNA Polymerase (Stratagene, La Jolla, Calif.), as shown below.

5'-CTTGGTACCGAGCTCGGATCCACTA-3'  (SEQ ID NO: 34)

5'-ATAGGGCGAATTGGGCCCTCTAGAT-3'  (SEQ ID NO: 35)

Fifty picomoles of each of the primers were used in a PCR reaction containing 10 ng of pPH27, pPH28, or pPH29, 1×Herculase Amplification Buffer (Stratagene, La Jolla, Calif.), 1 μl of 10 mM blend of dATP, dTTP, dGTP, and dCTP, and 2.5 units of Herculase DNA Polymerase in a final volume of 50 μl. The amplification conditions were one cycle at 94° C. for 1 minute; and 20 cycles each at 94° C. for 30 seconds, 55° C. for 30 seconds, and 72° C. for 1 minute. The heat block then went to a 4° C. soak cycle. The reaction products were isolated on a 1.0% agarose gel using TAE buffer where three <500 bp product bands were excised from the gel and purified using a QIAquick Gel Extraction Kit (QIAGEN Inc., Valencia, Calif.) according to the manufacturer's instructions. Twenty five ng of each fragment was radiolabeled with $^{32}$P using a Prime It II Kit (Stratagene, La Jolla, Calif.).

Approximately 90,000 plaques from the library described in Example 6 were screened by plaque-hybridization using the three labeled PCR fragments as the probes. The DNA was cross-linked onto membranes (Hybond N+, Amersham, Arlington Heights, Ill.) using a UV Stratalinker (Stratagene, La Jolla, Calif.). Each $^{32}$P-radiolabeled gene fragment was denatured by adding sodium hydroxide to a final concentration of 0.1 M, and added to a hybridization solution containing 6×SSPE, 7% SDS at an activity of approximately $1 \times 10^6$ cpm per ml of hybridization solution. Each of the mixtures was incubated overnight at 55° C. in a shaking water bath. Following incubation, the membranes were washed three times for fifteen minutes in 0.2×SSC with 0.1% SDS at 65° C. The membranes were dried on blotting paper for 15 minutes, wrapped in SaranWrap™, and exposed to X-ray film overnight at 70° C. with intensifying screens (Kodak, Rochester, N.Y.).

Figure 12:
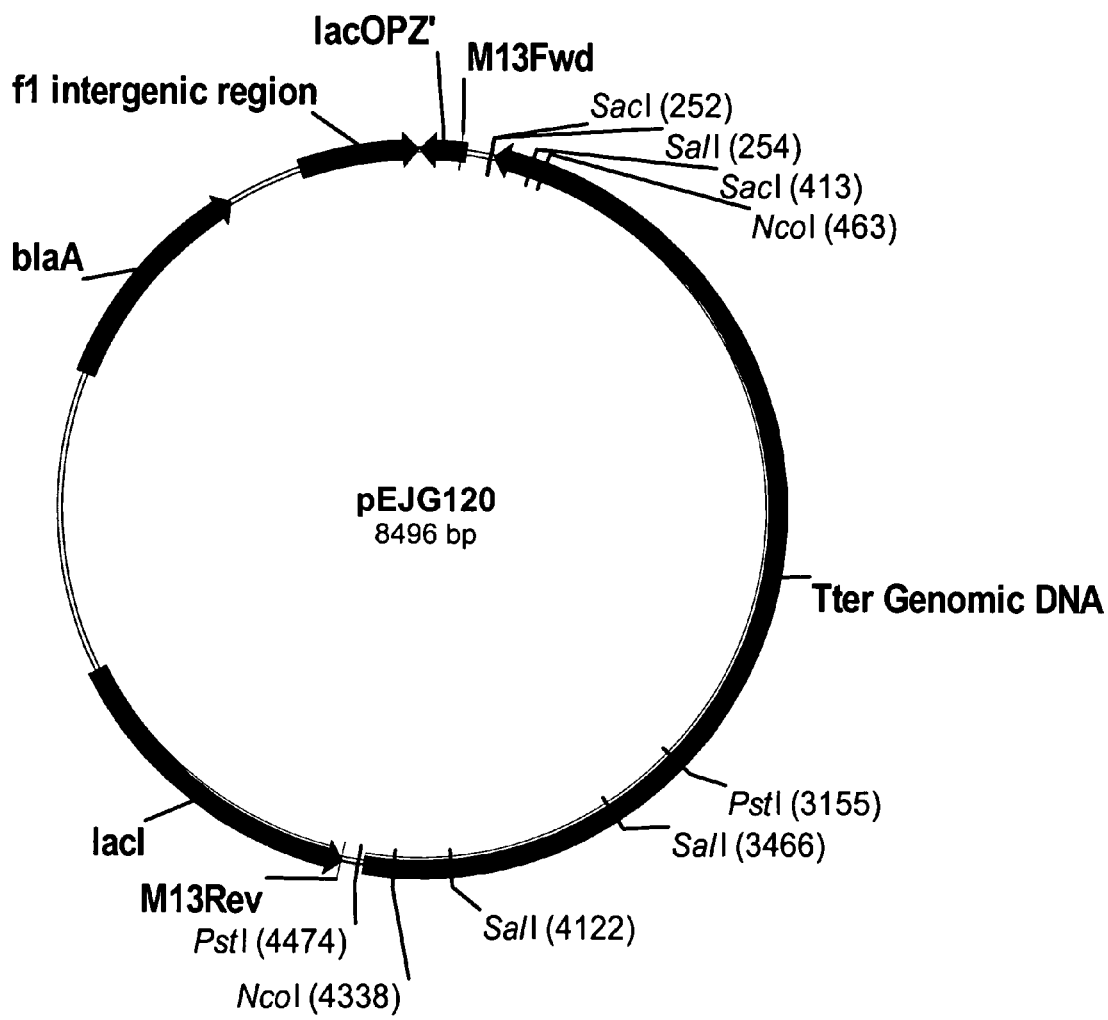
FIG. 12 shows a restriction map of pEJG120.

Based on the production of strong hybridization signals with the GH61 probes described above, several plaques were chosen for further study. The plaques were purified twice in *E. coli* Y1090ZL cells and the inserted genes and pZL1 plasmid were subsequently excised from the λZipLox vector as pZL1-derivatives (D'Alessio et al., 1992, Focus® 14:76) using in vivo excision by infection of *E. coli* DH10BZL cells (Life Technologies, Gaithersburg, Md.). The colonies were inoculated into three ml of LB plus 50 μg/ml ampicillin medium and grown overnight at 37° C. Miniprep DNA was prepared from each of these cultures using a BioRobot 9600 (QIAGEN Inc., Valencia, Calif.). Clone pEJG120 (FIG. 12) was shown by DNA sequencing to contain the full-length genomic gene for GH61B.

The full-length genomic genes for GH61C and GH61D were isolated in the same manner as described for GH61B.

*E. coli* pEJG120 containing plasmid pEJG120 was deposited with the Agricultural Research Service Patent Culture Collection, Northern Regional Research Center, 1815 University Street, Peoria, Ill., 61604, as NRRL B-30699, with a deposit date of Dec. 19, 2003.

Figure 13:
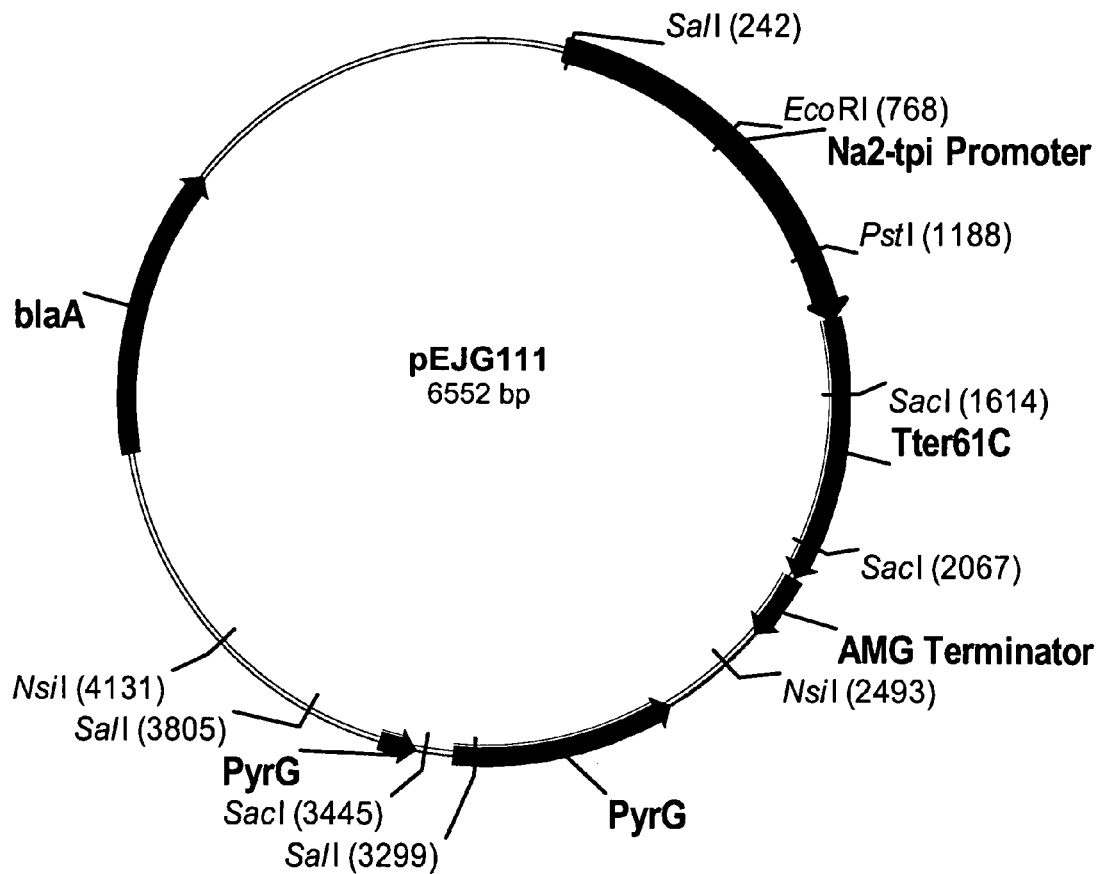
FIG. 13 shows a restriction map of pEJG111.

For deposit, the Tter61C gene was PCR amplified from its expression construct pEJG111 (see Example 13, FIG. 13) with the primers shown below.

In-Fusion Forward Primer:
                                 (SEQ ID NO: 36)
5'-ACAACTGGATTTACCATGCGGTTCGACGCCTC-3'

In-Fusion Reverse Primer:
                                 (SEQ ID NO: 37)
5'-GTCAGTCACCTCTAGTTACTAAAACTCGAAGCC-3'

Bold letters represent coding sequence. The remaining sequence contains sequence identity to the insertion sites of pAlLo2.

Fifty picomoles of each of the primers above were used in a PCR reaction containing 50 ng of pEJG111 DNA, 1×Pfx Amplification Buffer (Invitrogen, Carlsbad, Calif.), 6 μl of 10 mM blend of dATP, dTTP, dGTP, and dCTP, 1 μl of 50 mM MgSO$_4$, 5 μl of 10×pCRx Enhancer Solution (Invitrogen, Carlsbad, Calif.), and 2.5 units of Platinum Pfx DNA Polymerase (Invitrogen, Carlsbad, Calif.), in a final volume of 50 μl. An Eppendorf Mastercycler 5333 (Eppendorf Scientific, Inc., Westbury, N.Y.) was used to amplify the DNA fragment and was programmed for one cycle at 98° C. for 2 minutes; and 35 cycles each at 94° C. for 30 seconds, 60° C. for 30 seconds, and 68° C. for 1 minute. After the 35 cycles, the reaction was incubated at 68° C. for 10 minutes and then cooled to 10° C. until further processed. A PCR reaction product of approximately 800 bp was isolated on a 0.8% GTG-agarose gel (Cambrex Bioproducts, East Rutherford, N.J.) using TAE buffer and 0.1 μg of ethidium bromide per ml. The DNA band was visualized with the aid of a Dark Reader™ (Clare Chemical Research, Dolores, Colo.) to avoid UV-induced mutations. The 800 bp DNA band was excised with a disposable razor blade and purified with an Ultrafree-DA Spin Cup (Millipore, Billerica, Mass.) according to the manufacturer's instructions.

The purified DNA band was cloned into a pCR4-Blunt TOPO vector according to the manufacturer's instructions (Invitrogen, Carlsbad, Calif.). Two microliters of the TOPO-reaction were transformed into *E. coli* TOP10 cells according to the manufacturer's instructions (Invitrogen, Carlsbad, Calif.). The transformed cells were plated onto 2×YT agar plates supplemented with 100 μg of ampicillin per ml and incubated overnight at 37° C.

Figure 15:
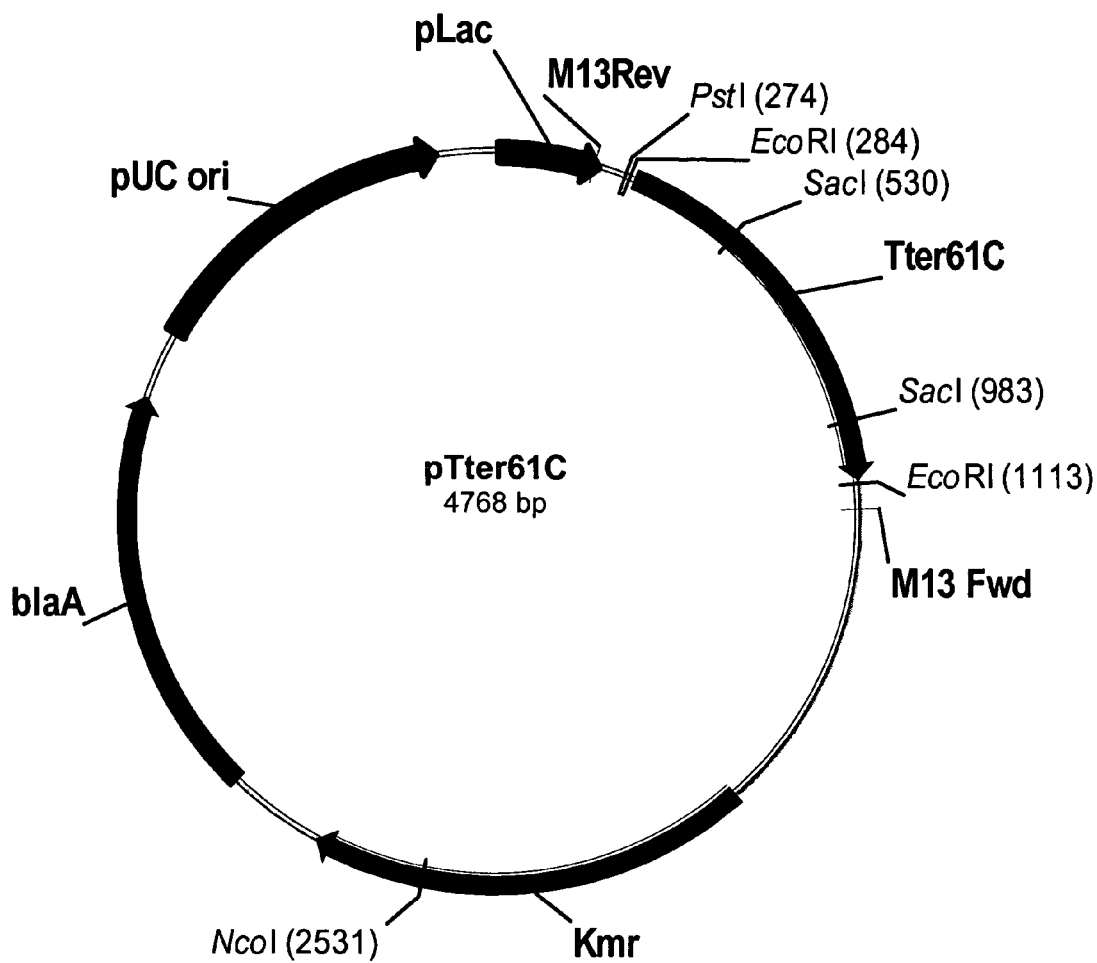
FIG. 15 shows a restriction map of pTter61C.

Eight colonies were selected at random for plasmid DNA preparation. Each colony was grown overnight on 3 ml of LB supplemented with 100 μg of ampicillin per ml. From these cultures, 10 μl were used to spot-inoculate a 2×YT agar plate supplemented with 100 μg of ampicillin per ml in order to have a bacterial stock of each colony. The rest of the culture was then used to prepare plasmid DNA with a QIAGEN BioRobot 9600. Clones were analyzed by EcoRI restriction enzyme digestion. Eight clones had the expected restriction digest pattern. From these clones, three were then sequenced with Big-Dye™ terminator chemistry as described above, using standard M13 forward and reverse primers. All three clones were show to have the correct sequence of the Tter61E gene. Clone #7 was renamed pTter61C (FIG. 15) and its bacterial stock re-streaked onto a fresh 2×YT plate supplemented with 100 μg of ampicillin per ml and incubated overnight at 37° C. From this plate, cells were used to inoculate two 1.8 ml cryovials containing about 1.5 ml of LB agarose supplemented with 100 μg of ampicillin per ml. The vials were sealed with PetriSeal™ (Diversified Biotech, Boston Mass.) and deposited with the Agricultural Research Service Patent Culture Collection, Northern Regional Research Center, 1815 University Street, Peoria, Ill., 61604, as pTter61G NRRL B-30811, with a deposit date of Jan. 21, 2005.

Figure 14:
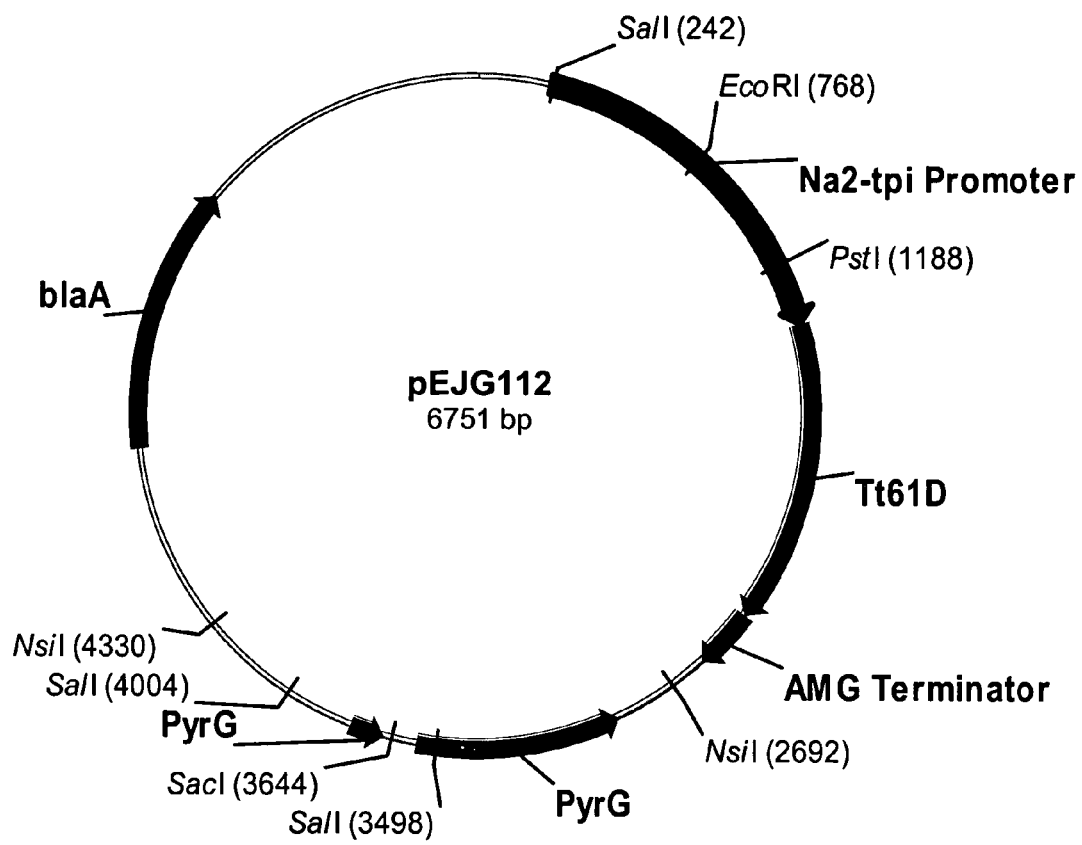
FIG. 14 shows a restriction map of pEJG112.

For deposit, the Tter61D gene was PCR amplified from its expression construct pEJG112 (see Example 13, FIG. 14) with the following primers.

```
Forward Primer:
5'-CATGCCATGGATGCTTCTCAC-3'      (SEQ ID NO: 38)

Reverse Primer:
5'-CCTTAATTAATCAGGCGGTGAAGTC-3'  (SEQ ID NO: 39)
```

Bold letters represent coding sequence. The remaining sequence contains unique restriction sites for future cloning experiments.

The PCR reaction was conducted as described above except with pEJG112. A PCR reaction product of approximately 1 kb was isolated on a 0.8% GTG-agarose gel using TAE buffer and 0.1 μg of ethidium bromide per ml. The DNA band was visualized with the aid of a Dark Reader™ to avoid UV-induced mutations. The 1 kb DNA band was excised with a disposable razor blade and purified with a QIAquick PCR Purification Kit according to the manufacture's instructions (QIAGEN Inc., Valencia, Calif.). The purified DNA band was cloned into the pCR4-Blunt TOPO vector according to the manufacturer's instructions and transformants of *E. coli* TOP10 cells isolated as described above.

Figure 16:
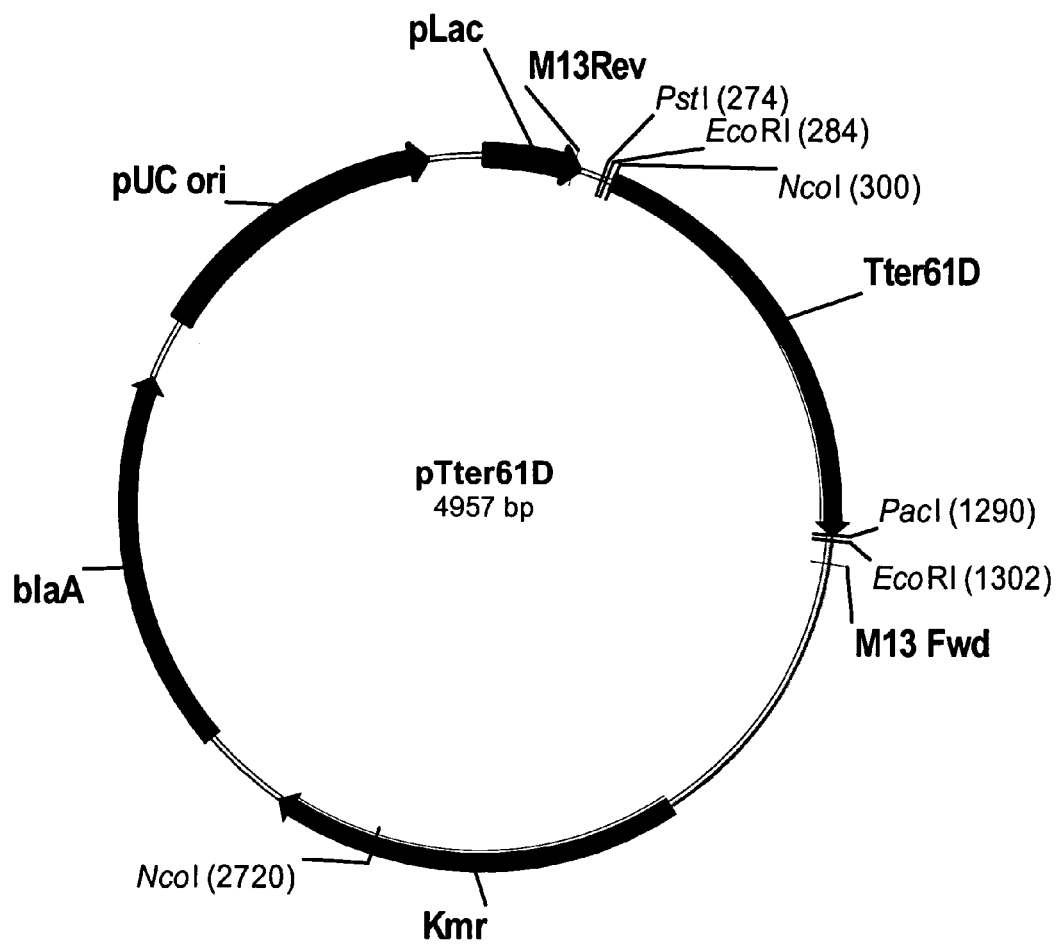
FIG. 16 shows a restriction map of pTter61D.

Ten colonies were selected at random for plasmid DNA preparation. Each colony was grown overnight on 3 ml of LB supplemented with 100 μg of ampicillin per ml and used to prepare plasmid DNA with a QIAGEN BioRobot 9600. Clones were analyzed by EcoRI restriction enzyme digestion to confirm the presence of the cloned insert. All ten clones had the expected restriction digest pattern. From these clones five were then sequenced with Big-Dye™ terminator chemistry as described above, using standard M13 forward and reverse primers. One of these clones was shown to have the correct sequence of the Tter61D gene. This clone was renamed pTter61D (FIG. 16) and re-transformed into *E. coli* TOP10 cells as described above. From a single colony streak, cells were used to inoculate two 1.8 ml cryovials containing about 1.5 ml of LB agarose supplemented with 100 μg/ml of ampicillin per ml. The vials were sealed with PetriSeal™ and deposited with the Agricultural Research Service Patent Culture Collection, Northern Regional Research Center, 1815 University Street, Peoria, Ill., 61604, as pTter61D NRRL B-30812, with a deposit date of Jan. 21, 2005.

Example 8

Expressed Sequence Tags (EST) cDNA Library Construction

A two ml aliquot from a 24-hour liquid culture (50 ml of NNCYPmod medium supplemented with 1% glucose in 250 ml flask, 45° C., 200 rpm) of *Thielavia terrestris* NRRL 8126 was used to seed a 500 ml flask containing 100 ml of NNCYPmod medium supplemented with 2% Sigmacell-20. The culture was incubated at 45° C., 200 rpm for 3 days. The mycelia were harvested by filtration through a disposable filtering unit with a glass fiber prefilter (Nalgene, Rochester N.Y.), washed twice with 10 mM Tris-HCl-1 mM EDTA pH 8 (TE), and quick frozen in liquid nitrogen.

Total RNA was isolated using the following method. Frozen mycelia of *Thielavia terrestris* NRRL 8126 were ground in an electric coffee grinder. The ground material was mixed 1:1 v/v with 20 ml of Fenazol (Ambion, Inc., Austin, Tex.) in a 50 ml Falcon tube. Once the mycelia were suspended, they were extracted with chloroform and three times with a mixture of phenol-chloroform-isoamyl alcohol 25:24:1 v/v/v. From the resulting aqueous phase, the RNA was precipitated by adding 1/10 volume of 3 M sodium acetate pH 5.2 and 1.25 volumes of isopropanol. The precipitated RNA was recovered by centrifugation at 12,000×g for 30 minutes at 4° C. The final pellet was washed with cold 70% ethanol, air dried, and resuspended in 500 ml of diethylpyrocarbonate-treated water (DEPC-water).

The quality and quantity of the purified RNA was assessed with an Agilent Bioanalyzer 2100 (Agilent Technologies, Inc., Palo Alto, Calif.). Polyadenylated mRNA was isolated from 360 μg of total RNA with the aid of a Poly(A) Purist Magnetic Kit (Ambion, Inc., Austin, Tex.) according to the manufacturer's instructions.

To create the cDNA library, a CloneMiner™ Kit (Invitrogen, Carlsbad, Calif.) was employed to construct a directional library that does not require the use of restriction enzyme cloning, thereby reducing the number of chimeric clones and size bias.

To insure the successful synthesis of the cDNA, two reactions were performed in parallel with two different concentrations of mRNA (2.2 and 4.4 μg of poly(A)⁺ mRNA). The mRNA samples were mixed with a Biotin-attB2-Oligo(dt) primer (CloneMiner™ Kit, Invitrogen, Carlsbad, Calif.), 1×first strand buffer (Invitrogen, Carlsbad, Calif.), 2 μl of 0.1 M DTT, 10 mM of each dNTP, and water to a final volume of 18 and 16 μl respectively.

The reaction mixtures were mixed carefully and then 2 and 4 μl of SuperScript™ reverse transcriptase (Invitrogen, Carlsbad, Calif.) were added and incubated at 45° C. for 60 minutes to synthesize the first complementary strand. For second strand synthesis, to each first strand reaction was added 30 μl of 5×second strand buffer (Invitrogen, Carlsbad, Calif.), 3 μl of 10 mM of each dNTP, 10 units of *E. coli* DNA ligase (Invitrogen, Carlsbad, Calif.), 40 units of *E. coli* DNA polymerase I (Invitrogen, Carlsbad, Calif.), and 2 units of *E. coli* RNase H (Invitrogen, Carlsbad, Calif.) in a total volume of 150 μl. The mixtures were then incubated at 16° C. for two hours. After the two-hour incubation, 2 μl of T4 DNA polymerase (Invitrogen, Carlsbad, Calif.) were added to each reaction and incubated at 16° C. for 5 minutes to create a bunt-ended cDNA. The cDNA reactions were extracted with a mixture of phenol-chloroform-isoamyl alcohol 25:24:1 v/v/v and precipitated in the presence of 20 μg of glycogen, 120 μl of 5 M ammonium acetate, and 660 μl of ethanol. After centrifugation at 12,000×g, 4° C. for 30 minutes, the cDNA pellets were washed with cold 70% ethanol, dried under vacuum for 2-3 minutes, and resuspended in 18 μl of DEPC-water. To each resuspended cDNA sample was added 10 μl of 5×adapted buffer (Invitrogen, Carlsbad, Calif.), 10 μg of attB1 adapter (Invitrogen, Carlsbad, Calif.), 7 μl of 0.1 M DTT, and 5 units of T4 DNA ligase (Invitrogen, Carlsbad, Calif.).

```
                                          (SEQ ID NO: 40)
5'-TCGTCGGGGACAACTTTGTACAAAAAAGTTGG-3'

(SEQ ID NO: 41)
3'-CCCCTGTTGAAACATGTTTTTTCAACCp-5'
```

Ligation reactions were incubated overnight at 16° C. Excess adapters were removed by size-exclusion chromatography with 1 ml of Sephacryl™ S-500 HR resin (Amersham Biosciences, Piscataway, N.J.). Column fractions were collected according to the CloneMiner™ Kit's instructions and fractions 3 to 14 were analyzed with an Agilent Bioanalyzer to determine the fraction at which the attB1 adapters started to elute. Analysis showed that the adapters started eluting around fraction 10 or 11. For the first library fractions 6 to 11 were pooled and for the second library fractions 4-11 were pooled.

Cloning of the cDNA was performed by homologous DNA recombination according to the Gateway System protocol (Invitrogen, Carlsbad, Calif.) using BP Clonase™ (Invitrogen, Carlsbad, Calif.) as the recombinase. Each BP Clonase™ recombination reaction contained approximately 70 ng of attB-flanked-cDNA, 250 ng of pDONR™222 (Invitrogen, Carlsbad, Calif.), 2 μl of 5×BP Clonase™ buffer (Invitrogen, Carlsbad, Calif.), 2 μl of TE, and 3 μl of BP Clonase™. Recombination reactions were incubated at 25° C. overnight.

Heat-inactivated BP recombination reactions were then divided into 6 aliquots and electroporated into Electro-Max™ DH10B electrocompetent cells (Invitrogen, Carlsbad, Calif.) using a BioRad Gene Pulser II (BioRad, Hercules, Calif.) with the following parameters: 2.0 kV, 200 Ω, and 25 μF. Electroporated cells were resuspended in 1 ml of SOC and incubated at 37° C. for 60 minutes with constant shaking (200 rpm). After the incubation period, the transformed cells were pooled and mixed 1:1 with freezing medium. A 200 μl aliquot was removed for library titration and then the rest of each library was aliquoted into 1.8 ml cryovials (Wheaton Science Products, Millville, N.J.) and stored frozen at −80° C.

Four serial dilutions of each library were prepared: 1/100, 1/1000, 1/10⁴, 1/10⁵. From each dilution, 100 μl were plated onto 150 mm LB plates supplemented with 50 μg of kanamycin per ml and incubated at 37° C. overnight. The number of colonies on each dilution plate were counted and used to calculate the total number of transformants in each library.

The first library was shown to have 5.4 million independent clones and the second library was show to have 9 million independent clones.

Example 9

Template Preparation and Nucleotide Sequencing of cDNA Clones

Aliquots from both libraries were mixed and plated onto 25×25 cm LB plates supplemented with 50 μg of kanamycin per ml. Individual colonies were arrayed onto 96-well plates containing 100 μl of LB medium supplemented with 50 μg of kanamycin per ml with the aid of a Genetix QPix robot (Genetix Inc., Boston, Mass.). Forty five 96-well plates were obtained for a total of 4320 individual clones. The plates were incubated overnight at 37° C. with shaking at 200 rpm. After incubation, 100 μl of sterile 50% glycerol was added to each well. The transformants were replicated with the aid of a 96-pin tool (Boekel, Feasterville, Pa.) into secondary, deep-dish 96-well microculture plates (Advanced Genetic Technologies Corporation, Gaithersburg, Md.) containing 1 ml of Magnificent Broth™ (MacConnell Research, San Diego, Calif.) supplemented with 50 μg of kanamycin per ml in each well. The primary microtiter plates were stored frozen at −80° C. The secondary deep-dish plates were incubated at 37° C. overnight with vigorous agitation (300 rpm) on a rotary shaker. To prevent spilling and cross-contamination, and to allow sufficient aeration, each secondary culture plate was covered with a polypropylene pad (Advanced Genetic Technologies Corporation, Gaithersburg, Md.) and a plastic microtiter dish cover. Plasmid DNA was prepared with a MWG Robot-Smart 384 (MWG Biotech Inc., High Point, N.C.) and Montage Plasmid Miniprep Kits (Millipore, Billerica, Mass.).

Sequencing reactions were performed using Big-Dye™ terminator chemistry (Giesecke et al., 1992, *Journal of Virology Methods* 38: 47-60) and a M13 Forward (−20) sequencing primer:

```
5'-GTAAAACGACGGCCAG-3'      (SEQ ID NO: 42)
```

The sequencing reactions were performed in a 384-well format with a Robot-Smart 384 (MWG Biotech Inc., High Point, N.C.). Terminator removal was conducted with Millipore MultiScreen Seq384 Sequencing Clean-up Kits (Millipore, Billerica, Mass.). Reactions contained 6 μl of plasmid DNA and 4 μl of sequencing master-mix containing 1 μl of 5×sequencing buffer (Millipore, Billerica, Mass.), 1 μl of Big-Dye™ terminator (Applied Biosystems, Inc., Foster City, Calif.), 1.6 μmoles of M13 Forward primer, and 1 μl of water. Single-pass DNA sequencing was performed with an ABI PRISM Automated DNA Sequencer Model 3700 (Applied Biosystems, Foster city, Calif.).

Example 10

Analysis of DNA Sequence Data of cDNA Clones

Base calling, quality value assignment, and vector trimming were performed with the assistance of PHRED/PHRAP software (University of Washington, Seattle, Wash.). Clustering analysis of the ESTs was performed with a Parcel Transcript Assembler v. 2.6.2. (Paracel, Inc., Pasadena, Calif.). Analysis of the EST clustering indicated the presence of 395 independent clusters.

Sequence homology analysis of the assembled EST sequences against the PIR database was performed with the Blastx program (Altschul et. al., 1990, *J. Mol. Biol.* 215: 403-410) on a 32-node Linux cluster (Paracel, Inc., Pasadena, Calif.) using the BLOSUM 62 matrix (Henikoff, 1992, *Proc. Natl. Acad. Sci. USA* 89: 10915-10919). From the 395 clusters, 246 had a significant identity to known genes in the public protein database and 149 had no significant identity against this database. Among these 246 clusters, 13 had hits against well characterized homologues of glycosyl hydrolase genes.

Example 11

Identification of cDNA Clones Encoding Two Family 61 Polypeptides Having Cellulolytic Enhancing Activity (GH61E and GH61G)

Two cDNA clones encoding Family 61 polypeptides having cellulolytic enhancing activity (GH61E and GH61G) were initially identified by their identity to the Family 61 protein from *Volvariella volvacea* (GenPept g49333361). This analysis indicated that the proteins were 41% and 38%, respectively, identical to the *V. volvacea* at the protein level over a 289 amino acid stretch (867 bp). After this initial identification, the EST clones Tter39E1 and Tter39H8 were retrieved from their original frozen stock plate and streaked onto LB plates supplemented with 50 µg of kanamycin per ml. The plates were incubated overnight at 37° C. and the next day a single colony from each plate was used to inoculate 3 ml of LB supplemented with 50 µg of kanamycin per ml. The liquid cultures were incubated overnight at 37° C. and plasmid DNA was prepared with a QIAGEN BioRobot 9600. Plasmid DNA from each EST clone was sequenced again with Big-Dye™ terminator chemistry as described above, using the M13 forward and a Poly-T primer shown below to sequence the 3' end of the clone.

```
5'-TTTTTTTTTTTTTTTTTTTTTVN-3'   (SEQ ID NO: 43)
```

Where V=G, A, or C and N=G, A, C, or T

Sequence analysis of clone Tter39E1 indicated that this clone was not full length and was missing some nucleotides at the 5' end since it did not have a start codon "ATG". In order to obtain a full length clone, a pair of primers were designed to amplify the 5' end of this gene from the original cDNA pool used to construct the library.

The forward or sense primer was designed to match the attB1 adapter used during the construction of the cDNA library and the reverse primer was designed to amplify from about 350 bp from the truncated 5' end, as shown below.

```
attB1 Primer:
5'-GGGGACAACTTTGTACAAAAAAGTTGG-3'   (SEQ ID NO: 44)

Reverse Primer:
5'-AAAGGTAGGATGGTCCTCGTACACCTT-3'   (SEQ ID NO: 45)
```

Fifty picomoles of each of the primers above were used in a PCR reaction containing 1 µl of the pooled cDNA, 1×Taq Amplification Buffer (New England BioLabs, Beverly, Mass.), 6 µl of 10 mM blend of dATP, dTTP, dGTP, and dCTP, and 2.5 units of Taq DNA Polymerase (New England BioLabs, Beverly, Mass.), in a final volume of 50 µl. An Eppendorf Mastercycler 5333 was used to amplify the fragment programmed for one cycle at 98° C. for 2 minutes; 5 cycles each at 96° C. for 30 seconds, 55° C. for 30 seconds, and 68° C. for 1 minute; and 35 cycles each at 96° C. for 30 seconds, 61° C. for 30 seconds, and 68° C. for 1 minute. After the 35 cycles, the reaction was incubated at 68° C. for 10 minutes and then cooled to 10° C. until further processed.

A PCR reaction product (approximately 400 bp) was isolated on a 0.8% GTG-agarose gel using TAE buffer and 0.1 µg of ethidium bromide per ml. The DNA band was visualized with the aid of a Dark Reader™ to avoid UV-induced mutations. The 400 bp DNA band was excised with a disposable razor blade and purified with an Ultrafree-DA Spin Cup according to the manufacturer's instructions. The purified DNA band was cloned into a pCR2.1 TA-TOPO vector according to the manufacturer's instructions (Invitrogen, Carlsbad, Calif.). Two microliters of the TA-reaction were transformed into *E. coli* TOP10 cells according to the manufacturer's instructions. The transformed cells were plated onto 2×YT agar plates supplemented with 100 µg/ml of ampicillin and incubated overnight at 37° C. Eight colonies were selected at random for plasmid DNA preparation. Each colony was grown overnight in 3 ml of LB medium supplemented with 100 µg of ampicillin per ml and plasmid DNA was prepared from each one using a QIAGEN BioRobot 9600. Clones were analyzed by EcoRI restriction enzyme digestion. All eight clones had the expected restriction digest pattern. From these clones three were then sequenced with Big-Dye™ terminator chemistry as described above, using a standard M13 reverse primer. Sequence analysis indicated that all three clones had a complete 5' end and that the original EST clone pTter39E1 was missing only five nucleotides at the 5' end.

From the full-length sequence of the Tter61E gene In-Fusion PCR primers were designed as shown below to amplify the truncated gene, for cloning into the expression vector pAlLo2, and add at the same time the missing 5 nucleotides at its 5' end.

```
In-Fusion Forward Primer:
                                    (SEQ ID NO: 46)
5'-ACTGGATTACCATGCTCGCAAACGGTGCCATCGTCT-3'

In-Fusion Reverse Primer:
                                    (SEQ ID NO: 47)
5'- TCACCTCTAGTTAATTAATCAGCAGCTGAAGACGGCCG-3'
```

Bold letters represent coding sequence. The Bold and underlined letters represent the missing five nucleotides from the 5' end of the gene as described above. The remaining sequence contains sequence identity to the insertion sites of pAlLo2.

The PCR reaction was conducted as described in Example 7 except with pTter39E1. A PCR reaction product of approximately 700 bp was isolated on a 0.8% GTG-agarose gel using TAE buffer and 0.1 µg of ethidium bromide per ml. The DNA band was visualized with the aid of a Dark Reader™ to avoid UV-induced mutations. The 700 bp DNA band was excised with a disposable razor blade and purified with an Ultrafree-DA Spin Cup according to the manufacturer's instructions.

Figure 17:
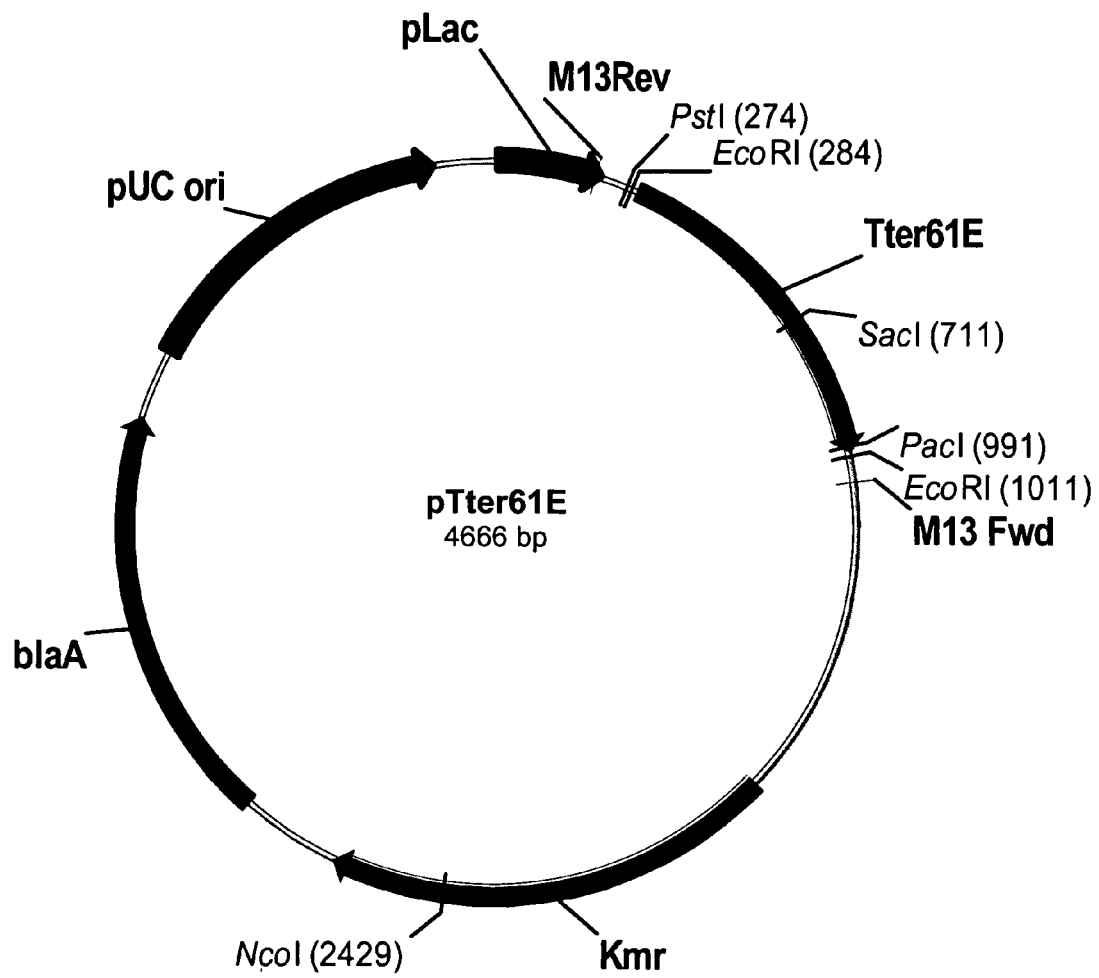
FIG. 17 shows a restriction map of pTter61E.

The purified DNA band was cloned into the pCR4-Blunt TOPO vector according to the manufacturer's instructions and transformants of *E. coli* TOP10 cells isolated as described in Example 7. Eight colonies were selected at random for plasmid DNA preparation. Each colony was grown overnight in 3 ml of LB supplemented with 100 µg of ampicillin per ml and used to prepare plasmid DNA with a QIAGEN BioRobot 9600. Clones were analyzed by PacI/PstI restriction enzyme digestion. Seven out of eight clones had the expected restriction digest pattern. From these seven clones, three were then sequenced with Big-Dye™ terminator chemistry as described above, using standard M13 forward and reverse primers. All three clones were show to have the correct sequence of the Tter61E gene. Clone #2 was renamed pTter61E (FIG. 17) and re-transformed into *E. coli* TOP10 cells as described above. From a single colony streak, cells were used to inoculate two 1.8 ml cryovials containing about 1.5 ml of LB agarose supplemented with 100 µg/ml of ampicillin per ml. The vials were sealed with PetriSeal™ and deposited with the Agricultural Research Service Patent Culture Collection, Northern Regional Research Center, 1815 University Street, Peoria, Ill., 61604, as pTter61E NRRL B-30814, with a deposit date of Jan. 21, 2005.

Figure 18:
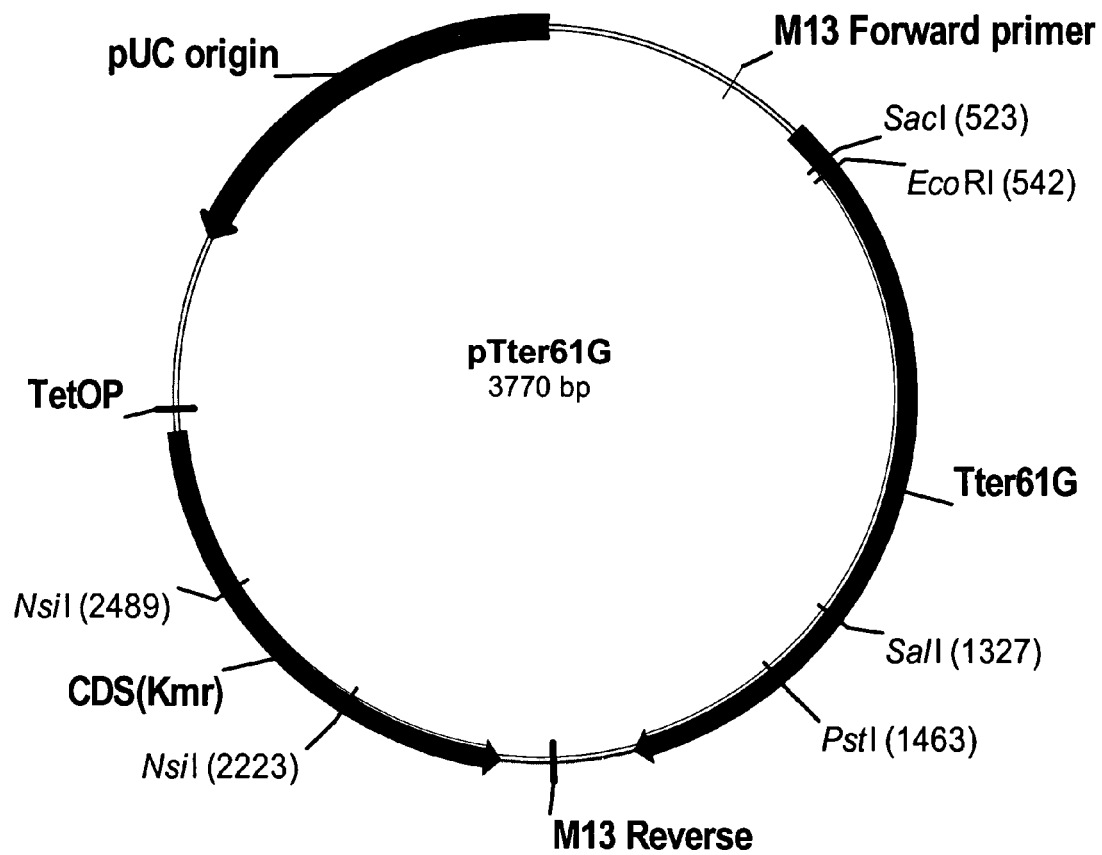
FIG. 18 shows a restriction map of pTter61G.

Once the identity of clone Tter39H8 was confirmed, the plasmid was renamed pTter61G (FIG. 18). A 0.5 µl aliquot of plasmid DNA from this clone was transferred into a vial of *E. coli* TOP10 cells, gently mixed, and incubated on ice for 10 minutes. The cells were then heat-shocked at 42° C. for 30 seconds and incubated again on ice for 2 minutes. The cells were resuspended in 250 µl of SOC and incubated at 37° C. for 60 minutes with constant shaking (200 rpm). After the incubation period, two 30 µl aliquots were plated onto LB plates supplemented with 50 µg of kanamycin per ml and incubated overnight at 37° C. The next day a single colony was picked and streaked onto a fresh 2×YT plate supplemented with 50 µg of kanamycin per ml and incubated overnight at 37° C. From this plate, cells were used to inoculate two 1.8 ml cryovials containing about 1.5 ml of LB agarose supplemented with 50 µg of kanamycin per ml. The vials were sealed with PetriSeal™ and deposited with the Agricultural Research Service Patent Culture Collection, Northern Regional Research Center, 1815 University Street, Peoria, Ill., 61604, as pTter61G NRRL B-30811, with a deposit date of Jan. 21, 2005.

Example 12

Characterization of the *Thielavia terrestris* Genomic Sequences Encoding Family GH61B, GH61C and GH61D Polypeptides Having Cellulolytic Enhancing Activity and cDNA Sequences Encoding Family GH61E and GH61G Polypeptides Having Cellulolytic Enhancing Activity DNA sequencing of the *Thielavia terrestris* GH61B genomic clone (clone 15) and multiple overlapping GH61C and GH61D genomic clones was performed with an Applied Biosystems Model 3700 Automated DNA Sequencer using version 3.1 BigDye™ terminator chemistry and dGTP chemistry (Applied Biosystems, Inc., Foster City, Calif.) and primer walking strategy. Nucleotide sequence data were scrutinized for quality and all sequences were compared to each other with assistance of PHRED/PHRAP software (University of Washington, Seattle, Wash.).

Gene models for the *Thielavia terrestris* GH61B, GH61C, and GH61D genomic DNA sequences were constructed based on similarity to homologous genes from *Diplodia gossypina, Trichophaea saccata,* and *Pseudoplectania nigrella*.

The nucleotide sequence (SEQ ID NO: 1) and deduced amino acid sequence (SEQ ID NO: 2) of the *Thielavia terrestris* GH61B gene are shown in FIG. 1. The coding sequence is 1104 bp including the stop codon and is interrupted by introns of 60 and 63 bp. The encoded predicted protein is 326 amino acids. The coding region is 65.8% G+C. Using the SignalP program (Nielsen et al., 1997, *Protein Engineering* 10: 1-6), a signal peptide of 19 residues was predicted. The predicted mature protein contains 307 amino acids with a molecular mass of 31.3 kDa.

Analysis of the deduced amino acid sequence of the GH61B gene with the Interproscan program (Zdobnov and Apweiler, 2001, *Bioinformatics* 17: 847-848) showed that the GH61B gene contained the sequence signature of the fungal cellulose binding domain. This sequence signature known as the Prosite pattern PS00562 (Sigrist et al., 2002, *Brief Bioinform.* 3: 265-274) was found from approximately residues 271 to 307 of the mature polypeptide.

A comparative alignment of amino acid sequences was determined using the Smith-Waterman algorithm (Waterman et al., 1976, *Adv. Math.* 20: 367) with gap open penalty of 11, gap extension penalty of 1, and the BLOSUM62 matrix. The alignment showed that the deduced amino acid sequence of the *Thielavia terrestris* gene encoding a Family GH61B polypeptide having cellulolytic enhancing activity shared 70% and 64% identity (including gaps) to the deduced amino acid sequences of two Family 61 proteins from *Neurospora crassa* (accession number EAA26873 and EAA36262).

The nucleotide sequence (SEQ ID NO: 3) and deduced amino acid sequence (SEQ ID NO: 4) of the *Thielavia terrestris* GH61C gene are shown in FIG. 2. The coding sequence is 778 bp including the stop codon and is interrupted by one intron of 58 bp. The encoded predicted protein is 240 amino acids. The coding region is 66.2% G+C. Using the SignalP program, a signal peptide of 17 residues was predicted. The predicted mature protein contains 223 amino acids with a molecular mass of 24.1 kDa.

A comparative alignment of amino acid sequences was determined using the Smith-Waterman algorithm (Waterman et al., 1976, *Adv. Math.* 20: 367) with gap open penalty of 11, gap extension penalty of 1, and the BLOSUM62 matrix. The alignment showed that the deduced amino acid sequence of the *Thielavia terrestris* gene encoding a Family GH61C polypeptide having cellulolytic enhancing activity shared 76% and 72% identity to the deduced amino acid sequences of two Family 61 proteins from *Neurospora crassa* (accession number Q9P3R7 and Q7RV41, respectively).

The nucleotide sequence (SEQ ID NO: 5) and deduced amino acid sequence (SEQ ID NO: 6) of the *Thielavia terrestris* GH61D gene are shown in FIG. 3. The coding sequence is 913 bp including the stop codon and is interrupted by introns of 70 and 66 bp. The encoded predicted protein is 258 amino acids. The coding region is 63.1% G+C. Using the SignalP program, a signal peptide of 19 residues was predicted. The predicted mature protein contains 239 amino acids with a molecular mass of 25.7 kDa.

A comparative alignment of amino acid sequences was determined using the Smith-Waterman algorithm (Waterman et al., 1976, *Adv. Math.* 20: 367) with gap open penalty of 11, gap extension penalty of 1, and the BLOSUM62 matrix. The alignment showed that the deduced amino acid sequence of the *Thielavia terrestris* gene encoding a Family GH61D polypeptide having cellulolytic enhancing activity shared 53% and 53% identity to the deduced amino acid sequences of two Family 61 proteins from *Neurospora crassa* (accession number Q9P3R7 and Q7RV41, respectively).

The cDNA sequence (SEQ ID NO: 7) and deduced amino acid sequence (SEQ ID NO: 8) of the *Thielavia terrestris* GH61E gene are shown in FIG. 4. The coding sequence is 681 bp including the stop codon. The encoded predicted protein is 226 amino acids. The % G+C content of the GH61E cDNA clone is 65.6% and of the mature protein coding region (nucleotides 55 to 681 of SEQ ID NO: 7) is 65.4%. Using the SignalP program, a signal peptide of 18 residues was predicted. The predicted mature protein contains 208 amino acids with a molecular mass of 22.3 kDa.

A comparative alignment of amino acid sequences was determined using the Smith-Waterman algorithm (Waterman et al., 1976, *Adv. Math.* 20: 367) with gap open penalty of 11, gap extension penalty of 1, and the BLOSUM62 matrix. The alignment showed that the deduced amino acid sequence of the *Thielavia terrestris* gene encoding a Family GH61E polypeptide having cellulolytic enhancing activity shared 73% and 53% identity to the deduced amino acid sequences of a Family 61 protein from *Neurospora crassa* (accession number Q873G1) and another from *Magnaporthe grisea* (accession number EAA54517), respectively.

The nucleotide sequence (SEQ ID NO: 9) and deduced amino acid sequence (SEQ ID NO: 10) of the *Thielavia terrestris* GH61G gene are shown in FIG. 5. The coding sequence is 915 bp including the stop codon. The encoded predicted protein is 304 amino acids. The % G+C content of the GH61G cDNA clone is 64.5% and of the mature protein coding region (nucleotides 58 to 912 of SEQ ID NO: 9) is 64.4%. Using the SignalP program, a signal peptide of 19 residues was predicted. The predicted mature protein contains 285 amino acids with a molecular mass of 30.0 kDa.

Analysis of the deduced amino acid sequence of the GH61G gene with the Interproscan program showed that the GH61G gene contained the sequence signature of the fungal cellulose binding domain. This sequence signature was present from approximately residues 271 to 304 of the mature polypeptide.

A comparative alignment of amino acid sequences was determined using the Smith-Waterman algorithm (Waterman et al., 1976, *Adv. Math.* 20: 367) with gap open penalty of 11, gap extension penalty of 1, and the BLOSUM62 matrix. The alignment showed that the deduced amino acid sequence of the *Thielavia terrestris* gene encoding a Family GH61G polypeptide having cellulolytic enhancing activity shared 61% and 61% identity to the deduced amino acid sequences of a Family 61 protein from *Neurospora crassa* (accession number Q7SCJ5) and another from *Gibberella zeae* (accession number EAA72972), respectively.

A comparative alignment of Family 61 sequences from *Thielavia terrestris* NRRL 8126 was determined using the MAFFT NW method with iterative refinement and default parameters (Katoh et al., 2002, *Nucleic Acids Research* 30: 3059). An identity matrix was calculated using LASERGENE™ MEGALIGN™ software (DNASTAR, Inc., Madison, Wis.). The alignment results are shown in Table 1.

TABLE 1

Alignment of *Thielavia terrestris* GH61 Polypeptide Sequences

| Divergence | Percent Identity | | | | | |
|---|---|---|---|---|---|---|
| | 1 | 2 | 3 | 4 | 5 | |
| 1 | | 59.6 | 35.2 | 33.2 | 31.2 | 1 *Thielavia terrestris* GH61C |
| 2 | 59.6 | | 32.2 | 27.5 | 26.7 | 2 *Thielavia terrestris* GH61D |
| 3 | 135.0 | 138.4 | | 43.3 | 41.7 | 3 *Thielavia terrestris* GH61G |
| 4 | 142.6 | 174.6 | 129.6 | | 42.1 | 4 *Thielavia terrestris* GH61E |
| 5 | 134.4 | 157.0 | 116.4 | 99.8 | | 5 *Thielavia terrestris* GH61B |
| | 1 | 2 | 3 | 4 | 5 | |

Example 13

Construction of an *Aspergillus oryzae* Expression Vector for the *Thielavia terrestris* Family GH61B, GH61C, Gh61D, GH61E, and GH61G Genes Two synthetic oligonucleotide primers shown below were designed to PCR amplify the *Thielavia terrestris* Family GH61B gene from the genomic clone. An InFusion Cloning Kit (BD Biosciences, Palo Alto, Calif.) was used to clone the fragment directly into the expression vector, pAlLo2, without the need for restriction digests and ligation.

```
Forward primer:
                                        (SEQ ID NO: 48)
5'-ACTGGATTTACCATGAAGTCGTTCACCATTG-3'

Reverse primer:
                                        (SEQ ID NO: 49)
5'-AGTCACCTCTAGTTAGAGGCACTGCGAGTAG-3'
```

Bold letters represent coding sequence. The remaining sequence is homologous to the insertion sites of pAlLo2.

Fifty picomoles of each of the primers above were used in a PCR reaction containing 100 ng of *Thielavia terrestris* genomic clone 15 DNA (prepared as described in Example 2), 1×Pfx Amplification Buffer, 1.5 µl of 10 mM blend of dATP, dTTP, dGTP, and dCTP, 2.5 units of Platinum Pfx DNA Polymerase, 1 µl of 50 mM MgSO$_4$ and 5 µl of 10×pCRx Enhancer Solution in a final volume of 50 µl. The amplification conditions were one cycle at 94° C. for 2 minutes; and 30 cycles each at 94° C. for 15 seconds, 55° C. for 30 seconds, and 68° C. for 3 minutes. The heat block then went to a 4° C. soak cycle.

The reaction products were isolated on a 1.0% agarose gel using TAE buffer where a 3 kb product band was excised from the gel and purified using a QIAquick Gel Extraction Kit according to the manufacturer's instructions.

Figure 19:
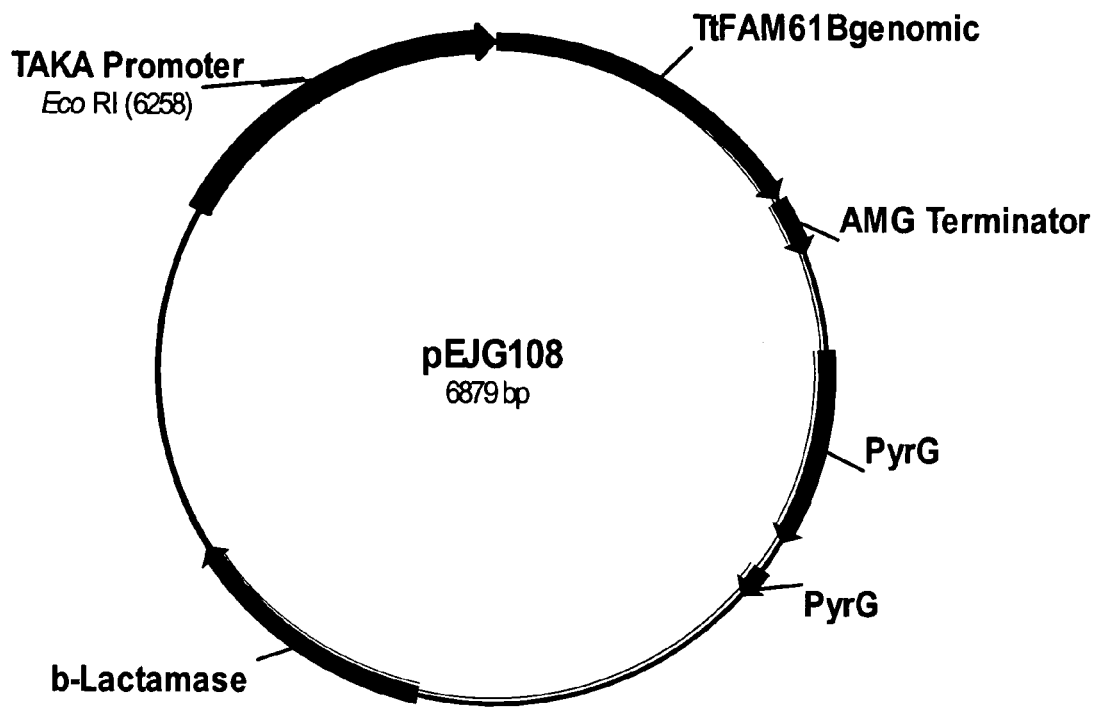
FIG. 19 shows a restriction map of pEJG108.

The fragment was then cloned into the pAlLo2 expression vector using an InFusion Cloning Kit. The vector was digested with restriction endonucleases Nco I and Pac I (using conditions specified by the manufacturer). The fragment was purified by gel electrophoresis and QIAquick gel purification. The gene fragment and the digested vector were ligated together in a reaction resulting in the expression plasmid pEJG108 (FIG. 19) in which transcription of the Family GH61B gene was under the control of the NA2-tpi promoter. The ligation reaction (20 µl) was composed of 1×InFusion Buffer (BD Biosciences, Palo Alto, Calif.), 1×BSA (BD Biosciences, Palo Alto, Calif.), 1 µl of InFusion enzyme (diluted 1:10) (BD Biosciences, Palo Alto, Calif.), 100 ng of pAlLo2 digested with Nco I and Pac I, and 100 ng of the *Thielavia terrestris* GH61B purified PCR product. The reaction was incubated at room temperature for 30 minutes. One µl of the reaction was used to transform *E. coli* XL10 Solopac Gold cells (Stratagene, La Jolla, Calif.). An *E. coli* transformant containing pEJG108 (GH61B gene) was detected by restriction enzyme digestion and plasmid DNA was prepared using a QIAGEN BioRobot 9600.

The *Thielavia terrestris* Family GH61C and GH61D genes were generated in the same manner as described above using the following primers.

```
For Tter61C:
In-Fusion Forward primer
                                        (SEQ ID NO: 50)
5'-ACAACTGGATTTACCATGCGGTTCGACGCCTC-3'

In-Fusion Reverse primer:
                                        (SEQ ID NO: 51)
5'-GTCAGTCACCTCTAGTTACTAAAACTCGAAGCC-3'

For Tter61D
In-Fusion Forward primer
                                        (SEQ ID NO: 52)
5'-ACTGGATTACCATGCTTCTCACATCAG-3'
```

-continued

In-Fusion Reverse primer:
(SEQ ID NO: 53)
5'-AGTCACCTCTAGTTATCAGGCGGTGAAGTC-3'

Bold letters represent coding sequence. The remaining sequence is homologous to the insertion sites of pAlLo2.

E. coli transformants containing the correct recombinant expressions constructs pEJG111 (GH61C gene) and pEJG112 (GH61D gene) were identified by restriction enzyme digestion analysis and plasmid DNA was prepared using a QIAGEN BioRobot 9600.

Two synthetic oligonucleotide primers, shown below, were designed to PCR amplify the full-length open reading frame from *Thielavia terrestris* EST pTter61G encoding the Family GH61G gene. An In-Fusion Cloning Kit (BD Biosciences, Palo Alto, Calif.) was used to clone the fragment directly into pAlLo2.

```
In-Fusion Forward primer:
(SEQ ID NO: 54)
5'-ACTGGATTACCATGAAGGGACTTTTCAGTGC-3'

In-Fusion Reverse primer:
(SEQ ID NO: 55)
5'-TCACCTCTAGTTAATTAATTACAAGCACTGCGAGTAGT-3'
```

Bold letters represent coding sequence. The remaining sequence contains sequence identity compared with the insertion sites of pAlLo2.

Fifty picomoles of each of the primers above were used in a PCR reaction containing 50 ng of pTter61G DNA, 1×Pfx Amplification Buffer, 6 µl of 10 mM blend of dATP, dTTP, dGTP, and dCTP, 2.5 units of Platinum Pfx DNA Polymerase, 1 µl of 50 mM MgSO$_4$, and 5 µl of 10×pCRx Enhancer Solution in a final volume of 50 µl. An Eppendorf Mastercycler 5333 was used to amplify the fragment programmed for one cycle at 98° C. for 2 minutes; and 35 cycles each at 94° C. for 30 seconds, 65° C. for 30 seconds, and 68° C. for 1.5 minutes. After the 35 cycles, the reaction was incubated at 68° C. for 10 minutes and then cooled at 10° C. until further processed. A 1 kb PCR reaction product was isolated on a 0.8% GTG-agarose gel using TAE buffer and 0.1 µg of ethidium bromide per ml. The DNA band was visualized with the aid of a Dark Reader™ to avoid UV-induced mutations. The 1 kb DNA band was excised with a disposable razor blade and purified with an Ultrafree-DA Spin Cup according to the manufacturer's instructions.

Figure 20:
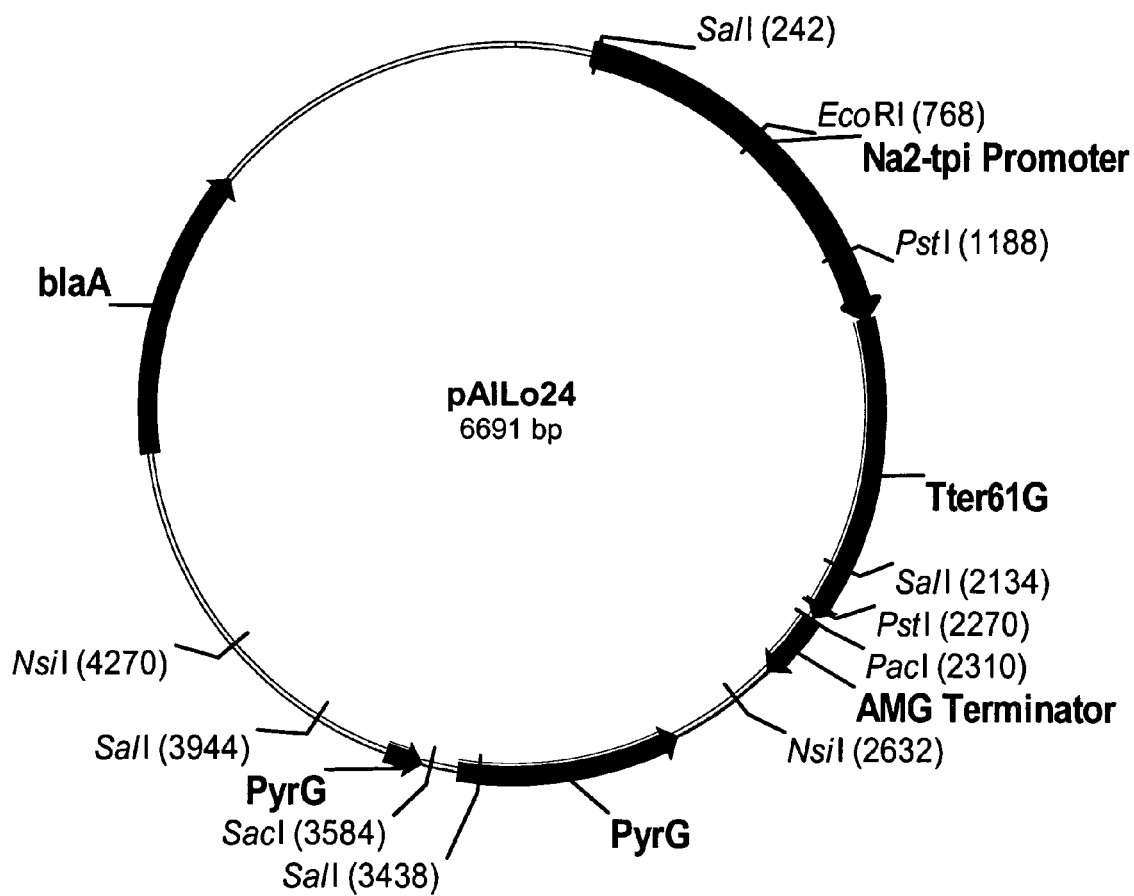
FIG. 20 shows a restriction map of pAlLo24.

The vector pAlLo2 was linearized by digestion with Nco I and Pac I. The fragment was purified by gel electrophoresis and ultrafiltration as described above. Cloning of the purified PCR fragment into the linearized and purified pAlLo2 vector was performed with an InFusion Cloning Kit. The reaction (20 µl) contained of 1×InFusion Buffer, 1×BSA, 1 µl of InFusion enzyme (diluted 1:10), 100 ng of pAlLo2 digested with Nco I and Pac I, and 50 ng of the *Thielavia terrestris* GH61G purified PCR product. The reaction was incubated at room temperature for 30 minutes. Two microliters of the reaction were used to transform E. coli XL10 SoloPac® Gold cells (Stratagene, La Jolla, Calif.) according to the manufacturer's instructions. After the recovery period, two 100 µl aliquots from the transformation reaction were plated onto 150 mm 2×YT plates supplemented with 100 µg of ampicillin per ml. The plates were incubated overnight at 37° C. Six putative recombinant clones were selected at random from the selection plates and plasmid DNA was prepared from each one using a QIAGEN BioRobot 9600. Clones were analyzed by PstI restriction enzyme digestion. Five out of six clones had the expected restriction digest pattern, two clones were then sequenced to confirm that there were no mutations in the cloned insert. Clone #1 was selected and designated pAlLo24 (FIG. 20).

Figure 21:
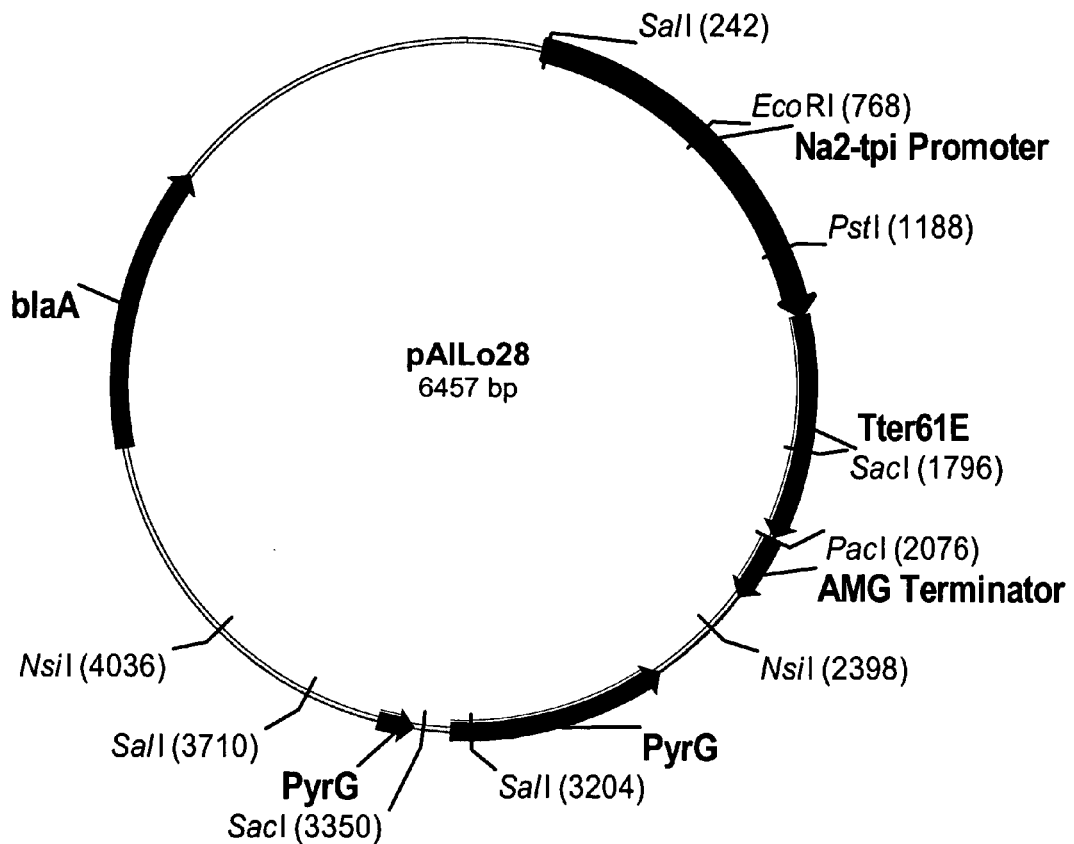
FIG. 21 shows a restriction map of pAlLo28.

The truncated Tter61E gene was PCR amplified with In-Fusion specific primers designed to add the missing 5 nucleotides at its 5' end as described in Example 11. The gel purified band was then cloned into pAlLo2 as described above. Two microliters of the TOPO reaction were transformed into E. coli TOP10 cells according to the manufacturer's instructions. The transformed cells were plated onto 2×YT agar plates supplemented with 100 µg/ml of ampicillin and incubated overnight at 37° C. Eight colonies were selected at random and plasmid DNA was prepared as described above. Clones were analyzed by SacI restriction enzyme digestion. Seven out of eight clones had the expected restriction digest pattern, four clones were then sequenced to confirm that there were no mutations in the cloned insert. Clone #5 was selected and designated pAlLo28 (FIG. 21).

Example 14

Expression of *Thielavia terrestris* Genes Encoding Family GH61B, GH61C, GH61D, GH61E, and GH61G Polypeptides Having Cellulolytic Enhancing Activity in *Aspergillus oryzae* JaL250

*Aspergillus oryzae* JaL250 protoplasts were prepared according to the method of Christensen et al., 1988, *Bio/Technology* 6: 1419-1422. Five µg of pEJG108 (as well as pAlLo2 as a vector control) was used to transform *Aspergillus oryzae* JaL250.

The transformation of *Aspergillus oryzae* JaL250 with pEJG108 (GH61B gene) yielded about 100 transformants. Ten transformants were isolated to individual PDA plates.

Confluent PDA plates of all transformants were washed with 5 ml of 0.01% Tween 80 and inoculated separately into 25 ml of MDU2BP medium in 125 ml glass shake flasks and incubated at 34° C., 200 rpm. Five days after incubation, 5 µl of supernatant from each culture was analyzed using 8-16% Tris-Glycine SDS-PAGE gels (Invitrogen, Carlsbad, Calif.) according to the manufacturer's instructions. SDS-PAGE profiles of the cultures showed that 9 of the 10 transformants had a new major band of approximately 42 kDa.

A confluent plate of transformant 10 (grown on PDA) was washed with 10 ml of 0.01% Tween 20 and inoculated into a 2 liter Fernbach containing 500 ml of MDU2BP medium to generate broth for characterization of the enzyme. The flask was harvested on day 5 and filtered using a 0.22 µm GP Express plus Membrane (Millipore, Bedford, Mass.).

Plasmids pEJG111 (GH61C gene) and pEJG112 (GH61D gene) were expressed in *Aspergillus oryzae* JaL250 using the same protocol described above.

*Aspergillus oryzae* Jal250 (WO 99/61651) protoplasts were prepared according to the method of Christensen et al., 1988, supra. Five micrograms of pAlLo24 and pAlLo28 (as well as pAlLo2 as a vector control) were used to transform *Aspergillus oryzae* JaL250 protoplasts.

The transformations of *Aspergillus oryzae* Jal250 yielded about 50 transformants per expression construct. Eight transformants were isolated from each transformation to individual PDA plates and incubated for five days at 34° C.

Confluent spore plates were washed with 3 ml of 0.01% Tween 80 and the spore suspension was used to inoculate 25 ml of MDU2BP medium in 125 ml glass shake flasks. Transformant cultures were incubated at 34° C. with constant shaking at 200 rpm. At day five post-inoculation, cultures were centrifuged at 6000×g and their supernatants collected. Five micro-liters of each supernatant were mixed with an equal volume of 2×loading buffer (10% 1-mercaptoethanol) and loaded onto a 1.5 mm 8%-16% Tris-Glycine SDS-PAGE gel and stained with Simply Blue SafeStain (Invitrogen, Carlsbad, Calif.). SDS-PAGE profiles of the culture broths showed that seven out of eight pAlLo24 transformants had a new protein band of approximately 45 kDa. This new protein runs on SDS-polyacrylamide gels as a fat smear rather than a well-defined band, suggesting the presence of multiple forms maybe due to post-translational modifications like glycosylation. This type of modifications would explain the difference between the deduced molecular weight of the *T. terrestris* GH61G—33.7 kDa—and the apparent molecular weigh of the new protein present on these transformants. Clone #3 was selected for further studies. In the case of the pAlLo28 transformants 6 out of eight pAlLo28 transformants had a new protein band of approximately 25 kDa very close to the calculated weight for the mature protein of 22.5 kDa.

Example 15

Construction of pMJ09

Vector pMJ04 was constructed by PCR amplifying the *Trichoderma reesei* Cel7A cellobiohydrolase 1 gene (cbh1) terminator from *Trichoderma reesei* RutC30 genomic DNA using primers 993429 (antisense) and 993428 (sense) shown below. The antisense primer was engineered to have a PacI site at the 5'-end and a SpeI site at the 5'-end of the sense primer.

```
Primer 993429 (antisense):
                             (SEQ ID NO: 56)
5'-AACGTTAATTAAGGAATCGTTTTGTGTTT-3'

Primer 993428 (sense):
                             (SEQ ID NO: 57)
5'-AGTACTAGTAGCTCCGTGGCGAAAGCCTG-3'
```

The amplification reactions (50 μl) were composed of 1×ThermoPol Reaction Buffer (New England BioLabs, Beverly, Mass.), 0.3 mM dNTPs, 100 ng of *Trichoderma reesei* RutC30 genomic DNA (which was isolated using a DNeasy Plant Maxi Kit, QIAGEN Inc., Valencia, Calif.), 0.3 μM primer 993429, 0.3 μM primer 993428, and 2 units of Vent polymerase (New England BioLabs, Beverly, Mass.). The reactions were incubated in an Eppendorf Mastercycler 5333 programmed as follows: 30 cycles each for 30 seconds at 94° C., 30 seconds at 55° C., and 30 seconds at 72° C. (15 minute final extension).

The reaction products were isolated on a 1.0% agarose gel using TAE buffer where a 229 bp product band was excised from the gel and purified using a QIAGEN QIAquick Gel Extraction Kit according to the manufacturer's instructions.

Figure 22:
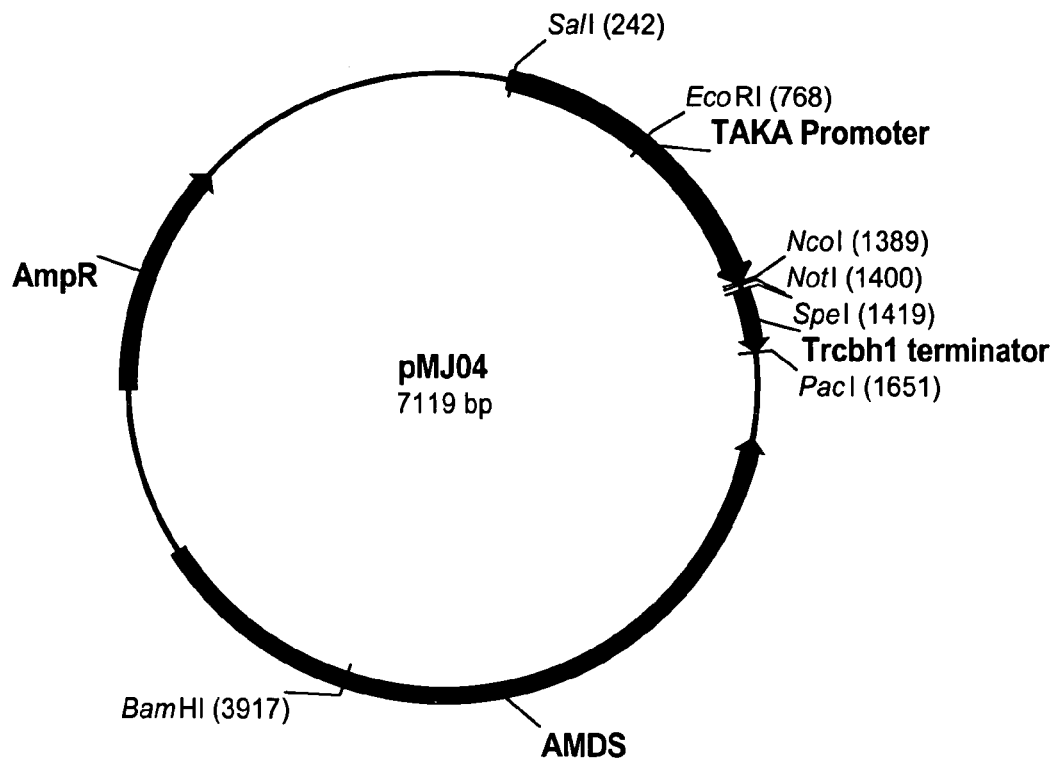
FIG. 22 shows a restriction map of pMJ04.

The resulting PCR fragment was digested with PacI and SpeI and ligated into pAlLo1 digested with the same restriction enzymes using a Rapid Ligation Kit (Roche, Indianapolis, Ind.), to generate pMJ04 (FIG. 22).

Vector pMJ06 was constructed by PCR amplifying the *Trichoderma reesei* Cel7A cellobiohydrolase 1 gene (cbh1) promoter from *Trichoderma reesei* RutC30 genomic DNA using primers 993696 (antisense) and 993695 (sense) shown below. The antisense primer was engineered to have a SalI site at the 5'-end of the sense primer and an NcoI site at the 5'-end of the antisense primer.

```
Primer 993695 (sense):
5'-ACTAGTCGACCGAATGTAGGATTGTT-3'   (SEQ ID NO: 58)

Primer 993696 (antisense):
5'-TGACCATGGTGCGCAGTCC-3'          (SEQ ID NO: 59)
```

The amplification reactions (50 μl) were composed of 1×ThermoPol Reaction Buffer, 0.3 mM dNTPs, 100 ng *Trichoderma reesei* RutC30 genomic DNA (which was prepared using a QIAGEN DNeasy Plant Maxi Kit), 0.3 μM primer 993696, 0.3 μM primer 993695, and 2 units of Vent polymerase. The reactions were incubated in an Eppendorf Mastercycler 5333 programmed as follows: 30 cycles each for 30 seconds at 94° C., 30 seconds at 55° C., and 60 seconds at 72° C. (15 minute final extension).

The reaction products were isolated on a 1.0% agarose gel using TAE buffer where a 988 bp product band was excised from the gel and purified using a QIAGEN QIAquick Gel Extraction Kit according to the manufacturer's instructions.

Figure 23:
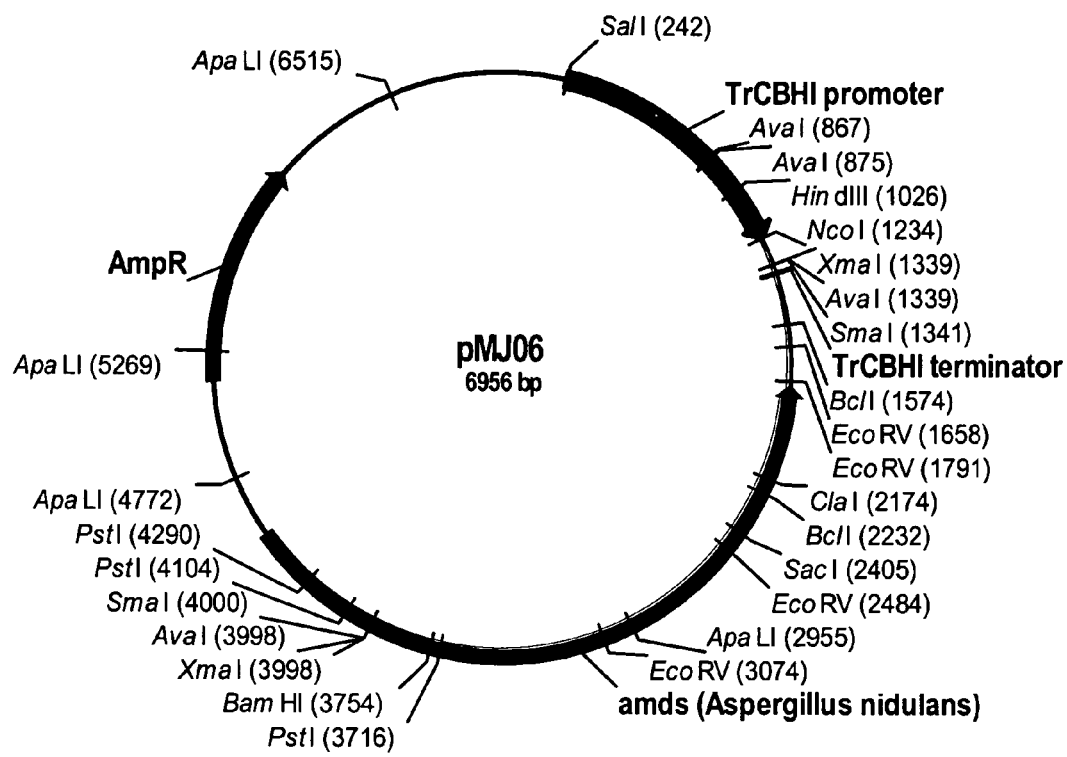
FIG. 23 shows a restriction map of pMJ06.

The resulting PCR fragment was digested with NcoI and SalI and ligated into pMJ04 digested with the same restriction enzymes, using a Rapid Ligation Kit, to generate pMJ06 (FIG. 23).

Expression vector pMJ09 was constructed by PCR amplifying the *Trichoderma reesei* Cel7A cellobiohydrolase 1 gene (cbh1) terminator from *Trichoderma reesei* RutC30 genomic DNA using primers 993843 (antisense) and 99344 (sense) shown below. The antisense primer was engineered to have a Pac I and a Spe I sites at the 5'-end and a PvuI site at the 5'-end of the sense primer.

```
Primer 993844 (sense):
5'-CGATCGTCTCCCTATGGGTCATTACC-3'   (SEQ ID NO: 60)

Primer 993843 (antisense):
5'-ACTAGTTAATTAAGCTCCGTGGCGAAAG-3' (SEQ ID NO: 61)
```

The amplification reactions (50 μl) were composed of 1×ThermoPol Reaction Buffer, 0.3 mM dNTPs, 100 ng of *Trichoderma reesei* RutC30 genomic DNA (which was extracted using a QIAGEN DNeasy Plant Maxi Kit), 0.3 μM primer 993844, 0.3 μM primer 993843, and 2 units of Vent polymerase. The reactions were incubated in an Eppendorf Mastercycler 5333 programmed as follows: 30 cycles each for 30 seconds at 94° C., 30 seconds at 55° C., and 60 seconds at 72° C. (15 minute final extension).

The reaction products were isolated on a 1.0% agarose gel using TAE buffer where a 473 bp product band was excised from the gel and purified using a QIAGEN QIAquick Gel Extraction Kit according to the manufacturer's instructions.

Figure 24:
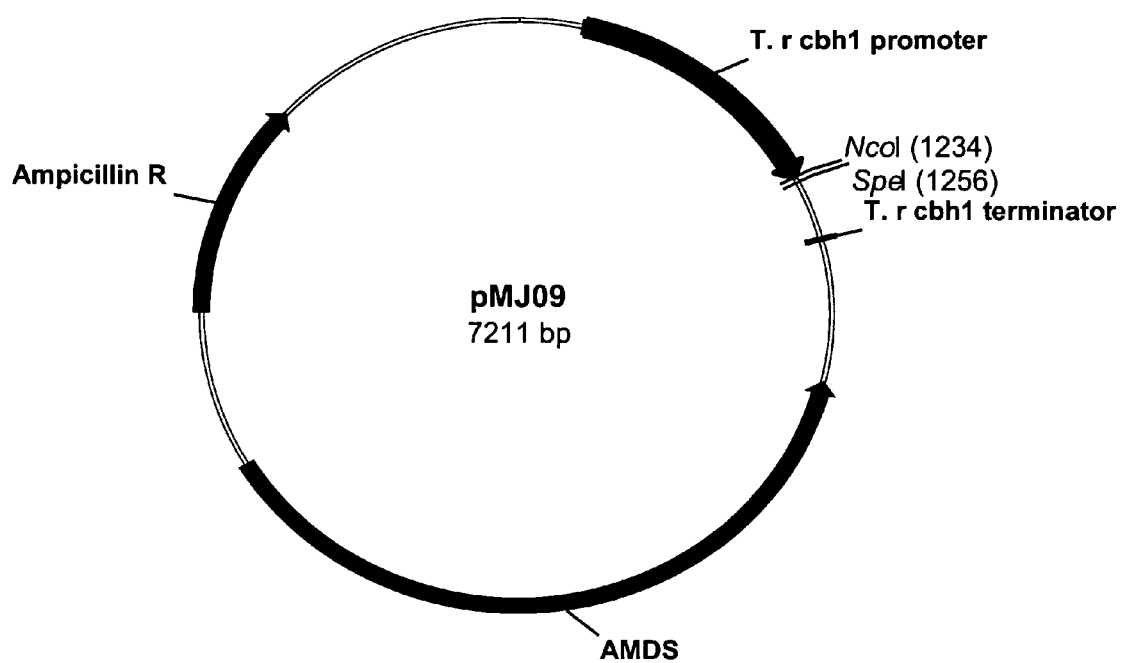
FIG. 24 shows a restriction map of pMJ09.

The resulting PCR fragment was digested with Pvu I and Spe I and ligated into pMJ06 digested with Pac I and Spe I using a Rapid Ligation Kit to generate pMJ09 (FIG. 24).

Example 16

Construction of Expression Vector pSMAi155

Based on the *E. coli* hpt gene found in plasmid pPHTI (Cummings et al., 1999, *Current Genetics* 36: 371-82) the following primers were designed for amplification:

```
Forward (993863):
5'-GGGttcgaaTTCATTTAAACGGCT-3'    (SEQ ID NO: 62)
    Bst BI Reverse (993864):
5'-GGGagcgctCAATATTCATCTCTC-3'    (SEQ ID NO: 63)
    Eco 47III
```

Figure 25:
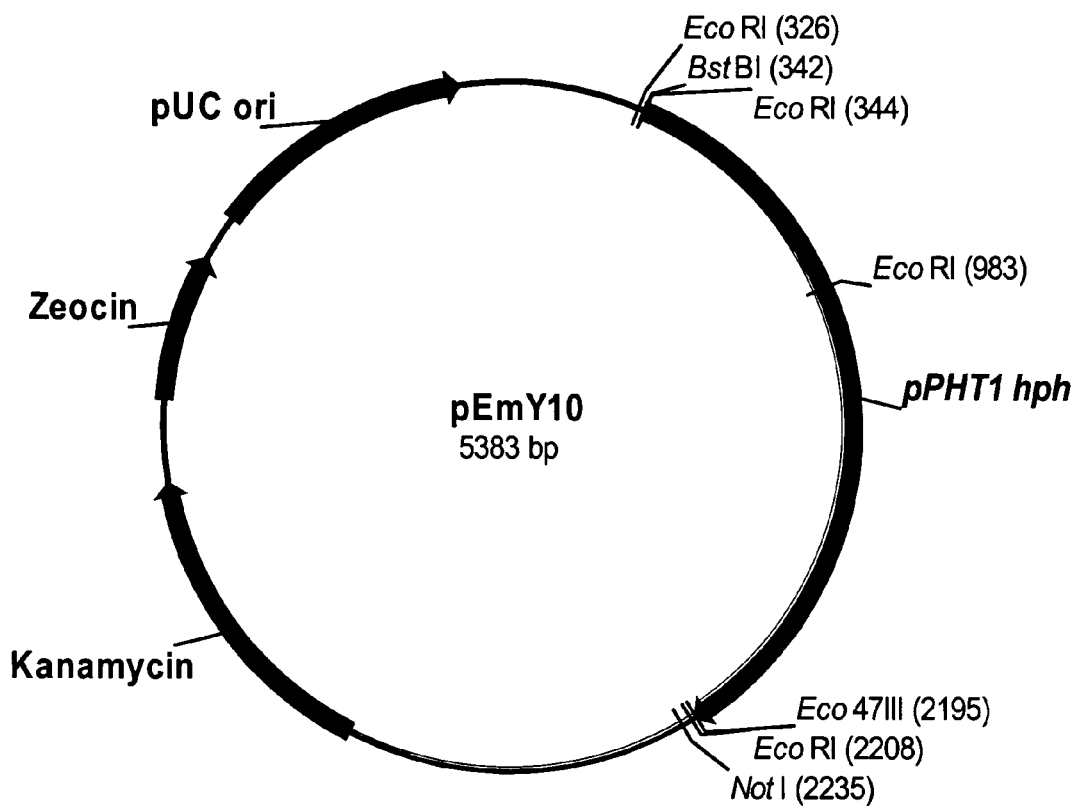
FIG. 25 shows a restriction map of pEmY10.

The Vent® DNA Polymerase System (New England BioLabs, Inc., Beverly, Mass.) was utilized to amplify the gene of interest under the following gradient thermocycling conditions using a Robocycler Gradient 40 (Stratagene, La Jolla, Calif.): a cycle at 95° C. for 2 minutes; 25 cycles each at 95° C. for 1 minutes, 51° C.-65° C. for 1 minutes, and 72° C. for 2 minutes; and 1 cycle at 72° C. for 7 minutes. The resulting 1.8 kb fragment was successfully amplified at 51° C. annealing temperature and gel purified using a QIAquick Gel Extraction Kit. The gel purified fragment was then cloned into pCR-BluntII-TOPO (Invitrogen, Carlsbad, Calif.) creating pEmY10 (FIG. 25).

Plasmid pMJ09 was digested with Nsi I to remove the amdS marker gene. The digest was fractionated on a 0.7% agarose gel using TAE buffer and a 3.9 kb band excised and purified using a QIAquick Gel Extraction Kit according to the manufacturer's suggested protocol. The vector was dephosphorylated using shrimp alkaline phosphatase (Roche Diagnostics Corporation, Indianapolis, Ind.) according to the manufacturer's protocol. The hygromycin resistance gene was removed from plasmid pEmY10 by digestion with NsiI and a 2.0 kb fragment purified as above. This fragment was ligated with the 3.9 kb fragment from pMJ09. The ligation mix was transformed into E. coli SURE cells (Stratagene, La Jolla, Calif.), and eight resulting colonies were screened for correct ligation by restriction analysis and DNA sequencing. One of the verified clones was designated pSMai149. The Nco I site in the hygromycin resistance gene was removed from pSMai149 using the Quickchange Site-Directed Mutagenesis Kit (Stratagene, La Jolla, Calif.) according to the manufacturer's protocol. The mutagenesis/amplification primers had the following sequences, where the underlined G represents the site of mutation.

```
5'-GGTCGCGGAGGCGATGGATGCGATCG-3'    (SEQ ID NO: 64)

5'-CGATCGCATCCATCGCCTCCGCGACC-3'    (SEQ ID NO: 65)
```

Figure 26:
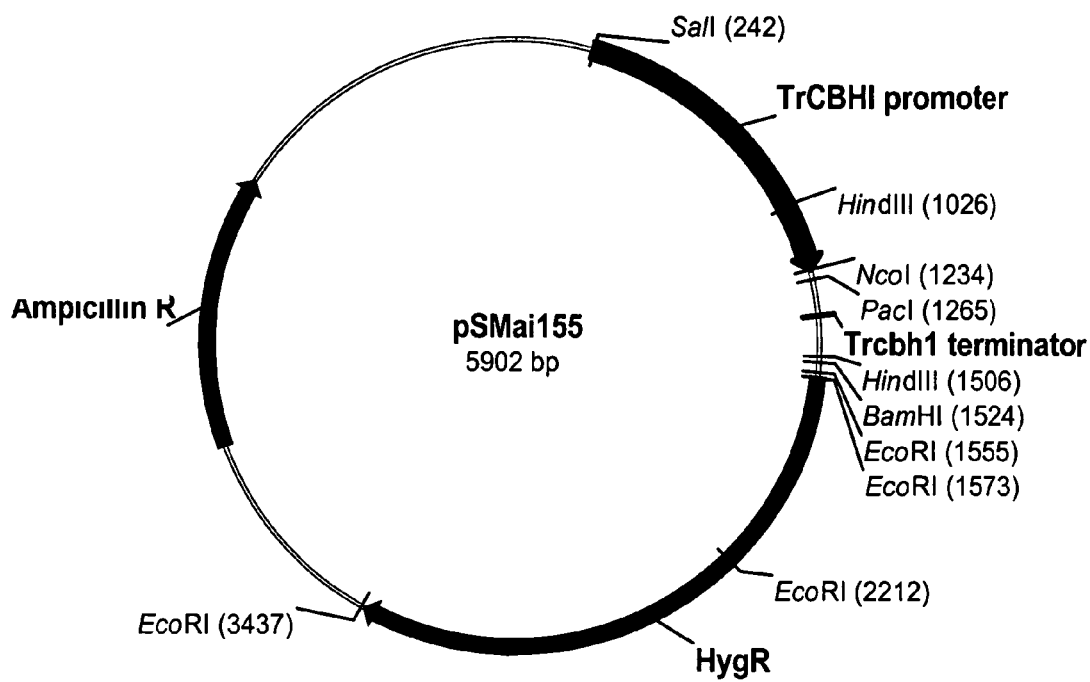
FIG. 26 shows a restriction map of pSMAI155.

Eight randomly selected colonies were screened by digestion with NcoI, and one of these, designated clone 7, that showed loss of the NcoI site was further verified by DNA sequencing and designated pSMai155 (FIG. 26).

Example 17

Expression of *Thielavia terrestris* Genes Encoding a Family GH61B, GH61C, GH61D, GH61E, and GH61G Polypeptides Having Cellulolytic Enhancing Activity in *Trichoderma reesei*

Two synthetic oligonucleotide primers shown below were designed to PCR amplify a *Thielavia terrestris* gene encoding a putative Family GH61B from the genomic clone. An InFusion Cloning Kit was used to clone the fragment directly into the expression vector, pSMAI155, without the need for restriction digests and ligation.

```
Forward primer:
                                   (SEQ ID NO: 66)
5'-cgcggactgcgcaccATGAAGTCGTTCACCATTG-3'

Reverse primer:
                                   (SEQ ID NO: 67)
5'-tcgccacggagcttaGAGGCACTGCGAGTAG-3'
```

Bold letters represent coding sequence. The remaining sequence is homologous to the insertion sites of pSMAI155 clone 7.

Fifty picomoles of each of the primers above were used in a PCR reaction containing 10 ng of *Thielavia terrestris* genomic clone 15 DNA, 1×Pfx Amplification Buffer, 1.5 µl of 10 mM blend of dATP, dTTP, dGTP, and dCTP, 2.5 units of Platinum Pfx DNA Polymerase, 1 µl of 50 mM MgSO$_4$ and 5 µl of 10×pCRx Enhancer Solution in a final volume of 50 µl. The amplification conditions were one cycle at 94° C. for 2 minutes; and 30 cycles each at 94° C. for 15 seconds, 55° C. for 30 seconds, and 68° C. for 3 minutes. The heat block then went to a 4° C. soak cycle.

The reaction products were isolated on a 1.0% agarose gel using TAE buffer where a 3 kb product band was excised from the gel and purified using a QIAquick Gel Extraction Kit according to the manufacturer's instructions.

Figure 27:
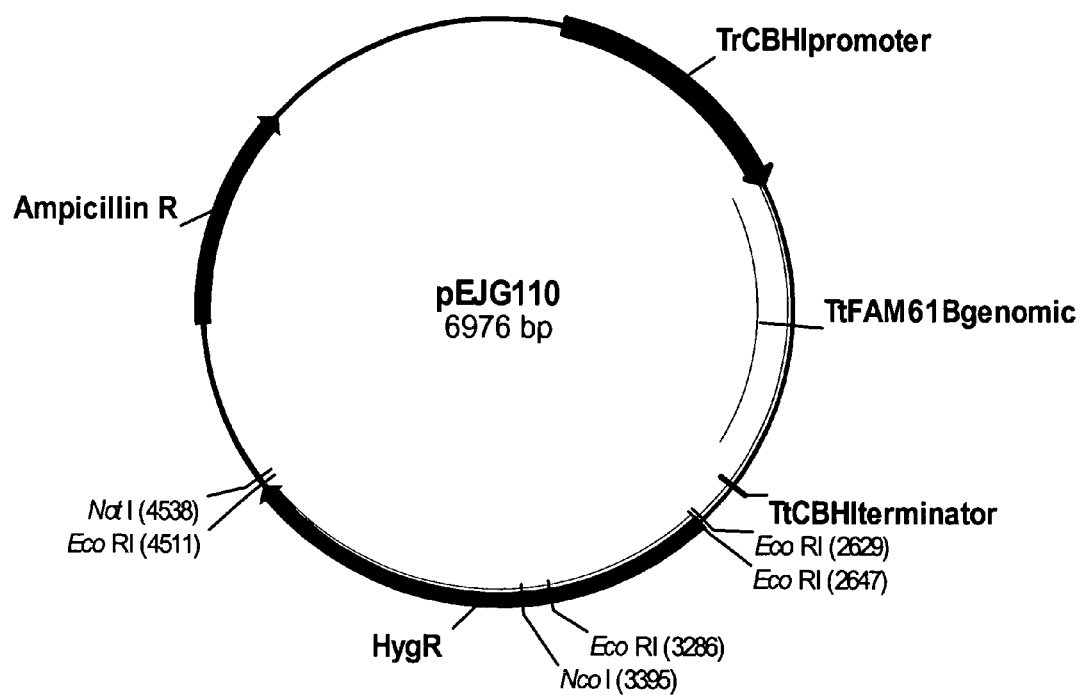
FIG. 27 shows a restriction map of pEJG110.

The fragment was then cloned into the pSMAI155 expression vector using an InFusion Cloning Kit. The vector was digested with restriction endonucleases NcoI and PacI. The fragment was purified by gel electrophoresis and QIAquick gel purification. The gene fragment and the digested vector were ligated together in a reaction resulting in the expression plasmid pEJG110 (FIG. 27) in which transcription of the Family GH61B gene was under the control of the *Trichoderma reesei* CBHI promoter and terminator. The ligation reaction (20 µl) was composed of 1×InFusion Buffer, 1×BSA (BD Biosciences, Palo Alto, Calif.), 11 µl of InFusion enzyme (diluted 1:10), 100 ng of pSma155 digested with Nco I and Pac I, and 100 ng of the *Thielavia terrestris* GH61B purified PCR product. The reaction was incubated at room temperature for 30 minutes. One µl of the reaction was used to transform E. coli XL10 Solopac Gold cells (Stratagene, La Jolla, Calif.). An E. coli transformant containing the pEJG110 plasmid was detected by restriction enzyme digestion and plasmid DNA was prepared using a QIAGEN BioRobot 9600.

DNA sequencing of pEJG110 was performed with an Applied Biosystems Model 3700 Automated DNA Sequencer using version 3.0 Big-Dye™ terminator (Applied Biosystems, Inc., Foster City, Calif.) and primer walking strategy. Nucleotide sequence data were scrutinized for quality and all sequences were compared to each other with assistance of PHRED/PHRAP software (University of Washington, Seattle, Wash.).

For expression in *T. reesei* the Tter61E gene was PCR amplified from its expression construct pAlLo28 with the following primers.

```
Forward Primer:
5'-GCCCATGGACCATGCTCGCAAAC-3'    (SEQ ID NO: 68)

Reverse Primer:
5'-CCTCTAGTTAATTAATCAGCAGC-3'    (SEQ ID NO: 69)
```

Likewise the Tter61G gene was PCR amplified from its expression construct pAlLo24 with the following primers.

```
Forward Primer:
5'-GCCCATGGACCATGAAGGGACTT-3'    (SEQ ID NO: 70)

Reverse Primer:
5'-CCTCTAGTTAATTAATTACAAGC-3'    (SEQ ID NO: 71)
```

Both experiments were carried as follows:

Fifty picomoles of each of the primers above were used in a PCR reaction containing 50 ng of pAlLo28 DNA, 1 µl of 10 mM blend of dATP, dTTP, dGTP, and dCTP, 5 µl of 10×AmpliTaq® DNA Polymerase Buffer I (Perkin-Elmer/Applied Biosystems, Inc., Foster City, Calif.), and 5 units of AmpliTaq® DNA Polymerase (Perkin-Elmer/Applied Biosystems, Inc., Foster City, Calif.), in a final volume of 50 µl. An Eppendorf Mastercycler 5333 was used to amplify the DNA fragment and was programmed for one cycle at 95° C. for 3 minutes; and 25 cycles each at 95° C. for 45 seconds, 55° C. for 60 seconds, and 72° C. for 1 minute 30 seconds. After the 25 cycles, the reaction was incubated at 72° C. for 10 minutes and then cooled at 4° C. until further processed. A PCR reaction product of approximately 681 bases was isolated on a 0.8% GTG-agarose gel using TAE buffer and 0.1 µg of ethidium bromide per ml. The DNA band was visualized with the aid of a Dark Reader™ to avoid UV-induced mutations. The appropriate DNA band was excised with a disposable razor blade and purified with a QIAquick PCR Purification Kit according to the manufacture's instructions. The purified DNA band was cloned into the pCR2.1-TOPO vector according to the manufacture's instructions (Invitrogen, Carlsbad, Calif.). Two microliters of the TOPO-reaction were transformed into *E. coli* TOP10 cells according to the manufacture's instructions. The transformed cells were plated onto 2×YT agar plates supplemented with 100 µg/ml of ampicillin and incubated overnight at 37° C. Eight colonies were selected at random for plasmid DNA preparation. Each colony was grown overnight on 3 ml of LB medium supplemented with 100 µg of ampicillin per ml and used to prepare plasmid DNA with a QIAGEN BioRobot 9600. The plasmid DNA was analyzed by restriction mapping to identify clones positive for GH61E or GH61G insertion using restriction endonucleases Pac I and Nco I. Once a clone was validated that there was successful insertion of the GH61E or GH61G gene, the clone was sequenced for fidelity using BigDye Terminator Version 3 and analyzed using ABI 3700 DNA Analyzer (Foster City, Calif.) according the manufacturer's instructions.

The *E. coli* TOPO clone DNA containing the confirmed GH61E or GH61G sequence was digested with PacI and NcoI and the reaction product was then resolved on a 0.8% agarose gel. The appropriate DNA band was excised with a disposable razor blade and purified with a QIAquick PCR Purification Kit according to the manufacture's instructions.

Plasmid pSMai155 was digested in the same manner with PacI and NcoI to create compatible ends with the GH61 fragments. The digestion product was resolved on a 0.8% agarose gel and the linear plasmid was excised and purified using QIAquick PCR Purification Kit according to the manufacture's instructions.

The Pac I/Nco I GH61E or GH61G gene fragment was ligated into the Pac I/Nco I digested pSMai155 plasmid using the Rapid DNA Ligation Kit (Roche, Indianapolis, Ind.) following the manufacturer's instructions. This ligation was then used to transform *E. coli* SURE cells following the manufacturer's instructions. Colonies were selected, cultured, and plasmid was prepared as described above. The plasmid DNA was analyzed by restriction mapping to identify clones positive for GH61E or GH61G insertion using PacI and NcoI. One of the clones that had the correct restriction pattern for the GH61E gene was designated pCW095 and one that had the correct pattern for the GH61G gene was designated pCW096.

Figure 28:
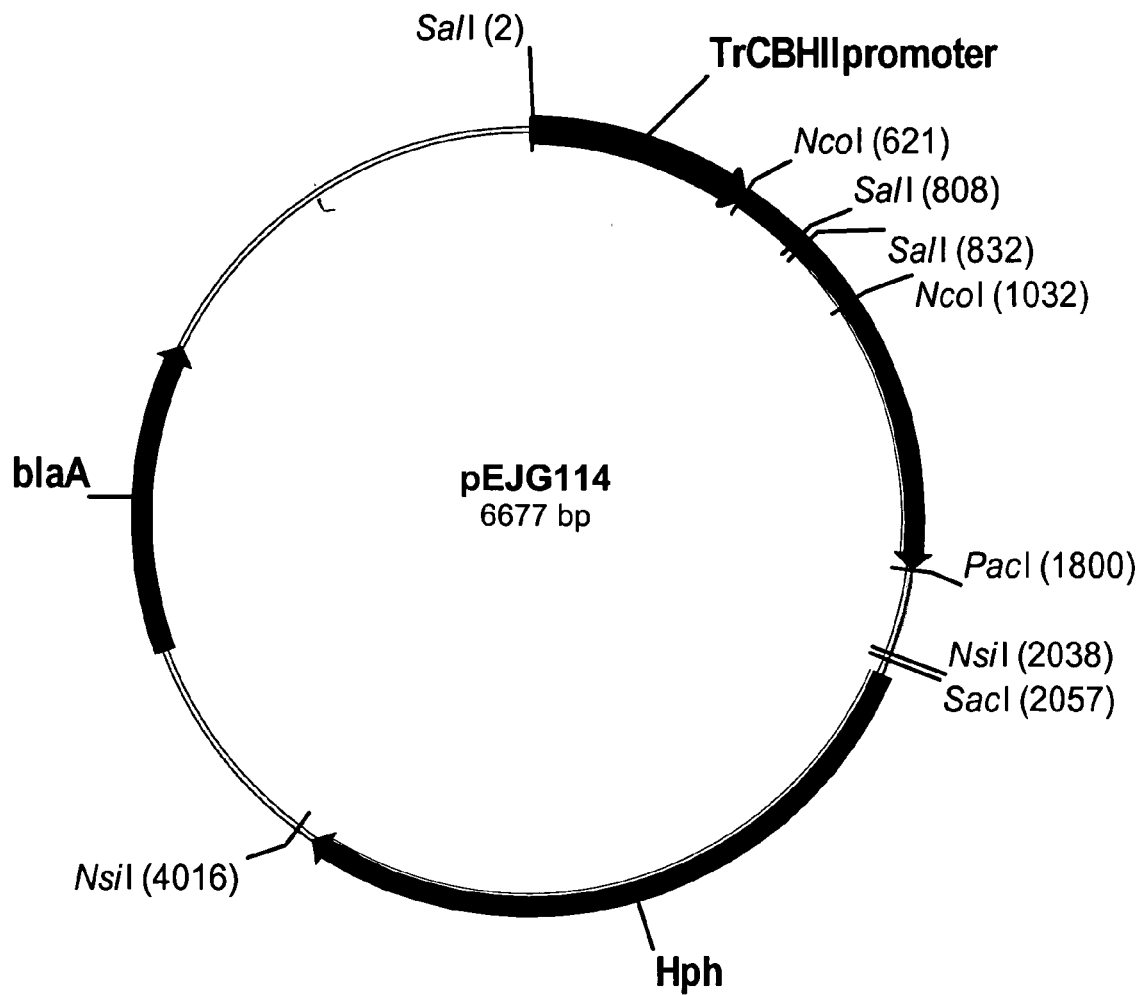
FIG. 28 shows a restriction map of pEJG114.

An expression vector, pCW076, was created to utilize the *Trichoderma reesei* CBHII promoter for gene expression. Expression vector pSMai155 was digested with restriction endonucleases Sal I and Nco I to remove the CBHI promoter fragment. Expression construct pEJG114 (FIG. 28) was also digested with Sal I and Nco I to isolate the CBHII promoter for ligation into the Sal I/Nco I digested pSMai155 plasmid.

Figure 29:
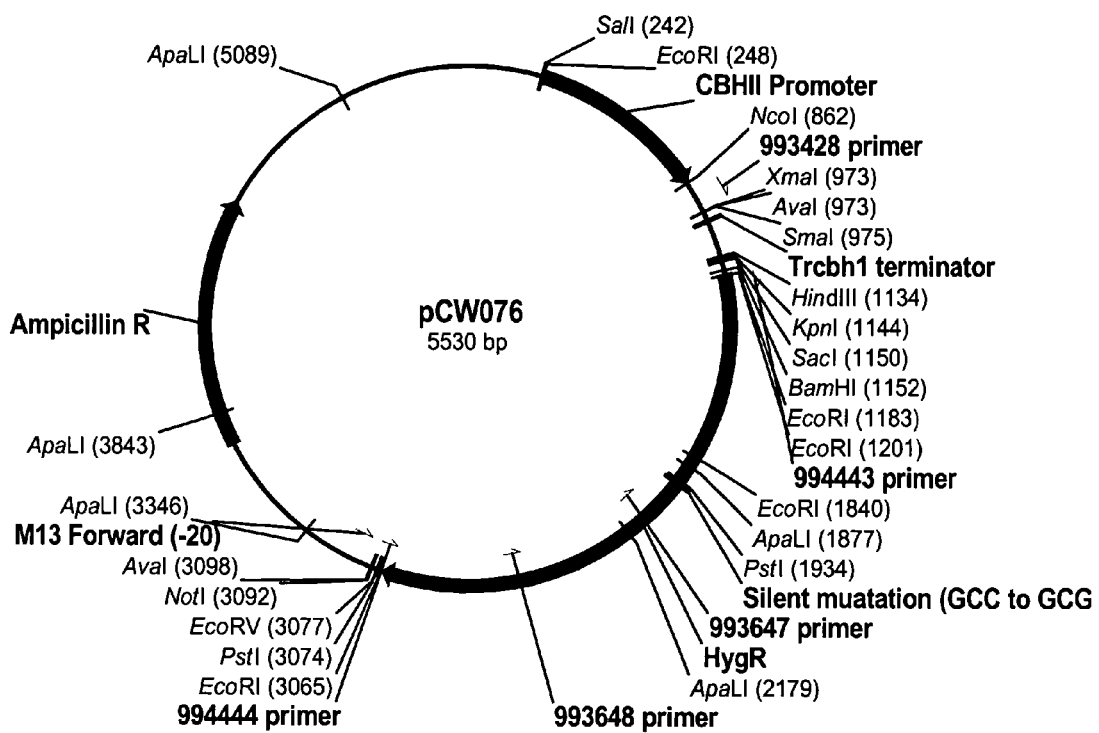
FIG. 29 shows a restriction map of pCW076.

The Sal I/Nco I CBHII promoter was ligated into the SalI/NcoI digested pSMai155 using the Rapid DNA Ligation Kit following the manufacturer's instructions. This ligation was then used to transform *E. coli* SURE Cells following the manufacturer's instructions. Colonies were selected, cultured, and plasmid was prepared as described above. The plasmid DNA was analyzed by restriction enzyme digestion to identify clones positive for CBHII promoter insertion using Sal I and Nco I. These clones were then sequenced using primer TrCBH2PrSeqF1, shown below, to confirm the presence of the CBHII promoter. One of the clones that had the correct sequence was designated pCW076 (FIG. 29).

```
TrCBH2PrSeqF1:
5'-GGATGAAGCTCATTAGCCG-3'    (SEQ ID NO: 72)
```

For expression in *Trichoderma reesei* the Tter61D gene was isolated from pTter61D (as described in Example 7 using restriction endonucleases Pac I and Nco I). Plasmid pCW076 was digested in the same manner with Pac I and Nco I to create compatible ends with the GH61D fragment. The digestion products were resolved on a 0.8% agarose gel using TAE buffer and the linear fragments were excised and purified using a QIAquick PCR Purification Kit according to the manufacture's instructions.

Figure 30:
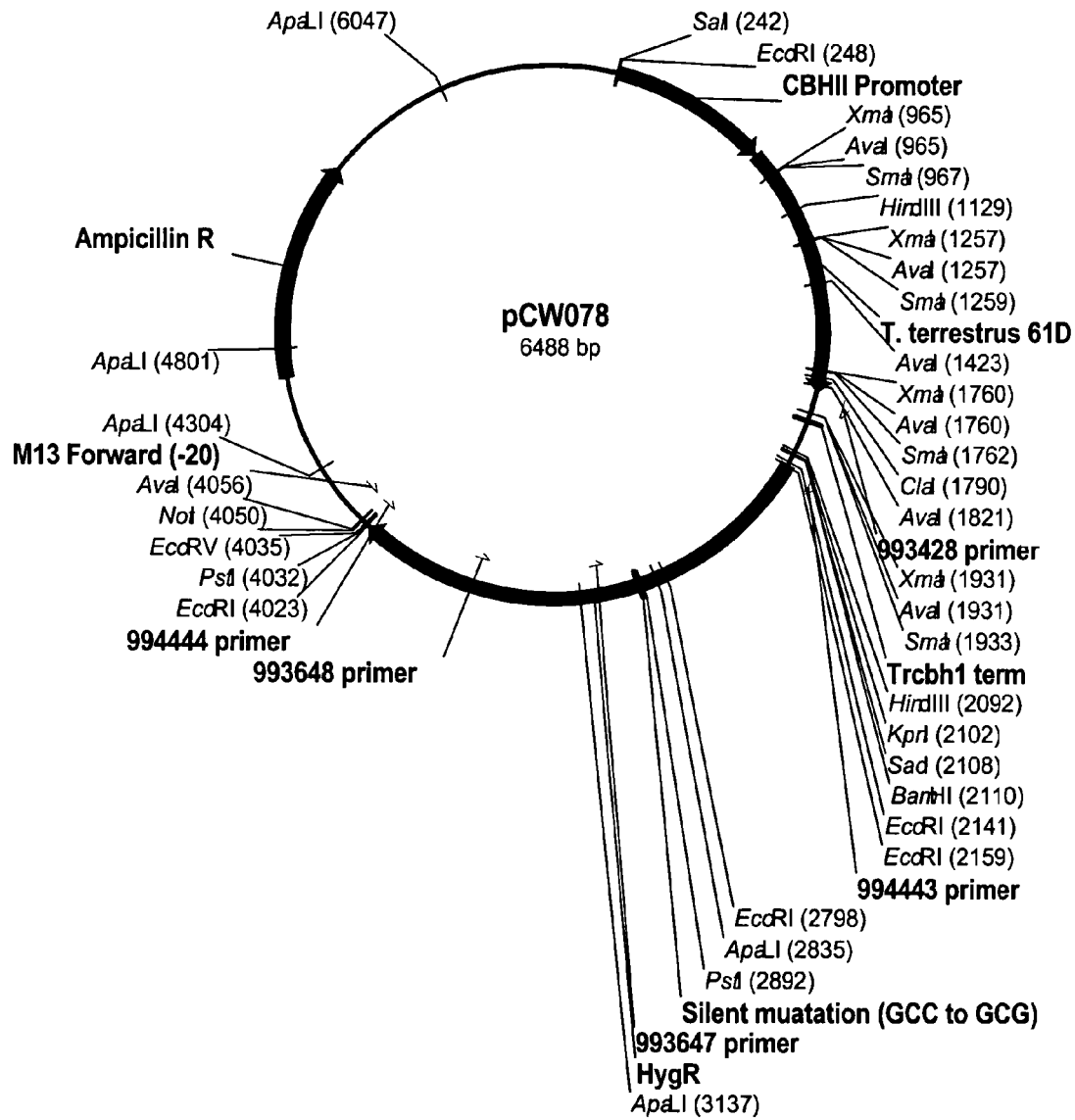
FIG. 30 shows a restriction map of pCW078.

The Pac I/Nco I GH61D gene fragment was ligated into Pac I/Nco I digested pCW076 using the Rapid DNA Ligation Kit following the manufacturer's instructions. One microliter of the ligation reaction was then used to transform *E. coli* SURE Cells following the manufacturer's instructions. Colonies were selected, cultured, and plasmid was prepared as described above. The plasmid DNA was analyzed by restriction enzyme digestion to identify clones positive for GH61D insertion using Pac I and Nco I. One of the clones that had the correct restriction pattern was designated pCW078 (FIG. 30).

*Trichoderma reesei* RutC30 protoplasts were prepared according to the method of Christensen et al., 1988, supra. Five µg of pEJG110, pCW095, pCW096, or pCW078 were used to transform *Trichoderma reesei* RutC30. Each individual transformation yielded about 100 transformants. Sixty transformants were isolated, from each transformation, to individual Cove/10 mM uridine plates and incubated at 28° C. for seven days.

Transformant strains were analyzed in batches of eight at a time. Spores were collected from eight individual plates with a sterile loop, inoculated separately into 25 ml of CIM medium in 125 ml glass shake flasks and incubated at 28° C., 250 rpm. Five days post-inoculation, 0.5 µl of supernatant from each culture was analyzed using 7.5% Tris SDS-PAGE gels (BioRad, Hercules, Calif.) according to the manufacturer's instructions. SDS-PAGE profiles of the cultures showed that 20% to 50% of the transformants produced a new protein band corresponding to the newly introduced gene. An appropriate transformant was selected from each expression construct for further studies.

Example 18

Identification of a Beta-glucosidase Family GH3A Gene in the Genomic Sequence of *Aspergillus fumigatus*

A Blast search (Altschul et al., 1997, *Nucleic Acids Res.* 25: 3389-3402) of the *Aspergillus fumigatus* partial genome sequence (The Institute for Genomic Research, Rockville, Md.) was carried out using as query a beta-glucosidase protein sequence from *Aspergillus aculeatus* (Accession No. P48825). Several genes were identified as putative Family GH3A homologs based upon a high degree of similarity to the query sequence at the amino acid level. One genomic region of approximately 3000 bp with greater than 70% identity to the query sequence at the amino acid level was chosen for further study.

Example 19

*Aspergillus fumigatus* Genomic DNA Extraction

*Aspergillus fumigatus* was grown in 250 ml of potato dextrose medium in a baffled shake flask at 37° C. and 240 rpm. Mycelia were harvested by filtration, washed twice in TE (10 mM Tris-1 mM EDTA), and frozen under liquid nitrogen. Frozen mycelia were ground, by mortar and pestle, to a fine powder, which was resuspended in pH 8.0 buffer containing 10 mM Tris, 100 mM EDTA, 1% Triton X-100, 0.5 M guanidine-HCl, and 200 mM NaCl. DNase-free RNase A was added at a concentration of 20 mg/liter and the lysate was incubated at 37° C. for 30 minutes. Cellular debris was removed by centrifugation, and DNA was isolated using a Maxi 500 column (QIAGEN Inc., Valencia, Calif.). The columns were equilibrated in 10 ml of QBT washed with 30 ml of QC, and eluted with 15 ml of QF (all buffers from QIAGEN Inc., Valencia, Calif.). DNA was precipitated in isopropanol, washed in 70% ethanol, and recovered by centrifugation. The DNA was resuspended in TE buffer.

Example 20

Cloning of the Family GH3A Beta-glucosidase Gene and Construction of an *Aspergillus oryzae* Expression Vector Two synthetic oligonucleotide primers shown below were designed to PCR amplify the *Aspergillus fumigatus* gene encoding the Family GH3A beta-glucosidase from the genomic DNA prepared in Example 19. An InFusion Cloning Kit was used to clone the fragment directly into the expression vector, pAILo2, without the need for restriction digests and ligation.

```
Forward primer:
                                          (SEQ ID NO: 73)
5'-ACTGGATTTACCATGAGATTCGGTTGGCTCG-3'

Reverse primer:
                                          (SEQ ID NO: 74)
5'-AGTCACCTCTAGTTACTAGTAGACACGGGGC-3'
```

Bold letters represent coding sequence. The remaining sequence is homologous to the insertion sites of pAILo2.

Fifty picomoles of each of the primers above were used in a PCR reaction containing 100 ng of *Aspergillus fumigatus* genomic DNA, 1×Pfx Amplification Buffer, 1.5 µl of 10 mM blend of dATP, dTTP, dGTP, and dCTP, 2.5 units of Platinum Pfx DNA Polymerase, 1 µl of 50 mM MgSO$_4$, and 2.5 µl of 10×pCRx Enhancer Solution in a final volume of 50 µl. The amplification conditions were one cycle at 94° C. for 2 minutes; and 30 cycles each at 94° C. for 15 seconds, 55° C. for 30 seconds, and 68° C. for 3 minutes. The heat block then went to a 4° C. soak cycle.

The reaction products were isolated on a 1.0% agarose gel using TAE buffer where a 3 kb product band was excised from the gel and purified using a QIAquick Gel Extraction Kit according to the manufacturer's instructions.

Figure 31:
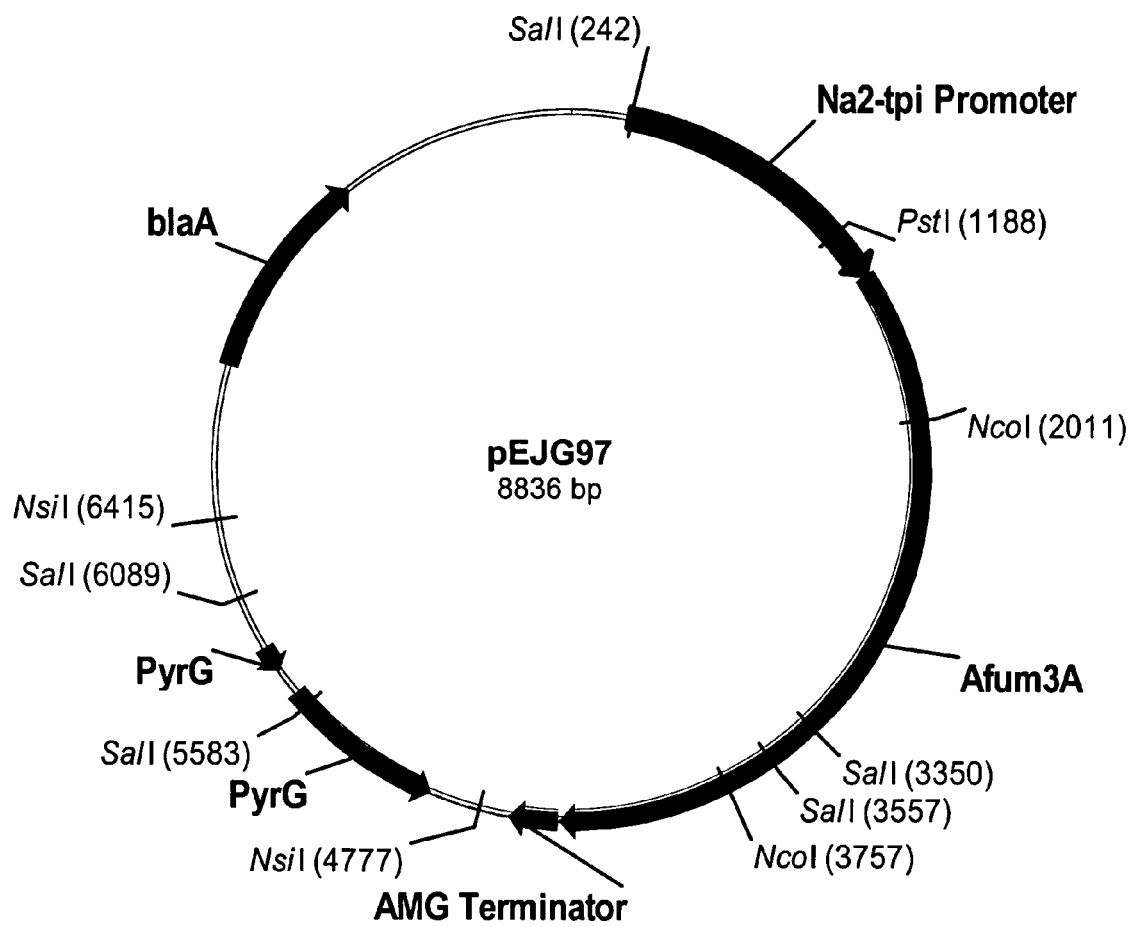
FIG. 31 shows a restriction map of pEJG97.

The fragment was then cloned into the pAILo2 expression vector using an InFusion Cloning Kit. The vector was digested with restriction endonucleases Nco I and Pac I (using conditions specified by the manufacturer). The fragment was purified by gel electrophoresis and QIAquick gel purification. The gene fragment and the digested vector were ligated together in a reaction resulting in the expression plasmid pEJG97 (FIG. 31) in which transcription of the Family GH3A beta-glucosidase gene was under the control of the NA2-tpi promoter. The ligation reaction (20 µl) was composed of 1×InFusion Buffer, 1×BSA (BD Biosciences, Palo Alto, Calif.), 1 µl of InFusion enzyme (diluted 1:10), 150 ng of pAILo2 digested with Nco I and Pac I, and 50 ng of the *Aspergillus fumigatus* beta-glucosidase purified PCR product. The reaction was incubated at room temperature for 30 minutes. One µl of the reaction was used to transform *E. coli* XL10 Solopac Gold cells (Stratagene, La Jolla, Calif.). An *E. coli* transformant containing the pEJG97 plasmid was detected by restriction enzyme digestion and plasmid DNA was prepared using a QIAGEN BioRobot 9600.

Example 21

Characterization of the *Aspergillus fumigatus* Genomic Sequence Encoding a Family GH3A Beta-glucosidase DNA sequencing of the *Aspergillus fumigatus* beta-glucosidase gene from pEJG97 was performed with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47-60) and primer walking strategy. Nucleotide sequence data were scrutinized for quality and all sequences were compared to each other with assistance of PHRED/PHRAP software (University of Washington, Seattle, Wash.).

Figure 32A:
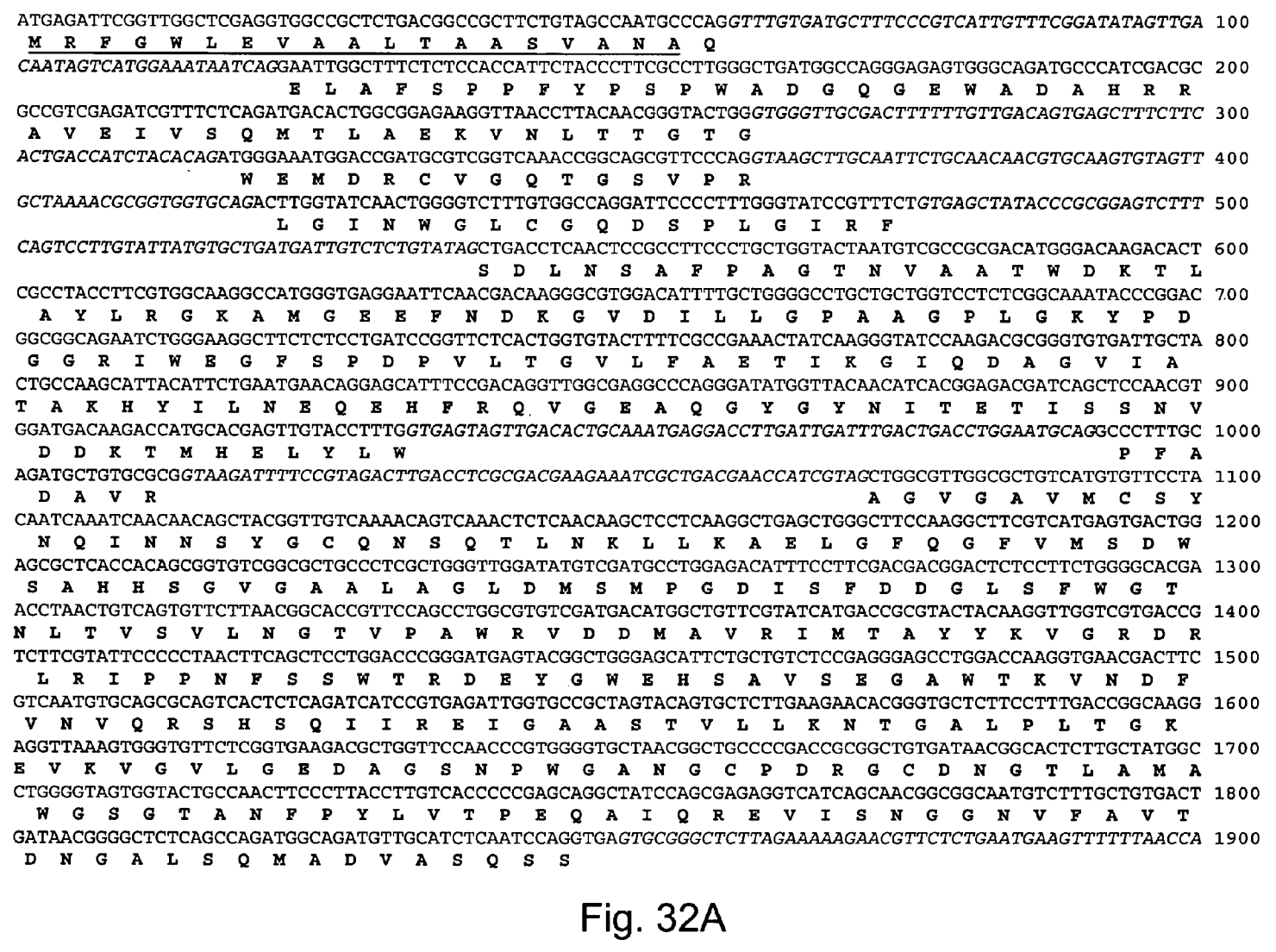

A gene model for the *Aspergillus fumigatus* sequence was constructed based on similarity to homologous genes from *Aspergillus aculeatus*, *Aspergillus niger*, and *Aspergillus kawachii*. The nucleotide sequence (SEQ ID NO: 75) and deduced amino acid sequence (SEQ ID NO: 76) are shown in FIGS. 32A and 32B. The genomic fragment encodes a polypeptide of 863 amino acids, interrupted by 8 introns of 62, 55, 58, 63, 58, 58, 63 and 51 bp. The % G+C content of the gene is 54.3%. Using the SignalP software program (Nielsen et al., 1997, supra), a signal peptide of 19 residues was predicted. The predicted mature protein contains 844 amino acids with a molecular mass of 91.7 kDa.

A comparative alignment of beta-glucosidase sequences was determined using the Clustal W method (Higgins, 1989, *CABIOS* 5: 151-153) using the LASERGENE™ MEGA-LIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus fumigatus* beta-glucosidase gene shared 78%, 76%, and 76% identity to the deduced amino acid sequences of the *Aspergillus aculeatus* (accession number P48825), *Aspergillus niger* (000089), and *Aspergillus kawachii* (P87076) beta-glucosidases.

Example 22

Expression of the *Aspergillus fumigatus* Family GH3A Beta-Glucosidase Gene in *Aspergillus oryzae* JaL250

*Aspergillus oryzae* JaL250 protoplasts were prepared according to the method of Christensen et al., 1988, supra. Five μg of pEJG97 (as well as pAILo2 as a vector control) was used to transform *Aspergillus oryzae* JaL250.

The transformation of *Aspergillus oryzae* JaL250 with pEJG97 yielded about 100 transformants. Ten transformants were isolated to individual PDA plates.

Confluent PDA plates of five of the ten transformants were washed with 5 ml of 0.01% Tween 80 and inoculated separately into 25 ml of MDU2BP medium in 125 ml glass shake flasks and incubated at 34° C., 200 rpm. Five days after incubation, 0.5 μl of supernatant from each culture was analyzed using 8-16% Tris-Glycine SDS-PAGE gels (Invitrogen, Carlsbad, Calif.) according to the manufacturer's instructions. SDS-PAGE profiles of the cultures showed that one of the transformants (designated transformant 1) had a major band of approximately 130 kDa.

A confluent plate of transformant 1 (grown on PDA) was washed with 10 ml of 0.01% Tween 20 and inoculated into a 2 liter Fernbach containing 400 ml of MDU2BP medium to generate broth for characterization of the enzyme. The flask was harvested on day 5 and filtered using a 0.22 μm GP Express plus Membrane (Millipore, Bedford, Mass.).

Example 23

Expression of the *Aspergillus fumigatus* Family GH3A Beta-glucosidase Gene in *Trichoderma reesei*

Two synthetic oligonucleotide primers shown below were designed to PCR amplify the *Aspergillus fumigatus* beta-glucosidase gene from pEJG97 described in Example 20. An InFusion Cloning Kit was used to clone the fragment directly into the expression vector, pMJ09, without the need for restriction digests and ligation.

```
Forward primer:
5-GGACTGCGCACCATGAGATTCGGTTGGCTC-3'   (SEQ ID NO: 77)

Reverse primer:
5-TCGCCACGGAGCTTACTAGTAGACACGGGG-3'   (SEQ ID NO: 78)
```

Bold letters represent coding sequence. The remaining sequence is homologous to the insertion sites of pMJ09.

Fifty picomoles of each of the primers above were used in a PCR reaction (50 μl) containing 100 ng of pEJG97 DNA, 1×Pfx Amplification Buffer, 1.5 μl of 10 mM blend of dATP, dTTP, dGTP, and dCTP, 2.5 units of Platinum Pfx DNA Polymerase, 1 μl of 50 mM $MgSO_4$, and 2.5 μl of 10×pCRx Enhancer Solution. The amplification conditions were one cycle at 94° C. for 2 minutes; and 30 cycles each at 94° C. for 15 seconds, 55° C. for 30 seconds, and 68° C. for 3 minutes. The heat block then went to a 4° C. soak cycle.

The reaction products were isolated on a 1.0% agarose gel using TAE buffer where a 3 kb product band was excised from the gel and purified using a QIAGEN QIAquick Gel Extraction Kit according to the manufacturer's instructions.

Figure 33:
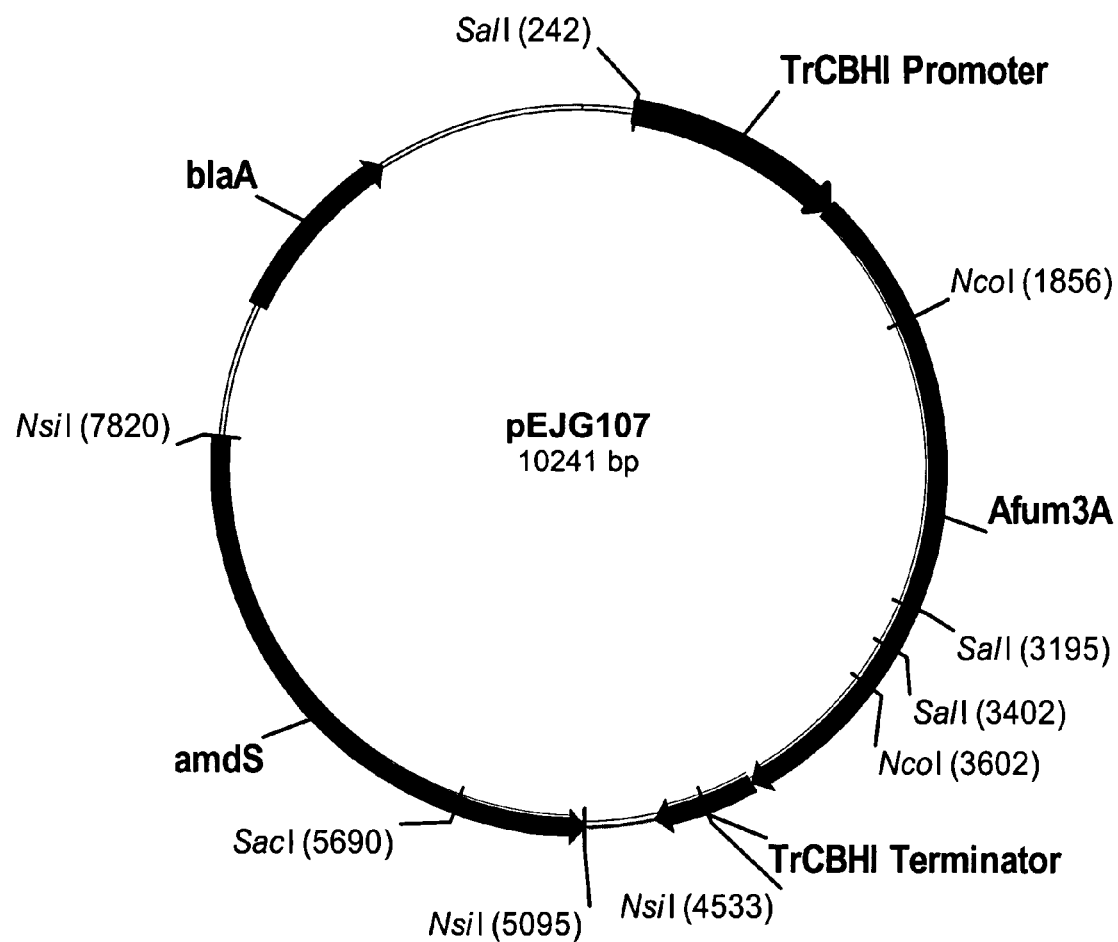
FIG. 33 shows a restriction map of pEJG107.

The purified 3 kb fragment was then cloned into pMJ09 using an InFusion Cloning Kit. The vector was digested with Nco I and Pac I. The fragment was purified by gel electrophoresis and QIAquick gel purification, as described above. The gene fragment and the digested vector were ligated together in a reaction resulting in the expression plasmid pEJG107 (FIG. 33) in which transcription of the Family GH3A beta-glucosidase gene was under the control of the *Trichoderma reesei cbhl* promoter. The ligation (50 μl) was composed of 1×InFusion Buffer, 1×BSA, 1 μl of InFusion enzyme (diluted 1:10), 100 ng of pMJ09 digested with Nco I and Pac I, and 100 ng of the *Aspergillus fumigatus* beta-glucosidase purified PCR product. The reaction was incubated at room temperature for 30 minutes. One μl of the reaction was used to transform *E. coli* electrocompetent SURE cells (Stratagene, La Jolla, Calif.). An *E. coli* transformant containing the pEJG107 plasmid was detected by restriction enzyme digestion and plasmid DNA was prepared using a QIAGEN BioRobot 9600.

DNA sequencing of the *Aspergillus fumigatus* beta-glucosidase gene from pEJG107 was done with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47-60) and primer walking strategy. Nucleotide sequence data were scrutinized for quality and all sequences were compared to each other with assistance of PHRED/PHRAP software (University of Washington, Seattle, Wash.).

*Trichoderma reesei* RutC30 protoplasts were prepared according to the method of Christensen et al., 1988, supra. Five μg of pEJG107 were used to transform *Trichoderma reesei* RutC30. The transformation yielded about 100 transformants. Sixty transformants were isolated to individual COVE/10 mM uridine plates and incubated at 28° C.

Spores were collected from plates from 8 of the 60 transformants swiping three times with a sterile loop and inoculated separately into 25 ml of CIM medium in 125 ml glass shake flasks and incubated at 28° C., 250 rpm. Five days after incubation, 0.5 μl of supernatant from each culture was analyzed using 7.5% Tris SDS-PAGE gels (Biorad, Hercules, Calif.) according to the manufacturer's instructions. SDS-PAGE profiles of the cultures showed that one of the transformants (designated transformant 1) had a new major band of approximately 130 kDa.

Example 24

Purification and Characterization of the *Thielavia terrestris* Polypeptides Having Cellulolytic Enhancing Activity

*Thielavia terrestris* NRRL 8126 shake flask cultures were grown in 100 ml of NNCYPmod medium in a 500 ml baffled shake flask at 44° C., 175 rpm. Flasks were inoculated with a plug (approximately 2 square cm) from a fresh agar plate of the same medium and allowed to grow for approximately 3-5 days before harvesting. Crude broth samples were obtained by centrifuging cultures for approximately 10 minutes at 9500×g to remove cellular matter and any residual carbon source. The resulting supernatant was then centrifuged again as described above. The supernatant was used as the starting material for biochemical analysis and when not in use stored at 4° C.

Thielavia terrestris fermentor cultures were grown by cultivating Thielavia terrestris on NNCYP medium with 52 g of cellulose per liter, which was batched in during fermentation (no additional carbon source) at 42° C. and maintained at pH 5.0. The fermentation was allowed to run until the batch cellulose had been exhausted (typically about 40 hours) at which time the broth was harvested and centrifuged to remove mycelia as described above.

Prior to performing protein purification experiments, small scale preparations of Thielavia terrestris broth were prepared by concentrating cleared supernatant samples using Centricon Plus 20 (Millipore, Bedford, Mass.) filtering devices on a swinging bucket rotor centrifuge (Sorvall, RC3B Plus). Approximately 3 ml of each concentrate was loaded onto a 10DG Econo PAC (BioRad, Hercules, Calif.) desalting column equilibrated with 50 mM sodium acetate pH 5.0, and samples eluted using 4 ml of 50 mM sodium acetate pH 5.0. For large scale preparations of Thielavia terrestris broth (approximately 0.5 liter to 10 liters), the protocol described below was utilized. Crude broth samples were cleared of cellular debris by centrifuging cultures for approximately 20 minutes at 9500×g. Cleared broth samples were then filtered (GP Express membrane, polyethersulfone, 0.22 µm, Millipore, Bedford, Mass.), buffer exchanged with 50 mM sodium acetate pH 5.0 (Pall Filtron, North Borough, Mass., 10 kDa polyethersulfone membrane, approximately 10-20 psi), and concentrated using an Amicon ultrafiltration device (Millipore, Bedford, Mass., 10 kDa membrane, 40 psi, 4° C.). Protein concentrations were determined using a BCA Protein Assay Kit (Pierce, Rockford, Ill.) in which bovine serum albumin was used as a protein standard. Aliquots from the desalting procedure were typically examined on 8-16% SDS-PAGE gels (Invitrogen, Carlsbad, Calif.; 200 V for 1 hour) in which Precision molecular weight standards (BioRad, Hercules, Calif.) were included. Gels were stained for protein using Biosafe Coomassie Stain (BioRad, Hercules, Calif.) and destained using deionized $H_2O$.

The Thielavia terrestris supernatants were loaded onto a Q Sepharose Big Bead column (Amersham Pharmacia, Uppsala Sweden) equilibrated with 20 mM Tris-HCl pH 8.2. Flow-through material was collected and stored at 4° C. until use. Prior to elution the column was washed with five column volumes of starting buffer. Bound material was eluted with a linear gradient of 0 to 0.40 M NaCl (15 column volumes; 10 ml fractions) in 20 mM Tris-HCl pH 8.2 buffer. Based on the UV profile ($A_{280\ nm}$) individual fractions representative of resolved protein peaks were pooled for characterization and buffer exchanged (Ultrafree Biomax 10 kDa NMWL membrane, Millipore, Bedford, Mass.) using 50 mM sodium acetate pH 5.0.

Designated Thielavia terrestris Q Sepharose Big Bead fractions were then further fractionated using a Phenyl Superose column (HR 16/10 Pharmacia Biotech, Uppsala Sweden) using the protocol described below. Solid ammonium sulfate was added to the sample to be fractionated to give a final concentration of 1.7 M $(NH_4)_2SO_4$. The sample was then centrifuged and filtered (10 minutes, 5,000×g, RT; 0.22 µm GP Express membrane, Millipore, Bedford, Mass.) to remove particulate matter prior to loading onto a Phenyl Superose column equilibrated with 1.7 M $(NH_4)_2SO_4$ in 20 mM Tris-HCl pH 8.2. Elution of bound material was achieved using a decreasing linear gradient (15 column volumes using deionized $H_2O$) of 1.7 M $(NH_4)_2SO_4$ in 20 mM Tris-HCl pH 8.2. Fractions were pooled based on $A_{280\ nm}$ absorbance to enrich resolved peak areas. Pools were buffer exchanged into 50 mM sodium acetate pH 5.0 using an Amicon Ultrafiltration device (polyethersulfone membrane, 5 kDa NMWL, Bedford, Mass.). Protein concentrations were determined using a BCA Protein Assay Kit and samples analyzed on 8-16% Tris-Glycine SDS-PAGE gels as described in Example 1.

Corn stover was pretreated at the U.S. Department of Energy National Renewable Energy Laboratory (NREL) using dilute sulfuric acid. The following conditions were used for the pretreatment: 1.4 wt % sulfuric acid at 165° C. and 107 psi for 8 minutes. According to NREL, the water-insoluble solids in the pretreated corn stover (PCS) contained 56.5% cellulose, 4.6% hemicellulose and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003. Prior to enzymatic hydrolysis, the PCS was washed with a large volume of DDI water on a glass filter; the dry weight of the water-washed PCS was found to be 24.54%. Milled PCS (dry weight 32.35%) was prepared from the water-washed PCS by milling in a coffee-grinder and subsequent washing with deionized water on a 22 µm Millipore Filter (6P Express Membrane, Stericup, Millipore, Bedford, Mass.).

Hydrolysis of PCS was conducted using 1.1 ml Immunoware microtubes (Pierce, Rockford, Ill.) using a total reaction volume of 1.0 ml. In this protocol hydrolysis of PCS (10 mg/ml in 50 mM sodium acetate pH 5.0 buffer) was performed using different protein loadings (expressed as mg of enzyme per gram of PCS) of a Thielavia terrestris broth or Celluclast® 1.5 L sample (Novozymes A/S, Bagsvaerd, Denmark) in the presence of 3% Aspergillus oryzae beta-glucosidase (recombinantly produced in Aspergillus oryzae according to WO 02/095014) or 3% Aspergillus fumigatus beta glucosidase (recombinantly produced in Aspergillus oryzae according to Example 22) of cellulase protein loading. Screening of Thielavia terrestris protein fractions for PCS hydrolyzing capability was performed at 50° C. (Isotemp 102S water baths or TS Autoflow $CO_2$ Jacketed Incubator). Typically, reactions were run in quadruplicate and aliquots taken during the course of hydrolysis. PCS hydrolysis reactions were stopped by mixing a 20 µl aliquot of each hydrolyzate with 180 µl of 0.11 M NaOH (stop reagent). Appropriate serial dilutions were generated for each sample and the reducing sugar content determined using a para-hydroxybenzoic acid hydrazide (PHBAH, Sigma, St. Louis, Mo.) assay adapted to a 96 well microplate format as described below. Briefly, a 90 µl aliquot of an appropriately diluted sample was placed in a 96 well conical bottomed microplate. Reactions were initiated by adding 60 µl of 1.5% (w/v) PHBAH in 2% NaOH to each well. Plates were heated uncovered at 95° C. for 10 minutes. Plates were allowed to cool to room temperature (RT) and 50 µl of distilled $H_2O$ added to each well. A 100 µl aliquot from each well was transferred to a flat bottomed 96 well plate and the absorbance at $A_{410\ nm}$ measured using a SpectraMax Microplate Reader (Molecular Devices, Sunnyvale, Calif.). Glucose standards (0.1-0.0125 mg/ml diluted with 0.4% sodium hydroxide) were used to prepare a standard curve to translate the obtained $A_{410\ nm}$ values into glucose equivalents. The resultant equivalents were used to calculate the percentage of PCS cellulose conversion for each reaction.

The degree of cellulose conversion to reducing sugar (conversion, %) was calculated using the following equation:

$$\text{Conversion}_{(\%)} = RS_{(mg/ml)} * 100 * 162/(\text{Cellulose}_{(mg/ml)} * 180) = RS_{(mg/ml)} * 100/(\text{Cellulose}_{(mg/ml)} * 1.111)$$

In this equation, RS is the concentration of reducing sugar in solution measured in glucose equivalents (mg/ml), and the factor 1.111 reflects the weight gain in converting cellulose to glucose.

In an attempt to reconstitute the original *Thielavia terrestris* broth PCS hydrolysis activity, selected pools from a Q Sepharose Big Bead column (pools A through F) were mixed at equal ratios and their PCS hydrolysis activity examined. The mixture most closely approaching the PCS activity of the original starting material (*Thielavia terrestris* broth, 5 mg enzyme loading=77% PCS Cellulose conversion) was a mixture consisting of pools A+B+C+E (5 mg enzyme loading=83% PCS Cellulose conversion).

An FPLC run (AKTA Design, Amersham Pharmacia Biotech, Uppsala Sweden) in which a *Thielavia terrestris* Q Sepharose Big Bead pool (Flow Through Material) was fractionated on a Phenyl Superose column generated multiple fractions which were subsequently pooled and buffer exchanged as described previously. Based on the protein concentrations for each of the pooled samples (BCA Protein Assay Kit) approximately 43% of the total protein loaded was recovered from this fractionation step.

To screen for *Thielavia terrestris* samples which could enhance Celluclast® 1.5 L performance, PCS hydrolysis reactions (1.0 ml protocol, 10 g of PCS per liter, 50° C., supplemented by addition of 3% of total loading of *Aspergillus oryzae* beta-glucosidase) were performed in which 2.5 mg enzyme loading Celluclast® 1.5 L was mixed with 2.5 mg enzyme loading of each pooled sample (5 mg enzyme loading Total protein per reaction). Celluclast® 1.5 L control reactions consisting of 10 mg enzyme loading, 5 mg enzyme loading and 2.5 mg enzyme loading gave PCS cellulose conversion values of 86%, 75% and 53%, respectively. Analysis of the resultant hydrolysis of PCS showed that one pooled sample when added to Celluclast® 1.5 L at a protein ratio of 50:50 and total loading of 5 mg enzyme surpassed the 5 mg enzyme loading Celluclast® 1.5 L control reaction (79% vs. 75%). This sample when analyzed on an 8-16% acrylamide gradient gel was shown to comprise a major protein band at approximately 42 kDa.

Example 25

Effect of *Thielavia terrestris* GH61B on Hydrolysis of Pretreated Corn Stover by *Trichoderma reesei* Fermentation Broth Expressing *Aspergillus fumigatus* Beta-Glucosidase

*Thielavia terrestris* GH61B (recombinantly produced in *Aspergillus oryzae* as described in Example 12) was desalted and exchanged to 50 mM sodium acetate pH 5.0 using a Centricon Plus-20 centrifugal filter with a Biomax-5 membrane (5000 NMWL; Millipore, Bedford, Mass.) before hydrolysis experiments. Cell-free *Trichoderma reesei* fermentation broth expressing *Aspergillus fumigatus* beta-glucosidase (see Example 23) was used in hydrolysis experiments without desalting or buffer exchange.

The protein concentration in the enzyme samples was determined by the BCA Microplate Assay as described in the instructions for BCA Protein Assay Reagent Kit (Pierce Chemical Co., Rockford, Ill.). Cell-free *Trichoderma reesei* fermentation broth expressing *Aspergillus fumigatus* beta-glucosidase (see Example 23) was additionally desalted by passing through Bio Spin 6 columns (Bio-Rad Laboratories, Hercules, Calif.) according to the manufacturer's instructions before measuring the protein concentration.

Enzyme dilutions were prepared fresh before each experiment from stock enzyme solutions, which were stored at −20° C.

Reducing sugars (RS) were determined using a p-hydroxybenzoic acid hydrazide (PHBAH) assay (Lever, M., 1972, A new reaction for colorimetric determination of carbohydrates, *Anal. Biochem.*, 47: 273-279), which was modified and adapted to a 96-well microplate format.

A 90-µl aliquot of the diluted sample was placed into each well of a 96-well conical-bottomed microplate (Corning Inc., Acton, Mass., Costar, clear polycarbonate). The assay was started by adding 60 µl of 1.25% PHBAH in 2% sodium hydroxide to each well. The uncovered plate was heated on a custom-made heating block for 10 minutes at 95° C. After the microplate was cooled to room temperature, 35 µl of deionized water was added to each well. A 100-µl aliquot was removed from each well and transferred to a flat-bottomed 96-well plate (Corning Inc., Acton, Mass., Costar, medium binding polystyrene). The absorbance at 410 nm ($A_{410}$) was measured using a SpectraMAX Microplate Reader (Molecular Devices, Sunnyvale, Calif.). The $A_{410}$ value was translated into glucose equivalents using a standard curve.

The standard curve was obtained with six glucose standards (0.005, 0.010, 0.025, 0.050, 0.075, and 0.100 mg/ml), which were treated similarly to the samples. Glucose standards were prepared by diluting 10 mg/ml stock glucose solution with deionized water.

The degree of cellulose conversion to reducing sugar (conversion, %) was calculated using the same equation described in Example 24.

Hydrolysis of milled PCS (1% w/v on a dry weight basis) by a cell-free *Trichoderma reesei* fermentation broth expressing *Aspergillus fumigatus* beta-glucosidase (see Example 23) at 2.5, 5, 10, and 20 mg protein per g of PCS was carried out in Deepwell Plates 96 (1.2 ml, Brinkmann, Westbury, N.Y.) capped with Deepwell Mats 96 (Brinkmann, Westbury, N.Y.). All reactions with the initial volume of 1 ml were run in 50 mM sodium acetate pH 5.0 with intermittent stirring at 50° C., 55° C., and 60° C.

Reactions containing the *Trichoderma reesei* fermentation broth at 5 mg per g of PCS were supplemented with *Thielavia terrestris* GH61B (recombinantly produced in *Aspergillus oryzae* as described herein) at 1 mg per g of PCS (20% of cellulase protein loading), and the results were compared with non-supplemented reactions.

Aliquots of 20 µl were removed from PCS hydrolysis reactions at specified time points using an 8-channel pipettor, and added to 180 µl of alkaline mixture (102 mM $Na_2CO_3$ and 58 mM $NaHCO_3$) in MultiScreen HV 96-well filtration plate (Millipore, Bedford, Mass.) to terminate the reaction. The samples were vacuum-filtered into another flat-bottomed microplate to remove the PCS residue. After appropriate dilution, the filtrates were analyzed for RS using the PHBAH assay as described in Example 24.

Figure 34:
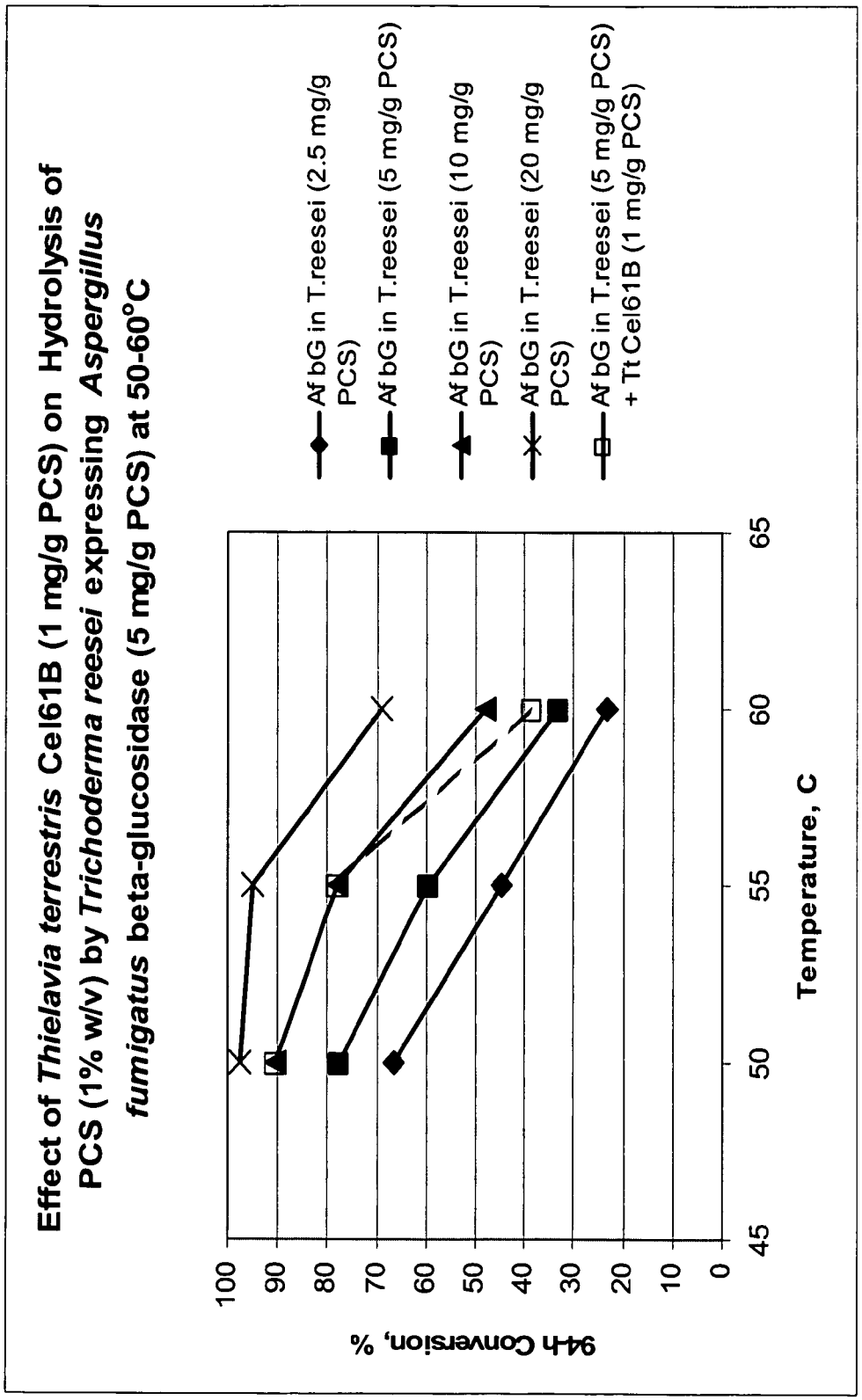
FIG. 34 shows the effect of a *Thielavia terrestris* GH61B polypeptide having cellulolytic enhancing activity (1 mg/g PCS) on hydrolysis of PCS (1% w/v) by fermentation broth of *Trichoderma reesei* expressing cellulolytic activity and an *Aspergillus fumigatus* beta-glucosidase (5 mg/g PCS) at 50-60° C.
Figure 35:
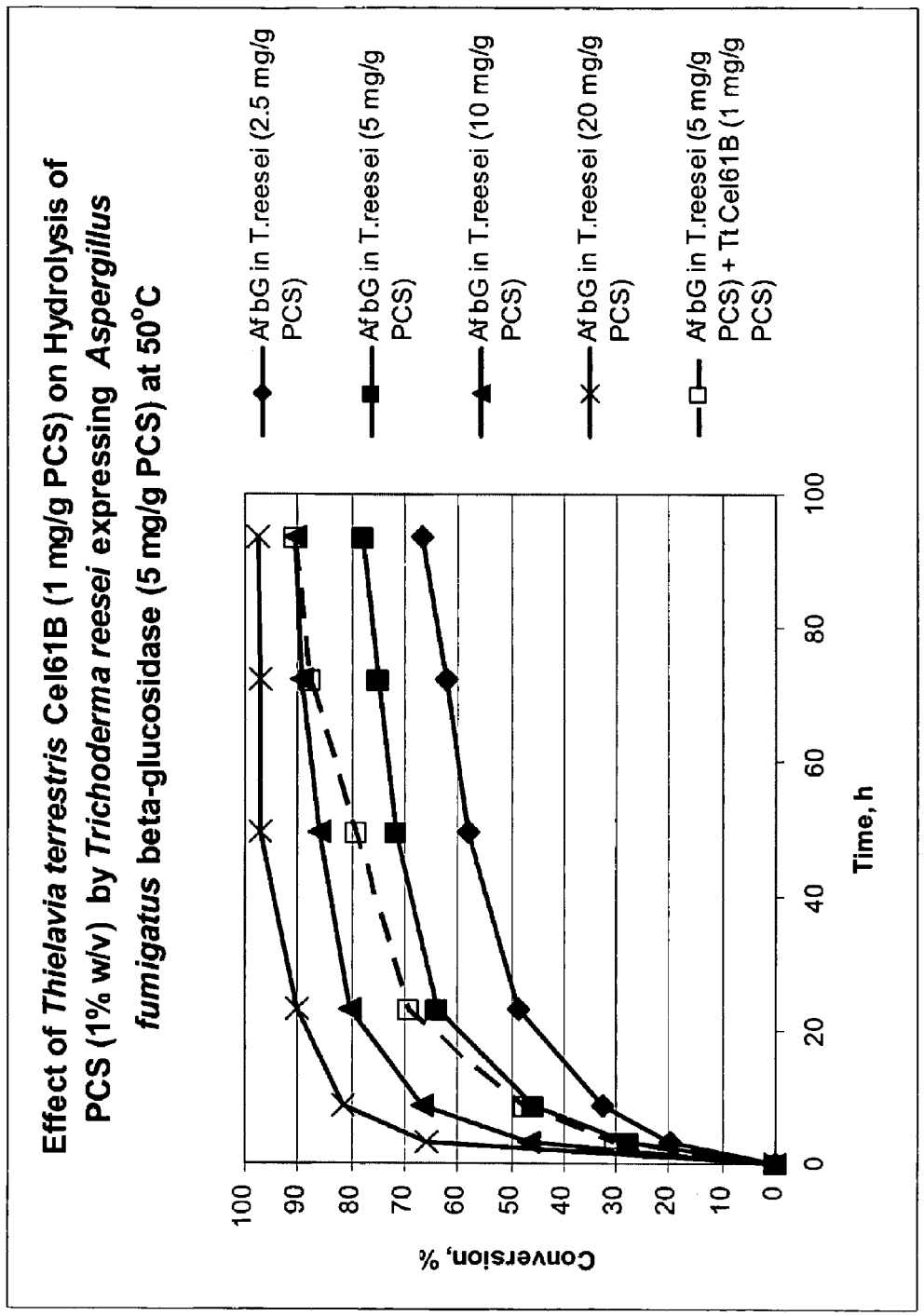
FIG. 35 shows the effect of a *Thielavia terrestris* GH61B polypeptide having cellulolytic enhancing activity (1 mg/g PCS) on hydrolysis of PCS (1% w/v) by fermentation broth of *Trichoderma reesei* fermentation broth expressing cellulolytic activity and an *Aspergillus fumigatus* beta-glucosidase (5 mg/g PCS) at 50° C.

The results as shown in FIGS. 34 and 35 indicated that supplementing *Trichoderma reesei* fermentation broth expressing *Aspergillus fumigatus* beta-glucosidase (see Example 23) with the *Thielavia terrestris* GH61B protein improved the 94 hour hydrolysis yield by 16-30% compared to non-supplemented broth and reduced enzyme loading requirements. At 50° C. and 55° C., the same cellulose conversion in 94 hours could be achieved using supplemented fermentation broth at total protein loading of 6 mg per g of PCS and non-supplemented fermentation broth at 10 mg per g of PCS.

Example 26

Hydrolysis of Pretreated Corn Stover (PCS) with Thielavia terrestris GH61B Recombinantly Produced in Aspergillus oryzae Aspergillus oryzae transformants expressing Thielavia terrestris GH61B were grown in shake flask (SF) cultures as follows. Spores were collected with 5 milliliters of an aqueous solution of 0.01% Tween 80 and one or two more washes with MDU2BP to maximize the number of spores collected. The spore suspension was then used to inoculate 500 milliliters of MDU2BP medium in a two-liter Fernbach flask. Transformant cultures were incubated at 34° C. with constant shaking (200 rpm). At day five post-inoculation the culture broths were collected by filtration on a 500 milliliter, 75 mm Nylon filter unit with a pore size of 0.45 μm. A 5 μl sample of the broth was analyzed by SDS-PAGE. The broth containing rGH61B contained one major band of approximately 42,000 MW.

The broths were stored at −20° C. prior to concentration by pressure ultrafiltration in stirred cells (Amicon, PM10 membrane with 10 kD MWCO) to approximately 15×concentration, followed by desalt/buffer exchange into citrate buffer (50 mM, pH 5.0) by use of Econo-Pac 10DG columns (BioRad). After assay of the protein concentration by a BCA Protein Assay Kit, the enzyme stocks were stored at −20° C. The proteins were not further purified, and stocks were added to reaction mixtures based on total protein measured.

Hydrolysis of PCS was conducted using 1.1 ml Immunoware microtubes or 1 ml deep-well blocks (VWR) using a total reaction volume of 1.0 ml. Hydrolysis of PCS (10 mg/ml in 50 mM sodium acetate pH 5.0 buffer) was performed using different protein loadings (expressed as mg enzyme per gram PCS) of recombinant Thielavia terrestris GH61B protein with or without added Celluclast® 1.5 L in the presence of 3% Aspergillus fumigatus beta-glucosidase (BG, 3% of cellulase protein loading). Incubation of hydrolysis mixtures was performed at 50° C. (Isotemp 102S water baths or TS Autoflow $CO_2$ Jacketed Incubator with humidification). Typically, reactions were run in triplicate and aliquots taken during the course of hydrolysis. Data reported was the mean of triplicates. PCS hydrolysis reactions were stopped by mixing a 20 μl aliquot of each hydrolyzate with 180 μl of PCS Stop Buffer (0.102 M $Na_2CO_3$, 0.058 M $NaHCO_3$, pH ~10). Samples were assayed immediately or stored frozen at −20° C. The reducing sugar content determined using a p-Hydroxybenzoic Acid Hydrazide (PHBAH) assay adapted to a 96 well microplate format. Briefly, a 100 μl aliquot of an appropriately diluted sample was placed in a 96 well conical bottomed microplate. Reactions were initiated by adding 50 μl of 1.5% (w/v) PHBAH in 2% NaOH to each well. Plates were heated uncovered at 95° C. for 10 minutes. Plates were allowed to cool to RT and 50 ul of $ddH_2O$ added to each well. A 100 μl aliquot from each well was transferred to a flat bottomed 96 well plate and the absorbance at $A_{410\ nm}$ measured using a SpectraMax Microplate Reader (Molecular Devices). Glucose standards (0.1-0.0125 mg/ml diluted with 0.4% sodium hydroxide) were used to prepare a standard curve to translate the obtained A410 values into glucose equivalents (based on the yield expected from the theoretical complete conversion of cellulose to glucose). The resultant equivalents were used to calculate the percentage of PCS cellulose conversion for each reaction. Results were plotted as glucose equivalents (percent conversion) vs. total protein loading (mg enzyme/g PCS).

To examine the ability of the Thielavia terrestris GH61B protein to enhance the activity of Celluclast® 1.5 L, the dose dependent hydrolysis of PCS was tested for mixtures of 2.5 mg of Celluclast® 1.5 L plus 0.078 to 1.25 mg of the GH61B protein per g of PCS using the 1.0 ml PCS micro protocol. For comparison purposes similar total protein loadings were also done for Celluclast® 1.5 L without addition of the GH61B protein. All samples had supplemental Aspergillus fumigatus beta-glucosidase at 3% of total cellulase loading.

The results shown in Table 2 demonstrated that the addition of various amounts of Thielavia terrestris GH61B protein to 2.5 mg/g PCS Celluclast® 1.5 L with a resulting total enzyme loading of 2.578 to 3.75 mg/g of PCS increased glucose conversion above that obtained by Celluclast® 1.5 L without the GH61B protein at 2.5 or 3.75 mg/g of PCS enzyme loading levels. Addition of as little as 0.078 mg of the GH61B protein to 2.5 mg of Celluclast® 1.5 L improved hydrolysis of PCS above the amount measured for 3.75 mg of Celluclast® 1.5 L without the GH61B protein. The addition of the GH61B protein to Celluclast® 1.5 L-containing solutions increased, therefore, the yield of reducing sugars (predominantly glucose and residual cellobiose) upon hydrolysis of acid-pretreated corn stover (PCS). The yield increase was higher than that achieved by addition of equal or lesser amounts of Celluclast® 1.5 L, resulting in reduced enzyme loading requirements and increased enzyme efficiency.

TABLE 2

Celluclast ® and GH61B values are in mg enzyme/g PCS, and glucose is in percent of theoretical yield. All mixtures contain 3% w/w added beta-glucosidase to enhance conversion of cellobiose to glucose. Glucose conversion is shown as percent of theoretical glucose available by hydrolysis of PCS.

| Celluclast ® | GH61B OD | Total enzyme (mg/g PCS) | Glucose conversion (%) |
|---|---|---|---|
| 2.5 | 0 | 2.5 | 59.3 |
| 2.5 | 0.078 | 2.578 | 65.4 |
| 2.5 | 0.16 | 2.66 | 65.3 |
| 2.5 | 0.31 | 2.81 | 66.9 |
| 2.5 | 0.63 | 3.13 | 67.8 |
| 2.5 | 1.25 | 3.75 | 66.8 |
| 0 | 1.25 | 1.25 | 2.6 |
| 3.75 | 0 | 3.75 | 62.7 |
| 6 | 0 | 6 | 70.9 |
| 8 | 0 | 8 | 73.7 |

Example 27

Hydrolysis of Pretreated Corn Stover (PCS) with GH61B, GH61E and GH61G Polypeptides Recombinantly Produced in Aspergillus oryzae Three Family 61 polypeptides, including Thielavia terrestris GH61B, GH61E, and GH61G were tested in the same series of PCS hydrolysis reactions as described in Examples 24 and 25. All the Family 61 polypeptides were expressed in Aspergillus oryzae as described in Example 14, and the broths were concentrated using an Amicon stirred cell equipped with a PM10 membrane, 10 kDa cutoff (Millipore, Billerica, Mass.), and desalted using an Econo-Pac 10DG column (BioRad Laboratories, Hercules, Calif.). After assay of the protein concentration by BCA (Pierce, BSA used as standard), these enzyme stocks were stored at −20° C. The proteins were not further purified, and stocks were added to reaction mixtures based on total protein measured.

Hydrolysis of PCS (10 mg/ml in 50 mM sodium acetate pH 5.0 buffer) was conducted using 1.1 ml Immunoware microtubes (Pierce, Rockford, Ill.) with a total reaction volume of 1.0 ml. The Family 61 polypeptides were tested for their ability to enhance the hydrolytic capability of a cellulase preparation derived from fermentation of *Trichoderma reesei* expressing a beta-glucosidase from *Aspergillus oryzae* (WO 02/095014), hereinafter called Tr/AoBG and obtained from Novozymes A/S, Bagsvaerd, Denmark. Hydrolysis of PCS was performed using 2.5 mg of Tr/AoBG per gram of PCS, supplemented with 0.2 mg of GH61 polypeptide per gram of PCS. PCS hydrolysis was performed at 50° C. (TS Autoflow $CO_2$ Jacketed Incubator). Reactions were run in duplicates and aliquots taken during the course of hydrolysis. PCS hydrolysis reactions were stopped by mixing a 20 µl aliquot of each hydrolyzate with 180 µl of 0.11 M NaOH (stop reagent). Appropriate serial dilutions were generated for each sample and the reducing sugar content determined using a para-hydroxybenzoic acid hydrazide (PHBAH, Sigma, St. Louis, Mo.) assay adapted to a 96 well microplate format as described below. Briefly, a 90 µl aliquot of an appropriately diluted sample was placed in a 96 well conical bottomed microplate. Reactions were initiated by adding 60 µl of 1.5% (w/v) PHBAH in 2% NaOH to each well. Plates were heated uncovered at 95° C. for 10 minutes. Plates were allowed to cool to room temperature (RT) and 50 µl of distilled $H_2O$ added to each well. A 100 µl aliquot from each well was transferred to a flat bottomed 96 well plate and the absorbance at $A_{410\ nm}$ measured using a SpectraMax Microplate Reader (Molecular Devices, Sunnyvale, Calif.). Glucose standards (0.1-0.0125 mg/ml diluted with 0.4% sodium hydroxide) were used to prepare a standard curve to translate the obtained $A_{410\ nm}$ values into glucose equivalents. The resultant equivalents were used to calculate the percentage of PCS cellulose conversion for each reaction.

The degree of cellulose conversion to reducing sugar (conversion, %) was calculated using the same equation described in Example 24.

Figure 36:
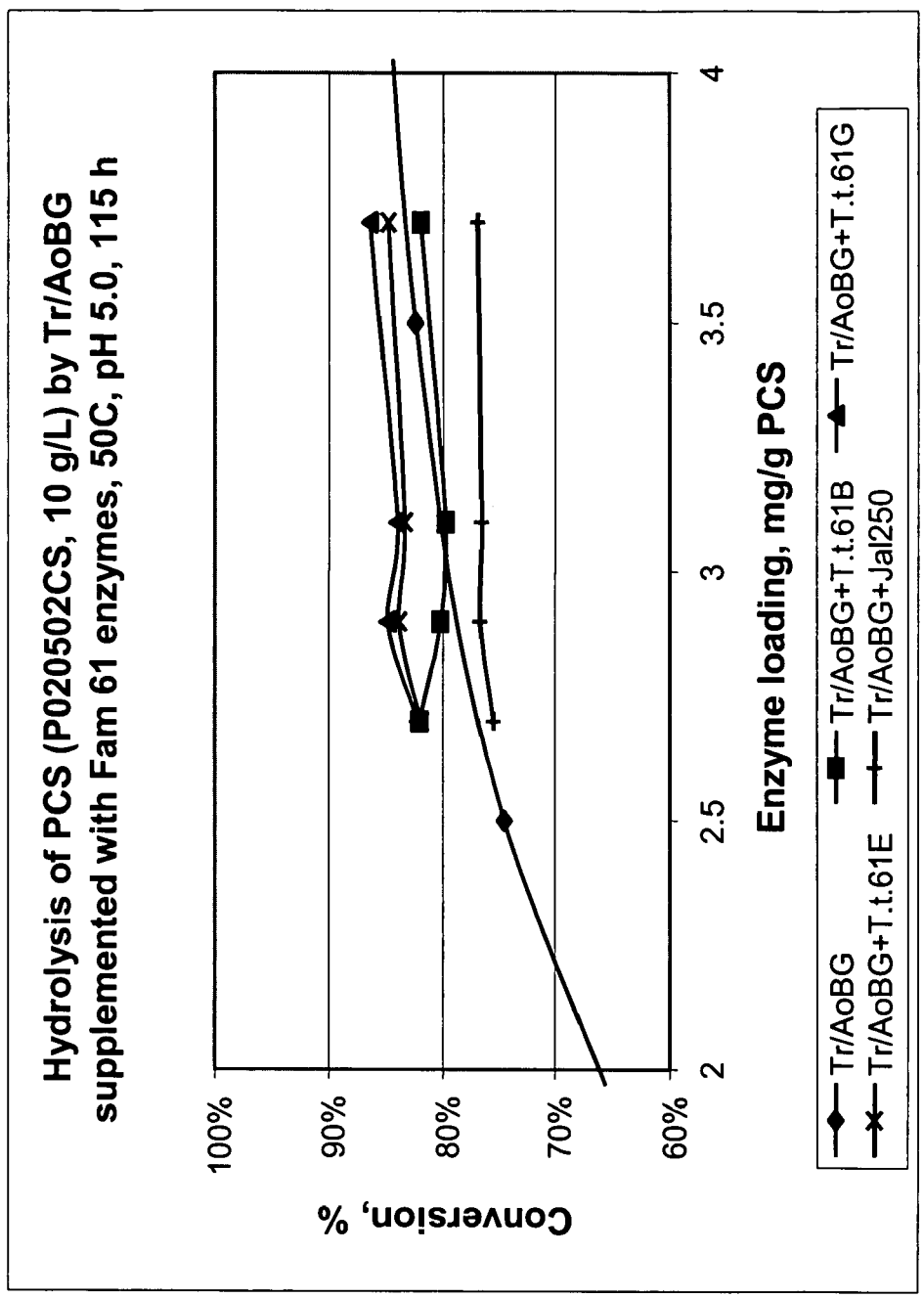
FIG. 36 shows cellulose conversion by Tr/AoBG alone or Tr/AoBG supplemented with *Thielavia terrestris* GH61 polypeptides having cellulolytic activity at 50° C., pH 5.0 for 115 hours.

Cellulose conversion by Tr/AoBG alone (2.5 mg/g PCS) or supplemented with each of the three GH61 polypeptides (0.2 mg/g PCS) are summarized in Table 3 and FIG. 36.

TABLE 3

Cellulose conversion by Tr/AoBG alone or Tr/AoBG supplemented with GH61 polypeptide at 115 h, 50° C., pH 5.0.

| Test # | Name | Loading, mg/g PCS | Conversion at 115 h, % |
|---|---|---|---|
| 1 | Tr/AoBG | 2.5 | 74.6 |
| 2 | Tr/AoBG + T.t.GH61B | 2.5 + 0.2 | 82.0 |
| 3 | Tr/AoBG + T.t.GH61E | 2.5 + 0.2 | 82.0 |
| 4 | Tr/AoBG + T.t.GH61G | 2.5 + 0.2 | 82.2 |
| 5 | Tr/AoBG | 3.5 | 82.4 |

Table 3 and FIG. 36 show that all three GH61 polypeptides enhanced the activity of Tr/AoBG on PCS. Supplementing 0.2 mg of Tt. GH61B, Tt. GH61E, or Tt GH61G to 2.5 mg of Tr/AoBG yielded a conversion level close to or higher than that by 3.5 mg of Tr/AoBG, indicating Tr/AoBG activity on PCS was boosted by the three GH61 polypeptides.

*Thielavia terrestris* GH61C was evaluated in a separate experiment using 2.5 mg/g PCS of Tr/AoBG and 0.125 mg/g PCS of Tt. GH61C with incubation for 120 hours. Conversion was 63.1% with Tr/AoBG alone and 66.2% with T.t. GH61C addition.

Example 28

Hydrolysis of Pretreated Corn Stover (PCS) with GH61D Polypeptide Recombinantly Produced in *Aspergillus oryzae*

Thielavia terrestris GH61D polypeptide was expressed in *Aspergillus oryzae* as described in Example 14 and the broths concentrated and desalted as in Example 27. Hydrolysis of PCS was conducted using 1 ml deep-well blocks (VWR) using a total reaction volume of 1.0 ml. Hydrolysis of PCS (10 mg/ml in 50 mM sodium acetate pH 5.0 buffer) was performed using different protein loadings (expressed as mg enzyme per gram PCS) of a recombinant *Thielavia terrestris* protein with or without added Celluclast® 1.5 L in the presence of 3% *Aspergillus fumigatus* β-glucosidase (BG, 3% of Cellulase protein loading). Incubation of hydrolysis mixtures was done at 50° C. (TS Autoflow $CO_2$ Jacketed Incubator with humidification). Typically, reactions were run in triplicate and aliquots taken during the course of hydrolysis. Data reported is the mean of triplicates. PCS hydrolysis reactions were stopped by mixing a 20 µl aliquot of each hydrolyzate with 180 µl of PCS Stop Buffer (0.102 M Na2Co3, 0.058 M NaHCO3, pH ~10). Samples were assayed immediately or stored frozen at −20° C. The reducing sugar content determined using a p-hydroxybenzoic acid hydrazide (PHBAH) assay adapted to a 96 well microplate format. Briefly, a 100 µl aliquot of an appropriately diluted sample was placed in a 96 well conical bottomed microplate. Reactions were initiated by adding 50 µl of 1.5% (w/v) PHBAH in 2% NaOH to each well. Plates were heated uncovered at 95° C. for 10 minutes. Plates were allowed to cool to RT and 50 µl of dd$H_2O$ added to each well. A 100 µl aliquot from each well was transferred to a flat bottomed 96 well plate and the absorbance at $A_{410\ nm}$ measured using a SpectraMax Microplate Reader (Molecular Devices). Glucose standards (0.1-0.0125 mg/ml diluted with 0.4% sodium hydroxide) were used to prepare a standard curve to translate the obtained $A_{410}$ values into glucose equivalents (based on the yield expected from the theoretical complete conversion of cellulose to glucose). The resultant equivalents were used to calculate the percentage of PCS cellulose conversion for each reaction. Results were plotted as glucose equivalents (percent conversion) vs. total protein loading (mg enzyme/g PCS). To examine the ability of GH61D to enhance the activity of Celluclast® 1.5 L, the dose dependent hydrolysis of PCS was tested for mixtures of 2.5 mg Celluclast® plus 0.1 to 0.8 mg GH61D/g PCS using the 1.0 ml PCS micro protocol. For comparison purposes similar total protein loadings were also done for Celluclast® 1.5 L without addition of GH61D. All samples had supplemental *Aspergillus fumigatus* α-glucosidase at 3% of total cellulase loading.

Addition of various amounts of GH61D to 2.5 mg/g PCS Celluclast® with a resulting total enzyme loading of 2.6 to 3.3 mg/g PCS increases glucose conversion above that obtained by Celluclast® without GH61D at 3.4 mg/g PCS enzyme loading levels (Table 4).

TABLE 4

Cellulose conversion by Celluclast® alone or Celluclast® supplemented with GH61D

| Celluclast® | GH61D | Total enzyme (mg/g PCS) | Glucose conversion (%) |
|---|---|---|---|
| 2.5 | 0 | 2.5 | 66.1 |
| 2.5 | 0.1 | 2.6 | 73.2 |
| 2.5 | 0.2 | 2.7 | 75.4 |
| 2.5 | 0.4 | 2.9 | 76.5 |
| 2.5 | 0.8 | 3.3 | 78.5 |
| 2.7 | 0 | 2.7 | 67.3 |
| 2.9 | 0 | 2.9 | 68.3 |
| 3.4 | 0 | 3.4 | 71.7 |
| 4.0 | 0 | 4.0 | 73.6 |

DEPOSIT OF BIOLOGICAL MATERIAL

The following biological material has been deposited under the terms of the Budapest Treaty with the Agricultural Research Service Patent Culture Collection, Northern Regional Research Center, 1815 University Street, Peoria, Ill., 61604, and given the following accession numbers:

| Deposit | Accession Number | Date of Deposit |
|---|---|---|
| E. coli strain pEJG120 | NRRL B-30699 | Dec. 19, 2003 |
| E. coli strain pTter61C | NRRL B-30823 | Jan. 21, 2005 |
| E. coli strain pTter61D | NRRL B-30812 | Jan. 21, 2005 |
| E. coli strain pTter61E | NRRL B-30814 | Jan. 21, 2005 |
| E. coli strain pTter61G | NRRL B-30811 | Jan. 21, 2005 |

The strains have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

---

What is claimed is:

1. An isolated polypeptide having cellulolytic enhancing activity, selected from the group consisting of:
   (a) a polypeptide comprising an amino acid sequence which has at least 95% sequence identity to amino acids 20 to 326 of SEQ ID NO: 2;
   (b) a polypeptide which is encoded by a polynucleotide which hybridizes under at least high stringency conditions with (i) nucleotides 388 to 1332 of SEQ ID NO: 1, (ii) the cDNA sequence contained in nucleotides 388 to 1332 of SEQ ID NO: 1, or (iii) a full-length complementary strand of (i) or (ii); and
   (c) a polypeptide which is encoded by a polynucleotide comprising a nucleotide sequence which has at least 95% sequence identity to nucleotides 388 to 1332 of SEQ ID NO: 1.

2. The polypeptide of claim 1, which comprises the amino acid sequence of SEQ ID NO: 2.

3. The polypeptide of claim 1, which comprises amino acids 20 to 326 of SEQ ID NO: 2.

4. The polypeptide of claim 1, which is encoded by the polynucleotide contained in plasmid pEJG120 which is contained in *E. coli* NRRL B-30699.

5. A detergent composition comprising the polypeptide having cellulolytic enhancing activity of claim 1, a polypeptide having cellulolytic activity, and a surfactant.

6. The polypeptide of claim 1, comprising an amino acid sequence which has at least 95% sequence identity to amino acids 20 to 326 of SEQ ID NO: 2.

7. The polypeptide of claim 6, comprising an amino acid sequence which has at least 97% sequence identity to amino acids 20 to 326 of SEQ ID NO: 2.

8. The polypeptide of claim 1, which is encoded by a polynucleotide which hybridizes under at least high stringency conditions with (i) nucleotides 388 to 1332 of SEQ ID NO: 1, (ii) the cDNA sequence contained in nucleotides 388 to 1332 of SEQ ID NO: 1, or (iii) a full-length complementary strand of (i) or (ii).

9. The polypeptide of claim 1, which is encoded by a polynucleotide which has at least 95% sequence identity to nucleotides 388 to 1332 of SEQ ID NO: 1.

10. The polypeptide of claim 9, which is encoded by a polynucleotide which has at least 97% sequence identity to nucleotides 388 to 1332 of SEQ ID NO: 1.

11. The polypeptide of claim 2, which consists of the amino acid sequence of SEQ ID NO: 2.

12. The polypeptide of claim 3, which consists of amino acids 20 to 326 of SEQ ID NO: 2.

13. The polypeptide of claim 1, which is encoded by a polynucleotide which comprises SEQ ID NO: 1.

14. The polypeptide of claim 1, which is encoded by a polynucleotide which comprises nucleotides 388 to 1332 of SEQ ID NO: 1.

15. The polypeptide of claim 13, which is encoded by a polynucleotide which consists of SEQ ID NO: 1.

16. The polypeptide of claim 14, which is encoded by a polynucleotide which consists of nucteotides 388 to 1332 of SEQ ID NO: 1.

* * * * *

SEQUENCE LISTING

```
<160> NUMBER OF SEQ ID NOS: 78

<210> SEQ ID NO 1
<211> LENGTH: 1846
<212> TYPE: DNA
<213> ORGANISM: Thielavia terrestris

<400> SEQUENCE: 1
aattgaagga gggagtggcg gagtggccac caagtcaggc ggctgtcaac taaccaagga    60
tgggaacagt tcggctcgcc ttgcccgagg gcagcgttcc ctgatgggga cgaaccatgg   120
gactggggtc agctgctgta taaagttca aatcgatgat ctctcagatg gcgctgctgg   180
ggtgttctgc gcttttccat cctcgcaacc tggtatccca ctagtccagc gttcggcacc   240
atgaagtcgt tcaccattgc cgccttggca gcccatatggg cccaggaggc cgccgcccac   300
gcgaccttcc aggacctctg gattgatgga gtcgactacg gctcgcaatg tgtccgcctc   360
ccggcgtcca actcccccgt caccaatgtt gcgtccgacg atatccgatg caatgtcggc   420
acctcgaggc ccaccgtcaa gtgcccggtc aaggccggct ccacggtcac gatcgagatg   480
caccaggttc gcacgcctct ctgcgtaggc ccccagcta ctatatggca ctaacacgac    540
ctccagcaac ctggcgaccg gtcttgcgcc aacgaggcta tcggcggcga ccactacggc   600
cccgtaatgg tgtacatgtc caaggtcgat gacgcggtga cagccgacgg ttcatcgggc   660
```

-continued

```
tggttcaagg tgttccagga cagctgggcc aagaacccgt cgggttcgac gggcgacgac      720
gactactggg gcaccaagga cctcaactcg tgctgcggca agatgaacgt caagatcccc      780
gaagacatcg agccgggcga ctacctgctc cgcgccgagg ttatcgcgct gcacgtggcc      840
gccagctcgg gcggcgcgca gttctacatg tcctgctacc agctgaccgt gacgggctcc      900
ggcagcgcca ccccctcgac cgtgaatttc ccgggcgcct actcggccag cgacccgggc      960
atcctgatca acatccacgc gcccatgtcg acctacgtcg tcccgggccc gaccgtgtac     1020
gcgggcggct cgaccaagtc ggctggcagc tcctgctccg gctgcgaggc gacctgcacg     1080
gttggttccg gccccagcgc gacactgacg cagcccacct ccaccgcgac cgcgacctcc     1140
gcccctggcg gcggcggctc cggctgcacg gcggccaagt accagcagtg cggcggcacc     1200
ggctacactg ggtgcaccac ctgcgctgta agttccctcg tgatatgcag cggaacaccg     1260
tctggactgt tttgctaact cgcgtcgtag tccgggtcta cctgcagcgc cgtctcgcct     1320
ccgtactact cgcagtgcct ctaagccggg agcgcttgct cagcgggctg ctgtgaagga     1380
gctccatgtc cccatgccgc catggccgga gtaccgggct gagcgcccaa ttcttgtata     1440
tagttgagtt ttcccaatca tgaatacata tgcatctgca tggactgttg cgtcgtcagt     1500
ctacatcctt tgctccactg aactgtgaga ccccatgtca tccggaccat tcgatcggtg     1560
ctcgctctac catctcggtt gatgggtctg ggcttgagag tcactggcac gtcctcggcg     1620
gtaatgaaat gtggaggaaa gtgtgagctg tctgacgcac tcggcgctga tgagacgttg     1680
agcgcggccc acactggtgt tctgtaagcc agcacacaaa agaatactcc aggatggccc     1740
atagcggcaa atatacagta tcagggatgc aaaaagtgca aagtaaggg  gctcaatcgg     1800 ggatcgaacc cgagacctcg cacatgactt atttcaagtc agggt                     1846
```

<210> SEQ ID NO 2
<211> LENGTH: 326
<212> TYPE: PRT
<213> ORGANISM: Thielavia terrestris

<400> SEQUENCE: 2

```
Met Lys Ser Phe Thr Ile Ala Ala Leu Ala Ala Leu Trp Ala Gln Glu
1               5                   10                  15

Ala Ala Ala His Ala Thr Phe Gln Asp Leu Trp Ile Asp Gly Val Asp
                20                  25                  30

Tyr Gly Ser Gln Cys Val Arg Leu Pro Ala Ser Asn Ser Pro Val Thr
            35                  40                  45

Asn Val Ala Ser Asp Asp Ile Arg Cys Asn Val Gly Thr Ser Arg Pro
        50                  55                  60

Thr Val Lys Cys Pro Val Lys Ala Gly Ser Thr Val Thr Ile Glu Met
65                  70                  75                  80

His Gln Gln Pro Gly Asp Arg Ser Cys Ala Asn Glu Ala Ile Gly Gly
                85                  90                  95

Asp His Tyr Gly Pro Val Met Val Tyr Met Ser Lys Val Asp Asp Ala
            100                 105                 110

Val Thr Ala Asp Gly Ser Ser Gly Trp Phe Lys Val Phe Gln Asp Ser
        115                 120                 125

Trp Ala Lys Asn Pro Ser Gly Ser Thr Gly Asp Asp Tyr Trp Gly
        130                 135                 140

Thr Lys Asp Leu Asn Ser Cys Cys Gly Lys Met Asn Val Lys Ile Pro
145                 150                 155                 160
```

| | | | | | | | | | | | |
|---|---|---|---|---|---|---|---|---|---|---|---|
|Glu|Asp|Ile|Glu|Pro|Gly|Asp|Tyr|Leu|Leu|Arg|Ala|Glu|Val|Ile|Ala|
| | |165| | | |170| | | |175| |

Leu His Val Ala Ala Ser Ser Gly Gly Ala Gln Phe Tyr Met Ser Cys
            180                 185                 190

Tyr Gln Leu Thr Val Thr Gly Ser Gly Ser Ala Thr Pro Ser Thr Val
        195                 200                 205

Asn Phe Pro Gly Ala Tyr Ser Ala Ser Asp Pro Gly Ile Leu Ile Asn
    210                 215                 220

Ile His Ala Pro Met Ser Thr Tyr Val Val Pro Gly Pro Thr Val Tyr
225                 230                 235                 240

Ala Gly Gly Ser Thr Lys Ser Ala Gly Ser Ser Cys Ser Gly Cys Glu
                245                 250                 255

Ala Thr Cys Thr Val Gly Ser Gly Pro Ser Ala Thr Leu Thr Gln Pro
            260                 265                 270

Thr Ser Thr Ala Thr Ala Thr Ser Ala Pro Gly Gly Gly Ser Gly
        275                 280                 285

Cys Thr Ala Ala Lys Tyr Gln Gln Cys Gly Gly Thr Gly Tyr Thr Gly
    290                 295                 300

Cys Thr Thr Cys Ala Ser Gly Ser Thr Cys Ser Ala Val Ser Pro Pro
305                 310                 315                 320

Tyr Tyr Ser Gln Cys Leu
                325

<210> SEQ ID NO 3
<211> LENGTH: 880
<212> TYPE: DNA
<213> ORGANISM: Thielavia terrestris

<400> SEQUENCE: 3

```
accccgggat cactgcccct aggaaccagc acacctcggt ccaatcatgc ggttcgacgc     60
cctctccgcc ctcgctcttg cgccgcttgt ggctggccac ggcgccgtga ccagctacat    120
catcggcggc aaaacctatc ccggctacga gggcttctcg cctgcctcga gcccgccgac    180
gatccagtac cagtggcccg actacaaccc gaccctgagc gtgaccgacc cgaagatgcg    240
ctgcaacggc ggcacctcgg cagagctcag cgcgcccgtc caggccggcg agaacgtgac    300
ggccgtctgg aagcagtgga cccaccagca aggcccgtc atggtctgga tgttcaagtg    360
ccccggcgac ttctcgtcgt gccacggcga cggcaagggc tggttcaaga tcgaccagct    420
gggcctgtgg ggcaacaacc tcaactcgaa caactgggc accgcgatcg tctacaagac    480
cctccagtgg agcaacccga tccccaagaa cctcgcgccg gcaactacc tcatccgcca    540
cgagctgctc gccctgcacc aggccaacac gccgcagttc tacgccgagt gcgcccagct    600
ggtcgtctcc ggcagcggct ccgccctgcc ccgtccgac tacctctaca gcatccccgt    660
ctacgcgccc cagaacgacc ccggcatcac cgtgagtggg cttccgttcc gcggcgagct    720
ctgtggaaat cttgctgacg atgggctagg ttgacatcta caacggcggg cttacctcct    780
acaccccgcc cggcggcccc gtctggtctg gcttcgagtt ttaggcgcat tgagtcgggg    840
gctacgaggg gaaggcatct gttcgcatga gcgtgggtac                          880
```

<210> SEQ ID NO 4
<211> LENGTH: 478
<212> TYPE: PRT
<213> ORGANISM: Thielavia terrestris

<400> SEQUENCE: 4

-continued

```
Met Arg Phe Asp Ala Leu Ser Ala Leu Ala Leu Ala Pro Leu Val Ala
1               5                   10                  15

Gly His Gly Ala Val Thr Ser Tyr Ile Ile Gly Gly Lys Thr Tyr Pro
            20                  25                  30

Gly Tyr Glu Gly Phe Ser Pro Ala Ser Pro Pro Thr Ile Gln Tyr
        35                  40                  45

Gln Trp Pro Asp Tyr Asn Pro Thr Leu Ser Val Thr Asp Pro Lys Met
    50                  55                  60

Arg Cys Asn Gly Gly Thr Ser Ala Glu Leu Ser Ala Pro Val Gln Ala
65                  70                  75                  80

Gly Glu Asn Val Thr Ala Val Trp Lys Gln Trp Thr His Gln Gln Gly
                85                  90                  95

Pro Val Met Val Trp Met Phe Lys Cys Pro Gly Asp Phe Ser Ser Ser
            100                 105                 110

His Gly Asp Gly Lys Gly Trp Phe Lys Ile Asp Gln Leu Gly Leu Trp
        115                 120                 125

Gly Asn Asn Leu Asn Ser Asn Asn Trp Gly Thr Ala Ile Val Tyr Lys
130                 135                 140

Thr Leu Gln Trp Ser Asn Pro Ile Pro Lys Asn Leu Ala Pro Gly Asn
145                 150                 155                 160

Tyr Leu Ile Arg His Glu Leu Leu Ala Leu His Gln Ala Asn Thr Pro
                165                 170                 175

Gln Phe Tyr Ala Glu Cys Ala Gln Leu Val Val Ser Gly Ser Gly Ser
            180                 185                 190

Ala Leu Pro Pro Ser Asp Tyr Leu Tyr Ser Ile Pro Val Tyr Ala Pro
        195                 200                 205

Gln Asn Asp Pro Gly Ile Thr Val Asp Ile Tyr Asn Gly Gly Leu Thr
210                 215                 220

Ser Tyr Thr Pro Pro Gly Gly Pro Val Trp Ser Gly Phe Glu Phe Met
225                 230                 235                 240

Arg Phe Asp Ala Leu Ser Ala Leu Ala Leu Ala Pro Leu Val Ala Gly
                245                 250                 255

His Gly Ala Val Thr Ser Tyr Ile Ile Gly Gly Lys Thr Tyr Pro Gly
            260                 265                 270

Tyr Glu Gly Phe Ser Pro Ala Ser Pro Pro Thr Ile Gln Tyr Gln
        275                 280                 285

Trp Pro Asp Tyr Asn Pro Thr Leu Ser Val Thr Asp Pro Lys Met Arg
    290                 295                 300

Cys Asn Gly Gly Thr Ser Ala Glu Leu Ser Ala Pro Val Gln Ala Gly
305                 310                 315                 320

Glu Asn Val Thr Ala Val Trp Lys Gln Trp Thr His Gln Gln Gly Pro
                325                 330                 335

Val Met Val Trp Met Phe Lys Cys Pro Gly Asp Phe Ser Ser Ser His
            340                 345                 350

Gly Asp Gly Lys Gly Trp Phe Lys Ile Asp Gln Leu Gly Leu Trp Gly
        355                 360                 365

Asn Asn Leu Asn Ser Asn Asn Trp Gly Thr Ala Ile Val Tyr Lys Thr
370                 375                 380

Leu Gln Trp Ser Asn Pro Ile Pro Lys Asn Leu Ala Pro Gly Asn Tyr
385                 390                 395                 400

Leu Ile Arg His Glu Leu Leu Ala Leu His Gln Ala Asn Thr Pro Gln
                405                 410                 415

Phe Tyr Ala Glu Cys Ala Gln Leu Val Val Ser Gly Ser Gly Ser Ala
```

```
                420             425             430
Leu Pro Pro Ser Asp Tyr Leu Tyr Ser Ile Pro Val Tyr Ala Pro Gln
            435                 440                 445

Asn Asp Pro Gly Ile Thr Val Asp Ile Tyr Asn Gly Gly Leu Thr Ser
        450                 455                 460

Tyr Thr Pro Pro Gly Gly Pro Val Trp Ser Gly Phe Glu Phe
465                 470                 475

<210> SEQ ID NO 5
<211> LENGTH: 1000
<212> TYPE: DNA
<213> ORGANISM: Thielavia terrestris

<400> SEQUENCE: 5
ctcctgttcc tgggccaccg cttgttgcct gcactattgg tagagttggt ctattgctag      60
agttggccat gcttctcaca tcagtcctcg gctcggctgc cctgcttgct agcggcgctg     120
cggcacacgg cgccgtgacc agctacatca tcgccggcaa gaattacccg gggtgggtag     180
ctgattattg agggcgcatt caaggttcat accggtgtgc atggctgaca accggctggc     240
agataccaag gcttttctcc tgcgaactcg ccgaacgtca tccaatggca atggcatgac     300
tacaaccccg tcttgtcgtg cagcgactcg aagcttcgct gcaacggcgg cacgtcggcc     360
accctgaacg ccacggccgc accgggcgac catcaccg ccatctgggc gcagtggacg       420
cacagccagg gccccatcct ggtgtggatg tacaagtgcc cgggctcctt cagtcctgt      480 gacggctccg gcgctggctg gttcaagatc gacgaggccg gcttccacgg cgacggcgtc     540
aaggtcttcc tcgacaccga aacccgtcc ggctgggaca tcgccaagct cgtcggcggc      600
aacaagcagt ggagcagcaa ggtccccgag ggcctcgccc ccggcaacta cctcgtccgc     660
cacgagttga tcgccctgca ccaggccaac aacccgcagt tctacccgga gtgcgcccag     720
gtcgtcatca ccggctccgg caccgcgcag ccggatgcct catacaaggc ggctatcccc     780
ggctactgca accagaatga cccgaacatc aaggtgagat ccaggcgtaa tgcagtctac     840
tgctggaaag aaagtggtcc aagctaaacc gcgctccagg tgcccatcaa cgaccactcc     900
atccctcaga cctacaagat tcccggccct cccgtcttca agggcaccgc cagcaagaag     960
gcccgggact tcaccgcctg aagttgttga atcgatggag                          1000

<210> SEQ ID NO 6
<211> LENGTH: 516
<212> TYPE: PRT
<213> ORGANISM: Thielavia terrestris

<400> SEQUENCE: 6

Met Leu Leu Thr Ser Val Leu Gly Ser Ala Ala Leu Leu Ala Ser Gly
1               5                   10                  15

Ala Ala Ala His Gly Ala Val Thr Ser Tyr Ile Ile Ala Gly Lys Asn
            20                  25                  30

Tyr Pro Gly Tyr Gln Gly Phe Ser Pro Ala Asn Ser Pro Asn Val Ile
        35                  40                  45

Gln Trp Gln Trp His Asp Tyr Asn Pro Val Leu Ser Cys Ser Asp Ser
    50                  55                  60

Lys Leu Arg Cys Asn Gly Gly Thr Ser Ala Thr Leu Asn Ala Thr Ala
65                  70                  75                  80

Ala Pro Gly Asp Thr Ile Thr Ala Ile Trp Ala Gln Trp Thr His Ser
                85                  90                  95
```

-continued

```
Gln Gly Pro Ile Leu Val Trp Met Tyr Lys Cys Pro Gly Ser Phe Ser
            100                 105                 110
Ser Cys Asp Gly Ser Gly Ala Gly Trp Phe Lys Ile Asp Glu Ala Gly
            115                 120                 125
Phe His Gly Asp Gly Val Lys Val Phe Leu Asp Thr Glu Asn Pro Ser
            130                 135                 140
Gly Trp Asp Ile Ala Lys Leu Val Gly Asn Lys Gln Trp Ser Ser
145                 150                 155                 160
Lys Val Pro Glu Gly Leu Ala Pro Gly Asn Tyr Leu Val Arg His Glu
                165                 170                 175
Leu Ile Ala Leu His Gln Ala Asn Asn Pro Gln Phe Tyr Pro Glu Cys
            180                 185                 190
Ala Gln Val Val Ile Thr Gly Ser Gly Thr Ala Gln Pro Asp Ala Ser
            195                 200                 205
Tyr Lys Ala Ala Ile Pro Gly Tyr Cys Asn Gln Asn Asp Pro Asn Ile
            210                 215                 220
Lys Val Pro Ile Asn Asp His Ser Ile Pro Gln Thr Tyr Lys Ile Pro
225                 230                 235                 240
Gly Pro Pro Val Phe Lys Gly Thr Ala Ser Lys Ala Arg Asp Phe
                245                 250                 255
Thr Ala Met Leu Leu Thr Ser Val Leu Gly Ser Ala Ala Leu Leu Ala
            260                 265                 270
Ser Gly Ala Ala Ala His Gly Ala Val Thr Ser Tyr Ile Ile Ala Gly
            275                 280                 285
Lys Asn Tyr Pro Gly Tyr Gln Gly Phe Ser Pro Ala Asn Ser Pro Asn
290                 295                 300
Val Ile Gln Trp Gln Trp His Asp Tyr Asn Pro Val Leu Ser Cys Ser
305                 310                 315                 320
Asp Ser Lys Leu Arg Cys Asn Gly Gly Thr Ser Ala Thr Leu Asn Ala
                325                 330                 335
Thr Ala Ala Pro Gly Asp Thr Ile Thr Ala Ile Trp Ala Gln Trp Thr
            340                 345                 350
His Ser Gln Gly Pro Ile Leu Val Trp Met Tyr Lys Cys Pro Gly Ser
            355                 360                 365
Phe Ser Ser Cys Asp Gly Ser Gly Ala Gly Trp Phe Lys Ile Asp Glu
            370                 375                 380
Ala Gly Phe His Gly Asp Gly Val Lys Val Phe Leu Asp Thr Glu Asn
385                 390                 395                 400
Pro Ser Gly Trp Asp Ile Ala Lys Leu Val Gly Asn Lys Gln Trp
                405                 410                 415
Ser Ser Lys Val Pro Glu Gly Leu Ala Pro Gly Asn Tyr Leu Val Arg
            420                 425                 430
His Glu Leu Ile Ala Leu His Gln Ala Asn Asn Pro Gln Phe Tyr Pro
            435                 440                 445
Glu Cys Ala Gln Val Val Ile Thr Gly Ser Gly Thr Ala Gln Pro Asp
            450                 455                 460
Ala Ser Tyr Lys Ala Ala Ile Pro Gly Tyr Cys Asn Gln Asn Asp Pro
465                 470                 475                 480
Asn Ile Lys Val Pro Ile Asn Asp His Ser Ile Pro Gln Thr Tyr Lys
                485                 490                 495
Ile Pro Gly Pro Pro Val Phe Lys Gly Thr Ala Ser Lys Lys Ala Arg
            500                 505                 510
Asp Phe Thr Ala
```

-continued

515

<210> SEQ ID NO 7
<211> LENGTH: 681
<212> TYPE: DNA
<213> ORGANISM: Thielavia terrestris

<400> SEQUENCE: 7

| | | |
|---|---|---|
| atgctcgcaa acggtgccat cgtcttcctg gccgccgccc tcggcgtcag tggccactac | 60 |
| acctggccac gggttaacga cggcgccgac tggcaacagg tccgtaaggc ggacaactgg | 120 |
| caggacaacg gctacgtcgg ggatgtcacg tcgccacaga tccgctgttt ccaggcgacc | 180 |
| ccgtccccgg ccccatccgt cctcaacacc acggccggct cgaccgtgac ctactgggcc | 240 |
| aaccccgacg tctaccaccc cgggcctgtg cagttttaca tggcccgcgt gcccgatggc | 300 |
| gaggacatca actcgtggaa cggcgacggc gccgtgtggt tcaaggtgta cgaggaccat | 360 |
| cctacctttg gcgctcagct cacatggccc agcacgggca gagctcgtt cgcggttccc | 420 |
| atccccccgt gcatcaagtc cggctactac ctcctccggg cggagcaaat cggcctgcac | 480 |
| gtcgcccaga gcgtaggcgg agcgcagttc tacatctcat gcgcccagct cagcgtcacc | 540 |
| ggcggcggca gcaccgagcc gccgaacaag gtggccttcc ccggcgctta cagtgcgacg | 600 |
| gacccgggca ttctgatcaa catctactac cctgttccca cgtcctacca gaaccccggc | 660 |
| ccggccgtct tcagctgctg a | 681 |

<210> SEQ ID NO 8
<211> LENGTH: 452
<212> TYPE: PRT
<213> ORGANISM: Thielavia terrestris

<400> SEQUENCE: 8

Met Leu Ala Asn Gly Ala Ile Val Phe Leu Ala Ala Ala Leu Gly Val
1               5                   10                  15

Ser Gly His Tyr Thr Trp Pro Arg Val Asn Asp Gly Ala Asp Trp Gln
            20                  25                  30

Gln Val Arg Lys Ala Asp Asn Trp Gln Asp Asn Gly Tyr Val Gly Asp
        35                  40                  45

Val Thr Ser Pro Gln Ile Arg Cys Phe Gln Ala Thr Pro Ser Pro Ala
    50                  55                  60

Pro Ser Val Leu Asn Thr Thr Ala Gly Ser Thr Val Thr Tyr Trp Ala
65                  70                  75                  80

Asn Pro Asp Val Tyr His Pro Gly Pro Val Gln Phe Tyr Met Ala Arg
                85                  90                  95

Val Pro Asp Gly Glu Asp Ile Asn Ser Trp Asn Gly Asp Gly Ala Val
            100                 105                 110

Trp Phe Lys Val Tyr Glu Asp His Pro Thr Phe Gly Ala Gln Leu Thr
        115                 120                 125

Trp Pro Ser Thr Gly Lys Ser Ser Phe Ala Val Pro Ile Pro Pro Cys
    130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
                165                 170                 175

Leu Ser Val Thr Gly Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile

```
                195                 200                 205
Tyr Tyr Pro Val Pro Thr Ser Tyr Gln Asn Pro Gly Pro Ala Val Phe
        210                 215                 220

Ser Cys Met Leu Ala Asn Gly Ala Ile Val Phe Leu Ala Ala Ala Leu
225                 230                 235                 240

Gly Val Ser Gly His Tyr Thr Trp Pro Arg Val Asn Asp Gly Ala Asp
            245                 250                 255

Trp Gln Gln Val Arg Lys Ala Asp Asn Trp Gln Asn Gly Tyr Val
                260                 265                 270

Gly Asp Val Thr Ser Pro Gln Ile Arg Cys Phe Gln Ala Thr Pro Ser
            275                 280                 285

Pro Ala Pro Ser Val Leu Asn Thr Thr Ala Gly Ser Thr Val Thr Tyr
        290                 295                 300

Trp Ala Asn Pro Asp Val Tyr His Pro Gly Pro Val Gln Phe Tyr Met
305                 310                 315                 320

Ala Arg Val Pro Asp Gly Glu Asp Ile Asn Ser Trp Asn Gly Asp Gly
                325                 330                 335

Ala Val Trp Phe Lys Val Tyr Glu Asp His Pro Thr Phe Gly Ala Gln
            340                 345                 350

Leu Thr Trp Pro Ser Thr Gly Lys Ser Ser Phe Ala Val Pro Ile Pro
        355                 360                 365

Pro Cys Ile Lys Ser Gly Tyr Tyr Leu Leu Arg Ala Glu Gln Ile Gly
        370                 375                 380

Leu His Val Ala Gln Ser Val Gly Gly Ala Gln Phe Tyr Ile Ser Cys
385                 390                 395                 400

Ala Gln Leu Ser Val Thr Gly Gly Gly Ser Thr Glu Pro Pro Asn Lys
                405                 410                 415

Val Ala Phe Pro Gly Ala Tyr Ser Ala Thr Asp Pro Gly Ile Leu Ile
            420                 425                 430

Asn Ile Tyr Tyr Pro Val Pro Thr Ser Tyr Gln Asn Pro Gly Pro Ala
        435                 440                 445

Val Phe Ser Cys
    450

<210> SEQ ID NO 9
<211> LENGTH: 960
<212> TYPE: DNA
<213> ORGANISM: Thielavia terrestris

<400> SEQUENCE: 9 atgaaggac tttttcagtgc cgccgccctc tccctggccg tcggccaggc ttcggcccat    60
tacatcttcc agcaactctc catcaacggg aaccagtttc ggtgtacca atatattcgc   120
aagaacacca attataacag tcccgttacc gatctcacgt ccgacgatct tcggtgcaat   180
gtcggcgccc agggtgctgg gacagacacc gtcacggtga aggccggcga ccagttcacc   240
ttcacccttg acacccctgt ttaccaccag gggcccatct ccatctacat gtccaaggcc   300
ccgggcgcgg cgtcagacta cgatggcagc ggcggctggt tcaagatcaa ggactggggc   360
ccgactttca cgccgacgg cacggccacc tgggacatgg ccggctcata cctacaac     420
atcccgacct gcattcccga cggcgactat ctgctccgca tccagtcgct ggccatccac   480
aaccctggc cggcgggcat cccgcagttc tacatctcct gcgcccagat caccgtgacc   540
ggcggcggca acggcaaccc tggcccgacg gccctcatcc ccggcgcctt caaggacacc   600
gacccgggct acacggtgaa catctacacg aacttccaca actacacggt tcccggcccg   660
```

-continued

```
gaggtcttca gctgcaacgg cggcggctcg aacccgcccc cgccggtgag tagcagcacg    720
cccgcgacca cgacgctggt cacgtcgacg cgcaccacgt cctccacgtc ctccgcctcg    780
acgccggcct cgaccggcgg ctgcaccgtc gccaagtggg gccagtgcgg cggcaacggg    840
tacaccggct gcacgacctg cgcggccggg tccacctgca gcaagcagaa cgactactac    900
tcgcagtgct gtaagggag gccgcaaagc atgaggtgtt tgaagaggag gagagggtc      960
```

<210> SEQ ID NO 10
<211> LENGTH: 608
<212> TYPE: PRT
<213> ORGANISM: Thielavia terrestris

<400> SEQUENCE: 10

```
Met Lys Gly Leu Phe Ser Ala Ala Ala Leu Ser Leu Ala Val Gly Gln
1               5                   10                  15

Ala Ser Ala His Tyr Ile Phe Gln Gln Leu Ser Ile Asn Gly Asn Gln
            20                  25                  30

Phe Pro Val Tyr Gln Tyr Ile Arg Lys Asn Thr Asn Tyr Asn Ser Pro
        35                  40                  45

Val Thr Asp Leu Thr Ser Asp Asp Leu Arg Cys Asn Val Gly Ala Gln
    50                  55                  60

Gly Ala Gly Thr Asp Thr Val Thr Val Lys Ala Gly Asp Gln Phe Thr
65                  70                  75                  80

Phe Thr Leu Asp Thr Pro Val Tyr His Gln Gly Pro Ile Ser Ile Tyr
                85                  90                  95

Met Ser Lys Ala Pro Gly Ala Ala Ser Asp Tyr Asp Gly Ser Gly Gly
            100                 105                 110

Trp Phe Lys Ile Lys Asp Trp Gly Pro Thr Phe Asn Ala Asp Gly Thr
        115                 120                 125

Ala Thr Trp Asp Met Ala Gly Ser Tyr Thr Tyr Asn Ile Pro Thr Cys
    130                 135                 140

Ile Pro Asp Gly Asp Tyr Leu Leu Arg Ile Gln Ser Leu Ala Ile His
145                 150                 155                 160

Asn Pro Trp Pro Ala Gly Ile Pro Gln Phe Tyr Ile Ser Cys Ala Gln
                165                 170                 175

Ile Thr Val Thr Gly Gly Gly Asn Gly Asn Pro Gly Pro Thr Ala Leu
            180                 185                 190

Ile Pro Gly Ala Phe Lys Asp Thr Asp Pro Gly Tyr Thr Val Asn Ile
        195                 200                 205

Tyr Thr Asn Phe His Asn Tyr Thr Val Pro Gly Pro Glu Val Phe Ser
    210                 215                 220

Cys Asn Gly Gly Gly Ser Asn Pro Pro Pro Val Ser Ser Ser Thr
225                 230                 235                 240

Pro Ala Thr Thr Thr Leu Val Ser Thr Arg Thr Thr Ser Ser Thr
                245                 250                 255

Ser Ser Ala Ser Thr Pro Ala Ser Thr Gly Gly Cys Thr Val Ala Lys
            260                 265                 270

Trp Gly Gln Cys Gly Gly Asn Gly Tyr Thr Gly Cys Thr Thr Cys Ala
        275                 280                 285

Ala Gly Ser Thr Cys Ser Lys Gln Asn Asp Tyr Tyr Ser Gln Cys Leu
    290                 295                 300

Met Lys Gly Leu Phe Ser Ala Ala Ala Leu Ser Leu Ala Val Gly Gln
305                 310                 315                 320
```

-continued

```
Ala Ser Ala His Tyr Ile Phe Gln Gln Leu Ser Ile Asn Gly Asn Gln
            325                 330                 335

Phe Pro Val Tyr Gln Tyr Ile Arg Lys Asn Thr Asn Tyr Asn Ser Pro
            340                 345                 350

Val Thr Asp Leu Thr Ser Asp Asp Leu Arg Cys Asn Val Gly Ala Gln
            355                 360                 365

Gly Ala Gly Thr Asp Thr Val Thr Val Lys Ala Gly Asp Gln Phe Thr
    370                 375                 380

Phe Thr Leu Asp Thr Pro Val Tyr His Gln Gly Pro Ile Ser Ile Tyr
385                 390                 395                 400

Met Ser Lys Ala Pro Gly Ala Ala Ser Asp Tyr Gly Ser Gly Gly
                405                 410                 415

Trp Phe Lys Ile Lys Asp Trp Gly Pro Thr Phe Asn Ala Asp Gly Thr
            420                 425                 430

Ala Thr Trp Asp Met Ala Gly Ser Tyr Thr Tyr Asn Ile Pro Thr Cys
            435                 440                 445

Ile Pro Asp Gly Asp Tyr Leu Leu Arg Ile Gln Ser Leu Ala Ile His
    450                 455                 460

Asn Pro Trp Pro Ala Gly Ile Pro Gln Phe Tyr Ile Ser Cys Ala Gln
465                 470                 475                 480

Ile Thr Val Thr Gly Gly Gly Asn Gly Asn Pro Gly Pro Thr Ala Leu
            485                 490                 495

Ile Pro Gly Ala Phe Lys Asp Thr Asp Pro Gly Tyr Thr Val Asn Ile
            500                 505                 510

Tyr Thr Asn Phe His Asn Tyr Thr Val Pro Gly Pro Glu Val Phe Ser
            515                 520                 525

Cys Asn Gly Gly Ser Asn Pro Pro Pro Val Ser Ser Ser Thr
530                 535                 540

Pro Ala Thr Thr Thr Leu Val Thr Ser Thr Arg Thr Thr Ser Ser Thr
545                 550                 555                 560

Ser Ser Ala Ser Thr Pro Ala Ser Thr Gly Gly Cys Thr Val Ala Lys
            565                 570                 575

Trp Gly Gln Cys Gly Gly Asn Gly Tyr Thr Gly Cys Thr Thr Cys Ala
            580                 585                 590

Ala Gly Ser Thr Cys Ser Lys Gln Asn Asp Tyr Tyr Ser Gln Cys Leu
            595                 600                 605
```

```
<210> SEQ ID NO 11
<211> LENGTH: 17
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: Xaa= Ile or Leu
<220> FEATURE:
<221> NAME/KEY: MISC_FEATURE
<222> LOCATION: (16)..(16)
<223> OTHER INFORMATION: Xaa= Ile or Leu

<400> SEQUENCE: 11

Xaa Pro Ala Ser Asn Ser Pro Val Thr Asn Val Ala Ser Asp Asp Xaa
1               5                   10                  15

Arg

<210> SEQ ID NO 12
<211> LENGTH: 13
<212> TYPE: PRT
```

```
<213> ORGANISM: Thielavia terrestris
<220> FEATURE:
<221> NAME/KEY: MISC_FEATURE
<222> LOCATION: (1)..(1)
<223> OTHER INFORMATION: Xaa= Ile or Leu
<220> FEATURE:
<221> NAME/KEY: MISC_FEATURE
<222> LOCATION: (5)..(5)
<223> OTHER INFORMATION: Xaa= Ile or Leu
<220> FEATURE:
<221> NAME/KEY: MISC_FEATURE
<222> LOCATION: (11)..(12)
<223> OTHER INFORMATION: Xaa= Ile or Leu

<400> SEQUENCE: 12

Xaa Pro Glu Asp Xaa Glu Pro Gly Asp Tyr Xaa Xaa Arg
 1               5                  10

<210> SEQ ID NO 13
<211> LENGTH: 17
<212> TYPE: PRT
<213> ORGANISM: Thielavia terrestris

<400> SEQUENCE: 13

Cys Pro Gly Ser Phe Ser Ser Cys Asp Gly Ser Gly Ala Gly Trp Phe
 1               5                  10                  15

Lys

<210> SEQ ID NO 14
<211> LENGTH: 12
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: Xaa= Ile or Leu

<400> SEQUENCE: 14

Xaa Asp Glu Ala Gly Phe His Gly Asp Gly Val Lys
 1               5                  10

<210> SEQ ID NO 15
<211> LENGTH: 10
<212> TYPE: PRT
<213> ORGANISM: Thielavia terrestris
<220> FEATURE:
<221> NAME/KEY: MISC_FEATURE
<222> LOCATION: (1)..(2)
<223> OTHER INFORMATION: Xaa= Any Aminio Acid
<220> FEATURE:
<221> NAME/KEY: MISC_FEATURE
<222> LOCATION: (8)..(9)
<223> OTHER INFORMATION: Xaa= Ile or Leu

<400> SEQUENCE: 15

Xaa Xaa Ala Pro Gly Asn Tyr Xaa Xaa Arg
 1               5                  10

<210> SEQ ID NO 16
<211> LENGTH: 22
<212> TYPE: DNA
<213> ORGANISM: Aspergillus nidulans

<400> SEQUENCE: 16
gtgccccatg atacgcctcc gg                                          22

<210> SEQ ID NO 17
<211> LENGTH: 26
```

```
<212> TYPE: DNA
<213> ORGANISM: Aspergillus nidulans

<400> SEQUENCE: 17
gagtcgtatt tccaaggctc ctgacc                                         26

<210> SEQ ID NO 18
<211> LENGTH: 24
<212> TYPE: DNA
<213> ORGANISM: Aspergillus nidulans

<400> SEQUENCE: 18
ggaggccatg aagtggacca acgg                                           24

<210> SEQ ID NO 19
<211> LENGTH: 45
<212> TYPE: DNA
<213> ORGANISM: Aspergillus niger

<400> SEQUENCE: 19
caccgtgaaa gccatgctct ttccttcgtg tagaagacca gacag                    45

<210> SEQ ID NO 20
<211> LENGTH: 45
<212> TYPE: DNA
<213> ORGANISM: Aspergillus niger

<400> SEQUENCE: 20
ctggtcttct acacgaagga aagagcatgg ctttcacggt gtctg                    45

<210> SEQ ID NO 21
<211> LENGTH: 44
<212> TYPE: DNA
<213> ORGANISM: Aspergillus niger

<400> SEQUENCE: 21
ctatatacac aactggattt accatgggcc cgcggccgca gatc                     44

<210> SEQ ID NO 22
<211> LENGTH: 44
<212> TYPE: DNA
<213> ORGANISM: Aspergillus niger

<400> SEQUENCE: 22
gatctgcggc cgcgggccca tggtaaatcc agttgtgtat atag                     44

<210> SEQ ID NO 23
<211> LENGTH: 17
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: Xaa= Ile or Leu
<220> FEATURE:
<221> NAME/KEY: MISC_FEATURE
<222> LOCATION: (16)..(16)
<223> OTHER INFORMATION: Xaa= Ile or Leu

<400> SEQUENCE: 23

Xaa Pro Ala Ser Asn Ser Pro Val Thr Asn Val Ala Ser Asp Asp Xaa
1               5                   10                  15

Arg
```

```
<210> SEQ ID NO 24
<211> LENGTH: 13
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: Xaa= Ile or Leu
<220> FEATURE:
<221> NAME/KEY: MISC_FEATURE
<222> LOCATION: (5)..(5)
<223> OTHER INFORMATION: Xaa= Ile or Leu
<220> FEATURE:
<221> NAME/KEY: MISC_FEATURE
<222> LOCATION: (11)..(12)
<223> OTHER INFORMATION: Xaa= Ile or Leu

<400> SEQUENCE: 24

Xaa Pro Glu Asp Xaa Glu Pro Gly Asp Tyr Xaa Xaa Arg
1               5                   10

<210> SEQ ID NO 25
<211> LENGTH: 28
<212> TYPE: DNA
<213> ORGANISM: Thielavia terrestris
<220> FEATURE:
<221> NAME/KEY: misc_feature
<222> LOCATION: (20)..(20)
<223> OTHER INFORMATION: N = A,C,G, OR T
<220> FEATURE:
<221> NAME/KEY: misc_feature
<222> LOCATION: (26)..(26)
<223> OTHER INFORMATION: N = A,C,G, OR T

<400> SEQUENCE: 25
cctccaactc ccccgtcacn aaygtngc                                          28

<210> SEQ ID NO 26
<211> LENGTH: 27
<212> TYPE: DNA
<213> ORGANISM: Thielavia terrestris
<220> FEATURE:
<221> NAME/KEY: misc_feature
<222> LOCATION: (19)..(19)
<223> OTHER INFORMATION: N=A,C,G, OR T
<220> FEATURE:
<221> NAME/KEY: misc_feature
<222> LOCATION: (22)..(22)
<223> OTHER INFORMATION: N=A,C,G, OR T

<400> SEQUENCE: 26
ggcgcggagg aggtartcnc cnggytc                                           27

<210> SEQ ID NO 27
<211> LENGTH: 16
<212> TYPE: PRT
<213> ORGANISM: Thielavia terrestris

<400> SEQUENCE: 27

Ser Gly Ala Gly Trp Phe Lys Ile Asp Glu Ala Gly Phe His Gly Asp
1               5                   10                  15

<210> SEQ ID NO 28
<211> LENGTH: 8
<212> TYPE: PRT
<213> ORGANISM: Thielavia terrestris
<220> FEATURE:
<221> NAME/KEY: MISC_FEATURE
<222> LOCATION: (6)..(7)
<223> OTHER INFORMATION: Xaa= Ile or Leu
```

```
<400> SEQUENCE: 28

Ala Pro Gly Asn Tyr Xaa Xaa Arg
1               5

<210> SEQ ID NO 29
<211> LENGTH: 11
<212> TYPE: PRT
<213> ORGANISM: Thielavia terrestris

<400> SEQUENCE: 29

Ala Pro Gly Asn Tyr Leu Ile Arg His Glu Leu
1               5                   10

<210> SEQ ID NO 30
<211> LENGTH: 11
<212> TYPE: PRT
<213> ORGANISM: Thielavia terrestris

<400> SEQUENCE: 30

Ala Pro Gly Asn Tyr Leu Val Arg His Glu Leu
1               5                   10

<210> SEQ ID NO 31
<211> LENGTH: 9
<212> TYPE: PRT
<213> ORGANISM: Thielavia terrestris

<400> SEQUENCE: 31

Gly Ala Gly Trp Phe Lys Ile Asp Glu
1               5

<210> SEQ ID NO 32
<211> LENGTH: 27
<212> TYPE: DNA
<213> ORGANISM: Thielavia terrestris
<220> FEATURE:
<221> NAME/KEY: misc_feature
<222> LOCATION: (19)..(19)
<223> OTHER INFORMATION: R= A or G
<220> FEATURE:
<221> NAME/KEY: misc_feature
<222> LOCATION: (22)..(22)
<223> OTHER INFORMATION: H= A, C, or T
<220> FEATURE:
<221> NAME/KEY: misc_feature
<222> LOCATION: (25)..(25)
<223> OTHER INFORMATION: Y= C or T

<400> SEQUENCE: 32
cggcgcgggc tggtttaara thgayga                                            27

<210> SEQ ID NO 33
<211> LENGTH: 32
<212> TYPE: DNA
<213> ORGANISM: Thielavia terrestris
<220> FEATURE:
<221> NAME/KEY: misc_feature
<222> LOCATION: (21)..(21)
<223> OTHER INFORMATION: R= A or G
<220> FEATURE:
<221> NAME/KEY: misc_feature
<222> LOCATION: (24)..(24)
<223> OTHER INFORMATION: N= A, C, G, or T
<220> FEATURE:
<221> NAME/KEY: misc_feature
<222> LOCATION: (27)..(27)
<223> OTHER INFORMATION: N= A, C, G, or T
<220> FEATURE:
<221> NAME/KEY: misc_feature
```

```
<222> LOCATION: (30)..(30)
<223> OTHER INFORMATION: N= A, C, G, or T

<400> SEQUENCE: 33
agttcatggc gaatcagata rttnccnggn gc                                    32

<210> SEQ ID NO 34
<211> LENGTH: 25
<212> TYPE: DNA
<213> ORGANISM: Thielavia terrestris

<400> SEQUENCE: 34
cttggtaccg agctcggatc cacta                                            25

<210> SEQ ID NO 35
<211> LENGTH: 25
<212> TYPE: DNA
<213> ORGANISM: Thielavia terrestris

<400> SEQUENCE: 35
atagggcgaa ttgggccctc tagat                                            25

<210> SEQ ID NO 36
<211> LENGTH: 32
<212> TYPE: DNA
<213> ORGANISM: Thielavia terrestris

<400> SEQUENCE: 36
acaactggat ttaccatgcg gttcgacgcc tc                                    32

<210> SEQ ID NO 37
<211> LENGTH: 33
<212> TYPE: DNA
<213> ORGANISM: Thielavia terrestris

<400> SEQUENCE: 37
gtcagtcacc tctagttact aaaactcgaa gcc                                   33

<210> SEQ ID NO 38
<211> LENGTH: 21
<212> TYPE: DNA
<213> ORGANISM: Thielavia terrestris

<400> SEQUENCE: 38
catgccatgg atgcttctca c                                                21

<210> SEQ ID NO 39
<211> LENGTH: 25
<212> TYPE: DNA
<213> ORGANISM: Thielavia terrestris

<400> SEQUENCE: 39
ccttaattaa tcaggcggtg aagtc                                            25

<210> SEQ ID NO 40
<211> LENGTH: 32
<212> TYPE: DNA
<213> ORGANISM: Thielavia terrestris

<400> SEQUENCE: 40
tcgtcgggga caactttgta caaaaaagtt gg                                    32

<210> SEQ ID NO 41
```

```
<211> LENGTH: 27
<212> TYPE: DNA
<213> ORGANISM: Thielavia terrestris

<400> SEQUENCE: 41
cccctgttga aacatgtttt ttcaacc                                            27

<210> SEQ ID NO 42
<211> LENGTH: 16
<212> TYPE: DNA
<213> ORGANISM: Thielavia terrestris

<400> SEQUENCE: 42
gtaaaacgac ggccag                                                       16

<210> SEQ ID NO 43
<211> LENGTH: 25
<212> TYPE: DNA
<213> ORGANISM: Escherichia coli
<220> FEATURE:
<221> NAME/KEY: misc_feature
<222> LOCATION: (24)..(27)
<223> OTHER INFORMATION: V= A, C, OR G
<220> FEATURE:
<221> NAME/KEY: misc_feature
<222> LOCATION: (25)..(25)
<223> OTHER INFORMATION: N=A, C, G, OR T

<400> SEQUENCE: 43
tttttttttt tttttttttt tttvn                                             25

<210> SEQ ID NO 44
<211> LENGTH: 27
<212> TYPE: DNA
<213> ORGANISM: Escherichia coli

<400> SEQUENCE: 44
ggggacaact ttgtacaaaa aagttgg                                           27

<210> SEQ ID NO 45
<211> LENGTH: 27
<212> TYPE: DNA
<213> ORGANISM: Escherichia coli

<400> SEQUENCE: 45
aaaggtagga tggtcctcgt acacctt                                           27

<210> SEQ ID NO 46
<211> LENGTH: 36
<212> TYPE: DNA
<213> ORGANISM: Thielavia terrestris

<400> SEQUENCE: 46
actggattac catgctcgca aacggtgcca tcgtct                                 36

<210> SEQ ID NO 47
<211> LENGTH: 38
<212> TYPE: DNA
<213> ORGANISM: Thielavia terrestris

<400> SEQUENCE: 47
tcacctctag ttaattaatc agcagctgaa gacggccg                               38

<210> SEQ ID NO 48
<211> LENGTH: 31
```

```
<212> TYPE: DNA
<213> ORGANISM: Thielavia terrestris

<400> SEQUENCE: 48
actggattta ccatgaagtc gttcaccatt g                                     31

<210> SEQ ID NO 49
<211> LENGTH: 31
<212> TYPE: DNA
<213> ORGANISM: Thielavia terrestris

<400> SEQUENCE: 49
agtcacctct agttagaggc actgcgagta g                                     31

<210> SEQ ID NO 50
<211> LENGTH: 32
<212> TYPE: DNA
<213> ORGANISM: Thielavia terrestris

<400> SEQUENCE: 50
acaactggat ttaccatgcg gttcgacgcc tc                                    32

<210> SEQ ID NO 51
<211> LENGTH: 33
<212> TYPE: DNA
<213> ORGANISM: Thielavia terrestris

<400> SEQUENCE: 51
gtcagtcacc tctagttact aaaactcgaa gcc                                   33

<210> SEQ ID NO 52
<211> LENGTH: 27
<212> TYPE: DNA
<213> ORGANISM: Thielavia terrestris

<400> SEQUENCE: 52
actggattac catgcttctc acatcag                                          27

<210> SEQ ID NO 53
<211> LENGTH: 30
<212> TYPE: DNA
<213> ORGANISM: Thielavia terrestris

<400> SEQUENCE: 53
agtcacctct agttatcagg cggtgaagtc                                       30

<210> SEQ ID NO 54
<211> LENGTH: 31
<212> TYPE: DNA
<213> ORGANISM: Thielavia terrestris

<400> SEQUENCE: 54
actggattac catgaaggga cttttcagtg c                                     31

<210> SEQ ID NO 55
<211> LENGTH: 31
<212> TYPE: DNA
<213> ORGANISM: Thielavia terrestris

<400> SEQUENCE: 55
agtcacctct agttagaggc actgcgagta g                                     31

<210> SEQ ID NO 56
```

```
<211> LENGTH: 29
<212> TYPE: DNA
<213> ORGANISM: Trichoderma reesei

<400> SEQUENCE: 56
aacgttaatt aaggaatcgt tttgtgttt                                29

<210> SEQ ID NO 57
<211> LENGTH: 29
<212> TYPE: DNA
<213> ORGANISM: Trichoderma reesei

<400> SEQUENCE: 57
agtactagta gctccgtggc gaaagcctg                                29

<210> SEQ ID NO 58
<211> LENGTH: 26
<212> TYPE: DNA
<213> ORGANISM: Trichoderma reesei

<400> SEQUENCE: 58
actagtcgac cgaatgtagg attgtt                                   26

<210> SEQ ID NO 59
<211> LENGTH: 19
<212> TYPE: DNA
<213> ORGANISM: Trichoderma reesei

<400> SEQUENCE: 59
tgaccatggt gcgcagtcc                                           19

<210> SEQ ID NO 60
<211> LENGTH: 26
<212> TYPE: DNA
<213> ORGANISM: Trichoderma reesei

<400> SEQUENCE: 60
cgatcgtctc cctatgggtc attacc                                   26

<210> SEQ ID NO 61
<211> LENGTH: 28
<212> TYPE: DNA
<213> ORGANISM: Trichoderma reesei

<400> SEQUENCE: 61
actagttaat taagctccgt ggcgaaag                                 28

<210> SEQ ID NO 62
<211> LENGTH: 24
<212> TYPE: DNA
<213> ORGANISM: Escherichia coli

<400> SEQUENCE: 62
gggttcgaat tcatttaaac ggct                                     24

<210> SEQ ID NO 63
<211> LENGTH: 24
<212> TYPE: DNA
<213> ORGANISM: Escherichia coli

<400> SEQUENCE: 63
gggagcgctc aatattcatc tctc                                     24
```

```
<210> SEQ ID NO 64
<211> LENGTH: 26
<212> TYPE: DNA
<213> ORGANISM: Escherichia coli

<400> SEQUENCE: 64
ggtcgcggag gcgatggatg cgatcg                                          26

<210> SEQ ID NO 65
<211> LENGTH: 26
<212> TYPE: DNA
<213> ORGANISM: Escherichia coli

<400> SEQUENCE: 65
cgatcgcatc catcgcctcc gcgacc                                          26

<210> SEQ ID NO 66
<211> LENGTH: 34
<212> TYPE: DNA
<213> ORGANISM: Thielavia terrestris

<400> SEQUENCE: 66
cgcggactgc gcaccatgaa gtcgttcacc attg                                 34

<210> SEQ ID NO 67
<211> LENGTH: 31
<212> TYPE: DNA
<213> ORGANISM: Thielavia terrestris

<400> SEQUENCE: 67
tcgccacgga gcttagaggc actgcgagta g                                    31

<210> SEQ ID NO 68
<211> LENGTH: 23
<212> TYPE: DNA
<213> ORGANISM: Thielavia terrestris

<400> SEQUENCE: 68
gcccatggac catgctcgca aac                                             23

<210> SEQ ID NO 69
<211> LENGTH: 23
<212> TYPE: DNA
<213> ORGANISM: Thielavia terrestris

<400> SEQUENCE: 69
cctctagtta attaatcagc agc                                             23

<210> SEQ ID NO 70
<211> LENGTH: 23
<212> TYPE: DNA
<213> ORGANISM: Thielavia terrestris

<400> SEQUENCE: 70
gcccatggac catgaaggga ctt                                             23

<210> SEQ ID NO 71
<211> LENGTH: 23
<212> TYPE: DNA
<213> ORGANISM: Thielavia terrestris

<400> SEQUENCE: 71
cctctagtta attaattaca agc                                             23
```

<210> SEQ ID NO 72
<211> LENGTH: 19
<212> TYPE: DNA
<213> ORGANISM: Trichoderma reesei

<400> SEQUENCE: 72
ggatgaagct cattagccg                                              19

<210> SEQ ID NO 73
<211> LENGTH: 31
<212> TYPE: DNA
<213> ORGANISM: Aspergillus fumigatus

<400> SEQUENCE: 73
actggattta ccatgagatt cggttggctc g                                31

<210> SEQ ID NO 74
<211> LENGTH: 31
<212> TYPE: DNA
<213> ORGANISM: Aspergillus fumigatus

<400> SEQUENCE: 74
agtcacctct agttactagt agacacgggg c                                31

<210> SEQ ID NO 75
<211> LENGTH: 3060
<212> TYPE: DNA
<213> ORGANISM: Aspergillus fumigatus

<400> SEQUENCE: 75
atgagattcg gttggctcga ggtggccgct ctgacggccg cttctgtagc caatgcccag      60
gtttgtgatg ctttcccgtc attgtttcgg atatagttga caatagtcat ggaaataatc     120
aggaattggc tttctctcca ccattctacc cttcgccttg ggctgatggc cagggagagt     180
gggcagatgc ccatcgacgc gccgtcgaga tcgtttctca gatgacactg gcggagaagg     240
ttaaccttac aacgggtact gggtgggttg cgactttttt gttgacagtg agctttcttc     300
actgaccatc tacacagatg ggaaatggac cgatgcgtcg gtcaaaccgg cagcgttccc     360
aggtaagctt gcaattctgc aacaacgtgc aagtgtagtt gctaaaacgc ggtggtgcag     420
acttggtatc aactggggtc tttgtggcca ggattcccct ttgggtatcc gtttctgtga     480
gctatacccg cggagtcttt cagtccttgt attatgtgct gatgattgtc tctgtatagc     540
tgacctcaac tccgccttcc ctgctggtac taatgtcgcc gcgacatggg acaagacact     600
cgcctacctt cgtggcaagg ccatgggtga ggaattcaac gacaagggcg tggacatttt     660
gctggggcct gctgctggtc ctctcggcaa atacccggac ggcggcagaa tctgggaagg     720
cttctctcct gatccggttc tcactggtgt acttttcgcc gaaactatca agggtatcca     780
agacgcgggt gtgattgcta ctgccaagca ttacattctg aatgaacagg agcatttccg     840
acaggttggc gaggcccagg gatatggtta acatcacg gagacgatca gctccaacgt     900
ggatgacaag accatgcacg agttgtacct ttggtgagta gttgacactg caaatgagga     960
ccttgattga tttgactgac ctggaatgca ggcccttgc agatgctgtg cgcggtaaga    1020 tttttccgtag acttgacctc gcgacgaaga aatcgctgac gaaccatcgt agctggcgtt    1080
ggcgctgtca tgtgttccta caatcaaatc aacaacagct acggttgtca aaacagtcaa    1140
actctcaaca agctcctcaa ggctgagctg ggcttccaag gcttcgtcat gagtgactgg    1200
agcgctcacc acagcggtgt cggcgctgcc ctcgctgggt tggatatgtc gatgcctgga    1260

```
gacatttcct tcgacgacgg actctccttc tggggcacga acctaactgt cagtgttctt    1320
aacggcaccg ttccagcctg gcgtgtcgat gacatggctg ttcgtatcat gaccgcgtac    1380
tacaaggttg gtcgtgaccg tcttcgtatt ccccctaact tcagctcctg gacccgggat    1440
gagtacggct gggagcattc tgctgtctcc gagggagcct ggaccaaggt gaacgacttc    1500
gtcaatgtgc agcgcagtca ctctcagatc atccgtgaga ttggtgccgc tagtacagtg    1560
ctcttgaaga cacgggtgc tcttcctttg accggcaagg aggttaaagt gggtgttctc    1620
ggtgaagacg ctggttccaa cccgtggggt gctaacggct gccccgaccg cggctgtgat    1680
aacggcactc ttgctatggc ctggggtagt ggtactgcca acttccctta ccttgtcacc    1740
cccgagcagg ctatccagcg agaggtcatc agcaacggcg gcaatgtctt tgctgtgact    1800
gataacgggg ctctcagcca gatggcagat gttgcatctc aatccaggtg agtgcgggct    1860
cttagaaaaa gaacgttctc tgaatgaagt ttttttaacca ttgcgaacag cgtgtctttg    1920
gtgtttgtca acgccgactc tggagagggt ttcatcagtg tcgacggcaa cgagggtgac    1980
cgcaaaaatc tcactctgtg gaagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgaggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaaccccct cctgaaggct ggcggcgctc ctggtggtaa ccctacccctt    2700 tatcaggatc ttgttagggt gtcggccacc ataaccaaca ctggtaacgt cgccggttat    2760
gaagtccctc aattggtgag tgaccccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc ctctgccccg tgtctactag    3060
```

<210> SEQ ID NO 76
<211> LENGTH: 863
<212> TYPE: PRT
<213> ORGANISM: Aspergillus fumigatus

<400> SEQUENCE: 76

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
                20                  25                  30

Trp Ala Asp Gly Gln Gly Glu Trp Ala Asp Ala His Arg Arg Ala Val
            35                  40                  45

Glu Ile Val Ser Gln Met Thr Leu Ala Glu Lys Val Asn Leu Thr Thr

-continued

```
                50                  55                  60
Gly Thr Gly Trp Glu Met Asp Arg Cys Val Gly Gln Thr Gly Ser Val
 65                  70                  75                  80

Pro Arg Leu Gly Ile Asn Trp Gly Leu Cys Gly Gln Asp Ser Pro Leu
                 85                  90                  95

Gly Ile Arg Phe Ser Asp Leu Asn Ser Ala Phe Pro Ala Gly Thr Asn
                100                 105                 110

Val Ala Ala Thr Trp Asp Lys Thr Leu Ala Tyr Leu Arg Gly Lys Ala
                115                 120                 125

Met Gly Glu Glu Phe Asn Asp Lys Gly Val Asp Ile Leu Leu Gly Pro
130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
                180                 185                 190

Ile Leu Asn Glu Gln Glu His Phe Arg Gln Val Gly Glu Ala Gln Gly
                195                 200                 205

Tyr Gly Tyr Asn Ile Thr Glu Thr Ile Ser Ser Asn Val Asp Asp Lys
                210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
                260                 265                 270

Gly Phe Gln Gly Phe Val Met Ser Asp Trp Ser Ala His His Ser Gly
                275                 280                 285

Val Gly Ala Ala Leu Ala Gly Leu Asp Met Ser Met Pro Gly Asp Ile
                290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
                340                 345                 350

Pro Pro Asn Phe Ser Ser Trp Thr Arg Asp Glu Tyr Gly Trp Glu His
                355                 360                 365

Ser Ala Val Ser Glu Gly Ala Trp Thr Lys Val Asn Asp Phe Val Asn
370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
                420                 425                 430

Ala Asn Gly Cys Pro Asp Arg Gly Cys Asp Asn Gly Thr Leu Ala Met
                435                 440                 445

Ala Trp Gly Ser Gly Thr Ala Asn Phe Pro Tyr Leu Val Thr Pro Glu
                450                 455                 460

Gln Ala Ile Gln Arg Glu Val Ile Ser Asn Gly Gly Asn Val Phe Ala
465                 470                 475                 480
```

Val Thr Asp Asn Gly Ala Leu Ser Gln Met Ala Asp Val Ala Ser Gln
              485                 490                 495

Ser Ser Val Ser Leu Val Phe Val Asn Ala Asp Ser Gly Glu Gly Phe
         500                 505                 510

Ile Ser Val Asp Gly Asn Glu Gly Asp Arg Lys Asn Leu Thr Leu Trp
         515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
             565                 570                 575

Gln Glu Ser Gly Asn Ser Leu Val Asp Val Leu Tyr Gly Arg Val Asn
             580                 585                 590

Pro Ser Ala Lys Thr Pro Phe Thr Trp Gly Lys Thr Arg Glu Ser Tyr
         595                 600                 605

Gly Ala Pro Leu Leu Thr Glu Pro Asn Asn Gly Asn Gly Ala Pro Gln
         610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
             645                 650                 655

Thr Phe Gly Tyr Ser His Leu Arg Val Gln Ala Leu Asn Ser Ser Ser
             660                 665                 670

Ser Ala Tyr Val Pro Thr Ser Gly Glu Thr Lys Pro Ala Pro Thr Tyr
         675                 680                 685

Gly Glu Ile Gly Ser Ala Ala Asp Tyr Leu Tyr Pro Glu Gly Leu Lys
         690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
             725                 730                 735

Pro Glu Gly Ala Arg Asp Gly Ser Pro Gln Pro Leu Leu Lys Ala Gly
         740                 745                 750

Gly Ala Pro Gly Gly Asn Pro Thr Leu Tyr Gln Asp Leu Val Arg Val
         755                 760                 765

Ser Ala Thr Ile Thr Asn Thr Gly Asn Val Ala Gly Tyr Glu Val Pro
    770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
             805                 810                 815

Thr Thr Thr Leu Asn Arg Arg Asp Leu Ala Asn Trp Asp Val Glu Ala
             820                 825                 830

Gln Asp Trp Val Ile Thr Lys Tyr Pro Lys Lys Val His Val Gly Ser
         835                 840                 845

Ser Ser Arg Lys Leu Pro Leu Arg Ala Pro Leu Pro Arg Val Tyr
    850                 855                 860

<210> SEQ ID NO 77
<211> LENGTH: 30
<212> TYPE: DNA
<213> ORGANISM: Aspergillus fumigatus

```
<400> SEQUENCE: 77
ggactgcgca ccatgagatt cggttggctc                                    30

<210> SEQ ID NO 78
<211> LENGTH: 30
<212> TYPE: DNA
<213> ORGANISM: Aspergillus fumigatus

<400> SEQUENCE: 78
tcgccacgga gcttactagt agacacgggg                                    30
```